US00RE46733E

(19) United States
(12) Reissued Patent
Gray et al.

(10) Patent Number: US RE46,733 E
(45) Date of Reissued Patent: Feb. 27, 2018

(54) XYLANASES, NUCLEIC ACIDS ENCODING THEM AND METHODS FOR MAKING AND USING THEM

(71) Applicant: BP Corporation North America Inc., Naperville, IL (US)

(72) Inventors: Kevin A. Gray, San Diego, CA (US); Richard Dirmeier, San Diego, CA (US)

(73) Assignee: BP Corporation North America Inc., Houston, TX (US)

(21) Appl. No.: 14/732,217

(22) Filed: Jun. 5, 2015

Related U.S. Patent Documents

Reissue of:
(64) Patent No.: 8,486,680
Issued: Jul. 16, 2013
Appl. No.: 12/681,604
PCT Filed: Aug. 1, 2008
PCT No.: PCT/US2008/072030
§ 371 (c)(1),
(2) Date: Sep. 14, 2010
PCT Pub. No.: WO2009/045627
PCT Pub. Date: Apr. 9, 2009

U.S. Applications:
(60) Provisional application No. 60/977,348, filed on Oct. 3, 2007.

(51) Int. Cl.
*C12N 9/24* (2006.01)
*C12P 19/02* (2006.01)
*C12P 19/14* (2006.01)
*D21H 17/22* (2006.01)

(52) U.S. Cl.
CPC ..... *C12N 9/248* (2013.01); *C12P 19/02* (2013.01); *C12P 19/14* (2013.01); *D21H 17/22* (2013.01); *Y02E 50/16* (2013.01); *Y02T 50/678* (2013.01); *Y10T 428/249921* (2015.04)

(58) Field of Classification Search
CPC ..... C12N 9/248; C12P 19/14; C12P 19/02; D21H 17/22; Y02E 50/16; Y10T 428/249921
USPC ..... 435/200, 18, 402; 530/18, 402
See application file for complete search history.

(56) References Cited

U.S. PATENT DOCUMENTS

| | | | |
|---|---|---|---|
| 5,736,384 | A | 4/1998 | Fukunaga |
| 5,916,795 | A | 6/1999 | Fukunaga |
| 5,935,836 | A | 8/1999 | Vehmaanperä et al. |
| 6,365,390 | B1 | 4/2002 | Blum et al. |
| 2005/0208178 | A1 | 9/2005 | Bauer et al. |
| 2007/0208178 | A1 | 9/2007 | Brand et al. |

FOREIGN PATENT DOCUMENTS

| | | | |
|---|---|---|---|
| WO | WO 94/24270 | A2 | 10/1994 |
| WO | WO 96/23062 | A1 | 8/1996 |
| WO | WO 97/13853 | A2 | 4/1997 |
| WO | WO 97/14803 | A1 | 4/1997 |
| WO | WO 97/22691 | A1 | 6/1997 |
| WO | WO 01/39289 | A2 | 7/2000 |
| WO | WO 01/66711 | A1 | 9/2001 |
| WO | WO 02/38746 | A2 | 5/2002 |
| WO | WO 03/020923 | A1 | 3/2003 |
| WO | WO 03/106654 | | 12/2003 |
| WO | WO 2004/066945 | | 8/2004 |
| WO | WO 2007/095398 | | 8/2007 |

OTHER PUBLICATIONS

Andrews, S. R. et al.: "*The Use of Forced Protein Evolution to Investigate and Improve Stability of Family 10 Xylanases*";Journal of Biological Chemistry (2004)—279—54369-54379.
Grepinet, O. et al.: "*Nucleotide Sequence and Deletion Analysis of the Xylanase Gene (xynZ) of Clostridium thermocellum*"; Journal of Bacteriology (1988)—170—4582-4588.
Japanese Office Action dated Jan. 27, 2016 regarding JP 2015-000134.
Japanese Office Action dated Oct. 24, 2016 regarding JP 2015-000134.
Andrews—Journal of Biological Chemistry (2004)—279—54369-54379.
Dalboge—Trends in Biotechnology (1998) 16—265-272.
EP 08797071.1—Extended EP Search Report—dated Aug. 10, 2010.
EP07751203.6—Extended EP Search Report—dated Jan. 22, 2010.
Grepinet—Journal of Bacteriology (1988)—170—4582-4588.
IN Patent Office—Dec. 22, 2010—First Examination Report—IN 0014/MUMNP/2005.
NCBI Accession No. AY502070—Nectria haematococca mpVl—Dec. 9, 2004.
UNIPROT Accession No. Q9KB30—Takami (2000).
EP08797071.1—Extended EP Search Report—dated Aug. 10, 2010.
Arase—FEBS Letters (1993)—316—123-127.
CIPO—Oct. 4, 2010—Office Action—CA 2488916.
Genbank Accession No. AAL57754—Nagy (2001).
Genbank Accession No. BAB79287—Kamei (2001).
Genbank Accession No. AF198618—Kanhiyur (1999).
Genbank Accession No. AB063255—Aoki (2001).
Genbank Accession No. AP001514—Takami (Jan. 10, 2001).
Genbank Accession No. BA000004—Takami (1999).
(Continued)

*Primary Examiner* — Gary Kunz
(74) *Attorney, Agent, or Firm* — DLA Piper LLP (US)

(57) ABSTRACT

The invention relates to enzymes having xylanase, mannanase and/or glucanase activity, e.g., catalyzing hydrolysis of internal β-1,4-xylosidic linkages or endo-β-1,4-glucanase linkages; and/or degrading a linear polysaccharide beta-1, 4-xylan into xylose. Thus, the invention provides methods and processes for breaking down hemicellulose, which is a major component of the cell wall of plants, including methods and processes for hydrolyzing hemicelluloses in any plant or wood or wood product, wood waste, paper pulp, paper product or paper waste or byproduct. In addition, methods of designing new xylanases, mannanases and/or glucanases and methods of use thereof are also provided. The xylanases, mannanases and/or glucanases have increased activity and stability at increased pH and temperature.

30 Claims, No Drawings

(56) References Cited

OTHER PUBLICATIONS

AUIP—Nov. 2, 2010—Examiner's First Report—AU 2008201402.
EPO—Dec. 17, 2010—Office Action—EP 03760440.2.
AUIP—Jan. 28, 2011—Examiner's Second Report—AU 2008201402.
EP10179289—Extended EP Search Report—dated Feb. 10, 2011.
EP10179307—Extended EP Search Report—dated Feb. 9, 2011.
EP10179325—Extended EP Search Report—dated Feb. 9, 2011.
Fushinobu—Protein Engineering (1998) 11—1121-1128.
PCT/US2008/072030—IPRP—dated Apr. 7, 2010.
PCT/US2008/072030—ISR & WO—dated Aug. 20, 2009.
NCBI Accession No. M22759—*Clostridium thermocellum*—Apr. 26, 1993.
U.S. Appl. No. 12/279,326—Notice of References Cited—dated Apr. 12, 2010.

XYLANASES, NUCLEIC ACIDS ENCODING THEM AND METHODS FOR MAKING AND USING THEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

[This application is the national phase application claiming the benefit of priority under 35 U.S.C. 371 to Patent Cooperation Treaty (PCT) Application No. PCT/US2008/072030 having an international filing date of Aug. 1, 2008 (published as WO 2009/045627, on Apr. 9, 2009); which claims the benefit of priority under 35 U.S.C. 119(e) to U.S. Provisional Application No. 60/977,348 filed 3 Oct. 2007. The contents of the above patent applications are incorporated by reference herein in their entirety.] *This application is a reissue application of U.S. application Ser. No. 12/681,604 filed Sep. 14, 2010, now issued as U.S. Pat. No. 8,486,680; which is a 35 USC § 371 National Stage application of International Application No. PCT/US2008/072030 filed Aug. 1, 2008, now expired; which claims the benefit under 35 USC § 119(e) to U.S. Application Ser. No. 60/977,348 filed Oct. 3, 2007. The disclosure of each of the prior applications is considered part of and is incorporated by reference in the disclosure of this application.*

STATEMENT AS TO RIGHTS TO INVENTIONS MADE UNDER FEDERALLY SPONSORED RESEARCH

This invention was made in part with Government support under Contract No. DOE 1435-04-03-CA-70224, awarded by the Department of Energy. The Government may have certain rights in the invention.

REFERENCE TO SEQUENCE LISTING SUBMITTED VIA EFS-WEB

This application was filed electronically via the USPTO EFS-WEB server, as authorized and set forth in MPEP § 502.05(IX), and this electronic filing includes an electronically submitted sequence (SEQ ID) listing; the entire content of this sequence listing is herein incorporated by reference all purposes. The sequence listing is identified on the electronically filed text file as follows:

| File Name | Date of Creation | Size |
|---|---|---|
| [D1680_5N_SUBSTITUTE_SequenceListing.txt] | [Sep. 28,] [2010] | [90,112] [bytes] |
| *BP1200-1_ST25.txt* | *Jun. 5, 2015* | *87 KB* |

FIELD OF THE INVENTION

This invention relates generally to enzymes, polynucleotides encoding the enzymes, the use of such polynucleotides and polypeptides and more specifically to enzymes having xylanase activity, e.g., endoxylanase activity, and/or catalyzing hydrolysis of internal β-1,4-xylosidic linkages or endo-β-1,4-glucanase linkages; and/or degrading a linear polysaccharide beta-1,4-xylan into xylose; or, a glucanase activity, e.g., an endoglucanase activity, for example, catalyzing hydrolysis of internal endo-β-1,4- and/or 1,3-glucanase linkages, a xylanase activity, and/or a mannanase activity. Thus, the invention provides methods and processes for breaking down hemicellulose, which is a major component of the cell wall of plants, including methods and processes for hydrolyzing hemicelluloses in any organic compound, plant or wood or wood product or byproduct, wood waste, paper pulp, paper product or paper waste or byproduct. The invention further provides methods and processes for breaking down plant matter containing cellulose and/or hemicellulose into simple sugars using the "cocktails" of the invention.

BACKGROUND

Xylanases (e.g., endo-1,4-beta-xylanase, EC 3.2.1.8) hydrolyze internal (β-1,4-xylosidic linkages in xylan to produce smaller molecular weight xylose and xylo-oligomers. Xylans are polysaccharides formed from 1,4-β-glycoside-linked D-xylopyranoses. Xylanases are of considerable commercial value, being used in the food industry, for baking and fruit and vegetable processing, breakdown of agricultural waste, in the manufacture of animal feed and in pulp and paper production. Xylanases are formed by fungi and bacteria.

Arabinoxylans are major non-starch polysaccharides of cereals representing 2.5-7.1% w/w depending on variety and growth conditions. The physicochemical properties of this polysaccharide are such that it gives rise to viscous solutions or even gels under oxidative conditions. In addition, arabinoxylans have high water-binding capacity and may have a role in protein foam stability. All of these characteristics present problems for several industries including brewing, baking, animal nutrition and paper manufacturing. In brewing applications, the presence of xylan results in wort filterability and haze formation issues. In baking applications (especially for cookies and crackers), these arabinoxylans create sticky doughs that are difficult to machine and reduce biscuit size. In addition, this carbohydrate is implicated in rapid rehydration of the baked product resulting in loss of crispiness and reduced shelf-life. For monogastric animal feed applications with cereal diets, arabinoxylan is a major contributing factor to viscosity of gut contents and thereby adversely affects the digestibility of the feed and animal growth rate. For ruminant animals, these polysaccharides represent substantial components of fiber intake and more complete digestion of arabinoxylans would facilitate higher feed conversion efficiencies.

There remains a need in the art for xylanases to be used in the paper and pulp industry, for example, where the enzyme is active in the temperature range of 65° C. to 75° C. and at a pH of approximately 10. Additionally, an enzyme useful in the paper and pulp industry would decrease the need for bleaching chemicals, such as chlorine dioxide.

Additionally, there remains a need to provide efficient, low cost processes and compositions for producing bioalcohols, biofuels and/or biofuel—(e.g., bioethanol-, propanol-, butanol- and/or methanol-) by conversion of biomass. An enzyme or enzyme "cocktail" could provide a route to convert biomass into sugars that could then be fermented into biofuels.

SUMMARY OF THE INVENTION

The invention provides enzymes having: xylanase activity, e.g., endoxylanase activity, and/or catalyzing hydrolysis of internal β-1,4-xylosidic linkages or endo-β-1,4-glucanase linkages; and/or, having a glucanase activity, e.g., an endoglucanase activity, for example, catalyzing hydrolysis of internal endo-β-1,4- and/or 1,3-glucanase linkages, a xylanase activity, and/or a mannanase activity; and, nucleic acids encoding them, vectors and cells comprising them, probes for amplifying and identifying these xylanase-encoding nucleic acids, and methods for making and using these polypeptides and peptides.

For example, the invention provides enzymes having xylanase (e.g., endoxylanase activity), and compositions and methods comprising them, for hydrolyzing internal β-1,4-xylosidic linkages or endo-β-1,4-glucanase linkages, or hemicelluloses, in a wood, wood product, paper pulp, paper product or paper waste. In one aspect, the xylanase activity comprises catalyzing hydrolysis of xylan, e.g., degrading a linear polysaccharide beta-1,4-xylan into a xylose. Thus, the invention provides methods and processes for breaking down a xylan-comprising composition and/or a hemicellulose, which is a major component of the cell wall of plants.

In one aspect, the glucanase activity of a polypeptide or peptide of the invention (which includes a protein or peptide encoded by a nucleic acid of the invention) comprises an endoglucanase activity, e.g., endo-1,4- and/or 1,3-beta-D-glucan 4-glucano hydrolase activity. In one aspect, the endoglucanase activity comprises catalyzing hydrolysis of 1,4-beta-D-glycosidic linkages. In one aspect, the glucanase, e.g., endoglucanase, activity comprises an endo-1,4- and/or 1,3-beta-endoglucanase activity or endo-β-1,4-glucanase activity. In one aspect, the glucanase activity (e.g., endo-1,4-beta-D-glucan 4-glucano hydrolase activity) comprises hydrolysis of 1,4-beta-D-glycosidic linkages in cellulose, cellulose derivatives (e.g., carboxy methyl cellulose and hydroxy ethyl cellulose) lichenin, beta-1,4 bonds in mixed beta-1,3 glucans, such as cereal beta-D-glucans and other plant material containing cellulosic parts. In one aspect, the glucanase, xylanase, or mannanase activity comprises hydrolyzing a glucan or other polysaccharide to produce a smaller molecular weight polysaccharide or oligomer. In one aspect, the glucan comprises a beta-glucan, such as a water soluble beta-glucan.

The invention provides enzymes, compositions, methods and processes for hydrolyzing hemicelluloses in any organic matter, including cells, plants and/or wood or wood products, wood waste, paper pulp, paper products or paper waste or byproducts. The invention further provides methods and processes for breaking down plant matter containing cellulose and/or hemicellulose into simple sugars using the "cocktails" of the invention.

In another aspect, the invention provides polypeptides having lignocellulolytic (lignocellulosic) activity, e.g., a ligninolytic and cellulolytic activity, including, e.g., having a hydrolase activity, e.g., a glycosyl hydrolase activity, including cellulase, glucanase, xylanase, and/or mannanase activity, and nucleic acids encoding them, and methods for making and using them. The invention provides enzymes for the bioconversion of any biomass, e.g., a lignocellulosic residue, into fermentable sugars or polysaccharides; and these sugars or polysaccharides can be used as a chemical feedstock for the production of alcohols such as ethanol, propanol, butanol and/or methanol, production of fuels, e.g., biofuels such as synthetic liquids or gases, such as syngas, and the production of other fermentation products, e.g. succinic acid, lactic acid, or acetic acid. Enzymes of the invention can be added to bioconversion and other industrial processes continuously, in batches or by fed-batch methods. In another aspect, enzymes of the invention can be recycled in bioconversion and other industrial processes, thereby lowering enzyme requirements.

In one aspect, the enzymes of the invention have an increased catalytic rate to improve the process of substrate (e.g., a lignocellulosic residue, cellulose, bagasse) hydrolysis. This increased efficiency in catalytic rate leads to an increased efficiency in producing sugars or polysaccharides, which can be useful in industrial, agricultural or medical applications, e.g., to make a biofuel or an alcohol such as ethanol, propanol, butanol and/or methanol. In one aspect, sugars produced by hydrolysis using enzymes of this invention can be used by microorganisms for alcohol (e.g., ethanol, propanol, butanol and/or methanol) production and/or fuel (e.g., biofuel) production. Additionally, the sugars produced by hydrolysis using the enzymes of the invention can be used by microorganisms for the production of other fermentation products, e.g. succinic acid, lactic acid, or acetic acid.

The invention provides industrial, agricultural or medical applications: e.g., biomass to biofuel, e.g., ethanol, propanol, butanol and/or methanol, using enzymes of the invention having decreased enzyme costs, e.g., decreased costs in biomass to biofuel conversion processes. Thus, the invention provides efficient processes for producing bioalcohols, biofuels and/or biofuel—(e.g., bioethanol-, propanol-, butanol- and/or methanol-) comprising compositions, including synthetic, liquid or gas fuels comprising a bioalcohol, from any biomass.

In one aspect, enzymes of the invention, including the enzyme "cocktails" of the invention ("cocktails" meaning mixtures of enzymes comprising at least one enzyme of this invention), are used to hydrolyze the major components of a lignocellulosic biomass, or any composition comprising cellulose and/or hemicellulose (lignocellulosic biomass also comprises lignin), e.g., seeds, grains, tubers, plant waste (such as a hay or straw, e.g., a rice straw or a wheat straw, or any the dry stalk of any cereal plant) or byproducts of food processing or industrial processing (e.g., stalks), corn (including cobs, stover, and the like), grasses (e.g., Indian grass, such as Sorghastrum nutans; or, switch grass, e.g., Panicum species, such as Panicum virgatum), wood (including wood chips, processing waste, such as wood waste), paper, pulp, recycled paper (e.g., newspaper); also including a monocot or a dicot, or a monocot corn, sugarcane or parts thereof (e.g., cane tops), rice, wheat, barley, switchgrass or Miscanthus; or a dicot oilseed crop, soy, canola, rapeseed, flax, cotton, palm oil, sugar beet, peanut, tree, poplar or lupine; or, woods or wood processing byproducts, such as wood waste, e.g., in the wood processing, pulp and/or paper industry, in textile manufacture and in household and industrial cleaning agents, and/or in biomass waste processing.

In one aspect, enzymes of the invention are used to hydrolyze cellulose comprising a linear chain of β-1,4-linked glucose moieties, and/or hemicellulose as a complex structure that varies from plant to plant. In one aspect, enzymes of the invention are used to hydrolyze hemicelluloses containing a backbone of β-1,4 linked xylose molecules with intermittent branches of arabinose, galactose, glucuronic acid and/or mannose. In one aspect, enzymes of the invention are used to hydrolyze hemicellulose containing non-carbohydrate constituents such as acetyl groups on xylose and ferulic acid esters on arabinose. In one aspect, enzymes of the invention are used to hydrolyze hemicelluloses covalently linked to lignin and/or coupled to other hemicellulose strands via diferulate crosslinks.

In one aspect, the compositions and methods of the invention are used in the enzymatic digestion of biomass and can comprise use of many different enzymes, including the cellulases and hemicellulases. Lignocellulosic enzymes used to practice the invention can digest cellulose to monomeric sugars, including glucose. In one aspect, compositions used to practice the invention can include mixtures of enzymes, e.g., glycosyl hydrolases, glucose oxidases, xylanases, xylosidases (e.g., β-xylosidases), cellobiohydrolases, and/or arabinofuranosidases or other enzymes that can digest hemicellulose to monomer sugars. Mixtures of the invention can comprise, or consist of, only enzymes of this invention, or can include at least one enzyme of this invention and another enzyme, which can also be a lignocellulosic enzyme and/or any other enzyme.

In one aspect, the enzymes of the invention have a glucanase, e.g., an endoglucanase, activity, e.g., catalyzing hydrolysis of internal endo-β-1,4- and/or β-1,3-glucanase linkages. In one aspect, the endoglucanase activity (e.g., endo-1,4-beta-D-glucan 4-glucano hydrolase activity) comprises hydrolysis of 1,4- and/or β-1,3-beta-D-glycosidic linkages in cellulose, cellulose derivatives (e.g., carboxy methyl cellulose and hydroxy ethyl cellulose) lichenin, beta-1,4 bonds in mixed beta-1,3 glucans, such as cereal beta-D-glucans or xyloglucans and other plant material containing cellulosic parts.

In alternative embodiments, the invention provides polypeptides (and the nucleic acids that encode them) having at least one conservative amino acid substitution and retaining its xylanase, a mannanase and/or a glucanase activity; or, wherein the at least one conservative amino acid substitution comprises substituting an amino acid with another amino acid of like characteristics; or, a conservative substitution comprises: replacement of an aliphatic amino acid with another aliphatic amino acid; replacement of a Serine with a Threonine or vice versa; replacement of an acidic residue with another acidic residue; replacement of a residue bearing an amide group with another residue bearing an amide group; exchange of a basic residue with another basic residue; or replacement of an aromatic residue with another aromatic residue;

In alternative embodiments, the invention provides polypeptides (and the nucleic acids that encode them) having a xylanase (e.g., an endoxylanase), a mannanase and/or a glucanase activity but lacking a signal sequence, a prepro domain, a dockerin domain, and/or a carbohydrate binding module (CBM); and in one aspect, the carbohydrate binding module (CBM) comprises, or consists of, a xylan binding module, a cellulose binding module, a lignin binding module, a xylose binding module, a mannanse binding module, a xyloglucan-specific module and/or a arabinofuranosidase binding module.

In alternative embodiments, the invention provides polypeptides (and the nucleic acids that encode them) having a xylanase (e.g., an endoxylanase), a mannanase and/or a glucanase activity further comprising a heterologous sequence; and in one aspect, the heterologous sequence comprises, or consists of a sequence encoding: (i) a heterologous signal sequence, a heterologous carbohydrate binding module, a heterologous dockerin domain, a heterologous catalytic domain (CD), or a combination thereof; (ii) the sequence of (ii), wherein the heterologous signal sequence, carbohydrate binding module or catalytic domain (CD) is derived from a heterologous enzyme; or, (iii) a tag, an epitope, a targeting peptide, a cleavable sequence, a detectable moiety or an enzyme; and in one aspect, the hcterologous carbohydrate binding module (CBM) comprises, or consists of, a xylan binding module, a cellulose binding module, a lignin binding module, a xylose binding module, a mannanse binding module, a xyloglucan-specific module and/or a arabinofuranosidase binding module; and in one aspect, the heterologous signal sequence targets the encoded protein to a vacuole, the endoplasmic reticulum, a chloroplast or a starch granule.

The invention provides isolated, synthetic or recombinant nucleic acids comprising (a) a nucleic acid (polynucleotide) encoding at least one polypeptide, wherein the nucleic acid comprises a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete (100%) sequence identity to:

(i) the nucleic acid (polynucleotide) sequence of SEQ ID NO:1 having one or more nucleotide residue changes (or the equivalent thereof) as set forth in Table 1, or having at least one, two, three, four, five, six, seven, eight, nine, ten, eleven, twelve, thirteen, fourteen, fifteen, sixteen, seventeen or eighteen, or some or all of the following nucleotide residue changes: the codon encoding amino acid residue 4 changed from ACC to AAC; the codon encoding amino acid residue 4 changed from ACC to CGC; the codon encoding amino acid residue 4 changed from ACC to CAC; the codon encoding amino acid residue 9 changed from CCC to GAC; the codon encoding amino acid residue 17 changed from TTC to GTC; the codon encoding amino acid residue 21 changed from TTC to TAC; the codon encoding amino acid residue 33 changed from CTG to GCG; the codon encoding amino acid residue 38 changed from CGT to CAC; the codon encoding amino acid residue 44 changed from AGC to ACG; the codon encoding amino acid residue 63 changed from ATC to GTC; the codon encoding amino acid residue 73 changed from GGC to TAC; the codon encoding amino acid residue 73 changed from GGC to GAG; the codon encoding amino acid residue 73 changed from GGC to GTC; the codon encoding amino acid residue 108 changed from TTC to AAG; the codon encoding amino acid residue 125 changed from CAG to TAC; the codon encoding amino acid residue 150 changed from GTA to GCC; the codon encoding amino acid residue 188 changed from AGC to GAG; and/or, the codon encoding amino acid residue 189 changed from TCC to CAG; or (ii) the nucleic acid (polynucleotide) sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21 or SEQ ID NO:23;

wherein the nucleic acid of (i) or (ii) encodes at least one polypeptide having a xylanase, a mannanase and/or a glucanase activity, or encodes a polypeptide or peptide capable of generating a xylanase, a mannanase and/or a glucanase specific antibody (a polypeptide or peptide that acts as an epitope or immunogen), (b) the nucleic acid (polynucleotide) of (a), wherein the sequence identities are determined: (A) by analysis with a sequence comparison algorithm or by a visual inspection, or (B) over a region of at least about 20, 30, 40, 50, 75, 100, 150, 200, 250, 300, 350, 400, 450, 500, 550, 600, 650, 700, 750, 800, 850, 900, 950, 1000, 1050, 1100, 1150 or more residues, or over the full length of a cDNA, transcript (mRNA) or gene;

(c) the nucleic acid (polynucleotide) of (a) or (b), wherein the sequence comparison algorithm is a BLAST version 2.2.2 algorithm where a filtering setting is set to blastall -p blastp -d "nr pataa"-F F, and all other options are set to default;

(d) a nucleic acid (polynucleotide) encoding at least one polypeptide or peptide, wherein the nucleic acid comprises a sequence that hybridizes under stringent conditions to a nucleic acid comprising the nucleic acid (polynucleotide) sequence of SEQ ID NO:1 having one or more nucleotide residue changes (or the equivalent thereof) as set forth in Table 1, or having at least one, two, three, four, five, six, seven, eight, nine, ten, eleven, twelve, thirteen, fourteen, fifteen, sixteen, seventeen or eighteen, or some or all of the following nucleotide residue changes: the codon encoding amino acid residue 4 changed from ACC to AAC; the codon encoding amino acid residue 4 changed from ACC to CGC; the codon encoding amino acid residue 4 changed from ACC to CAC; the codon encoding amino acid residue 9 changed from CCC to GAC; the codon encoding amino acid residue 17 changed from TTC to GTC; the codon encoding amino acid residue 21 changed from TTC to TAC; the codon encoding amino acid residue 33 changed from CTG to GCG; the codon encoding amino acid residue 38 changed from CGT to CAC; the codon encoding amino acid residue 44 changed from AGC to ACG; the codon encoding amino acid residue 63 changed from ATC to GTC; the codon encoding amino acid residue 73 changed from GGC to TAC; the codon encoding amino acid residue 73 changed from GGC to GAG; the codon encoding amino acid residue 73 changed from GGC to GTC; the codon encoding amino acid residue 108 changed from TTC to AAG; the codon encoding amino acid residue 125 changed from CAG to TAC; the codon encoding amino acid residue 150 changed from GTA to GCC; the codon encoding amino acid residue 188 changed from AGC to GAG; and/or, the codon encoding amino acid residue 189 changed from TCC to CAG, wherein the polypeptide or peptide has a xylanase, a mannanase and/or a glucanase activity or is capable of generating a xylanase, a mannanase and/or a glucanasc specific antibody (a polypeptide or peptide that acts as an epitope or immunogen), and the stringent conditions comprise a wash step comprising a wash in 0.2×SSC at a temperature of about 65° C. for about 15 minutes;

(e) a nucleic acid (polynucleotide) encoding at least one polypeptide or peptide, wherein the nucleic acid comprises a sequence that hybridizes under stringent conditions to a nucleic acid comprising the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21 or SEQ ID NO:23, and the stringent conditions comprise a wash step comprising a wash in 0.2×SSC at a temperature of about 65° C. for about 15 minutes;

(f) the nucleic acid (polynucleotide) of any of (a) to (d) having a length of at least about 20, 25, 30, 50, 75, 100, 125, 150, 175, 200, 225, 300, 350, 400, 450, 500, 550, 600, 650, 700, 750, 800, 850, 900, 950, 1000, 1050, 1100, 1150 or more nucleotide residues, or the full length of a gene or a transcript;

(g) a nucleic acid (polynucleotide) encoding at least one polypeptide having a xylanase, a mannanase and/or a glucanase activity, wherein the polypeptide comprises the sequence of SEQ ID NO:2, or enzymatically active fragments thereof, has at least one, two, three, four, five, six, seven, eight, nine, ten, eleven, twelve, thirteen, fourteen, fifteen, sixteen, seventeen or eighteen or some or all of the following amino acid residue changes:

(h) a nucleic acid (polynucleotide) encoding at least one polypeptide having a xylanase, a mannanase and/or a glucanase activity, wherein the polypeptide comprises the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or enzymatically active fragments thereof;

(i) (A) the nucleic acid (polynucleotide) of any of (a) to (h) and encoding a polypeptide having at least one conservative amino acid substitution and retaining its xylanase, a mannanase and/or a glucanase activity; or, (B) the nucleic acid of (i)(A), wherein the at least one conservative amino acid substitution comprises substituting an amino acid with another amino acid of like characteristics; or, a conservative substitution comprises: replacement of an aliphatic amino acid with another aliphatic amino acid; replacement of a Serine with a Threonine or vice versa; replacement of an acidic residue with another acidic residue; replacement of a residue bearing an amide group with another residue bearing an amide group; exchange of a basic residue with another basic residue; or replacement of an aromatic residue with another aromatic residue;

(j) the nucleic acid (polynucleotide) of any of (a) to (i) encoding a polypeptide having a xylanase, a mannanase and/or a glucanase activity but lacking a signal sequence, a prepro domain, a dockerin domain, and/or a carbohydrate binding module (CBM);

(k) the nucleic acid (polynucicotide) of (j), wherein the carbohydrate binding module (CBM) comprises, or consists of, a xylan binding module, a cellulose binding module, a lignin binding module, a xylose binding module, a mannanse binding module, a xyloglucan-specific module and/or a arabinofuranosidase binding module;

(l) the nucleic acid (polynucleotide) of any of (a) to (k) encoding a polypeptide having a xylanase, a mannanase and/or a glucanase activity further comprising a heterologous sequence;

(m) the nucleic acid (polynucleotide) of (l), wherein the heterologous sequence comprises, or consists of a sequence encoding: (A) a heterologous signal sequence, a heterologous carbohydrate binding module, a heterologous dockerin domain, a heterologous catalytic domain (CD), or a combination thereof; (B) the sequence of (l), wherein the heterologous signal sequence, carbohydrate binding module or catalytic domain (CD) is derived from a heterologous enzyme; or, (C) a tag, an epitope, a targeting peptide, a cleavable sequence, a detectable moiety or an enzyme;

(n) the nucleic acid (polynucleotide) of (l), wherein the heterologous carbohydrate binding module (CBM) comprises, or consists of, a xylan binding module, a cellulose binding module, a lignin binding module, a xylose binding module, a mannanse binding module, a xyloglucan-specific module and/or a arabinofuranosidase binding module;

(o) the nucleic acid (polynucleotide) of (l), wherein the heterologous signal sequence targets the encoded protein to a vacuole, the endoplasmic reticulum, a chloroplast or a starch granule; or (p) a nucleic acid sequence (polynucleotide) fully (completely) complementary to the sequence of any of (a) to (o).

The invention provides isolated, synthetic or recombinant nucleic acids comprising a nucleic acid encoding at least one polypeptide having a xylanase (e.g., an endoxylanase), a mannanase and/or a glucanase activity, wherein the polypeptide has a sequence as set forth in SEQ ID NO:2 having one or more changes as described herein and in Table 1, or enzymatically active fragments thereof, including the sequences described herein and in Table 1, and the Sequence Listing (all of these sequences are "exemplary enzymes/polypeptides of the invention"), and enzymatically active subsequences (fragments) thereof and/or immunologically active subsequences thereof (such as epitopes or immunogens) (all "peptides of the invention") and variants thereof (all of these sequences encompassing polypeptide and peptide sequences of the invention) (or, hereinafter referred to as the exemplary polypeptide sequences of the inventions).

The invention provides isolated, synthetic or recombinant nucleic acids comprising sequences completely complementary to all of these nucleic acid sequences of the invention (complementary (non-coding) and coding sequences also hereinafter collectively referred to as nucleic acid sequences of the invention).

In one aspect, the sequence identity is at least about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (complete) sequence identity (homology). In one aspect, the sequence identity is over a region of at least about 150, 175, 200, 225, 250, 275, 300, 350, 400, 450, 500, 550, 600, 650, 700, 750, 800, 850, 900, 950, 1000, 1050, 1100, 1150 or more residues, or the full length of a gene or a transcript. For example, the invention provides isolated, synthetic or recombinant nucleic acids comprising a nucleic acid sequence of SEQ ID NO:1 having one or more mutations as described herein, e.g., as described in Tablet 1 (the exemplary polynucleotide sequences of this invention). The invention provides isolated, synthetic or recombinant nucleic acids encoding a polypeptide comprising a sequence of SEQ ID NO:2 having one or more amino acid change as described herein, e.g., as set forth in Table 1 (the exemplary polypeptide sequences of this invention), and enzymatically active fragments thereof.

The invention provides isolated, synthetic or recombinant nucleic acids encoding a polypeptide having xylanase (e.g., an endoxylanase), a mannanase and/or a glucanase activity, wherein the nucleic acid has at least one sequence modification of an exemplary sequence of the invention, or, any sequence of the invention.

The invention provides isolated, synthetic or recombinant nucleic acids encoding a polypeptide having xylanase (e.g., an endoxylanase), a mannanase and/or a glucanase activity, wherein the nucleic acid has at least one sequence modification of an exemplary nucleic acid of the invention, wherein in one aspect the modifications (changes) are set forth in Table 1.

In one aspect, the invention also provides enzyme-encoding nucleic acids with a common novelty in that they encode a novel subset of xylanases, or a Glade, comprising the "X14 module" (J Bacteriol. 2002 August; 184(15): 4124-4133). In one aspect, the invention also provides enzyme-encoding nucleic acids with a common novelty in that they encode a novel subset of xylanases, or a Glade, comprising the "X14 module". Thus, in one aspect, the invention provides a novel genus of xylanases comprising xylanase members of SEQ ID NO:2 having one or more mutations as described herein, e.g., in Table 1.

In one aspect (optionally), the isolated, synthetic or recombinant nucleic acids of the invention have a xylanase (e.g., an endoxylanase), a mannanase and/or a glucanase activity, e.g., wherein the xylanase activity comprises catalyzing hydrolysis of internal β-1,4-xylosidic linkages; comprises an endo-1,4-beta-xylanase activity; comprises hydrolyzing a xylan or an arabinoxylan to produce a smaller molecular weight xylose and xylo-oligomer; comprises hydrolyzing a polysaccharide comprising a 1,4-β-glycoside-linked D-xylopyranose; comprises hydrolyzing a cellulose or a hemicellulose; comprises hydrolyzing a cellulose or a hemicellulose in a wood, wood product, paper pulp, paper product or paper waste; comprises catalyzing hydrolysis of a xylan or an arabinoxylan in a feed or a food product; or, comprises catalyzing hydrolysis of a xylan or an arabinoxylan in a microbial cell or a plant cell. In one aspect, the xylanase activity comprises hydrolyzing polysaccharides comprising 1,4-β-glycoside-linked D-xylopyranoses or hydrolyzing hemicelluloses, e.g., hydrolyzing hemicelluloses in a wood, wood product, paper pulp, paper product or paper waste. In one aspect, the arabinoxylan is a cereal arabinoxylan, such as a wheat arabinoxylan.

In one aspect, the xylanase, a mannanase and/or a glucanase activity comprises catalyzing hydrolysis of polysaccarides, e.g., mannans or xylans, in a feed or a food product, such as a cereal-based animal feed, a wort or a beer, a milk or a milk product, a fruit or a vegetable. In one aspect, the xylanase, a mannanase and/or a glucanase activity comprises catalyzing hydrolysis of polysaccarides, e.g., mannans or xylans, in a microbial cell or a plant cell.

In one aspect, the xylanase, a mannanase and/or a glucanase activity is thermostable, e.g., wherein the polypeptide retains a xylanase, a mannanase and/or a glucanase activity under conditions comprising a temperature range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermostable polypeptides according to the invention retains activity, e.g., a xylanase, a mannanase and/or a glucanase activity, at a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In one aspect, the xylanase, a mannanase and/or a glucanase activity is thermotolerant, e.g., wherein the polypeptide retains a xylanase, a mannanase and/or a glucanase activity after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. The thermotolerant polypeptides according to the invention can retain activity, e.g. a xylanase, a mannanase and/or a glucanase activity, after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermotolerant polypeptides according to the invention retains activity, e.g. a xylanase, a mannanase and/or a glucanase activity, after exposure to a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In one aspect, the xylanase, a mannanase and/or a glucanase activity of polypeptides encoded by nucleic acids of the invention retain activity under acidic conditions comprising about pH 6.5, pH 6, pH 5.5, pH 5, pH 4.5, pH 4.0, pH 3.5, pH 3.0 or less (more acidic) pH, or, retain a xylanase, a mannanase and/or a glucanase activity after exposure to acidic conditions comprising about pH 6.5, pH 6, pH 5.5, pH 5, pH 4.5, pH 4.0, pH 3.5, pH 3.0 or less (more acidic) pH; or, retain activity under basic conditions comprising about pH 7, pH 7.5 pH 8.0, pH 8.5, pH 9, pH 9.5, pH 10, pH 10.5, pH 11, pH 11.5, pH 12, pH 12.5 or more (more basic) or, retain a xylanase, a mannanase and/or a glucanase activity after exposure to basic conditions comprising about pH 7, pH 7.5 pH 8.0, pH 8.5, pH 9, pH 9.5, pH 10, pH 10.5, pH 11, pH 11.5, pH 12, pH 12.5 or more (more basic). In one aspect, xylanase, a mannanase and/or a glucanase activity of polypeptides encoded by nucleic acids of the invention retain activity at a temperature of at least about 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 7.5 pH 8.0, pH 8.5, pH 9, pH 9.5, pH 10, pH 10.5, pH 11, pH 11.5, pH 12, pH 12.5 or more (more basic).

The invention provides expression cassettes, cloning vehicles, or a vector (e.g., expression vectors) comprising a nucleic acid comprising a sequence of the invention. The cloning vehicle can comprise a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise an artificial chromosome comprising a bacterial artificial chromosome (BAC), a bacteriophage P1-derived vector (PAC), a yeast artificial chromosome (YAC), or a mammalian artificial chromosome (MAC).

The invention provides nucleic acid probes for identifying a nucleic acid encoding a polypeptide with a xylanase, a mannanase and/or a glucanase activity, wherein the probe comprises at least about 10, 15, 20, 25, 30, 35, 40, 45, 50, 55, 60, 65, 70, 75, 100, 125, 150, 175, 200, 225, 250, 275, 300 or more consecutive bases of a nucleic acid comprising an exemplary sequence of the invention, or, any sequence of the invention (as defined herein), wherein in one aspect (optionally) the probe comprises an oligonucleotide comprising between at least about 10 to 300, about 25 to 250, about 10 to 50, about 20 to 60, about 30 to 70, about 40 to 80, about 60 to 100, or about 50 to 150 or more consecutive bases.

The invention provides amplification primer pairs for amplifying a nucleic acid encoding a polypeptide having a xylanase, a mannanase and/or a glucanase activity, wherein the primer pair is capable of amplifying a nucleic acid comprising an exemplary sequence of the invention, or, any sequence of the invention (as defined herein), or a subsequence thereof, wherein optionally a member of the amplification primer sequence pair comprises an oligonucleotide comprising at least about 10 to 50 consecutive bases of the sequence, or, about 10, 11, 12, 13, 14, 15, 16, 17, 18, 19, 20, 21, 22, 23, 24, 25, 26, 27, 28, 29, 30, 31, 32, 33, 34, 35 or more consecutive bases of the sequence. The invention provides amplification primer pairs wherein the primer pair comprises a first member having a sequence as set forth by about the first (the 5') 10, 11, 12, 13, 14, 15, 16, 17, 18, 19, 20, 21, 22, 23, 24, 25, 26, 27, 28, 29, 30, 31, 32, 33, 34, 35 or more residues of an exemplary sequence of the invention, or, any sequence of the invention (as defined herein), and a second member having a sequence as set forth by about the first (the 5') 10, 11, 12, 13, 14, 15, 16, 17, 18, 19, 20, 21, 22, 23, 24, 25, 26, 27, 28, 29, 30, 31, 32, 33, 34, 35 or more residues of the complementary strand of the first member.

The invention provides xylanase- and/or a glucanase-encoding nucleic acids generated by amplification of a polynucleotide using an amplification primer pair of the invention, wherein optionally the amplification is by polymerase chain reaction (PCR). In one aspect, the nucleic acid is generated by amplification of a gene library, wherein in one aspect (optionally) the gene library is an environmental library. The invention provides isolated, synthetic or recombinant xylanases and/or a glucanases encoded by a xylanase- and/or a glucanase-encoding nucleic acid generated by amplification of a polynucleotide using an amplification primer pair of the invention. The invention provides methods of amplifying a nucleic acid encoding a polypeptide having a xylanase, a mannanase and/or a glucanase activity, the methods comprising the step of amplification of a template nucleic acid with an amplification primer sequence pair capable of amplifying an exemplary sequence of the invention, or, any sequence of the invention (as defined herein), or a subsequence thereof.

The invention provides expression cassette, a vector or a cloning vehicle comprising a nucleic acid comprising a sequence of the invention, wherein optionally the cloning vehicle comprises a viral vector, a plasmid, a phage, a phagemid, a cosmid, a fosmid, a bacteriophage or an artificial chromosome. The viral vector can comprise an adenovirus vector, a retroviral vector or an adeno-associated viral vector, or, the artificial chromosome comprises a bacterial artificial chromosome (BAC), a bacteriophage P1-derived vector (PAC), a yeast artificial chromosome (YAC), or a mammalian artificial chromosome (MAC).

The invention provides transformed cells comprising a nucleic acid or vector of the invention, or an expression cassette or cloning vehicle of the invention. The transformed cell can be a bacterial cell, a mammalian cell, a fungal cell, a yeast cell, an insect cell or a plant cell.

The invention provides transgenic non-human animals comprising a sequence of the invention. The transgenic non-human animal can be a mouse, a rat, a rabbit, a sheep, a pig, a chicken, a goat, a fish, a dog, or a cow. The invention provides transgenic plants comprising a sequence of the invention, e.g., wherein the plant is a corn plant, a sorghum plant, a potato plant, a tomato plant, a wheat plant, an oilseed plant, a rapeseed plant, a soybean plant, a rice plant, a barley plant, a grass, or a tobacco plant. The invention provides transgenic seeds comprising a sequence of the invention, e.g., wherein the seed is a corn seed, a wheat kernel, an oilseed, a rapeseed, a soybean seed, a palm kernel, a sunflower seed, a sesame seed, a rice, a barley, a peanut or a tobacco plant seed.

The invention provides antisense oligonucleotides comprising a nucleic acid sequence complementary to or capable of hybridizing under stringent conditions to a sequence of the invention (including, e.g., exemplary sequences of the invention), or a subsequence thereof, wherein optionally the antisense oligonucleotide is between about 10 to 50, about 20 to 60, about 30 to 70, about 40 to 80, or about 60 to 100 bases in length, and in one aspect (optionally) the stringent conditions comprise a wash step comprising a wash in 0.2×SSC at a temperature of about 65° C. for about 15 minutes.

The invention provides methods of inhibiting the translation of a xylanase, a mannanase and/or a glucanase message in a cell comprising administering to the cell or expressing in the cell an antisense oligonucleotide comprising a nucleic acid sequence complementary to or capable of hybridizing under stringent conditions to a sequence of the invention (including, e.g., exemplary sequences of the invention).

The invention provides double-stranded inhibitory RNA (RNAi) molecules comprising a subsequence of a sequence of the invention (including, e.g., exemplary sequences of the invention). The double-stranded inhibitory RNA (RNAi) molecule can be about 10, 11, 12, 13, 14, 15, 16, 17, 18, 19, 20, 21, 22, 23, 24, 25, 26, 27, 28, 29, or 30 or more duplex nucleotides in length. The invention provides methods of inhibiting the expression of a xylanase, a mannanase and/or a glucanase in a cell comprising administering to the cell or expressing in the cell a double-stranded inhibitory RNA (iRNA), wherein the RNA comprises a subsequence of a sequence of the invention (including, e.g., exemplary sequences of the invention).

The invention provides isolated, synthetic or recombinant polypeptides having a xylanase, a mannanase and/or a glucanase activity, or polypeptides capable of generating an immune response specific for a xylanase (e.g., an endoxylanase), a mannanase and/or a glucanase (e.g., an epitope); and in alternative aspects peptide and polypeptide of the invention comprise a sequence:

(a) comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or has 100% (complete) sequence identity to:

(i) the amino acid sequence of SEQ ID NO:2, or enzymatically active fragments thereof, and having at least one amino acid residue change (or the equivalent thereof) as set forth in Table 1, or having at least one, two, three, four, five, six, seven, eight, nine, ten, eleven, twelve, thirteen, fourteen, fifteen, sixteen, seventeen or eighteen or some or all of the following amino acid residue changes: amino acid residue 4 is changed from a T (or thr, or threonine) to an N (or asn, or asparagine); amino acid residue 4 is changed from a T (or thr, or threonine) to an R (or arg, or arginine); amino acid residue 4 is changed from a T (or thr, or threonine) to an H (or his, or histidine); amino acid residue 9 is changed from a P (or pro, or proline) to an D (or asp, or aspartic acid); amino acid residue 17 is changed from a F (or phe, or phenylalanine) to an V (or val, or valine); amino acid residue 21 is changed from a F (or phe, or phenylalanine) to an Y (or tyr, or tyrosine); amino acid residue 33 is changed from a L (or leu, or leucine) to an A (or ala, or alanine); amino acid residue 38 is changed from a R (or arg, or arginine) to an H (or his, or histidine); amino acid residue 44 is changed from a S (or ser, or serine) to an T (or thr, or threonine); amino acid residue 63 is changed from a I (or ile, or isoleucine) to an V (or val, or valine); amino acid residue 73 is change from a G (or gly, or glycine) to an Y (or tyr, or tyrosine); amino acid residue 73 is changed from a G (or gly, or glycine) to an V (or val, or valine); amino acid residue 73 is changed from a G (or gly, or glycine) to an E (or gin, or glutamic acid); amino acid residue 108 is changed from a F (or phe, or phenylalaine) to an K (or lys, or lysine); amino acid residue 125 is change from a Q (or gln, or glutamine) to an Y (or tyr, or tyrosine); amino acid residue 150 is change from a V (or val, or valine) to an A (or ala, or alanine); amino acid residue 188 is changed from a S (or ser, or serine) to an E (or glu, or glutamic acid); and/or amino acid residue 189 is changed from a S (or ser, or serine) to an Q (or gln, or glutamine), or (ii) the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 or SEQ ID NO:24;

wherein the polypeptide or peptide of (i) or (ii) has a xylanase, a mannanase and/or a glucanase activity, or the polypeptide or peptide is capable of generating a xylanase, a mannanase and/or a glucanase specific antibody (a polypeptide or peptide that acts as an epitope or immunogen), (b) the polypeptide or peptide of (a), wherein the sequence identities are determined: (A) by analysis with a sequence comparison algorithm or by a visual inspection, or (B) over a region of at least about 20, 25, 30, 35, 40, 45, 50, 55, 60, 75, 100, 150, 200, 250, 300 or more amino acid residues, or over the full length of the polypeptide or peptide or enzyme, and/or enzymatically active subsequences (fragments) thereof, (c) the polypeptide or peptide of (a) of (b), wherein the sequence identities are determined by analysis with a sequence comparison algorithm or by a visual inspection, and optionally the sequence comparison algorithm is a BLAST version 2.2.2 algorithm where a filtering setting is set to blastall -p blastp -d "nr pataa"-F F, and all other options are set to default;

(d) an amino acid sequence encoded by the nucleic acid of claim 1, wherein the polypeptide has (i) a xylanase, a mannanase and/or a glucanase activity, or, (ii) has immunogenic activity in that it is capable of generating an antibody that specifically binds to a polypeptide having a sequence of (a), and/or enzymatically active subsequences (fragments) thereof;

(e) the amino acid sequence of any of (a) to (d), and comprising at least one amino acid residue conservative substitution, and the polypeptide or peptide retains xylanase, a mannanase and/or a glucanase activity;

(e) the amino acid sequence of (e), wherein the conservative substitution comprises replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or, replacement of an aromatic residue with another aromatic residue, or a combination thereof, (f) the amino acid sequence of (e), wherein the aliphatic residue comprises Alanine, Valine, Leucine, Isoleucine or a synthetic equivalent thereof, the acidic residue comprises Aspartic acid, Glutamic acid or a synthetic equivalent thereof; the residue comprising an amide group comprises Aspartic acid, Glutamic acid or a synthetic equivalent thereof, the basic residue comprises Lysine, Arginine or a synthetic equivalent thereof; or, the aromatic residue comprises Phenylalanine, Tyrosine or a synthetic equivalent thereof;

(g) the polypeptide of any of (a) to (f) having a xylanase, a mannanase and/or a glucanase activity but lacking a signal sequence, a prepro domain, a dockerin domain, and/or a carbohydrate binding module (CBM), (h) the polypeptide of (g) wherein the carbohydrate binding module (CBM) comprises, or consists of, a xylan binding module, a cellulose binding module, a lignin binding module, a xylose binding module, a mannanse binding module, a xyloglucan-specific module and/or a arabinofuranosidase binding module;

(i) the polypeptide of any of (a) to (h) having a xylanase, a mannanase and/or a glucanase activity further comprising a heterologous sequence;

(j) the polypeptide of (i), wherein the heterologous sequence comprises, or consists of: (A) a heterologous signal sequence, a heterologous carbohydrate binding module, a heterologous dockerin domain, a heterologous catalytic domain (CD), or a combination thereof; (B) the sequence of (A), wherein the heterologous signal sequence, carbohydrate binding module or catalytic domain (CD) is derived from a heterologous lignocellulosic enzyme; and/or, (C) a tag, an epitope, a targeting peptide, a cleavable sequence, a detectable moiety or an enzyme;

(k) the polypeptide of (i) or (j), wherein the heterologous sequence or the heterologous carbohydrate binding module (CBM) comprises, or consists of, a xylan binding module, a cellulose binding module, a lignin binding module, a xylose binding module, a mannan binding module, a xyloglucan-specific module and/or a arabinofuranosidase binding module;

(l) polypeptide of (i), wherein the heterologous signal sequence targets the encoded protein to a vacuole, the endoplasmic reticulum, a chloroplast or a starch granule; or (m) comprising an amino acid sequence encoded any nucleic acid sequence of this invention.

In one aspect, the isolated, synthetic or recombinant peptides of the invention have a xylanase activity, e.g., wherein the xylanase activity comprises catalyzing hydrolysis of internal β-1,4-xylosidic linkages; comprises an endo-1,4-beta-xylanase activity; comprises hydrolyzing a xylan or an arabinoxylan to produce a smaller molecular weight xylose and xylo-oligomer; comprises hydrolyzing a polysaccharide comprising a 1,4-β-glycoside-linked D-xylopyranose; comprises hydrolyzing a cellulose or a hemicellulose; comprises hydrolyzing a cellulose or a hemicellulose in a wood, wood product, paper pulp, paper product or paper waste; comprises catalyzing hydrolysis of a xylan or an arabinoxylan in a feed or a food product; or, comprises catalyzing hydrolysis of a xylan or an arabinoxylan in a microbial cell or a plant cell. The xylan can comprises an arabinoxylan, e.g., a water soluble arabinoxylan, e.g., a water soluble arabinoxylan in a dough or a bread product.

In one aspect, the xylanase, a mannanase and/or a glucanase activity comprises hydrolyzing polysaccharides, for example, comprising 1,4-β-glycoside-linked D-xylopyranoses, or hydrolyzing hemicelluloses, e.g., hydrolyzing hemicelluloses in a wood, wood product, paper pulp, paper product or paper waste.

In one aspect, the xylanase, a mannanase and/or a glucanase activity comprises catalyzing hydrolysis of polysaccharides, e.g., xylans, in a feed or a food product, such as a cereal-based animal feed, a wort or a beer, a milk or a milk product, a fruit or a vegetable. In one aspect, the xylanase activity comprises catalyzing hydrolysis of xylans in a microbial cell or a plant cell.

The invention provides isolated, synthetic or recombinant polypeptides comprising a polypeptide of the invention and lacking a signal sequence or a prepro sequence. The invention provides isolated, synthetic or recombinant polypeptides comprising a polypeptide of the invention and having a heterologous signal sequence or a heterologous prepro sequence.

In one aspect, a polypeptide of the invention has xylanase, a mannanase and/or a glucanase activity comprising a specific activity at about 37° C. in the range from about 100 to about 1000 units per milligram of protein, from about 500 to about 750 units per milligram of protein, from about 500 to about 1200 units per milligram of protein, or from about 750 to about 1000 units per milligram of protein. In one aspect, units are defined as 0.1 to 20 units/g of pulp, where a unit equals umol of xylose released per minute per mg of enzyme, using arabinoxylan as a substrate as described in the Nelson Somogyi assay, described in detail below. In alternative aspects, polypeptides of the invention have xylanase, a mannanase and/or a glucanase activity in the range of between about 0.05 to 20 units per gram of pulp, or 0.05, 0.10, 0.20, 0.30, 0.40, 0.50, 0.60, 0.70, 0.80, 0.90, 1.0, 1.5, 2.0, 2.5, 3.0, 3.5, 4.0, 4.5, 5.0, 5.5, 6.0, 6.5, 7, 8, 9, 10, 11, 12, 13, 14, 15, 16, 17, 18, 19 or 20 or more units per gram of pulp (where a unit equals umol of xylose released per minute per mg of enzyme, using arabinoxylan as a substrate as described in the Nelson Somogyi assay).

In one aspect, the thermotolerance comprises retention of at least half of the specific activity of the xylanase, a mannanase and/or a glucanase at 37° C. after being heated to an elevated temperature, such as a temperature from about 0° C. to about 20° C., about 20° C. to about 37° C., about 37° C. to about 50° C., about 50° C. to about 70° C., about 70° C. to about 75° C., about 75° C. to about 80° C., about 80° C. to about 85° C., about 85° C. to about 90° C., about 90° C. to about 95° C., about 95° C. to about 100° C., about 100° C. to about 110° C., or higher. The thermotolerance can comprise retention of specific activity at 37° C. in the range from about 500 to about 1200 units per milligram of protein after being heated to an elevated temperature, such as a temperature from about 0° C. to about 20° C., about 20° C. to about 37° C., about 37° C. to about 50° C., about 50° C. to about 70° C., about 70° C. to about 75° C., about 75° C. to about 80° C., about 80° C. to about 85° C., about 85° C. to about 90° C., about 90° C. to about 95° C., about 95° C. to about 100° C., about 100° C. to about 110° C., or higher.

In one aspect, the polypeptides of the invention comprise at least one glycosylation site or further comprises a polysaccharide. The glycosylation can be an N-linked glycosylation, e.g., wherein the polypeptide is glycosylated after being expressed in a P. pastoris or a S. pombe.

In one aspect, the xylanase, a mannanase and/or a glucanase activity of polypeptides of the invention retain activity under acidic conditions comprising about pH 6.5, pH 6, pH 5.5, pH 5, pH 4.5 or pH 4 or less (more acidic), or, retain a xylanase, a mannanase and/or a glucanase activity after exposure to acidic conditions comprising about pH 6.5, pH 6, pH 5.5, pH 5, pH 4.5 or pH 4 or less (more acidic); or, retain activity under basic conditions comprising about pH 7, pH 7.5 pH 8.0, pH 8.5, pH 9, pH 9.5, pH 10, pH 10.5, pH 11, pH 11.5, pH 12, pH 12.5 or more (more basic) or, retain a xylanase, a mannanase and/or a glucanase activity after exposure to basic conditions comprising about pH 7, pH 7.5 pH 8.0, pH 8.5, pH 9, pH 9.5, pH 10, pH 10.5, pH 11, pH 11.5, pH 12, pH 12.5 or more (more basic). In one aspect, xylanase, a mannanase and/or a glucanase activity of polypeptides of the invention retain activity at a temperature of at least about 80° C., 81° C., 82° C., 83° C., 84° C., 85° C., 86° C., 87° C., 88° C., 89° C. or 90° C., and a basic pH of at least about pH 7.5 pH 8.0, pH 8.5, pH 9, pH 9.5, pH 10, pH 10.5, pH 11, pH 11.5, pH 12, pH 12.5 or more (more basic).

The invention provides protein preparation comprising a polypeptide of the invention, wherein the protein preparation comprises a liquid, a slurry, a solid or a gel. The invention provides heterodimers comprising a polypeptide of the invention and a second domain. The second domain can be a polypeptide and the heterodimer is a fusion protein. the second domain can be an epitope or a tag. The invention provides homodimers or heterodimers comprising a polypeptide of the invention. The invention provides immobilized polypeptides, wherein the polypeptide comprises a sequence of the invention, or a subsequence thereof, or a polypeptide encoded by a nucleic acid of the invention, or a polypeptide comprising a polypeptide of the invention and a second domain, e.g., wherein the polypeptide is immobilized on or inside a cell, a vesicle, a liposome, a film, a membrane, a metal, a resin, a polymer, a ceramic, a glass, a microelectrode, a graphitic particle, a bead, a gel, a plate, an array, a capillary tube, a crystal, a tablet, a pill, a capsule, a powder, an agglomerate, a surface, a porous structure, or materials such as wood chips, brownstock, pulp, paper, and materials deriving therefrom.

The xylanases and/or a glucanases of the invention can be used or formulated alone or as mixture (a "cocktail") of xylanases and/or a glucanases, and other hydrolytic enzymes such as cellulases, mannanases, proteases, lipases, amylases, or redox enzymes such as laccases, peroxidases, catalases, oxidases, or reductases. They can be used formulated in a solid form such as a powder, a lyophilized preparation, a granule, a tablet, a bar, a crystal, a capsule, a pill, a pellet, or in a liquid form such as in an aqueous solution, an aerosol, a gel, a paste, a slurry, an aqueous/oil emulsion, a cream, a capsule, or in a vesicular or micellar suspension. The formulations of the invention can comprise any or a combination of the following ingredients: polyols such as a polyethylene glycol, a polyvinylalcohol, a glycerol, a sugar such as a sucrose, a sorbitol, a trehalose, a glucose, a fructose, a maltose, a mannose, a gelling agent such as a guar gum, a carageenan, an alginate, a dextrans, a cellulosic derivative, a pectin, a salt such as a sodium chloride, a sodium sulfate, an ammonium sulfate, a calcium chloride, a magnesium chloride, a zinc chloride, a zinc sulfate, a salt of a fatty acid and a fatty acid derivative, a metal chelator such as an EDTA, an EGTA, a sodium citrate, an antimicrobial agent such as a fatty acid or a fatty acid derivative, a paraben, a sorbate, a benzoate, an additional modulating compound to block the impact of an enzyme such as a protease, a bulk proteins such as a BSA, a wheat hydrolysate, a borate compound, an amino acid or a peptide, an appropriate pH or temperature modulating compound, an emulsifier such as a non-ionic and/or an ionic detergent, a redox agent such as a cystine/cysteine, a glutathione, an oxidized glutathione, a reduced or an antioxidant compound such as an ascorbic acid, or a dispersant. Cross-linking and protein modification such as pegylation, fatty acid modification, glycosylation can also be used to improve enzyme stability.

The invention provides arrays comprising immobilized polypeptide(s) and/or nucleic acids of the invention, and arrays comprising an immobilized oligonucleotide of the invention. The enzymes, fragments thereof and nucleic acids which encode the enzymes, or probes of the invention, and fragments thereof, can be affixed to a solid support; and these embodiments can be economical and efficient in the use of enzymes and nucleic acids of the invention in industrial, medical, research, pharmaceutical, food and feed and food and feed supplement processing and other applications and processes. For example, a consortium or cocktail of enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, the isolated nucleic acid is affixed to a solid support. In another embodiment of the invention, the solid support is selected from the group of a gel, a resin, a polymer, a ceramic, a glass, a microelectrode and any combination thereof.

For example, solid supports useful in this invention include gels. Some examples of gels include sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof. Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof. Another type of solid support useful in the present invention is ceramic. Some examples include non-porous ceramic, porous ceramic, $SiO_2$, $Al_2O_3$. Another type of solid support useful in the present invention is glass. Some examples include non-porous glass, porus glass, aminopropyl glass or any combination thereof. Another type of solid support which can be used is a mcroelectrode. An example is a polyethyleneimine-coated magnetite. Graphitic particles can be used as a solid support. Another example of a solid support is a cell, such as a red blood cell.

There are many methods which would be known to one of skill in the art for immobilizing enzymes or fragments thereof, or nucleic acids, onto a solid support. Some examples of such methods include electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Edited by G. F. Bickerstaff. Series: Methods in Biotechnology, Edited by J. M. Walker.

The invention provides isolated, synthetic or recombinant antibodies that specifically binds to a polypeptide of the invention. The antibody can be a monoclonal or a polyclonal antibody, or is a single chained antibody. The invention provides hybridomas comprising an antibody that specifically binds to a polypeptide of the invention.

The invention provides methods of isolating or identifying a polypeptide with a xylanase, a mannanase and/or a glucanase activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having a xylanase, a mannanase and/or a glucanase activity. The invention provides methods of making an anti-xylanase and/or anti-glucanase antibody comprising administering to a non-human animal a nucleic acid of the invention or a subsequence thereof in an amount sufficient to generate a humoral immune response, thereby making an anti-xylanase and/or anti-glucanase antibody. The invention provides methods of making an anti-xylanase and/or anti-glucanase antibody comprising administering to a non-human animal a polypeptide of the invention or a subsequence thereof in an amount sufficient to generate a humoral immune response, thereby making an anti-xylanase and/or anti-glucanase antibody.

The invention provides methods of producing a recombinant polypeptide comprising the steps of: (a) providing a nucleic acid operably linked to a promoter, wherein the nucleic acid comprises a sequence of the invention; and (b) expressing the nucleic acid of step (a) under conditions that allow expression of the polypeptide, thereby producing a recombinant polypeptide. The method can further comprise transforming a host cell with the nucleic acid of step (a) followed by expressing the nucleic acid of step (a), thereby producing a recombinant polypeptide in a transformed cell.

The invention provides methods for identifying a polypeptide having a xylanase, a mannanase and/or a glucanase activity comprising: (a) providing a polypeptide of the invention; (b) providing a xylanase, a mannanase and/or a glucanase substrate; and (c) contacting the polypeptide with the substrate of step (b) and detecting a decrease in the amount of substrate or an increase in the amount of a reaction product, wherein a decrease in the amount of the substrate or an increase in the amount of the reaction product detects a polypeptide having a xylanase, a mannanase and/or a glucanase activity.

The invention provides methods for identifying a xylanase, a mannanase and/or a glucanase substrate comprising: (a) providing a polypeptide of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a xylanase, a mannanase and/or a glucanase substrate.

The invention provides methods of determining whether a test compound specifically binds to a polypeptide comprising: (a) expressing a nucleic acid or a vector comprising the nucleic acid under conditions permissive for translation of the nucleic acid to a polypeptide, wherein the nucleic acid has a sequence of the invention; (b) providing a test compound; (c) contacting the polypeptide with the test compound; and (d) determining whether the test compound of step (b) specifically binds to the polypeptide.

The invention provides methods of determining whether a test compound specifically binds to a polypeptide comprising: (a) providing a polypeptide of the invention; (b) providing a test compound; (c) contacting the polypeptide with the test compound; and (d) determining whether the test compound of step (b) specifically binds to the polypeptide.

The invention provides methods for identifying a modulator of a xylanase, a mannanase and/or a glucanase activity comprising: (a) providing a polypeptide of the invention; (b) providing a test compound; (c) contacting the polypeptide of step (a) with the test compound of step (b) and measuring an activity of the xylanase, a mannanase and/or a glucanase, wherein a change in the xylanase, a mannanase and/or a glucanase activity measured in the presence of the test compound compared to the activity in the absence of the test compound provides a determination that the test compound modulates the xylanase, a mannanase and/or a glucanase activity. The xylanase, a mannanase and/or a glucanase activity can be measured by providing a xylanase, a mannanase and/or a glucanase substrate and detecting a decrease in the amount of the substrate or an increase in the amount of a reaction product, or, an increase in the amount of the substrate or a decrease in the amount of a reaction product. In one aspect, a decrease in the amount of the substrate or an increase in the amount of the reaction product with the test compound as compared to the amount of substrate or reaction product without the test compound identifies the test compound as an activator of a xylanase, a mannanase and/or a glucanase activity. In one aspect, an increase in the amount of the substrate or a decrease in the amount of the reaction product with the test compound as compared to the amount of substrate or reaction product without the test compound identifies the test compound as an inhibitor of a xylanase, a mannanase and/or a glucanase activity.

The invention provides computer systems comprising a processor and a data storage device wherein said data storage device has stored thereon a polypeptide sequence or a nucleic acid sequence, wherein the polypeptide sequence comprises sequence of the invention, a polypeptide encoded by a nucleic acid of the invention. The computer systems can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program. The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

The invention provides methods for isolating or recovering a nucleic acid encoding a polypeptide having a xylanase, a mannanase and/or a glucanase activity from an environmental sample comprising the steps of: (a) providing an amplification primer sequence pair for amplifying a nucleic acid encoding a polypeptide having a xylanase, a mannanase and/or a glucanase activity, wherein the primer pair is capable of amplifying a nucleic acid of the invention; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide having a xylanase, a mannanase and/or a glucanase activity from an environmental sample. One or each member of the amplification primer sequence pair can comprise an oligonucleotide comprising at least about 10 to 50 consecutive bases of a sequence of the invention. In one aspect, the amplification primer sequence pair is an amplification pair of the invention.

The invention provides methods for isolating or recovering a nucleic acid encoding a polypeptide having a xylanase, a mannanase and/or a glucanase activity from an environmental sample comprising the steps of: (a) providing a polynucleotide probe comprising a nucleic acid of the invention or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide having a xylanase, a mannanase and/or a glucanase activity from an environmental sample. The environmental sample can comprise a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide having a xylanase, a mannanase and/or a glucanase activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant xylanase, a mannanase and/or a glucanase polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly (e.g., GeneReassembly, see, e.g., U.S. Pat. No. 6,537,776), Gene Site Saturation Mutagenesis (GSSM), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until a xylanase, a mannanase and/or a glucanase having an altered or different activity or an altered or different stability from that of a polypeptide encoded by the template nucleic acid is produced. In one aspect, the variant xylanase, a mannanase and/or a glucanase polypeptide is thermotolerant, and retains some activity after being exposed to an elevated temperature. In another aspect, the variant xylanase, a mannanase and/or a glucanase polypeptide has increased glycosylation as compared to the xylanase, a mannanase and/or a glucanase encoded by a template nucleic acid. Alternatively, the variant xylanase, a mannanase and/or a glucanase polypeptide has a xylanase, a mannanase and/or a glucanase activity under a high temperature, wherein the xylanase, a mannanase and/or a glucanase encoded by the template nucleic acid is not active under the high temperature. In one aspect, the method can be iteratively repeated until a xylanase, a mannanase and/or a glucanase coding sequence having an altered codon usage from that of the template nucleic acid is produced. In another aspect, the method can be iteratively repeated until a xylanase, a mannanase and/or a glucanase gene having higher or lower level of message expression or stability from that of the template nucleic acid is produced. In another aspect, formulation of the final xylanase, a mannanase and/or a glucanase product enables an increase or modulation of the performance of the xylanase, a mannanase and/or a glucanase in the product.

The invention provides methods for modifying codons in a nucleic acid encoding a polypeptide having a xylanase, a mannanase and/or a glucanase activity to increase its expression in a host cell, the method comprising: (a) providing a nucleic acid of the invention encoding a polypeptide having a xylanase, a mannanase and/or a glucanase activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide having a xylanase, a mannanase and/or a glucanase activity; the method comprising: (a) providing a nucleic acid of the invention; and, (b) identifying a codon in the nucleic acid of step (a) and replacing it with a different codon encoding the same amino acid as the replaced codon, thereby modifying codons in a nucleic acid encoding a xylanase, a mannanase and/or a glucanase.

The invention provides methods for modifying codons in a nucleic acid encoding a polypeptide having a xylanase, a mannanase and/or a glucanase activity to increase its expression in a host cell, the method comprising: (a) providing a nucleic acid of the invention encoding a xylanase, a mannanase and/or a glucanase polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having a xylanase, a mannanase and/or a glucanase activity to decrease its expression in a host cell, the method comprising: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified xylanase, a mannanase and/or a glucanase active sites or substrate binding sites, wherein the modified active sites or substrate binding sites are derived from a first nucleic acid comprising a sequence encoding a first active site or a first substrate binding site the method comprising: (a) providing a first nucleic acid encoding a first active site or first substrate binding site, wherein the first nucleic acid sequence comprises a sequence that hybridizes under stringent conditions to a sequence of the invention, or a subsequence thereof, and the nucleic acid encodes a xylanase, a mannanase and/or a glucanase active site or a xylanase, a mannanase and/or a glucanase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified xylanase, a mannanase and/or a glucanase active sites or substrate binding sites. In one aspect, the method comprises mutagenizing the first nucleic acid of step (a) by a method comprising an optimized directed evolution system, Gene Site Saturation Mutagenesis (GSSM), or a synthetic ligation reassembly (SLR). In one aspect, the method comprises mutagenizing the first nucleic acid of step (a) or variants by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly (GeneReassembly, U.S. Pat. No. 6,537,776), Gene Site Saturation Mutagenesis (GSSM), synthetic ligation reassembly (SLR) and a combination thereof. In one aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising: (a) providing a plurality of biosynthetic enzymes capable of synthesizing or modifying a small molecule, wherein one of the enzymes comprises a xylanase, a mannanase and/or a glucanase enzyme encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. The invention provides methods for modifying a small molecule comprising: (a) providing a xylanase, a mannanase and/or a glucanase enzyme, wherein the enzyme comprises a polypeptide of the invention, or, a polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the xylanase, a mannanase and/or a glucanase enzyme, thereby modifying a small molecule by a xylanase, a mannanase and/or a glucanase enzymatic reaction. In one aspect, the method can comprise a plurality of small molecule substrates for the enzyme of step (a), thereby generating a library of modified small molecules produced by at least one enzymatic reaction catalyzed by the xylanase, a mannanase and/or a glucanase enzyme. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule that exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of a xylanase, a mannanase and/or a glucanase enzyme comprising the steps of: (a) providing a xylanase, a mannanase and/or a glucanase enzyme, wherein the enzyme comprises a polypeptide of the invention, or a polypeptide encoded by a nucleic acid of the invention, or a subsequence thereof; and (b) deleting a plurality of amino acid residues from the sequence of step (a) and testing the remaining subsequence for a xylanase, a mannanase and/or a glucanase activity, thereby determining a functional fragment of a xylanase, a mannanase and/or a glucanase enzyme. In one aspect, the xylanase, a mannanase and/or a glucanase activity is measured by providing a xylanase, a mannanase and/or a glucanase substrate and detecting a decrease in the amount of the substrate or an increase in the amount of a reaction product.

The invention provides methods for whole cell engineering of new or modified phenotypes by using real-time metabolic flux analysis, the method comprising: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides isolated, synthetic or recombinant signal sequences consisting of, or comprising, a sequence as set forth in residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43 or 1 to 44, of a polypeptide of the invention, including exemplary polypeptide sequences of the invention.

The invention provides chimeric polypeptides comprising at least a first domain comprising a signal peptide (SP) and at least a second domain comprising a heterologous polypeptide or peptide comprising a sequence of the invention, or a subsequence thereof, wherein the heterologous polypeptide or peptide is not naturally associated with the signal peptide (SP). In one aspect, the signal peptide (SP) is not derived from a xylanase, a mannanase and/or a glucanase. The heterologous polypeptide or peptide can be amino terminal to, carboxy terminal to or on both ends of the signal peptide (SP) or a xylanase, a mannanase and/or a glucanase catalytic domain (CD). The invention provides isolated, synthetic or recombinant nucleic acids encoding a chimeric polypeptide, wherein the chimeric polypeptide comprises at least a first domain comprising signal peptide (SP) and at least a second domain comprising a heterologous polypeptide or peptide comprising a sequence of the invention, or a subsequence thereof, wherein the heterologous polypeptide or peptide is not naturally associated with the signal peptide (SP).

The invention provides methods of increasing thermotolerance or thermo stability of a xylanase, a mannanase and/or a glucanase polypeptide, the method comprising glycosylating a xylanase, a mannanase and/or a glucanase polypeptide, wherein the polypeptide comprises at least thirty contiguous amino acids of a polypeptide of the invention; or a polypeptide encoded by a nucleic acid sequence of the invention, thereby increasing the thermotolerance or thermostability of the xylanase, a mannanase and/or a glucanase polypeptide. In one aspect, the xylanase, a mannanase and/or a glucanase specific activity can be thermostable or thermotolerant at a temperature in the range from greater than about 0° C. to about 20° C., about 20° C. to about 37° C., about 37° C. to about 50° C., about 50° C. to about 70° C., about 70° C. to about 75° C., about 75° C. to about 80° C., about 80° C. to about 85° C., about 85° C. to about 90° C., about 90° C. to about 95° C., about 95° C. to about 100° C., about 100° C. to about 110° C., or higher.

The invention provides methods for overexpressing a recombinant xylanase, a mannanase and/or a glucanase polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides methods of making a transgenic plant and seeds comprising: (a) introducing a heterologous nucleic acid sequence into the cell, wherein the heterologous nucleic sequence comprises a nucleic acid sequence of the invention, thereby producing a transformed plant or seed cell; and (b) producing a transgenic plant from the transformed cell or seed. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an Agrobacterium tumefaciens host. In one aspect, the plant cell can be a potato, corn, rice, wheat, tobacco, or barley cell.

The invention provides methods of expressing a heterologous nucleic acid sequence in a plant cell comprising: (a) transforming the plant cell with a heterologous nucleic acid sequence operably linked to a promoter, wherein the heterologous nucleic sequence comprises a nucleic acid of the invention; (b) growing the plantunder conditions wherein the heterologous nucleic acids sequence is expressed in the plant cell. The invention provides methods of expressing a heterologous nucleic acid sequence in a plant cell comprising: (a) transforming the plant cell with a heterologous nucleic acid sequence operably linked to a promoter, wherein the heterologous nucleic sequence comprises a sequence of the invention; (b) growing the plant under conditions wherein the heterologous nucleic acids sequence is expressed in the plant cell.

The invention provides methods for hydrolyzing, breaking up or disrupting a xylan-comprising composition comprising: (a) providing a polypeptide of the invention having a xylanase, a mannanase and/or a glucanase activity, or a polypeptide encoded by a nucleic acid of the invention; (b) providing a composition comprising a xylan; and (c) contacting the polypeptide of step (a) with the composition of step (b) under conditions wherein the xylanase, a mannanase and/or a glucanase hydrolyzes, breaks up or disrupts the xylan-comprising composition. In one aspect, the composition comprises a plant cell, a bacterial cell, a yeast cell, an insect cell, or an animal cell. Thus, the composition can comprise any plant or plant part, any xylan-containing food or feed, a waste product and the like.

The invention provides methods for liquefying or removing a xylan-comprising composition comprising: (a) providing a polypeptide of the invention having a xylanase activity, or a polypeptide encoded by a nucleic acid of the invention; (b) providing a composition comprising a xylan; and (c) contacting the polypeptide of step (a) with the composition of step (b) under conditions wherein the xylanase removes, softens or liquefies the xylan-comprising composition.

The invention provides detergent compositions comprising a polypeptide of the invention, or a polypeptide encoded by a nucleic acid of the invention, wherein the polypeptide has a xylanase, a mannanase and/or a glucanase activity. The xylanase can be a nonsurface-active xylanase, a mannanase and/or a glucanase or a surface-active xylanase, a mannanase and/or a glucanase. The xylanase, a mannanase and/or a glucanase can be formulated in a non-aqueous liquid composition, a cast solid, a granular form, a particulate form, a compressed tablet, a gel form, a paste or a slurry form. The invention provides methods for washing an object comprising: (a) providing a composition comprising a polypeptide of the invention having a xylanase, a mannanase and/or a glucanase activity, or a polypeptide encoded by a nucleic acid of the invention; (b) providing an object; and (c) contacting the polypeptide of step (a) and the object of step (b) under conditions wherein the composition can wash the object.

The invention provides textiles or fabrics, including, e.g., threads, comprising a polypeptide of the invention, or a polypeptide encoded by a nucleic acid of the invention. In one aspect, the textiles or fabrics comprise xylan-containing fibers. The invention provides methods for treating a textile or fabric (e.g., removing a stain from a composition) comprising: (a) providing a composition comprising a polypeptide of the invention having a xylanase, a mannanase and/or a glucanase activity, or a polypeptide encoded by a nucleic acid of the invention; (b) providing a textile or fabric comprising a xylan; and (c) contacting the polypeptide of step (a) and the composition of step (b) under conditions wherein the xylanase, a mannanase and/or a glucanase can treat the textile or fabric (e.g., remove the stain). The invention provides methods for improving the finish of a fabric comprising: (a) providing a composition comprising a polypeptide of the invention having a xylanase, a mannanase and/or a glucanase activity, or a polypeptide encoded by a nucleic acid of the invention; (b) providing a fabric; and (c) contacting the polypeptide of step (a) and the fabric of step (b) under conditions wherein the polypeptide can treat the fabric thereby improving the finish of the fabric. In one aspect, the fabric is a wool or a silk. In another aspect, the fabric is a cellulosic fiber or a blend of a natural fiber and a synthetic fiber.

The invention provides feeds or foods comprising a polypeptide of the invention, or a polypeptide encoded by a nucleic acid of the invention. The invention provides methods for hydrolyzing xylans in a feed or a food prior to consumption by an animal comprising: (a) obtaining a feed material comprising a xylanase, a mannanase and/or a glucanase of the invention, or a xylanase, a mannanase and/or a glucanase encoded by a nucleic acid of the invention; and (b) adding the polypeptide of step (a) to the feed or food material in an amount sufficient for a sufficient time period to cause hydrolysis of the xylan and formation of a treated food or feed, thereby hydrolyzing the xylans in the food or the feed prior to consumption by the animal. In one aspect, the invention provides methods for hydrolyzing xylans in a feed or a food after consumption by an animal comprising: (a) obtaining a feed material comprising a xylanase, a mannanase and/or a glucanase of the invention, or a xylanase, a mannanase and/or a glucanase encoded by a nucleic acid of the invention; (b) adding the polypeptide of step (a) to the feed or food material; and (c) administering the feed or food material to the animal, wherein after consumption, the xylanase, a mannanase and/or a glucanase causes hydrolysis of xylans in the feed or food in the digestive tract of the animal. The food or the feed can be, e.g., a cereal, a grain, a corn and the like.

The invention provides dough or bread products comprising a polypeptide having a xylanase, a mannanase and/or a glucanase activity, wherein the polypeptide comprises a sequence of the invention, or the polypeptide is encoded by a nucleic acid comprising a sequence of the invention, or an enzymatically active fragment thereof. The invention provides methods of dough conditioning comprising contacting a dough or a bread product with at least one polypeptide-having a xylanase, a mannanase and/or a glucanase activity, wherein the polypeptide comprises a sequence of the invention, or the polypeptide is encoded by a nucleic acid comprising a sequence of the invention, or an enzymatically active fragment thereof, under conditions sufficient for conditioning the dough.

The invention provides beverages comprising a polypeptide having a xylanase, a mannanase and/or a glucanase activity, wherein the polypeptide comprises a sequence of the invention, or the polypeptide is encoded by a nucleic acid comprising a sequence of the invention. The invention provides methods of beverage production comprising administration of at least one polypeptide having a xylanase, a mannanase and/or a glucanase activity, wherein the polypeptide comprises a sequence of the invention, or the polypeptide is encoded by a nucleic acid comprising a sequence of the invention, or an enzymatically active fragment thereof, to a beverage or a beverage precursor under conditions sufficient for decreasing the viscosity of the beverage, wherein in one aspect (optionally) the beverage or beverage precursor is a wort or a beer.

The invention provides food or nutritional supplements for an animal comprising a polypeptide of the invention, e.g., a polypeptide encoded by the nucleic acid of the invention. In one aspect, the polypeptide in the food or nutritional supplement can be glycosylated. The invention provides edible enzyme delivery matrices comprising a polypeptide of the invention, e.g., a polypeptide encoded by the nucleic acid of the invention. In one aspect, the delivery matrix comprises a pellet. In one aspect, the polypeptide can be glycosylated. In one aspect, the xylanase, a mannanase and/or a glucanaseactivity is thermotolerant. In another aspect, the xylanase, a mannanase and/or a glucanase activity is thermostable.

The invention provides a food, a feed or a nutritional supplement comprising a polypeptide of the invention. The invention provides methods for utilizing a xylanase, a mannanase and/or a glucanase as a nutritional supplement in an animal diet, the method comprising: preparing a nutritional supplement containing a xylanase, a mannanase and/or a glucanase enzyme comprising at least thirty contiguous amino acids of a polypeptide of the invention; and administering the nutritional supplement to an animal to increase utilization of a xylan contained in a feed or a food ingested by the animal. The animal can be a human, a ruminant or a monogastric animal. The xylanase, a mannanase and/or a glucanase enzyme can be prepared by expression of a polynucleotide encoding the xylanase, a mannanase and/or a glucanase in an organism selected from the group consisting of a bacterium, a yeast, a plant, an insect, a fungus and an animal. The organism can be selected from the group consisting of an S. pombe, S. cerevisiae, Pichia pastoris, Pseudomonas sp., E. coli, Streptomyces sp., Bacillus sp. and Lactobacillus sp.

The invention provides edible enzyme delivery matrix comprising a thermostable recombinant xylanase, a mannanase and/or a glucanase enzyme, e.g., a polypeptide of the invention. The invention provides methods for delivering a xylanase, a mannanase and/or a glucanase supplement to an animal, the method comprising: preparing an edible enzyme delivery matrix in the form of pellets comprising a granulate edible carrier and a thermostable recombinant xylanase, a mannanase and/or a glucanase enzyme, wherein the pellets readily disperse the xylanase, a mannanase and/or a glucanase enzyme contained therein into aqueous media, and administering the edible enzyme delivery matrix to the animal. The recombinant xylanase, a mannanase and/or a glucanase enzyme can comprise a polypeptide of the invention. The granulate edible carrier can comprise a carrier selected from the group consisting of a grain germ, a grain germ that is spent of oil, a hay, an alfalfa, a timothy, a soy hull, a sunflower seed meal and a wheat midd. The edible carrier can comprise grain germ that is spent of oil. The xylanase, a mannanase and/or a glucanase enzyme can be glycosylated to provide thermostability at pelletizing conditions. The delivery matrix can be formed by pelletizing a mixture comprising a grain germ and a xylanase, a mannanase and/or a glucanase. The pelletizing conditions can include application of steam. The pelletizing conditions can comprise application of a temperature in excess of about 80° C. for about 5 minutes and the enzyme retains a specific activity of at least 350 to about 900 units per milligram of enzyme.

The invention provides methods for improving texture and flavor of a dairy product comprising: (a) providing a polypeptide of the invention having a xylanase, a mannanase and/or a glucanase activity, or a xylanase, a mannanase and/or a glucanase encoded by a nucleic acid of the invention; (b) providing a dairy product; and (c) contacting the polypeptide of step (a) and the dairy product of step (b) under conditions wherein the xylanase, a mannanase and/or a glucanase can improve the texture or flavor of the dairy product. In one aspect, the dairy product comprises a cheese or a yogurt. The invention provides dairy products comprising a xylanase, a mannanase and/or a glue anase of the invention, or is encoded by a nucleic acid of the invention.

The invention provides methods for improving the extraction of oil from an oil-rich plant material comprising: (a) providing a polypeptide of the invention having a xylanase, a mannanase and/or a glucanase activity, or a xylanase, a mannanase and/or a glucanase encoded by a nucleic acid of the invention; (b) providing an oil-rich plant material; and (c) contacting the polypeptide of step (a) and the oil-rich plant material. In one aspect, the oil-rich plant material comprises an oil-rich seed. The oil can be a soybean oil, an olive oil, a rapeseed (canola) oil or a sunflower oil.

The invention provides methods for preparing a fruit or vegetable juice, syrup, puree or extract comprising: (a) providing a polypeptide of the invention having a xylanase, a mannanase and/or a glucanase activity, or a xylanase, a mannanase and/or a glucanase encoded by a nucleic acid of the invention; (b) providing a composition or a liquid comprising a fruit or vegetable material; and (c) contacting the polypeptide of step (a) and the composition, thereby preparing the fruit or vegetable juice, syrup, puree or extract.

The invention provides papers or paper products or paper pulp comprising a xylanase, a mannanase and/or a glucanase of the invention, or a polypeptide encoded by a nucleic acid of the invention. The invention provides methods for treating a biomass, e.g., any paper or a paper or wood pulp comprising: (a) providing a polypeptide of the invention having a xylanase, a mannanase and/or a glucanase activity, or a xylanase, a mannanase and/or a glucanase encoded by a nucleic acid of the invention; (b) providing a composition, e.g, a biomass, comprising a paper or a paper or wood pulp; and (c) contacting the polypeptide of step (a) and the composition of step (b) under conditions wherein the xylanase, a mannanase and/or a glucanase can treat the paper or paper or wood pulp.

The invention provides methods for reducing the amount of lignin (delignification), or solubilizing a lignin, in a paper or paper product, a paper waste, a wood, wood pulp or wood product, or a wood or paper recycling composition, comprising contacting the paper or paper product, wood, wood pulp or wood product, or wood or paper recycling composition with a polypeptide of the invention, or an enzymatically active fragment thereof.

The invention provides methods for hydrolyzing hemicelluloses in a wood, wood product, paper pulp, paper product or paper waste comprising contacting the wood, wood product, paper pulp, paper product or paper waste with a polypeptide of the invention, or an enzymatically active fragment thereof.

The invention provides methods for enzymatic decoloring (e.g., bleaching) of paper, hemp or flax pulp comprising contacting the paper, hemp or flax pulp with a xylanase, a mannanase and/or a glucanase and a decoloring (e.g., bleaching) agent, wherein the xylanase, a mannanase and/or a glucanase comprises a polypeptide of the invention, or an enzymatically active fragment thereof. The decoloring (e.g., bleaching) agent can comprise oxygen or hydrogen peroxide.

The invention provides methods for of decoloring (e.g., bleaching) a lignocellulose pulp comprising contacting the lignocellulose pulp with a xylanase, a mannanase and/or a glucanase, wherein the xylanase, a mannanase and/or a glucanase comprises a polypeptide of the invention, or an enzymatically active fragment thereof.

The invention provides methods for enzymatic deinking of paper, paper waste, paper recycled product, deinking toner from non-contact printed wastepaper or mixtures of non-contact and contact printed wastepaper, comprising contacting the paper, paper waste, paper recycled product, non-contact printed wastepaper or contact printed wastepaper with a xylanase, a mannanase and/or a glucanase, wherein the xylanase, a mannanase and/or a glucanase comprises a polypeptide of the invention, or an enzymatically active fragment thereof.

The invention provides methods for decoloring (e.g., bleaching) a thread, fabric, yarn, cloth or textile comprising contacting the fabric, yarn, cloth or textile with a xylanase, a mannanase and/or a glucanase under conditions suitable to produce a whitening of the textile, wherein the xylanase, a mannanase and/or a glucanase comprises a polypeptide of the invention, or an enzymatically active fragment thereof. The thread, fabric, yarn, cloth or textile can comprise a non-cotton cellulosic thread, fabric, yarn, cloth or textile. The invention provides fabrics, yarns, cloths or textiles comprising a polypeptide having a sequence of the invention, or a polypeptide encoded by a nucleic acid comprising a sequence of the invention, or an enzymatically active fragment thereof, wherein in one aspect (optionally) the fabric, yarn, cloth or textile comprises a non-cotton cellulosic fabric, yarn, cloth or textile.

The invention provides methods for decoloring (e.g., bleaching) or deinking newspaper comprising contacting the newspaper, wherein the xylanase, a mannanase and/or a glucanase comprises a polypeptide of the invention, or an enzymatically active fragment thereof.

The invention provides wood, wood chips, wood pulp, wood products, paper pulps, paper products, newspapers or paper waste comprising a polypeptide of the invention, or an enzymatically active fragment thereof. The invention provides thread, fabric, yarn, cloth or textile comprising a polypeptide of the invention, or an enzymatically active fragment thereof.

The invention provides methods for reducing lignin in a wood or wood product comprising contacting the wood or wood product with a polypeptide having a xylanase, a mannanase and/or a glucanase activity, wherein the polypeptide has a sequence of the invention, or the polypeptide is encoded by a nucleic acid comprising a sequence of the invention, or an enzymatically active fragment thereof.

The invention provides methods for reducing a lignin in a biomass, e.g., in a wood, a wood pulp, a Kraft pulp, a paper, a paper product or a paper pulp under high temperature and basic pH conditions, the method comprising: (a) providing at least one polypeptide having a xylanase, a mannanase and/or a glucanase activity, wherein the polypeptide retains xylanase, a mannanase and/or a glucanase activity under conditions comprising a temperature of at least about 80° C., 85° C., 90° C. or more, and a basic pH of at least about pH 10.5, pH 11, pH 12, pH 12.5 or more (basic) wherein the polypeptide comprises a xylanase, a mannanase and/or a glucanase having a sequence of the invention, or the xylanase, a mannanase and/or a glucanase is encoded by a nucleic acid comprising a sequence of the invention, or an enzymatically active fragment thereof; (b) providing a lignin-comprising biomass, e.g., a lignin-comprising wood, wood pulp, Kraft pulp, paper, paper product or paper pulp; and (c) contacting the wood, wood pulp, Kraft pulp, paper, paper product or paper pulp with the polypeptide of step (a) under conditions comprising a temperature of at least about 80° C., 85° C., 90° C. or more, and a basic pH of at least about pH 10.5, pH 11, pH 12, pH 12.5 or more (basic), wherein the polypeptide reduces the lignin-comprising biomass, e.g., the lignin in the wood, wood pulp, Kraft pulp, paper, paper product or paper pulp.

The invention provides methods for treating a lignin-comprising biomass, e.g., a wood, a wood pulp, a Kraft pulp, a paper product, a paper or a paper pulp under high temperature and basic pH conditions, the method comprising: (a) providing at least one polypeptide having a xylanase, a mannanase and/or a glucanase activity, wherein the polypeptide retains xylanase, a mannanase and/or a glucanase activity under conditions comprising a temperature of at least about 80° C., 85° C., 90° C. or more, and a basic pH of at least about pH 10.5, pH 11, pH 12, pH 12.5 or more (basic), wherein the polypeptide comprises a xylanase, a mannanase and/or a glucanase having a sequence of the invention, or the xylanase, a mannanase and/or a glucanase is encoded by a nucleic acid comprising a sequence of the invention, or an enzymatically active fragment thereof; (b) providing a lignin-comprising biomass, e.g., a wood, a wood pulp, a Kraft pulp, a paper, a paper product or a paper pulp; and (c) contacting the wood, wood pulp, Kraft pulp, paper, paper product or paper pulp with the polypeptide of step (a) under conditions comprising a temperature of at least about 80° C., 85° C., 90° C. or more, and a basic pH of at least about pH 10.5, pH 11, pH 12, pH 12.5 or more (basic), wherein the polypeptide catalyzes hydrolysis of compounds in the lignin-comprising biomass, e.g., wood, wood pulp, Kraft pulp, paper, paper product or paper pulp, and wherein in one aspect (optionally) the wood, wood pulp, Kraft pulp, paper, paper product or paper pulp comprises a softwood and hardwood, or the wood, wood pulp, Kraft pulp, paper or paper pulp is derived from a softwood and hardwood; and wherein in one aspect (optionally) after the treatment the pulp has a consistency of at least about 10%, or at least about 32%.

The invention provides methods for decoloring a biomass, e.g., a wood, a wood pulp, a Kraft pulp, a paper, a paper product or a paper pulp under high temperature and basic pH conditions, the method comprising: (a) providing at least one polypeptide having a xylanase, a mannanase and/or a glucanase activity, wherein the polypeptide retains xylanase, a mannanase and/or a glucanase activity under conditions comprising a temperature of at least about 80° C., 85° C., 90° C. or more, and a basic pH of at least about pH 10.5, pH 11, pH 12, pH 12.5 or more (basic), wherein the polypeptide comprises a xylanase, a mannanase and/or a glucanase having a sequence of the invention, or the xylanase, a mannanase and/or a glucanase is encoded by a nucleic acid comprising a sequence of the invention, or an enzymatically active fragment thereof; (b) providing a biomass, e.g., a wood, a wood pulp, a Kraft pulp, a paper, a paper product or a paper pulp; and (c) contacting the wood, wood pulp, Kraft pulp, paper, paper product or paper pulp with the polypeptide of step (a) under conditions comprising a temperature of at least about 80° C., 85° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 9.5, pH 10.0, pH 10.5, pH 11, pH 12, pH 12.5 or more (basic), wherein the polypeptide catalyzes hydrolysis of compounds in the biomass, e.g., a wood, wood pulp, Kraft pulp, paper, paper product or paper pulp, thereby decoloring (e.g., bleaching) the biomass, e.g., a wood, wood pulp, Kraft pulp, paper, paper product or paper pulp.

The invention provides methods for reducing the use of decoloring (e.g., bleaching) chemicals in a biomass, e.g., a wood, a wood pulp, a Kraft pulp, a paper, a paper product or a paper pulp decoloring (e.g., bleaching) process under high temperature and basic pH conditions, the method comprising: (a) providing at least one polypeptide having a xylanase, a mannanase and/or a glucanase activity, wherein the polypeptide retains xylanase, a mannanase and/or a glucanase activity under conditions comprising a temperature of at least about 80° C., 85° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 10.5, pH 11, pH 12, pH 12.5 or more (basic), wherein the polypeptide comprises a xylanase, a mannanase and/or a glucanase having a sequence of the invention, or the xylanase, a mannanase and/or a glucanase is encoded by a nucleic acid comprising a sequence of the invention, or an enzymatically active fragment thereof; (b) providing a biomass, e.g., a wood, a wood pulp, a Kraft pulp, a paper, a paper product or a paper pulp; and (c) contacting the wood, wood pulp, Kraft pulp, paper, paper product or paper pulp with the polypeptide of step (a) under conditions comprising a temperature of at least about 80° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 10.5, pH 11, pH 12, pH 12.5 or more (basic), wherein the polypeptide catalyzes hydrolysis of compounds in the biomass, e.g., wood, wood pulp, Kraft pulp, paper, paper product or paper pulp, thereby biobleaching the biomass, e.g., wood, wood pulp, Kraft pulp, paper, paper product or paper pulp and reducing the use of decoloring (e.g., bleaching) chemicals in the decoloring (e.g., bleaching) process; wherein in one aspect (optionally) the decoloring (e.g., bleaching) chemical comprises a chlorine, a chlorine dioxide, a caustic, a peroxide, or any combination thereof.

The invention provides methods for paper or pulp deinking under high temperature and basic pH conditions, the method comprising: (a) providing at least one polypeptide having a xylanase, a mannanase and/or a glucanase activity, wherein the polypeptide retains xylanase, a mannanase and/or a glucanase activity under conditions comprising a ° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 11, wherein the polypeptide comprises a xylanase, a mannanase and/or a glucanase having a sequence of the invention, or the xylanase, a mannanase and/or a glucanase is encoded by a nucleic acid comprising a sequence of the invention, or an enzymatically active fragment thereof; (b) providing an ink-comprising biomass, e.g., a wood, wood pulp, Kraft pulp, paper, a paper product or paper pulp; and (c) contacting the biomass, e.g., wood, wood pulp, Kraft pulp, paper, paper product or paper pulp with the polypeptide of step (a) under conditions comprising a temperature of at least about 85° C. and a basic pH of at least about pH 11, wherein the polypeptide catalyzes hydrolysis of compounds in the biomass, e.g., wood, wood pulp, Kraft pulp, paper or paper pulp, thereby facilitating deinking of the biomass, e.g., wood, wood pulp, Kraft pulp, paper, paper product or paper pulp.

The invention provides methods for releasing a lignin from a biomass, e.g., a wood, a wood pulp, a Kraft pulp, a paper, a paper product or a paper pulp under high temperature and basic pH conditions, the method comprising: (a) providing at least one polypeptide having a xylanase, a mannanase and/or a glucanase activity, wherein the polypeptide retains xylanase, a mannanase and/or a glucanase activity under conditions comprising a temperature of at least about 80° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 11, wherein the polypeptide comprises a xylanase, a mannanase and/or a glucanase having a sequence of the invention, or the xylanase, a mannanase and/or a glucanase is encoded by a nucleic acid comprising a sequence of the invention, or an enzymatically active fragment thereof; (b) providing a lignin-comprising biomass, e.g., wood, wood pulp, Kraft pulp, paper, paper product or paper pulp; and (c) contacting the wood, wood pulp, Kraft pulp, paper, paper product or a paper pulp of step (b) with the polypeptide of step (a) under conditions comprising a temperature of at least about 80° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 11, wherein the polypeptide catalyzes hydrolysis of compounds in the wood, wood pulp, Kraft pulp, paper, paper product or paper pulp, thereby facilitating release of lignin from the biomass, e.g., wood, wood pulp, Kraft pulp, paper, paper product or paper pulp; wherein in one aspect (optionally) after the treatment the pulp has a consistency of about 10%.

The invention provides compositions comprising a biomass, e.g., wood, a wood pulp, a Kraft pulp, a paper, a paper product or a paper pulp comprising a polypeptide having a xylanase, a mannanase and/or a glucanase activity, wherein the polypeptide has a sequence of the invention, or the polypeptide is encoded by a nucleic acid comprising a sequence of the invention, or an enzymatically active fragment thereof, wherein in one aspect (e.g., optionally) the biomass, e.g., wood, wood pulp, Kraft pulp, paper, paper product or paper pulp comprises a softwood and hardwood, or the wood, wood pulp, Kraft pulp, paper, paper product or paper pulp derived from a softwood and hardwood.

The invention provides methods for making ethanol comprising contacting a starch-comprising composition with a polypeptide having a xylanase, a mannanase and/or a glucanase activity, wherein the polypeptide has a sequence of the invention, or the polypeptide is encoded by a nucleic acid comprising a sequence of the invention, or an enzymatically active fragment thereof. The invention provides compositions compositions comprising an ethanol and a polypeptide having a xylanase, a mannanase and/or a glucanase activity, wherein the polypeptide has a sequence of the invention, or the polypeptide is encoded by a nucleic acid comprising a sequence of the invention, or an enzymatically active fragment thereof. The invention provides methods for making ethanol under high temperature and basic pH conditions, the method comprising: (a) providing at least one polypeptide having a xylanase, a mannanase and/or a glucanase activity, wherein the polypeptide retains xylanase, a mannanase and/or a glucanase activity under conditions comprising a temperature of at least about 80° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 11, wherein the polypeptide comprises a xylanase, a mannanase and/or a glucanase having a sequence of the invention, or the xylanase, a mannanase and/or a glucanase is encoded by a nucleic acid comprising a sequence of the invention, or an enzymatically active fragment thereof; (b) providing a starch-comprising composition comprising a wood, wood pulp, Kraft pulp, paper, a paper product or paper pulp; and (c) contacting the composition of step (b) with the polypeptide of step (a) under conditions comprising a temperature of at least about 80° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 11, wherein the polypeptide catalyzes hydrolysis of compounds in the wood, wood pulp, Kraft pulp, paper or paper pulp, thereby generating ethanol from the wood, wood pulp, Kraft pulp, paper, paper product or paper pulp.

The invention provides pharmaceutical compositions comprising a polypeptide having a xylanase, a mannanase and/or a glucanase activity, wherein the polypeptide comprises a sequence of the invention, or the polypeptide is encoded by a nucleic acid comprising a sequence of the invention, or an enzymatically active fragment thereof. In one aspect, the invention provides methods for eliminating or protecting animals from a microorganism comprising a xylan comprising administering a polypeptide of the invention. The microorganism can be a bacterium comprising a xylan, e.g., Salmonella.

In one aspect, the pharmaceutical composition acts as a digestive aid or an anti-microbial (e.g., against Salmonella). In one aspect, the treatment is prophylactic. In one aspect, the invention provides oral care products comprising a polypeptide of the invention having a xylanase, a mannanase and/or a glucanase activity, or a xylanase, a mannanase and/or a glucanase encoded by a nucleic acid of the invention. The oral care product can comprise a toothpaste, a dental cream, a gel or a tooth powder, an odontic, a mouth wash, a pre- or post brushing rinse formulation, a chewing gum, a lozenge or a candy. The invention provides contact lens cleaning compositions comprising a polypeptide of the invention having a xylanase, a mannanase and/or a glucanase activity, or a xylanase, a mannanase and/or a glucanase encoded by a nucleic acid of the invention.

The invention provides chimeric glycosidases, xylanases and/or glucanases comprising a polypeptide (e.g., xylanase, a mannanase and/or a glucanase) sequence of the invention and at least one heterologous carbohydrate-binding module (CBM), wherein in one aspect (optionally) the CBM comprises a CBM3a, CBM3b, CBM4, CBM6, CBM22 or X14, or a CBM as listed and discussed, below. The invention also provides chimeric glycosidases, xylanases and/or glucanases comprising at least one heterologous carbohydrate-binding module (CBM), wherein the CBM comprises a carbohydrate-binding subsequence of a xylanase sequence of the invention, or a carbohydrate-binding subsequence comprising a X14. The invention provides methods for designing a chimeric glycosidase, xylanase, a mannanase and/or a glucanase having a new carbohydrate-binding specificity or an enhanced carbohydrate-binding specificity, comprising inserting a heterologous or an additional endogenous carbohydrate-binding module (CBM) into a glycosidases, xylanases and/or glucanases, wherein the CBM comprises a carbohydrate-binding subsequence of a glycosidase, xylanase, mannanase and/or glucanase sequence of the invention, or a carbohydrate-binding subsequence comprising a X14, or alternatively a heterologous CBM, or an additional endogenous CBM, is inserted into a xylanase, a mannanase and/or a glucanase sequence of the invention.

The invention provides enzyme mixtures, or "cocktails" comprising at least one enzyme of the invention and one or more other enzyme(s), which can be another xylanase, mannanase and/or glucanase, or any other enzyme; for example, the "cocktails" of the invention, in addition to at least one enzyme of this invention, can comprise any other enzyme, such as xylanase (not of this invention), cellulases, lipases, esterases, proteases, or endoglycosidases, endo-beta.-1,4-glucanases, beta-glucanases, endo-beta-1,3(4)-glucanases, cutinases, peroxidases, catalases, laccases, amylases, glucoamylases, pectimases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases and/or transglutaminases, to name just a few examples. In alternative embodiments, these enzyme mixtures, or "cocktails" comprising at least one enzyme of the invention can be used in any process or method of the invention, or composition of the invention, e.g., in foods or feeds, food or feed supplements, textiles, papers, processed woods, etc. and methods for making them, and in compositions and methods for treating paper, pulp, wood, paper, pulp or wood waste or by-products, and the like, and in the final products thereof.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of aspects of the invention and are not meant to limit the scope of the invention as encompassed by the claims.

The patent or application file contains at least one drawing executed in color. Copies of this patent or patent application publication with color drawing(s) will be provided by the Office upon request and payment of the necessary fee.

FIG. 1 is a block diagram of a computer system.

FIG. 2 is a flow diagram illustrating one aspect of a process for comparing a new nucleotide or protein sequence with a database of sequences in order to determine the homology levels between the new sequence and the sequences in the database.

FIG. 3 is a flow diagram illustrating one aspect of a process in a computer for determining whether two sequences are homologous.

FIG. 4 is a flow diagram illustrating one aspect of an identifier process 300 for detecting the presence of a feature in a sequence.

FIG. 5 is a schematic flow diagram of an exemplary routine screening protocol to determine whether a xylanase of the invention is useful in pretreating paper pulp, as described in detail in Example 3, below.

FIG. 6 illustrates a biobleaching industrial process of the invention, as described in detail in Example 5, below.

Like reference symbols in the various drawings indicate like elements.

DETAILED DESCRIPTION OF THE INVENTION

The invention provides glycosyl hydrolases, including xylanases (e.g., endoxylanases) and/or a glucanases, and polynucleotides encoding them and methods of making and using them. Glycosyl hydrolase, including xylanase, mannanase and/or glucanase activity, of the polypeptides of the invention encompasses enzymes having hydrolase activity, for example, enzymes capable of hydrolyzing glycosidic linkages in a polysaccharide, for example a glycosidic linkage present in xylan, e.g., catalyzing hydrolysis of internal fβ-1,4-xylosidic linkages. The xylanases and/or a glucanases of the invention can be used to make and/or process foods, feeds, nutritional supplements, textiles, detergents and the like. The xylanases and/or a glucanases of the invention can be used in pharmaceutical compositions and dietary aids.

Xylanases and/or a glucanases of the invention are particularly useful in baking, animal feed, beverage and wood, wood pulp, Kraft pulp, paper, paper product or paper pulp processes. In one aspect, an enzyme of the invention is thermotolerant and/or tolerant of high and/or low pH conditions. For example, in one aspect, a xylanase, a mannanase and/or a glucanase of the invention retains activity under conditions comprising a temperature of at least about 80° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 11, or more.

The invention provides isolated, synthetic or recombinant nucleic acids comprising a nucleic acid encoding at least one polypeptide having a xylanase (e.g., an endoxylanase), a mannanase and/or a glucanase activity, or other activity as described herein, wherein the nucleic acid comprises a sequence having at least about 50% to 99%, or more, or complete (100%) sequence identity (homology) to SEQ ID NO:1 having one or more nucleotide residue changes (modifications, mutations) as set forth in Table 1, and as described herein, over a region of between about 10 to 2500, or more residues, or the full length of a cDNA, transcript (mRNA) or gene. Nucleic acids of the invention includes those encoding a polypeptide of this invention, which includes, e.g., SEQ ID NO:2 having one or more amino acid residue changes (mutations) as set forth in Table 1 and as described herein, and also including a genus of polypeptides having various sequence identities based on the exemplary SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 or SEQ ID NO:24.

TABLE 1

| Clone Name (Xyl 11 and 11 mutants) | Xyl Residue | Original Codon | Changed To | Other Codons for same AA change | original AA | changed to AA | Average A560 | Average WT-A560 | Average % of WT |
|---|---|---|---|---|---|---|---|---|---|
| Xyl 11 | WT | | | | | | | 100 | 100 |
| Xyl 11 mutant 1 | 108 | TTC | AAG | AAA | F | K | 0.655 | 0.740 | 87.5 |
| Xyl 11 mutant 2 | 21 | TTC | TAC | TAT | F | Y | 0.815 | 0.813 | 100.3 |
| Xyl 11 mutant 3 | 189 | TCC | CAG | CAA | S | Q | 0.909 | 0.906 | 100.4 |
| Xyl 11 mutant 4 | 150 | GTA | GCC | GCT, GCA, GCG | V | A | 0.634 | 0.623 | 101.8 |
| Xyl 11 mutant 5 | 9 | CCC | CAC | GAT | p | D | 0.570 | 0.556 | 102.5 |
| Xyl 11 mutant 6 | 188 | AGC | GAG | GAA | S | E | 0.749 | 0.722 | 104.1 |
| Xyl 11 mutant 7 | 125 | CAG | TAC | TAT | Q | Y | 0.936 | 0.902 | 104.2 |
| Xyl 11 mutant 8 | 73 | GGC | GTC | GTT, GTA, GTG | G | V | 0.769 | 0.736 | 104.6 |
| Xyl 11 mutant 9 | 73 | GGC | GAG | GAA | G | E | 0.965 | 0.902 | 106.6 |
| Xyl 11 mutant 10 | 33 | CTG | GCG | GCT, GCC, GCA | L | A | 0.795 | 0.736 | 108.0 |
| Xyl 11 mutant 11 | 38 | CGT | CAC | CAT | R | H | 0.969 | 0.894 | 108.3 |
| Xyl 11 mutant 12 | 17 | TTC | GTC | GTT, GTA, GTG | F | V | 0.981 | 0.901 | 109.0 |
| Xyl 11 mutant 13 | 62 | ATC | GTC | GTT, GTA, GTG | I | V | 0.996 | 0.901 | 110.5 |
| Xyl 11 mutant 14 | 44 | AGC | ACG | ACT, ACC, ACA | S | T | 1.008 | 0.894 | 112.7 |
| Xyl 11 mutant 15 | 73 | GGC | TAC | TAT | G | Y | 0.958 | 0.813 | 118.2 |
| Xyl 11 mutant 16 | 4 | ACC | CAC | CAT | T | H | 1.057 | 0.881 | 119.9 |
| Xyl 11 mutant 17 | 4 | ACC | CGC | CGT, CGA, CGG, AGA, AGG | T | R | 1.087 | 0.906 | 120.1 |
| Xyl 11 mutant 18 | 4 | ACC | AAC | AAT | T | N | 1.092 | 0.881 | 123.7 |

The invention provides variants of polynucleotides or polypeptides of the invention, which comprise sequences modified at one or more base pairs, codons, introns, exons, or amino acid residues (respectively) yet still retain the biological activity of a xylanase, a mannanase and/or a glucanase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly (e.g., GeneReassembly, see, e.g., U.S. Pat. No. 6,537,776), GSSM and any combination thereof.

The term "saturation mutagenesis", "gene site saturation mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

Generating and Manipulating Nucleic Acids

The invention provides nucleic acids (e.g., nucleic acids encoding polypeptides having glycosyl hydrolase activity, e.g., a xylanase, a mannanase and/or a glucanase activity; including enzymes having at least one sequence modification of an exemplary nucleic acid sequence of the invention (as defined above), wherein the sequence modification comprises one or more nucleotide residue changes (or the equivalent thereof) as set forth in Table 1, or at least one, two, three, four, five, six, seven, eight, nine, ten, eleven, twelve, thirteen, fourteen, fifteen, sixteen, seventeen or eighteen, or some or all of the following nucleotide residue changes: the codon encoding amino acid residue 4 changed from ACC to AAC; the codon encoding amino acid residue 4 changed from ACC to CGC; the codon encoding amino acid residue 4 changed from ACC to CAC; the codon encoding amino acid residue 9 changed from CCC to GAC; the codon encoding amino acid residue 17 changed from TTC to GTC; the codon encoding amino acid residue 21 changed from TTC to TAC; the codon encoding amino acid residue 33 changed from CTG to GCG; the codon encoding amino acid residue 38 changed from CGT to CAC; the codon encoding amino acid residue 44 changed from AGC to ACG; the codon encoding amino acid residue 63 changed from ATC to GTC; the codon encoding amino acid residue 73 changed from GGC to TAC; the codon encoding amino acid residue 73 changed from GGC to GAG; the codon encoding amino acid residue 73 changed from GGC to GTC; the codon encoding amino acid residue 108 changed from TTC to AAG; the codon encoding amino acid residue 125 changed from CAG to TAC; the codon encoding amino acid residue 150 changed from GTA to GCC; the codon encoding amino acid residue 188 changed from AGC to GAG; and/or, the codon encoding amino acid residue 189 changed from TCC to CAG, including expression cassettes such as expression vectors, encoding the polypeptides of the invention.

The invention also includes methods for discovering new xylanase, mannanase and/or glucanase sequences using the nucleic acids of the invention. The invention also includes methods for inhibiting the expression of xylanase, mannanase and/or glucanase genes, transcripts and polypeptides using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like.

In one aspect, the invention also provides xylanase- and/or glucanase-encoding nucleic acids with a common novelty in that they are derived from an environmental source, or a bacterial source, or an archaeal source.

In practicing the methods of the invention, homologous genes can be modified by manipulating a template nucleic acid, as described herein. The invention can be practiced in conjunction with any method or protocol or device known in the art, which are well described in the scientific and patent literature.

One aspect of the invention is an isolated nucleic acid comprising one of the sequences of The invention and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of a Sequence of the invention (or the sequences complementary thereto). The isolated, nucleic acids may comprise DNA, including cDNA, genomic DNA and synthetic DNA. The DNA may be double-stranded or single-stranded and if single stranded may be the coding strand or non-coding (anti-sense) strand. Alternatively, the isolated nucleic acids may comprise RNA.

Accordingly, another aspect of the invention is an isolated nucleic acid which encodes one of the polypeptides of the invention, or fragments comprising at least 5, 10, 15, 20, 25, 30, 35, 40, 50, 75, 100, or 150 consecutive amino acids of one of the polypeptides of the invention. The coding sequences of these nucleic acids may be identical to one of the coding sequences of one of the nucleic acids of the invention, or a fragment thereof or may be different coding sequences which encode one of the polypeptides of the invention, sequences substantially identical thereto and fragments having at least 5, 10, 15, 20, 25, 30, 35, 40, 50, 75, 100, or 150 consecutive amino acids of one of the polypeptides of the invention, as a result of the redundancy or degeneracy of the genetic code. The genetic code is well known to those of skill in the art and can be obtained, for example, on page 214 of B. Lewin, Genes VI, Oxford University Press, 1997.

The isolated nucleic acid which encodes one of the polypeptides of the invention and sequences substantially identical thereto, may include, but is not limited to: only the coding sequence of a nucleic acid of the invention and sequences substantially identical thereto and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only the coding sequence for the polypeptide as well as a polynucleotide which includes additional coding and/or non-coding sequence.

Alternatively, the nucleic acid sequences of the invention and sequences substantially identical thereto, may be mutagenized using conventional techniques, such as site directed mutagenesis, or other techniques familiar to those skilled in the art, to introduce silent changes into the polynucleotides of the invention and sequences substantially identical thereto. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of the invention and sequences substantially identical thereto. Such nucleotide changes may be introduced using techniques such as site directed mutagenesis, random chemical mutagenesis, exonuclease III deletion and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive hases of one of the sequences of The invention and sequences substantially identical thereto (or the sequences complementary thereto) under conditions of high, moderate, or low stringency as provided herein.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides (e.g., glycosyl hydrolases of the invention) generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. The phrases "nucleic acid" or "nucleic acid sequence" includes oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., e.g., double stranded iRNAs, e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. "Oligonucleotide" includes either a single stranded polydeoxynucleotide or two complementary polydeoxynucleotide strands that may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

A "coding sequence of" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons). "Operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" as used herein refers to a nucleotide sequence which is capable of affecting expression of a structural gene (i.e., a protein coding sequence, such as a xylanase, mannanase and/or glucanase of the invention) in a host compatible with such sequences. Expression cassettes include at least a promoter operably linked with the polypeptide coding sequence; and, in one aspect, with other sequences, e.g., transcription termination signals. Additional factors necessary or helpful in effecting expression may also be used, e.g., enhancers. Thus, expression cassettes also include plasmids, expression vectors, recombinant viruses, any form of recombinant "naked DNA" vector, and the like. A "vector" comprises a nucleic acid that can infect, transfect, transiently or permanently transduce a cell. It will be recognized that a vector can be a naked nucleic acid, or a nucleic acid complexed with protein or lipid. The vector in one aspect comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

As used herein, the term "promoter" includes all sequences capable of driving transcription of a coding sequence in a cell, e.g., a plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, e.g., in plants or animals. Tissue-specific regulation may be achieved by certain intrinsic factors that ensure that genes encoding proteins specific to a given tissue are expressed. Such factors are known to exist in mammals and plants so as to allow for specific tissues to develop.

As used herein, the term "isolated" means that the material (e.g., a nucleic acid, a polypeptide, a cell) is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment. As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$-$10^6$ fold. However, the term "purified" also includes nucleic acids that have been purified from the remainder of the genomic DNA or from other sequences in a library or other environment by at least one order of magnitude, typically two or three orders and more typically four or five orders of magnitude.

As used herein, the term "recombinant" means that the nucleic acid is adjacent to a "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one aspect, the enriched nucleic acids represent 90% or more of the number of nucleic acid inserts in the population of recombinant backbone molecules.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan. "Plasmids" can be commercially available, publicly available on an unrestricted basis, or can be constructed from available plasmids in accord with published procedures. Equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion, gel electrophoresis may be performed to isolate the desired fragment.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature and are well known in the art. In particular, stringency can be increased by reducing the concentration of salt, increasing the concentration of formamide, or raising the hybridization temperature. In alternative aspects, nucleic acids of the invention are defined by their ability to hybridize under various stringency conditions (e.g., high, medium, and low), as set forth herein.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS and 200 ug/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lad, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I. A promoter sequence is "operably linked to" a coding sequence when RNA polymerase which initiates transcription at the promoter will transcribe the coding sequence into mRNA. Promoters suitable for expressing a polypeptide in bacteria include the E. coli lac or trp promoters, the lad promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used. Promoters suitable for expressing the polypeptide or fragment thereof in bacteria include the E. coli lac or trp promoters, the lad promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK) and the acid phosphatase promoter. Fungal promoters include the ∀ factor promoter. Eukaryotic promoters include the CMV immediate early promoter, the HSV thymidine kinase promoter, heat shock promoters, the early and late SV40 promoter, LTRs from retroviruses and the mouse metallothionein-I promoter. Other promoters known to control expression of genes in prokaryotic or eukaryotic cells or their viruses may also be used.

Tissue-Specific Plant Promoters

The invention provides expression cassettes that can be expressed in a tissue-specific manner, e.g., that can express a xylanase, mannanase and/or glucanase of the invention in a tissue-specific manner. The invention also provides plants or seeds that express a xylanase, mannanase and/or glucanase of the invention in a tissue-specific manner. The tissue-specificity can be seed specific, stem specific, leaf specific, root specific, fruit specific and the like.

In one aspect, a constitutive promoter such as the CaMV 35S promoter can be used for expression in specific parts of the plant or seed or throughout the plant. For example, for overexpression, a plant promoter fragment can be employed which will direct expression of a nucleic acid in some or all tissues of a plant, e.g., a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of Agrobacterium tumefaciens, and other transcription initiation regions from various plant genes known to those of skill. Such genes include, e.g., ACT11 from Arabidopsis (Huang (1996) Plant Mol. Biol. 33:125-139); Cat3 from Arabidopsis (GenBank No. U43147, Zhong (1996) Mol. Gen. Genet. 251:196-203); the gene encoding stearoylacyl carrier protein desaturase from Brassica napus (Genbank No. X74782, Solocombe (1994) Plant Physiol. 104:1167-1176); GPc1 from maize (GenBank No. X15596; Martinez (1989) J. Mol. Biol. 208:551-565); the Gpc2 from maize (GenBank No. U45855, Manjunath (1997) Plant Mol. Biol. 33:97-112); plant promoters described in U.S. Pat. Nos. 4,962,028; 5,633,440.

The invention uses tissue-specific or constitutive promoters derived from viruses which can include, e.g., the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassaya vein mosaic virus (CVMV) promoter, with highest activity in vascular elements, in leaf mesophyll cells, and in root tips (Verdaguer (1996) Plant Mol. Biol. 31:1129-1139).

Alternatively, the plant promoter may direct expression of xylanase- and/or glucanase-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. For example, the invention incorporates the drought-inducible promoter of maize (Busk (1997)

supra); the cold, drought, and high salt inducible promoter from potato (Kirch (1997) Plant Mol. Biol. 33:897 909).

Tissue-specific promoters can promote transcription only within a certain time frame of developmental stage within that tissue. See, e.g., Blazquez (1998) Plant Cell 10:791-800, characterizing the Arabidopsis LEAFY gene promoter. See also Cardon (1997) Plant J 12:367-77, describing the transcription factor SPL3, which recognizes a conserved sequence motif in the promoter region of the A. thaliana floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells. In one aspect, the nucleic acids of the invention are operably linked to a promoter active primarily during the stages of cotton fiber cell elongation, e.g., as described by Rinehart (1996) supra. The nucleic acids can be operably linked to the Fb12A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60). Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF13 promoter from Agrobacterium rhizogenes (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

Alternatively, plant promoters which are inducible upon exposure to plant hormones, such as auxins, are used to express the nucleic acids of the invention. For example, the invention can use the auxin-response elements E1 promoter fragment (AuxREs) in the soybean (Glycine max L.) (Liu (1997) Plant Physiol. 115:397-407); the auxin-responsive Arabidopsis GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant. Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the Avena sativa L. (oat) arginine decarboxylase gene (Masgrau (1997) Plant J. 11:465-473); or, a salicylic acid-responsive element (Stange (1997) Plant J. 11:1315-1324). Using chemically—(e.g., hormone- or pesticide-) induced promoters, i.e., promoter responsive to a chemical which can be applied to the transgenic plant in the field, expression of a polypeptide of the invention can be induced at a particular stage of development of the plant. Thus, the invention also provides for transgenic plants containing an inducible gene encoding for polypeptides of the invention whose host range is limited to target plant species, such as corn, rice, barley, wheat, potato or other crops, inducible at any stage of development of the crop.

One of skill will recognize that a tissue-specific plant promoter may drive expression of operably linked sequences in tissues other than the target tissue. Thus, a tissue-specific promoter is one that drives expression preferentially in the target tissue or cell type, but may also lead to some expression in other tissues as well.

The nucleic acids of the invention can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the xylanase- and/or glucanase-producing nucleic acids of the invention will allow the grower to select plants with the optimal xylanase, mannanase and/or glucanase expression and/or activity. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences of the invention are also under the control of a tetracycline-inducible promoter, e.g., as described with transgenic tobacco plants containing the Avena sativa L. (oat) arginine decarboxylase gene (Masgrau (1997) Plant J. 11:465-473); or, a salicylic acid-responsive element (Stange (1997) Plant J. 11:1315-1324).

In some aspects, proper polypeptide expression may require polyadenylation region at the 3'-end of the coding region. The polyadenylation region can be derived from the natural gene, from a variety of other plant (or animal or other) genes, or from genes in the Agrobacterial T-DNA.

The term "plant" (e.g., as in a transgenic plant or plant seed of this invention, or plant promoter used in a vector of the invention) includes whole plants, plant parts (e.g., leaves, stems, flowers, roots, etc.), plant protoplasts, seeds and plant cells and progeny of same; the classes of plants that can be used to practice this invention (including compositions and methods) can be as broad as the class of higher plants, including plants amenable to transformation techniques, including angiosperms (monocotyledonous and dicotyledonous plants), as well as gymnosperms; also including plants of a variety of ploidy levels, including polyploid, diploid, haploid and hemizygous states. As used herein, the term "transgenic plant" includes plants or plant cells into which a heterologous nucleic acid sequence has been inserted, e.g., the nucleic acids and various recombinant constructs (e.g., expression cassettes, such a vectors) of the invention. Transgenic plants of the invention are also discussed, below.

Expression Vectors and Cloning Vehicles

The invention provides expression vectors and cloning vehicles comprising nucleic acids of the invention, e.g., sequences encoding the xylanases and/or glucanases of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, Aspergillus and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSV-LSV40 (Pharmacia). However, any other plasmid or other vector may be used so long as they are replicable and viable in the host. Low copy number or high copy number vectors may be employed with the present invention.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP 1 gene. Promoter regions can be selected from any desired gene using chloramphenicol transferase (CAT) vectors or other vectors with selectable markers.

Vectors for expressing the polypeptide or fragment thereof in eukaryotic cells can also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described inAusubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV,pMSG, and pSVL (Pharmacia). However, any other vector may be used as long as it is replicable and viable in the host cell.

The nucleic acids of the invention can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal minichromosome containing supercoiled DNA, see, e.g., Covey (1990) Proc. Natl. Acad. Sci. USA 87:1633-1637. Alternatively, coding sequences, i.e., all or sub-fragments of sequences of the invention can be inserted into a plant host cell genome becoming an integral part of the host chromosomal DNA. Sense or antisense transcripts can be expressed in this manner. A vector comprising the sequences (e.g., promoters or coding regions) from nucleic acids of the invention can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from Agrobacterium spp., potato virus X (see, e.g., Angell (1997) EMBO J. 16:3675-3684), tobacco mosaic virus (see, e.g., Casper (1996) Gene 173: 69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant. Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Mammalian expression vectors may also comprise an origin of replication, any necessary ribosome binding sites, a polyadenylation site, splice donor and acceptor sites, transcriptional termination sequences and 5' flanking nontranscribed sequences. In some aspects, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli and the S. cerevisiae TRP1 gene.

In some aspects, the nucleic acid encoding one of the polypeptides of the invention and sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. The nucleic acid can encode a fusion polypeptide in which one of the polypeptides of the invention and sequences substantially identical thereto, or fragments comprising at least 5, 10, 15, 20, 25, 30,35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., Molecular Cloning: A Laboratory Manual 2nd Ed., Cold Spring Harbor Laboratory Press (1989. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus and pseudorabies. A variety of cloning and expression vectors for use with prokaryotic and eukaryotic hosts are described by Sambrook, et al., Molecular Cloning: A Laboratory Manual, 2nd Ed., Cold Spring Harbor, N.Y., (1989).

Host Cells and Transformed Cells

The invention also provides transformed cells comprising a nucleic acid sequence of the invention, e.g., a sequence encoding a xylanase, a mannanase and/or a glucanase of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera Escherichia, Bacillus, Streptomyces, Salmonella, Pseudomonas and Staphylococcus, including, e.g., Escherichia coli, Lactococcus lactis, Bacillus subtilis, Bacillus cereus, Salmonella typhimurium, Pseudomonas fluorescens. Exemplary fungal cells include any species of Aspergillus. Exemplary yeast cells include any species of Pichia, Saccharomyces, Schizosaccharomyces, or Schwanniomyces, including Pichia pastoris, Saccharomyces cerevisiae, or Schizosaccharomyces pombe. Exemplary insect cells include any species of Spodoptera or Drosophila, including Drosophila S2 and Spodoptera Sf9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477; U.S. Pat. No. 5,750,870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are can be used.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Host cells containing the polynucleotides of interest, e.g., nucleic acids of the invention, can be cultured in conventional nutrient media modified as appropriate for activating promoters, selecting transformants or amplifying genes. The culture conditions, such as temperature, pH and the like, are those previously used with the host cell selected for expression and will be apparent to the ordinarily skilled artisan. The clones which are identified as having the specified enzyme activity may then be sequenced to identify the polynucleotide sequence encoding an enzyme having the enhanced activity.

The invention provides a method for overexpressing a recombinant xylanase, mannanase and/or glucanase in a cell comprising expressing a vector comprising a nucleic acid of the invention, e.g., a nucleic acid comprising a nucleic acid sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to a sequence of The invention over a region of at least about 100 residues, wherein the sequence identities are determined by analysis with a sequence comparison algorithm or by visual inspection, or, a nucleic acid that hybridizes under stringent conditions to a nucleic acid sequence of The invention, or a subsequence thereof. The overexpression can be effected by any means, e.g., use of a high activity promoter, a dicistronic vector or by gene amplification of the vector.

The nucleic acids of the invention can be expressed, or overexpressed, in any in vitro or in vivo expression system. Any cell culture systems can be employed to express, or over-express, recombinant protein, including bacterial, insect, yeast, fungal or mammalian cultures. Over-expression can be effected by appropriate choice of promoters, enhancers, vectors (e.g., use of replicon vectors, dicistronic vectors (see, e.g., Gurtu (1996) Biochem. Biophys. Res. Commun. 229:295-8), media, culture systems and the like. In one aspect, gene amplification using selection markers, e.g., glutamine synthetase (see, e.g., Sanders (1987) Dev. Biol. Stand. 66:55-63), in cell systems are used to overexpress the polypeptides of the invention.

Additional details regarding this approach are in the public literature and/or are known to the skilled artisan. In a particular non-limiting exemplification, such publicly available literature includes EP 0659215 (WO 9403612 A1) (Nevalainen et al.); Lapidot, A., Mechaly, A., Shoham, Y., "Overexpression and single-step purification of a thermostable xylanasc from Bacillus stearothermophilus T-6," J. Biotechnol. November 51:259-64 (1996); Lüthi, E., Jasmat, N. B., Bergquist, P. L., "Xylanase from the extremely thermophilic bacterium Caldocellum saccharolyticum: overexpression of the gene in Escherichia coli and characterization of the gene product," Appl. Environ. Microbiol. September 56:2677-83 (1990); and Sung, W. L., Luk, C. K., Zahab, D. M., Wakarchuk, W., "Overexpression of the Bacillus subtilis and circulans xylanases in Escherichia coli," Protein Expr. Purif. June 4:200-6 (1993), although these references do not teach the inventive enzymes of the instant application.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as E. coli, Streptomyces, Bacillus subtilis, Bacillus cereus, Salmonella typhimurium and various species within the genera Pseudomonas, Streptomyces and Staphylococcus, fungal cells, such as Aspergillus, yeast such as any species of Pichia, Saccharomyces, Schizosaccharomyces, Schwanniomyces, including Pichia pastoris, Saccharomyces cerevisiae, or Schizosaccharomyces pombe, insect cells such as Drosophila S2 and Spodoptera SP, animal cells such as CHO, COS or Bowes melanoma and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981) and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of amino acid sequences of the invention, or fragments comprising at least 5, 10, 15, 20, 25, 30, 35, 40, 50, 75, 100, or 150 consecutive amino acids thereof can be synthetically produced by conventional peptide synthesizers. In other aspects, fragments or portions of the polypeptides may be employed for producing the corresponding full-length polypeptide by peptide synthesis; therefore, the fragments may be employed as intermediates for producing the foil-length polypeptides.

Cell-free translation systems can also be employed to produce one of the polypeptides of amino acid sequences of the invention, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

Amplification of Nucleic Acids

In practicing the invention, nucleic acids of the invention and nucleic acids encoding the xylanases and/or glucanases of the invention, or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

In one aspect, the invention provides a nucleic acid amplified by a primer pair of the invention, e.g., a primer pair as set forth by about the first (the 5') 12, 13, 14, 15, 16, 17, 18, 19, 20, 21, 22, 23, 24, or 25 residues of a nucleic acid of the invention, and about the first (the 5') 15, 16, 17, 18, 19, 20, 21, 22, 23, 24, or 25 residues of the complementary strand.

The invention provides an amplification primer sequence pair for amplifying a nucleic acid encoding a polypeptide having a xylanase, mannanase and/or glucanase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence, or about 12, 13, 14, 15, 16, 17, 18, 19, 20, 21, 22, 23, 24, or 25 consecutive bases of the sequence. The invention provides amplification primer pairs, wherein the primer pair comprises a first member having a sequence as set forth by about the first (the 5') 12, 13, 14, 15, 16, 17, 18, 19, 20, 21, 22, 23, 24, or 25 residues of a nucleic acid of the invention, and a second member having a sequence as set forth by about the first (the 5') 12, 13, 14, 15, 16, 17, 18, 19, 20, 21, 22, 23, 24, or 25 residues of the complementary strand of the first member. The invention provides xylanases and/or glucanases generated by amplification, e.g., polymerase chain reaction (PCR), using an amplification primer pair of the invention. The invention provides methods of making a xylanase, mannanase and/or glucanase by amplification, e.g., polymerase chain reaction (PCR), using an amplification primer pair of the invention. In one aspect, the amplification primer pair amplifies a nucleic acid from a library, e.g., a gene library, such as an environmental library.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and ncludc, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989)

Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention (as defined above) over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters.

As used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

The phrase "substantially identical" in the context of two nucleic acids or polypeptides, refers to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleoti de or amino acid residue (sequence) identity, when compared and aligned for maximum correspondence, as measured using one of the known sequence comparison algorithms or by visual inspection. Typically, the substantial identity exists over a region of at least about 100 residues and most commonly the sequences are substantially identical over at least about 150-200 residues. In some aspects, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a xylanase, mannanase and/or glucanase polypeptide, resulting in modification of the structure of the polypeptide, without significantly altering its biological activity. For example, amino- or carboxyl-terminal amino acids that are not required for xylanase, mannanase and/or glucanase biological activity can be removed. Modified polypeptide sequences of the invention can be assayed for xylanase, mannanase and/or glucanase biological activity by any number of methods, including contacting the modified polypeptide sequence with a xylanase, mannanase and/or glucanase substrate and determining whether the modified polypeptide decreases the amount of specific substrate in the assay or increases the bioproducts of the enzymatic reaction of a functional xylanase, mannanase and/or glucanase polypeptide with the substrate.

Nucleic acid sequences of the invention can comprise at least 10, 15, 20, 25,30,35, 40, 50, 75,100, 150, 200,300, 400, or 500 consecutive nucleotides of an exemplary sequence of the invention and sequences substantially identical thereto. Nucleic acid sequences of the invention can comprise homologous sequences and fragments of nucleic acid sequences and sequences substantially identical thereto, refer to a sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity (homology) to these sequences. Homology may be determined using any of the computer programs and parameters described herein, including FASTA version 3.0t78 with the default parameters. Homologous sequences also include RNA sequences in which uridines replace the thymines in the nucleic acid sequences of the invention. The homologous sequences may be obtained using any of the procedures described herein or may result from the correction of a sequencing error. It will be appreciated that the nucleic acid sequences of the invention and sequences substantially identical thereto, can be represented in the traditional single character format (See the inside back cover of Stryer, Lubert. Biochemistry, 3rd Ed., W.H. Freeman & Co., New York.) or in any other format which records the identity of the nucleotides in a sequence.

Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analyses Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project. At least twenty-one other genomes have already been sequenced, including, for example, M. genitalium (Fraser et al., 1995), M. jannaschii (Bult et al., 1996), H. influenzae (Fleischmann et al., 1995), E. coli (Blattner et al., 1997) and yeast (S. cerevisiae) (Mewes et al., 1997) and D. melanogaster (Adams et al., 2000). Significant progress has also been made in sequencing the genomes of model organism, such as mouse, C. elegans and Arabadopsis sp. Several databases containing genomic information annotated with some functional information are maintained by different organization and are accessible via the internet One example of a useful algorithm is BLAST and BLAST 2.0 algorithms, which are described in Altschul et al., Nuc. Acids Res. 25:3389-3402, 1977 and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3 and expectations (E) of 10 and the BLOSUM62 scoring matrix (see Henikoff & Henikoff, Proc. Natl. Acad. Sci. USA 89:10915, 1989) alignments (B) of 50, expectation (E) of 10, M=5, N=−4 and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01 and most preferably less than about 0.001.

In one aspect, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation). BLAST programs are accessible through the U.S. National Library of Medicine.

The parameters used with the above algorithms may be adapted depending on the sequence length and degree of homology studied. In some aspects, the parameters may be the default parameters used by the algorithms in the absence of instructions from the user.

Computer Systems and Computer Program Products

To determine and identify sequence identities, structural homologies, motifs and the like in silico, a nucleic acid or polypeptide sequence of the invention can be stored, recorded, and manipulated on any medium which can be read and accessed by a computer.

Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

The polypeptides of the invention include the exemplary sequences of the invention, and sequences substantially identical thereto, and fragments of any of the preceding sequences. Substantially identical, or homologous, polypeptide sequences refer to a polypeptide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary sequence of the invention, e.g., a polypeptide sequences of the invention.

Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least about 10, 15, 20, 25, 30, 35, 40, 45, 50, 75, 100, 150, 200, 250, 300, 350, 400, 450, 500 or more consecutive amino acids of the polypeptides of the invention and sequences substantially identical thereto. It will be appreciated that the polypeptide codes of amino acid sequences of the invention and sequences substantially identical thereto, can be represented in the traditional single character format or three letter format (See Stryer, Lubert. Biochemistry, 3rd Ed., supra) or in any other format which relates the identity of the polypeptides in a sequence.

A nucleic acid or polypeptide sequence of the invention can be stored, recorded and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences of the invention and sequences substantially identical thereto, one or more of the polypeptide sequences of the invention and sequences substantially identical thereto. Another aspect of the invention is a computer readable medium having recorded thereon at least 2, 5, 10, 15, or 20 or more nucleic acid sequences of the invention and sequences substantially identical thereto.

Another aspect of the invention is a computer readable medium having recorded thereon one or more of the nucleic acid sequences of the invention and sequences substantially identical thereto. Another aspect of the invention is a computer readable medium having recorded thereon one or more of the polypeptide sequences of the invention and sequences substantially identical thereto. Another aspect of the invention is a computer readable medium having recorded thereon at least 2, 5, 10, 15, or 20 or more of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), particularly computer systems which store and manipulate the sequence information described herein. One example of a computer system 100 is illustrated in block diagram form in FIG. 1. As used herein, "a computer system" refers to the hardware components, software components and data storage components used to analyze a nucleotide sequence of a nucleic acid sequence of the invention and sequences substantially identical thereto, or a polypeptide sequence as set forth in the amino acid sequences of the invention. The computer system 100 typically includes a processor for processing, accessing, and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data and one or more data retrieving devices for retrieving the data stored on the data storage components. A skilled artisan can readily appreciate that any one of the currently available computer systems are suitable.

In one particular aspect, the computer system 100 includes a processor 105 connected to a bus which is connected to a main memory 115 (preferably implemented as RAM) and one or more internal data storage devices 110, such as a hard drive and/or other computer readable media having data recorded thereon. In some aspects, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internes) etc. In some aspects, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of a nucleic acid sequence of the invention and sequences substantially identical thereto, or a polypeptide sequence of the invention and sequences substantially identical thereto, (such as search tools, compare tools and modeling tools etc.) may reside in main memory 115 during execution.

In some aspects, the computer system 100 may further comprise a sequence comparison algorithm for comparing a nucleic acid sequence of the invention and sequences substantially identical thereto, or a polypeptide sequence of the invention and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence of the invention and sequences substantially identical thereto, or a polypeptide sequence of the invention and sequences substantially identical thereto, stored on a computer readable medium to reference sequences stored on a computer readable medium to identify homologies or structural motifs.

FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence of the invention and sequences substantially identical thereto, or a polypeptide sequence of the invention and sequences substantially identical thereto, a data storage device having retrievably stored thereon reference nucleotide sequences or polypeptide sequences to be compared to a nucleic acid sequence of the invention and sequences substantially identical thereto, or a polypeptide sequence of the invention and sequences substantially identical thereto and a sequence comparer for conducting the comparison. The sequence comparer may indicate a homology level between the sequences compared or identify structural motifs in the above described nucleic acid code of nucleic acid sequences of the invention and sequences substantially identical thereto, or a polypeptide sequence of the invention and sequences substantially identical thereto, or it may identify structural motifs in sequences which are compared to these nucleic acid codes and polypeptide codes. In some aspects, the data storage device may have stored thereon the sequences of at least 2, 5, 10, 15, 20, 25, 30 or 40 or more of the nucleic acid sequences of the invention and sequences substantially identical thereto, or the polypeptide sequences of the invention and sequences substantially identical thereto.

Another aspect of the invention is a method for determining the level of homology between a nucleic acid sequence of the invention and sequences substantially identical thereto, or a polypeptide sequence of the invention and sequences substantially identical thereto and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences of the invention, or the polypeptide sequences of the invention through use of the computer program and determining homology between the nucleic acid codes or polypeptide codes and reference nucleotide sequences or polypeptide sequences.

FIG. 3 is a flow diagram illustrating one aspect of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of a nucleic acid sequence of the invention and sequences substantially identical thereto, differs from a reference nucleic acid sequence at one or more positions. In one aspect such a program records the length and identity of inserted, deleted or substituted nucleotides with respect to the sequence of either the reference polynucleotide or a nucleic acid sequence of the invention and sequences substantially identical thereto. In one aspect, the computer program may be a program which determines whether a nucleic acid sequence of the invention and sequences substantially identical thereto, contains a single nucleotide polymorphism (SNP) with respect to a reference nucleotide sequence.

Another aspect of the invention is a method for determining whether a nucleic acid sequence of the invention and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some aspects, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences of the invention and sequences substantially identical thereto and the reference nucleotide sequences through the use of the computer program and identifying differences between the nucleic acid codes and the reference nucleotide sequences with the computer program.

In other aspects the computer based system may further comprise an identifier for identifying features within a nucleic acid sequence of the invention or a polypeptide sequence of the invention and sequences substantially identical thereto.

An "identifier" refers to one or more programs which identifies certain features within a nucleic acid sequence of the invention and sequences substantially identical thereto, or a polypeptide sequence of the invention and sequences substantially identical thereto. In one aspect, the identifier may comprise a program which identifies an open reading frame in a nucleic acid sequence of the invention and sequences substantially identical thereto.

FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group.

Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence of the invention and sequences substantially identical thereto, or a polypeptide sequence of the invention and sequences substantially identical thereto, comprising reading the nucleic acid code(s) or polypeptide code(s) through the use of a computer program which identifies features therein and identifying features within the nucleic acid code(s) with the computer program. In one aspect, computer program comprises a computer program which identifies open reading frames. The method may be performed by reading a single sequence or at least 2, 5, 10, 15, 20, 25, 30, or 40 of the nucleic acid sequences of the invention and sequences substantially identical thereto, or the polypeptide sequences of the invention and sequences substantially identical thereto, through the use of the computer program and identifying features within the nucleic acid codes or polypeptide codes with the computer program.

A nucleic acid sequence of the invention and sequences substantially identical thereto, or a polypeptide sequence of the invention and sequences substantially identical thereto, may be stored and manipulated in a variety of data processor programs in a variety of formats. For example, a nucleic acid sequence of the invention and sequences substantially identical thereto, or a polypeptide sequence of the invention and sequences substantially identical thereto, may be stored as text in a wordprocessing file, such as Microsoft WORD™ or WORDPERFECT™ or as an ASCII file in a variety of database programs familiar to those of skill in the art, such as DB2™, SYBASE™, or ORACLE™ In addition, many computer programs and databases may be used as sequence comparison algorithms, identifiers, or sources of reference nucleotide sequences or polypeptide sequences to be compared to a nucleic acid sequence of the invention and sequences substantially identical thereto, or a polypeptide sequence of the invention and sequences substantially identical thereto. The following list is intended not to limit the invention but to provide guidance to programs and databases which are useful with the nucleic acid sequences of the invention and sequences substantially identical thereto, or the polypeptide sequences of the invention and sequences substantially identical thereto.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents's World Drug Index database, the BioByteMasterFile database, the Genbank database and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices and beta sheets, signal sequences encoding signal peptides which direct the secretion of the encoded proteins, sequences implicated in transcription regulation such as homeoboxes, acidic stretches, enzymatic active sites, substrate binding sites and enzymatic cleavage sites.

Hybridization of Nucleic Acids

The invention provides isolated, synthetic or recombinant nucleic acids that hybridize under stringent conditions to an exemplary sequence of the invention. The stringent conditions can be highly stringent conditions, medium stringent conditions and/or low stringent conditions, including the high and reduced stringency conditions described herein. In one aspect, it is the stringency of the wash conditions that set forth the conditions which determine whether a nucleic acid is within the scope of the invention, as discussed below.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, iRNA (single or double stranded), antisense or sequences encoding antibody binding peptides (epitopes), motifs, active sites and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C.

Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-I or salmon sperm DNA (e.g., 200 ug/ml sheared and denatured salmon sperm DNA). In one aspect, nucleic acids of the invention are defined by their ability to hybridize under reduced stringency conditions comprising 35% formamide at a reduced temperature of 35° C.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content) and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's and 0.5 mg/ml polyriboadenylic acid. Approximately $2\times10^7$ cpm (specific activity $4\text{-}9\times10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at $T_m$-10° C. for the oligonucleotide probe. The membrane is then exposed to auto-radiographic film for detection of hybridization signals.

All of the foregoing hybridizations would be considered to be under conditions of high stringency.

Following hybridization, a filter can be washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content) and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1 M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

These methods may be used to isolate nucleic acids of the invention. For example, the preceding methods may be used to isolate nucleic acids having a sequence with at least about 97%, at least 95%, at least 90%, at least 85%, at least 80%, at least 75%, at least 70%, at least 65%, at least 60%, at least 55%, or at least 50% homology to a nucleic acid sequence selected from the group consisting of one of the sequences of The invention and sequences substantially identical thereto, or fragments comprising at least about 10, 15, 20, 25, 30, 35, 40, 50, 75, 100, 150, 200, 300, 400, or 500 consecutive bases thereof and the sequences complementary thereto. Homology may be measured using the aligmnent algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of The invention or the sequences complementary thereto.

Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% homology to a polypeptide having the sequence of one of amino acid sequences of the invention, or fragments comprising at least 5, 10, 15, 20, 25, 30,35, 40, 50, 75, 100, or 150 consecutive amino acids thereof as determined using a sequence alignment algorithm (e.g., such as the FASTA version 3.0t78 algorithm with the default parameters).

Oligonucleotides Probes and Methods for Using them

The invention also provides nucleic acid probes that can be used, e.g., for identifying nucleic acids encoding a polypeptide with a xylanase, mannanase and/or glucanase activity or fragments thereof or for identifying xylanase, mannanase and/or glucanase genes. In one aspect, the probe comprises at least 10 consecutive bases of a nucleic acid of the invention. Alternatively, a probe of the invention can be at least about 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below, including, e.g., capillary arrays. The probes of the invention can also be used to isolate other nucleic acids or polypeptides.

The isolated nucleic acids of The invention and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of The invention and sequences substantially identical thereto, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acidwas isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures and dot blots. Protocols for each of these procedures are provided in Ausubel et al. Current Protocols in Molecular Biology, John Wiley 503 Sons, Inc. (1997) and Sambrook et al., Molecular Cloning: A Laboratory Manual 2nd Ed., Cold Spring Harbor Laboratory Press (1989.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one aspect, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", PCR Methods and Applications 1:5-16, 1991; E. Fahy et al., "Self-sustained Sequence Replication (3SR): An Isothermal Transcription-based Amplification System Alternative to PCR", PCR Methods and Applications 1:25-33, 1991; and Walker G. T. et al., "Strand Displacement Amplification—an Isothermal in vitro DNA Amplification Technique", Nucleic Acid Research 20:1691-1696, 1992). In such procedures, the nucleic acids in the sample are contacted with the probes, the amplification reaction is performed and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of The invention and sequences substantially identical thereto, may also be used in chromosome walking procedures to identify clones containing genomic sequences located adjacent to the sequences of The invention and sequences substantially identical thereto. Such methods allow the isolation of genes which encode additional proteins from the host organism.

The isolated nucleic acids of the invention and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of the invention and sequences substantially identical thereto, or the sequences complementary thereto may be used as probes to identify and isolate related nucleic acids. In some aspects, the related nucleic acids maybe cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m$=81.5+16.6(log [Na+])+0.41 (fraction G+C)−(600/N where N is the length of the probe.

If the hybridization is carried out in a solution containing formamide, the melting temperature may be calculated using the equation: $T_m$=81.5+16.6(log [Na+])+0.41 (fraction G+C)−(0.63% formamide)−(600/N) where N is the length of the probe.

Prehybridization may be carried out in 6×SSC, 5×Denhardt's reagent, 0.5% SDS, 100 μg/ml denatured fragmented salmon sperm DNA or 6×SSC, 5×Denhardt's reagent, 0.5% SDS, 100 μg/ml denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the $T_m$. For shorter probes, such as oligonucleotide probes, the hybridization may be conducted at 5-10° C. below the $T_m$. Typically, for hybridizations in 6×SSC, the hybridization is conducted at approximately 68° C. Usually, for hybridizations in 50% formamide containing solutions, the hybridization is conducted at approximately 42° C.

Inhibiting Expression of Glycosyl Hydrolases

The invention provides nucleic acids complementary to (e.g., antisense sequences to) the nucleic acids of the invention, e.g., xylanase- and/or glucanase-encoding nucleic acids. Antisense sequences are capable of inhibiting the transport, splicing or transcription of xylanase- and/or glucanase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind xylanase, mannanase and/or glucanase gene or message, in either case preventing or inhibiting the production or function of xylanase, mannanase and/or glucanase. The association can be through sequence specific hybridization. Another useful class of inhibitors includes oligonucleotides which cause inactivation or cleavage of xylanase, mannanase and/or glucanase message. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity. Thus, the invention provides various compositions for the inhibition of xylanase, mannanase and/or glucanase expression on a nucleic acid and/or protein level, e.g., antisense, iRNA and ribozymes comprising xylanase, mannanase and/or glucanase sequences of the invention and the anti-xylanase and/or anti-glucanase antibodies of the invention.

Inhibition of xylanase, mannanase and/or glucanase expression can have a variety of industrial, medical, pharmaceutical, research, food and feed and food and feed supplement processing and other applications and processes. For example, inhibition of xylanase, mannanase and/or glucanase expression can slow or prevent spoilage. Spoilage can occur when polysaccharides, e.g., structural polysaccharides, are enzymatically degraded. This can lead to the deterioration, or rot, of fruits and vegetables. In one aspect, use of compositions of the invention that inhibit the expression and/or activity of xylanases and/or glucanases, e.g., antibodies, antisense oligonucleotides, ribozymes and RNAi, are used to slow or prevent spoilage. Thus, in one aspect, the invention provides methods and compositions comprising application onto a plant or plant product (e.g., a cereal, a grain, a fruit, seed, root, leaf, etc.) antibodies, antisense oligonucleotides, ribozymes and RNAi of the invention to slow or prevent spoilage. These compositions also can be expressed by the plant (e.g., a transgenic plant) or another organism (e.g., a bacterium or other microorganism transformed with a xylanase, mannanase and/or glucanase gene of the invention).

The compositions of the invention for the inhibition of xylanase, mannanase and/or glucanase expression (e.g., antisense, iRNA, ribozymes, antibodies) can be used as pharmaceutical compositions, e.g., as anti-pathogen agents or in other therapies, e.g., as anti-microbials for, e.g., Salmonella.

Antisense Oligonucleotides

The invention provides antisense oligonucleotides capable of binding xylanase, mannanase and/or glucanase message which can inhibit xylan hydrolase activity (e.g., catalyzing hydrolysis of internal β-1,4-xylosidic linkages) by targeting mRNA. Strategies for designing antisense oligonucleotides are well described in the scientific and patent literature, and the skilled artisan can design such xylanase, mannanase and/or glucanase oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be preent at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense xylanase, mannanase and/or glucanase sequences of the invention (see, e.g., Gold (1995) J. of Biol. Chem. 270:13581-13584).

Inhibitory Ribozymes

The invention provides ribozymes capable of binding xylanase, mannanase and/or glucanase message. These ribozymes can inhibit xylanase, mannanase and/or glucanase activity by, e.g., targeting mRNA. Strategies for designing ribozymes and selecting the xylanasc- and/or glucanase-specific antisense sequence for targeting are well described in the scientific and patent literature, and the skilled artisan can design suchribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme of the invention, e.g., an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting. Those skilled in the art will recognize that a ribozyme of the invention, e.g., an enzymatic RNA molecule of this invention, can have a specific substrate binding site complementary to one or more of the target gene RNA regions. A ribozyme of the invention can have a nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising a xylanase, mannanase and/or glucanase enzyme sequence of the invention. The RNAi molecule can comprise a double-stranded RNA (dsRNA) molecule, e.g., siRNA, miRNA and/or short hairpin RNA (shRNA) molecules. The RNAi molecule, e.g., siRNA (small inhibitory RNA) can inhibit expression of a xylanase, mannanase and/or glucanase enzyme gene, and/or miRNA (micro RNA) to inhibit translation of a xylanase, mannanase and/or glucanase message. In one aspect, the RNAi molecule, e.g., siRNA and/or miRNA, is about 11, 12, 13, 14, 15, 16, 17, 18, 19, 20, 21, 22, 23, 24, 25, 26, 27, 28, 29 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's molecules, e.g., siRNA and/or miRNA, of the invention. The process may be practiced in vitro, ex vivo or in vivo. In one aspect, the RNAi molecules of the invention can be used to generate a loss-of-function mutation in a cell, an organ or an animal.

In one aspect, intracellular introduction of the RNAi is by internalization of a target cell specific ligand bonded to an RNA binding protein comprising an RNAi (e.g., microRNA) is adsorbed. The ligand is specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, the invention provides lipid-based formulations for delivering, e.g., introducing nucleic acids of the invention as nucleic acid-lipid particles comprising an RNAi molecule to a cell, see e.g., U.S. Patent App. Pub. No. 20060008910.

Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding a xylanase, mannanase and/or glucanase. These methods can be repeated or used in various combinations to generate xylanases and/or glucanases having an altered or different activity or an altered or different stability from that of a xylanase, mannanase and/or glucanase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photo-activated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly (e.g., GeneReassembly, see, e.g., U.S. Pat. No. 6,537,776), gene site saturation mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94: 4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-45'7; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortie (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller (1987) Oligonucleotide-directed mutagenesis: a simple method using two oligonucleotide primers and a single-stranded DNA template" Methods in Enzymol. 154: 329-350); phosphorothioate-modified DNA mutagenesis (Taylor (1985) "The use of phosphorothioate-modified DNA in restriction enzyme reactions to prepare nicked DNA" Nucl. Acids Res. 13: 8749-8764; Taylor (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer (1988) "Improved enzymatic in vitro reactions in the gapped duplex DNA approach to oligonucleotide-directed construction of mutations" Nucl. Acids Res. 16: 7207; and Fritz (1988) "Oligonucleotide-directed construction of mutations: a gapped duplex DNA procedure without enzymatic reactions in vitro" Nucl. Acids Res. 16: 6987-6999).

Additional protocols that can be used to practice the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of Escherichia coli: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Protocols that can be used to practice the invention are described, e.g., in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used to practice the invention (providing details regarding various diversity generating methods) are described, e.g., in U.S. patent application Ser. No. 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, e.g., saturationmutagenesis (GSSM), synthetic ligation reassembly (SLR), or a combination thereof are used to modify the nucleic acids of the inventionto generate xylanases and/or glucanases with new or altered properties (e.g., activity under highly acidic or alkaline conditions, high or low temperatures, and the like). Polypeptides encoded by the modified nucleic acids can be screened for an activity before testing for xylan hydrolysis or other activity. Any testing modality or protocol can be used, e.g., using a capillary array platform. See, e.g., U.S. Pat. Nos. 6,361,974; 6,280,926; 5,939,250.

Gene Site Saturation Mutagenesis, or, GSSM

The invention also provides methods for making enzyme using Gene Site Saturation mutagenesis, or, GSSM, as described herein, and also in U.S. Pat. Nos. 6,171,820 and 6,579,258. In one aspect, codon primers containing a degenerate N,N,G/T sequence are used to introduce point mutations into a polynucleotide, e.g., a xylanase, mannanase and/or glucanase or an antibody of the invention, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, in one aspect, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence (s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per positionX 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can in one aspect be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., xylanases and/or glucanases) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., E. coli host, using, e.g., an expression vector) and subjected to expression screening. When an individual progeny polypeptide is identified by screening to display a favorable change in property (when compared to the parental polypeptide, such as increased xylan hydrolysis activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined −6 single point mutations (i.e. 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (gene site saturation mutagenesis (GSSM)). The oligos used are comprised contiguously of a first homologous sequence, a degenerate N,N,N sequence and preferably but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions and/or substitutions.

In a particular exemplification, it is possible to simultaneously mutagenize two or more contiguous amino acid positions using an oligo that contains contiguous N,N,N triplets, i.e. a degenerate $(N,N,N)_n$ sequence.

In another aspect, the present invention provides for the use of degenerate cassettes having less degeneracy than the N,N,N sequence. For example, it may be desirable in some instances to use (e.g. in an oligo) a degenerate triplet sequence comprised of only one N, where the N can be in the first second or third position of the triplet. Any other bases including any combinations and pennutations thereof canoe used in the remaining two positions of the triplet. Alternatively, it may be desirable in some instances to use (e.g., in an oligo) a degenerate N,N,N triplet sequence, N,N,G/T, or an N,N, G/Ctriplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can in one aspect be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes and point mutations that cause the generation of stop codons and the corresponding expression of polypeptide fragments.

Thus, in one aspect of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable E. coli host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid and each of two favorable changes) and 3 positions. Thus, there are 3×3×3 or 27 total possibilities, including 7 that were previously examined −6 single point mutations (i.e., 2 at each of three positions) and no change at any position.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every or a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Exemplary cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is preferably about 1-500 bases in length) in defined polynucleotide sequence to be mutagenized (wherein the sequence to be mutagenized is preferably from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons and groupings of particular nucleotide cassettes.

Defined sequences to be mutagenized include a whole gene, pathway, cDNA, an entire open reading frame (ORF) and entire promoter, enhancer, repressor/transactivator, origin of replication, intron, operator, or any polynucleotide functional group. Generally, a "defined sequences" for this purpose may be any polynucleotide that a 15 base-polynucleotide sequence and polynucleotide sequences of lengths between 15 bases and 15,000 bases (this invention specifically names every integer in between). Considerations in choosing groupings of codons include types of amino acids encoded by a degenerate mutagenic cassette.

In one exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19 and 20 amino acids at each position and a library of polypeptides encoded thereby.

Synthetic Ligation Reassembly (SLR)

The invention provides a non-stochastic gene modification system termed "synthetic ligation reassembly," or simply "SLR," a "directed evolution process," to generate polypeptides, e.g., xylanases and/or glucanases, or antibodies of the invention, with new or altered properties.

SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. Pat. Nos. 6,773,900; 6,740,506; 6,713,282; 6,635,449; 6,605,449; 6,537,776. In one aspect, SLR comprises: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

Synthetic Gene Reassembly

In one aspect, the present invention provides a non-stochastic method termed synthetic gene reassembly (e.g., GeneReassembly, see, e.g., U.S. Pat. No. 6,537,776), which differs from stochastic shuffling in that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends and assembling these nucleic acid building blocks, such that a designed overall assembly order is achieved.

In one aspect, synthetic gene reassembly comprises a method of: 1) preparing a progeny generation of molecule(s) (including a molecule comprising a polynucleotide sequence, e.g., a molecule comprising a polypeptide coding sequence), that is mutagenized to achieve at least one point mutation, addition, deletion, &/or chimerization, from one or more ancestral or parental generation template(s); 2) screening the progeny generation molecule(s), e.g., using a high throughput method, for at least one property of interest (such as an improvement in an enzyme activity); 3) in one aspect obtaining &/or cataloguing structural &/or and functional information regarding the parental &/or progeny generation molecules; and 4) in one aspect repeating any of steps 1) to 3). In one aspect, there is generated (e.g., from a parent polynucleotide template), in what is termed "codon site-saturation mutagenesis," a progeny generation of polynucleotides, each having at least one set of up to three contiguous point mutations (i.e. different bases comprising a new codon), such that every codon (or every family of degenerate codons encoding the same amino acid) is represented at each codon position. Corresponding to, and encoded by, this progeny generation of polynucleotides, there is also generated a set of progeny polypeptides, each having at least one single amino acid point mutation. In a one aspect, there is generated, in what is termed "amino acid site-saturation mutagenesis", one such mutant polypeptide for each of the 19 naturally encoded polypeptide-forming alpha-amino acid substitutions at each and every amino acid position along the polypeptide. This yields, for each and every amino acid position along the parental polypeptide, a total of 20 distinct progeny polypeptides including the original amino acid, or potentially more than 21 distinct progeny polypeptides if additional amino acids are used either instead of or in addition to the 20 naturally encoded amino acids Thus, in another aspect, this approach is also serviceable for generating mutants containing, in addition to &/or in combination with the 20 naturally encoded polypeptide-forming alpha-amino acids, other rare &/or not naturally-encoded amino acids and amino acid derivatives. In yet another aspect, this approach is also serviceable for generating mutants by the use of, in addition to &/or in combination with natural or unaltered codon recognition systems of suitable hosts, altered, mutagenized, &/or designer codon recognition systems (such as in a host cell with one or more altered tRNA molecules.

In yet another aspect, this invention relates to recombination and more specifically to a method for preparing polynucleotides encoding a polypeptide by a method of in vivo reassortment of polynucleotide sequences containing regions of partial homology, assembling the polynucleotides to form at least one polynucleotide and screening the polynucleotides for the production of polypeptide(s) having a useful property.

In yet another aspect, this invention is serviceable for analyzing and cataloguing, with respect to any molecular property (e.g. an enzymatic activity) or combination of properties allowed by current technology, the effects of any mutational change achieved (including particularly saturation mutagenesis). Thus, a comprehensive method is provided for determining the effect of changing each amino acid in a parental polypeptide into each of at least 19 possible substitutions. This allows each amino acid in a parental polypeptide to be characterized and catalogued according to its spectrum of potential effects on a measurable property of the polypeptide.

In one aspect, an intron may be introduced into a chimeric progeny molecule by way of a nucleic acid building block. Introns often have consensus sequences at both termini in order to render them operational. In addition to enabling gene splicing, introns may serve an additional purpose by providing sites of homology to other nucleic acids to enable homologous recombination. For this purpose, and potentially others, it may be sometimes desirable to generate a large nucleic acid building block for introducing an intron.

If the size is overly large easily generating by direct chemical synthesis of two single stranded oligos, such a specialized nucleic acid building block may also be generated by direct chemical synthesis of more than two single stranded oligos or by using a polymerase-based amplification reaction The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one aspect of the invention, the annealed building pieces are treated with an enzyme, such as a ligase (e.g., T4 DNA ligase) to achieve covalent bonding of the building pieces.

Coupling can occur in a manner that does not make use of every nucleotide in a participating overhang. The coupling is particularly lively to survive (e.g. in a transformed host) if the coupling reinforced by treatment with a ligase enzyme to form what may be referred to as a "gap ligation" or a "gapped ligation". This type of coupling can contribute to generation of unwanted background product(s), but it can also be used advantageously increase the diversity of the progeny library generated by the designed ligation reassembly. Certain overhangs are able to undergo self-coupling to form a palindromic coupling. A coupling is strengthened substantially if it is reinforced by treatment with a ligase enzyme. Lack of 5' phosphates on these overhangs can be used advantageously to prevent this type of palindromic self-ligation. Accordingly, this invention provides that nucleic acid building blocks can be chemically made (or ordered) that lack a 5' phosphate group. Alternatively, they can be removed, e.g. by treatment with a phosphatase enzyme, such as a calf intestinal alkaline phosphatase (CTAP), in order to prevent palindromic self-ligations in ligation reassembly processes.

In a another aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. The xylanases and/or glucanoses of the present invention can be mutagenized in accordance with the methods described herein.

Thus according to one aspect of the invention, the sequences of a plurality of progenitor nucleic acid templates (e.g., polynucleotides of The invention) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates and preferably at almost all of the progenitor templates. Even more preferably still a serviceable demarcation point is an area of homology that is shared by all of the progenitor templates.

In a one aspect, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another aspect, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated preferably comprise a library of finalized chimeric nucleic acid molecules having an overall assembly order that is chosen by design. In a particularly aspect, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one aspect, this polynucleotide is a gene, which may be a man-made gene. According to another aspect, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be in one aspect removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another aspect, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a one aspect, the recombination is facilitated by, or occurs at, areas of homology between the man-made, intron-containing gene and a nucleic acid, which serves as a recombination partner. In one aspect, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic gene reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order inwhich the nucleic acid building blocks are assembled to form a finalized chimeric nucleic acid molecule is determined by purposeful experimental design and is not random.

In one aspect, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Exemplary sizes for building block range from 1 base pair (not including any overhangs) to 100,000 base pairs (not including any overhangs). Other exemplary size ranges are also provided, which have lower limits of from 1 bp to 10,000 bp (including every integer value in between) and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another aspect, the two strands of a double-stranded nucleic acid building block are complementary at fewer than every nucleotide apart from any that form an overhang. Thus, according to this aspect, a double-stranded nucleic acid building block can be used to introduce codon degeneracy. The codon degeneracy can be introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins thorough recombination.

Optimized Directed Evolution System

The invention provides anon-stochastic gene modification system termed "optimized directed evolution system" to generate polypeptides, e.g., xylanases and/or glucanases, or antibodies of the invention, with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found, e.g., in U.S. Ser. No. 09/332,835; U.S. Pat. No. 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332,835.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLAB™ (The Mathworks, Natick, Mass.) a programming language and development environment for technical computing.

Iterative Processes

In practicing the invention, these processes can be iteratively repeated. For example, a nucleic acid (or, the nucleic acid) responsible for an altered or new xylanase, mannanase and/or glucanase phenotype is identified, re-isolated, again modified, re-tested for activity. This process can be iteratively repeated until a desired phenotype is engineered. For example, an entire biochemical anabolic or catabolic pathway can be engineered into a cell, including, e.g., xylanase, mannanase and/or glucanase activity.

Similarly, if it is determined that a particular oligonucleotide has no affect at all on the desired trait (e.g., a new xylanase, mannanase and/or glucanase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, xylanases, and the like. Invivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another aspect, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, novel polynucleotides can be generated by the process of reductive reassortment. The method involves the generation of constructs containing consecutive sequences (original encoding sequences), their insertion into an appropriate vector and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences and results in the production of novel molecular species. Various treatments may be applied to enhance the rate of reassortment. These could include treatment with ultra-violet light, or DNA damaging chemicals and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:

a) Primers that include a poly-A head and poly-T tail which when made single-stranded would provide orientation can be utilized. This is accomplished by having the first few bases of the primers made from RNA and hence easily removed RNAseH.
b) Primers that include unique restriction cleavage sites can be utilized. Multiple sites, a battery of unique sequences and repeated synthesis and ligation steps would be required.
c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:

1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.

3) The recovery of vectors containing interrupted genes which can be selected when insert size decreases.

4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intramolecular" mechanism, or mediated by recombination-like events through "inter-molecular" mechanisms is immaterial. The end result is a reassortment of the molecules into all possible combinations.

In one aspect (optionally), the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, virion, or other predetermined compound or structure.

The polypeptides that are identified from such libraries can be used for therapeutic, diagnostic, research and related purposes (e.g., catalysts, solutes for increasing osmolarity of an aqueous solution and the like) and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N-3-Adenine (See Sun and Hurley, (1992); an N-acetylated or deacetylated 4'-fluoro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl) phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(11) halogen salt, N-hydroxy-2-amino-3-methylimidazo[4,5-f]-quinoline ("N-hydroxy-IQ") and N-hydroxy-2-amino-1-methyl-6-phenylimidazo[4,5-f]-pyridine ("N-hydroxy-PhIP"). Exemplary means for slowing or halting PCR amplification consist of UV light (+)-CC-1065 and (+)-CC-1065-(N-3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

Producing Sequence Variants

The invention also provides additional methods for making sequence variants of the nucleic acid (e.g., xylanase) sequences of the invention. The invention also provides additional methods for isolating xylanases using the nucleic acids and polypeptides of the invention. In one aspect, the invention provides for variants of a xylanase coding sequence (e.g., a gene, cDNA or message) of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate new nucleic acids which encode polypeptides having characteristics which enhance their value in industrial, medical, laboratory (research), pharmaceutical, food and feed and food and feed supplement processing and other applications and processes. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids are evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/μl in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an E. coil strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations".

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811-7815, 1992.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S, and Youvan, D. C., Biotechnology Research, 11:1548-1552, 1993. Random and site-directed mutagenesis are described in Arnold, F. H., Current Opinion in Biotechnology, 4:450-455, 1993.

In some aspects, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis" and U.S. Pat. No. 5,939,250, filed May 22, 1996, entitled, "Production of Enzymes Having Desired Activities by Mutagenesis.

The variants of the polypcptides of the invention may be variants in which one or more of the amino acid residues of the polypeptides of the invention are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue.

Other variants are those in which one or more of the amino acid residues of the polypeptides of the invention includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some aspects, the fragments, derivatives and analogs retain the same biological function or activity as the polypeptides of the invention and sequences substantially identical thereto. In other aspects, the fragment, derivative, or analog includes a proprotein, such that the fragment, derivative, or analog can be activated by cleavage of the proprotein portion to produce an active polypeptide.

Optimizing Codons to Achieve High Levels of Protein Expression in Host Cells

The invention provides methods for modifying xylanase-encoding nucleic acids to modify codon usage. In one aspect, the invention provides methods for modifying codons in a nucleic acid encoding a xylanase to increase or decrease its expression in a host cell. The invention also provides nucleic acids encoding a xylanase modified to increase its expression in a host cell, xylanase so modified, and methods of making the modified xylanases. The method comprises identifying a "non-preferred" or a "less preferred" codon in xylanase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as Escherichia coli and Pseudomonas fluorescens; gram positive bacteria, such as Lactobacillus gasseri, Lactococcus lactis, Lactococcus crentoris, Bacillus subtilis. Exemplary host cells also include eukaryotic organisms, e.g., various yeast, such as Saccharomyces sp., including Saccharomyces cerevisiae, Schizosaccharomyces pombe, Pichia pastoris, and Kluyveromyces lactis, Hansenula polymorpha, Aspergillus niger, and mammalian cells and cell lines and insect cells and cell lines. Other exemplary host cells include bacterial cells, such as E. coli, Streptomyces, Bacillus subtilis, Bacillus cereus, Salmonella typhimurium and various species within the genera Pseudomonas, Streptomyces and Staphylococcus, fungal cells, such as Aspergillus, yeast such as any species of Pichia, Saccharomyces, Schizosaccharomyces, Schwanniomyces, including Pichia pastoris, Saccharomyces cerevisiae, or Schizosaccharomyces pombe, insect cells such as Drosophila S2 and Spodoptera Sf9, animal cells such as CHO, COS or Bowes melanoma and adenoviruses. The selection of an appropriate host is within the abilities of those skilled in the art. Thus, the invention also includes nucleic acids and polypeptides optimized for expression in these organisms and species.

For example, the codons of a nucleic acid encoding a xylanase isolated from a bacterial cell are modified such that the nucleic acid is optimally expressed in a bacterial cell different from the bacteria from which the xylanase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif 24:18-24, describing optimizing codons in yeast; Feng (2000) Biochemistry 39:15399-15409, describing optimizing codons in E. coli; Humphreys (2000) Protein Expr. Purif. 20:252-264, describing optimizing codon usage that affects secretion in E. coli.

Transgenic Non-Human Animals

The invention provides transgenic non-human animals comprising a nucleic acid, a polypeptide (e.g., a xylanase), an expression cassette or vector or a transfected or transformed cell of the invention. The invention also provides methods of making and using these transgenic non-human animals.

The transgenic non-human animals can be, e.g., goats, rabbits, sheep, pigs, cows, rats, horses, dogs, fish and mice, comprising the nucleic acids of the invention. These animals can be used, e.g., as invivo models to study xylanase activity, or, as models to screen for agents that change the xylanase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs, chickens, goats, fish and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudopregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express an endogenous gene, which is replaced with a gene expressing a xylanase of the invention, or, a fusion protein comprising a xylanase of the invention.

Transgenic Plants and Seeds

The invention provides transgenic plants and seeds comprising a nucleic acid, a polypeptide (e.g., a xylanase), an expression cassette or vector or a transfected or transformed cell of the invention. The invention also provides plant products or byproducts, e.g., fruits, oils, seeds, leaves, extracts and the like, including any plant part, comprising a nucleic acid and/or a polypeptide (e.g., a xylanase) of the invention, e.g., wherein the nucleic acid or polypeptide of the invention is heterologous to the plant, plant part, seed etc. The transgenic plant (which includes plant parts, fruits, seeds etc.) can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's xylanase production is regulated by endogenous transcriptional or translational control elements. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on starch-producing plants, such as potato, wheat, rice, barley, and the like. Nucleic acids of the invention can be used to manipulate metabolic pathways of a plant in order to optimize or alter host's expression of xylanase. The can change xylanase activity in a plant. Alternatively, a xylanase of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium, containing the appropriate antibiotic or herbicide. As for other inserted genes, marker genes also require promoter and termination sequences for proper function.

In one aspect, making transgenic plants or seeds comprises incorporating sequences of the invention and, in one aspect (optionally), marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional Agrobacterium tumefaciens host vector. The virulence functions of the Agrobacterium tumefaciens host will direct the insertion of the construct and adjacent marker into the plant cell DNA when the cell is infected by the bacteria. Agrobacterium tumefaciens-mediated transformation techniques, including disarming and use of binary vectors, are well described in the scientific literature. See, e.g., Horsch (1984) Science 233:496-498; Fraley (1983) Proc. Natl. Acad. Sci. USA 80:4803 (1983); Gene Transfer to Plants, Potrykus, ed. (Springer-Verlag, Berlin 1995). The DNA in an A. tumefaciens cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. A. tumefaciens can only infect a plant through wounds: when a plant root or stem is wounded it gives off certain chemical signals, in response to which, the vir genes of A. tumefaciens become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use A. tumefaciens as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci. USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., a xylanase) of the invention. The desired effects can be passed to future plant generations by standard propagation means.

The nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, Poa), forage grass such as festuca, lolium, temperate grass, such as Agrostis, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism Arabidopsis thaliana. Thus, the transgenic plants and seeds of the invention include a broad range of plants, including, but not limited to, species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea. Transgenic plants and seeds of the invention can be any monocot or dicot, e.g., a monocot corn, sugarcane, rice, wheat, barley, switchgrass or Miscanthus; or a dicot oilseed crop, soy, canola, rapeseed, flax, cotton, palm oil, sugar beet, peanut, tree, poplar or lupine.

In alternative embodiments, the nucleic acids of the invention are expressed in plants (and/or their seeds) which contain fiber cells, including, e.g., cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants of the invention can be members of the genus Gossypium, including members of any Gossypium species, such as G. arboreum; G. herbaceum, G. barbadense, and G. hirsutum.

The invention also provides for transgenic plants (and/or their seeds) to be used for producing large amounts of the polypeptides (e.g., a xylanase or antibody) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas 1',2') promoter with Agrobacterium tumefaciens-mediated leaf disc transformation methods).

Using known procedures, one of skill can screen for plants (and/or their seeds) of the invention by detecting the increase or decrease of transgene mRNA or protein in transgenic plants. Means for detecting and quantitation of mRNAs or proteins are well known in the art.

Polypeptides and Peptides

In one aspect, the invention provides isolated, synthetic or recombinant polypeptides and peptides having xylanase, a mannanase and/or a glucanase activity, or polypeptides and peptides capable of generating an antibody that specifically binds to a xylanase or a glucanase, including an enzyme of this invention, including the amino acid sequences of the invention, which include those having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, or 100% (complete) sequence identity to an exemplary polypeptide of the invention (as defined above, including SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 and SEQ ID NO:24), or any polypeptide of this invention, including for example SEQ ID NO:2 having one or more amino acid residue changes (mutations) as set forth in Table 1 and as described herein, also including a genus of polypeptides having various sequence identities based on the exemplary SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 or SEQ ID NO:24; and these exemplary polypeptides have the following enzymatic activity (e.g., the xylanase of SEQ ID NO:2, is encoded e.g , by SEQ ID NO:1; the arabinofuranosidase of SEQ ID NO:14, is encoded e.g., by SEQ ID NO:13, and the like):

| SEQ ID NO: | Name | Activity |
|---|---|---|
| 1, 2 | xyl 11 | Xylanase |
| 11, 12 | control xylanase | Xylanase |
| 13, 14 | | Arabinofuranosidase |
| 15, 16 | | Xylanase |
| 17, 18 | | Oligomerase |
| 19, 20 | | B-glucosidase |
| 21, 22 | | Arabinofuranosidase |
| 23, 24 | | Beta-xylosidase |
| 3, 4 | | Endoglucanase |
| 5, 6 | | Oligomerase |
| 7, 8 | | Cellobiohydrolase |
| 9, 10 | | Cellobiohydrolase |

The invention also provides enzyme-encoding nucleic acids with a common novelty in that they encode a subset of xylanases, or a Glade, comprising the "X14 module". In one aspect, the invention also provides enzyme-encoding nucleic acids with a common novelty in that they encode a Glade comprising the "X14 module" (see, e.g., J. Bacteriol. 2002 August; 184(15): 4124-4133). X14-comprising xylanase members include SEQ ID NO:2 having one or more amino acid residue changes (mutations) as set forth in Table 1 and as described herein.

In one aspect, the invention provides chimeric enzymes, including xylanases, glucanases and/or glycosidases, having heterologous carbohydrate-binding modules (CBMs), e.g., for use in the processes of the invention and in various industrial, medical, pharmaceutical, research, food and feed and food and feed supplement processing and other applications. For example, in one aspect the invention provides enzymes, e.g., hydrolases, including glycosyl hydrolases (such as xylanases, glucanases) comprising one or more CBMs of an enzyme of the invention, including the CBM-like X14 module discussed above. In another aspect, CBMs, e.g., X14 modules, between different enzymes of the invention can be swapped; or, alternatively, one or more CBMs of one or more enzymes of the invention can be spliced into an enzyme, e.g., a hydrolase, e.g., any glycosyl hydrolase, such as a xylanase.

Glycosyl hydrolases that utilize insoluble substrates are modular, usually comprising catalytic modules appended to one or more non-catalytic carbohydrate-binding modules (CBMs). In nature, CBMs are thought to promote the interaction of the glycosyl hydrolase with its target substrate polysaccharide. For example, as discussed above, X14 is a xylan binding module. Thus, the invention provides chimeric enzymes having heterologous, non-natural substrates; including chimeric enzymes having multiple substrates by nature of their "spliced-in" heterologous CBMs, e.g., a spliced-in X14 module of the invention—thus giving the chimeric enzyme new specificity for xylan and galactan, or enhanced binding to xylan and galactan. The heterologous CBMs of the chimeric enzymes of the invention can be designed to be modular, i.e., to be appended to a catalytic module or catalytic domain (e.g., an active site), which also can be heterologous or can be homologous to the enzyme.

Utilization of just the catalytic module of a xylanase or a glucanase (e.g., an enzyme of the invention) has been shown to be effective. Thus, the invention provides peptides and polypeptides consisting of, or comprising, modular CBM/active site modules (e.g., X14), which can be homologously paired or joined as chimeric (heterologous) active site-CBM pairs. Thus, these chimeric polypeptides/peptides of the invention can be used to improve or alter the performance of an individual enzyme, e.g., a xylanase enzyme. A chimeric catalytic module of the invention (comprising, e.g., at least one CBM of the invention, e.g., X14) can be designed to target the enzyme to particular regions of a substrate, e.g., to particular regions of a pulp. For example, in one aspect, this is achieved by making fusions of the xylanase and various CBMs (either a xylanase of the invention with a heterologous CBM, or, a CBM of the invention with another enzyme, e.g., a hydrolase, such as a xylanase. For example, CBM4, CBM6, and CBM22 are known to bind xylan and may enhance the effectiveness of the xylanase in pulp biobleaching (see, e.g., Czjzek (2001) J. Biol. Chem. 276 (51):48580-7, noting that CBM4, CBM6, and CBM22 are related and CBM interact primarily with xylan). In another embodiment, fusion of xylanase and CBM3a or CBM3b, which bind crystalline cellulose, may help the xylanase penetrate the complex polysaccharide matrix of pulp and reach inaccessible xylans. Any CBM can be used to practice the instant invention, e.g., as reviewed by Boraston (2004) Biochem. J. 382:769-781:

| Family | Protein | PDB code |
|---|---|---|
| CBM1 | Cellulase 7A (Trichoderma reesei) | 1CBH |
| CBM2 | Xylanase 10A (Cellulomonas fimi) | 1EXG |
| | Xylanase 11A (Cellulomonas fimi) | 2XBD |
| | Xylanase 11A (Cellulomonas fimi) | 1HEH |
| CBM3 | Scaffoldin (Clostridium cellulolyticum) | 1G43 |
| | Scaffoldin (Clostridium thermocellum) | 1NBC |
| | Cellulase 9A (Thermobifida fusca) | 1TF4 |
| CBM4 | Laminarinase 16A (Thermotoga maritima) | 1GUI |
| | Cellulase 9B (Cellulomonas fimi) | 1ULO; 1GU3 |
| | Cellulase 9B (Cellulomonas fimi) | 1CX1 |
| | Xylanase 10A (Rhodothermus marinus) | 1K45 |
| CBM5 | Cellulase 5A (Erwinia chrysanthemi) | 1AIW |
| | Chitinase B (Serratia marcescens) | 1E15 |
| CBM6 | Xylanase 11A (Clostridium thermocellum) | 1UXX |
| | Xylanase 11A (Clostridium stercorarium) | 1NAE |
| | Xylanase 11A (Clostridium stercorarium) | 1UY4 |
| | Endoglucanase 5A (Cellvibrio mixtus) | 1UZO |
| CBM9 | Xylanase 10A (Thermotoga maritima) | 1I8A |
| CBM10 | Xylanase 10A (Cellvibrio japonicus) | 1QLD |
| CBM12 | Chitinase Chi1 (Bacillus circulans) | 1ED7 |
| CBM13* | Xylanase 10A (Streptomyces olivaceoviridis) | 1XYF |
| | Xylanase 10A (Streptomyces lividans) | 1MC9 |
| | Ricin toxin B-chain (Ricinus communis) | 2AAI |
| | Abrin (Abrus precatorius) | 1ABR |
| CBM14 | Tachycitin (Tachypleus tridentatus) | 1DQC |
| CBM15 | Xylanase 10C (Cellvibrio japonicus) | 1GNY |
| CBM17 | Cellulase 5A (Clostridium cellulovorans) | 1J83 |
| CBM18* | Agglutinin (Triticum aestivum) | 1WGC |
| | Antimicrobial peptide (Amaranthus caudatus) | 1MMC |
| | Chitinase/agglutinin (Urtica dioica) | 1EIS |
| CBM20* | Glucoamylase (Aspergillus niger) | 1AC0 |
| | β-amylase (Bacillus cereus) | 1CQY |
| CBM22 | Xylanase 10B (Clostridium thermocellum) | 1DYO |
| CBM27 | Mannanase 5A (Thermotoga maritima) | 1OF4 |

-continued

| Family | Protein | PDB code |
|---|---|---|
| CBM28 | Cellulase 5A (Bacillus sp. 1139) | 1UWW |
| CBM29 | Non-catalytic protein 1 (Pyromyces equi) | 1GWK |
| CBM32 | Sialidase 33A (Micromonospora viridifaciens) | 1EUU |
| | Galactose oxidase (Cladobotryum dendroides) | 1GOF |
| CBM34* | α-Amylase 13A (Thermoactinomyces vulgaris) | 1UH2 |
| | Neopullulanase (Geobacillus stearothermophilus) | 1J0H |
| CBM36 | Xylanase 43A (Paenibacillus polymyxa) | 1UX7 |

*These families contain too many structure entries to list them all so only representatives are given.

Thus, the invention provides chimeric hydrolases, e.g., a fusion of a glycosidase with different (e.g., heterologous) CBMs to target the enzyme to particular insoluble polysaccharides to enhance performance in an application. In one aspect, the chimeric glycosidase comprises an enzyme of the invention. In one aspect, the chimeric enzyme comprises fusions of different CBMs to enhance pulp bio bleaching performance, e.g., to achieve greater percentage reduction of bleaching chemicals. The invention also provides methods comprising recombining different CBMs with different xylanases (e.g., CBMs of the invention and/or xylanases of the invention) and screening the resultant chimerics to find the best combination for a particular application or substrate.

Other variations also are within the scope of this invention, e.g., where one, two, three, four or five or more residues are removed from the carboxy- or amino-terminal ends of any polypeptide of the invention. Another variation includes modifying any residue to increase or decrease pI of a polypeptide, e.g., removing or modifying (e.g., to another amino acid) a glutamate. This method was used as a general scheme for improving the enzyme's properties without creating regulatory issues since no amino acids are mutated; and this general scheme can be used with any polypeptide of the invention.

The invention provides isolated, synthetic or recombinant polypeptides having xylanase activity, wherein the polypeptide has a sequence modification of any polypeptide of the invention, including any exemplary amino acid sequence of the invention, including SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and also including SEQ ID NO:2 having amino acid residue changes (mutations) as set forth in Table 1 and as described herein. The sequence change(s) can also comprise any amino acid modification to change the pI of a polypeptide, e.g., deletion or modification of a glutamate, or changing from a glutamate to another residue.

The invention further provides isolated, synthetic or recombinant polypeptides having a sequence identity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention.

In one aspect, the polypeptide has a xylanase or a glucanase activity; for example, wherein the xylanase activity can comprise hydrolyzing a glycosidic bond in a polysaccharide, e.g., a xylan. In one aspect, the polypeptide has a xylanase activity comprising catalyzing hydrolysis of internal β-1,4-xylosidic linkages. In one aspect, the xylanase activity comprises an endo-1,4-beta-xylanase activity. In one aspect, the xylanase activity comprises hydrolyzing a xylan to produce a smaller molecular weight xylose and xylo-oligomer. In one aspect, the xylan comprises an arabinoxylan, such as a water soluble arabinoxylan.

The invention provides polypeptides having glucanase activity. In one aspect, the glucanase activity of a polypeptide or peptide of the invention (which includes a protein or peptide encoded by a nucleic acid of the invention) comprises an endoglucanase activity, e.g., endo-1,4- and/or 1,3-beta-D-glucan 4-glucano hydrolase activity. In one aspect, the endoglucanase activity comprises catalyzing hydrolysis of 1,4-beta-D-glycosidic linkages. In one aspect, the glucanase, e.g., endoglucanase, activity comprises an endo-1,4- and/or 1,3-beta-endoglucanase activity or endo-β-1,4-glucanase activity. In one aspect, the glucanase activity (e.g., endo-1,4-beta-D-glucan 4-glucano hydrolase activity) comprises hydrolysis of 1,4-beta-D-glycosidic linkages in cellulose, cellulose derivatives (e.g., carboxy methyl cellulose and hydroxy ethyl cellulose) lichenin, beta-1,4 bonds in mixed beta-1,3 glucans, such as cereal beta-D-glucans and other plant material containing cellulosic parts. In one aspect, the glucanase, xylanase, or mannanase activity comprises hydrolyzing a glucan or other polysaccharide to produce a smaller molecular weight polysaccharide or oligomer. In one aspect, the glucan comprises a beta-glucan, such as a water soluble beta-glucan.

The invention provides polypeptides having mannanase (e.g., endo-1,4-beta-D-mannanase) activity, for example, catalyzing the hydrolysis of a beta-1,4-mannan, e.g., an unsubstituted linear beta-1,4-mannan. Mannanase activity determination can be determined using any known methods, e.g., the Congo Red method, as described e.g., by Downie (1994) "A new assay for quantifying endo-beta-mannanase activity using Congo red dye. Phytochemistry, July 1994, vol. 36, no. 4, p. 829-835; or, as described in U.S. Pat. No. 6,060,299, e.g., by applying a solution to be tested to 4 mm diameter holes punched out in agar plates containing 0.2% AZCL galactomannan (carob) or any substrate for the assay of endo-1,4-beta-D-mannanase.

Any xylanase, glue anase and/or mannanase assay known in the art can be used to determine if a polypeptide has xylanase, glucanase and/or mannanase activity and is within scope of the invention. For example, reducing sugar assays such as the Nelson-Somogyi method or the dinitrosalicylic acid (DNS) method can be used to assay for the product sugars (and thus, xylanase activity). In one aspect, reactions are carried out by mixing and incubating a dilution of the enzyme preparation with a known amount of substrate at a buffered pH and set temperature. Xylanase assays are similar to cellulase assays except that a solution of xylan (e.g., oat spelts or birch) is substituted for CMC or filter paper. The DNS assay is easier to use than the Nelson-Somogyi assay. The DNS assay is satisfactory for cellulase activities, but tends to over estimate xylanase activity. The Somogyi-Nelson procedure is more accurate in the determination of reducing sugars, to measure specific activities and to quantify the total amount of xylanase produced in the optimized growth conditions, see, e.g., Breuil (1985) Comparison of the 3,5-dinitrosalicylic acid and Nelson-Somogyi methods of assaying for reducing sugars and determining cellulase activity, Enzyme Microb. Technol. 7:327-332; Somogyi, M. 1952, Notes on sugar determination, J. Biol. Chem. 195:19-23. The invention incorporates use of any reducing sugar assay, e.g., by Nelson-Somogyi, e.g., based on references Nelson, N. (1944) J. Biol. Chem. 153:375-380, and Somogyi, M. (1952) J. Biol. Chem. 195:19-23.

The polypeptides of the invention include xylanases in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include xylanases inactive for other reasons, e.g., before "activation" by a post-translational processing event, e.g., an endo- or exo-peptidase or proteinase action, a phosphorylation event, an amidation, a glycosylation or a sulfation, a dimerization event, and the like. The polypeptides of the invention include all active forms, including active subsequences, e.g., catalytic domains or active sites, of the xylanase.

Methods for identifying "prepro" domain sequences and signal sequences are well known in the art, see, e.g., Van de Ven (1993) Crit. Rev. Oncog. 4(2):115-136. For example, to identify a prepro sequence, the protein is purified from the extracellular space and the N-terminal protein sequence is determined and compared to the unprocessed form.

The invention includes polypeptides with or without a signal sequence and/or a prepro sequence. The invention includes polypeptides with heterologous signal sequences and/or prepro sequences. The prepro sequence (including a sequence of the invention used as a heterologous prepro domain) can be located on the amino terminal or the carboxy terminal end of the protein. The invention also includes isolated, synthetic or recombinant signal sequences, prepro sequences and catalytic domains (e.g., "active sites") comprising sequences of the invention.

The percent sequence identity can be over the full length of the polypeptide, or, the identity can be over a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides. In alternative aspects, the invention provides polypeptides (peptides, fragments) ranging in size between about 5 and the full length of a polypeptide, e.g., an enzyme, such as a xylanase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary xylanase of the invention.

Peptides of the invention (e.g., a subsequence of an exemplary polypeptide of the invention) can be useful as, e.g., labeling probes, antigens, toleragens, motifs, xylanase active sites (e.g., "catalytic domains"), signal sequences and/or prepro domains.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431 A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

"Amino acid" or "amino acid sequence" as used herein refer to an oligopeptide, peptide, polypeptide, or protein sequence, or to a fragment, portion, or subunit of any of these and to naturally occurring or synthetic molecules. "Amino acid" or "amino acid sequence" include an oligopeptide, peptide, polypeptide, or protein sequence, or to a fragment, portion, or subunit of any of these, and to naturally occurring or synthetic molecules. The term "polypeptide" as used herein, refers to amino acids joined to each other by peptide bonds or modified peptide bonds, i.e., peptide isosteres and may contain modified amino acids other than the 20 gene-encoded amino acids. The polypeptides may be modified by either natural processes, such as post-translational processing, or by chemical modification techniques that are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a home moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, xylan hydrolase processing, phosphorylation, prenylation, racemization, selenoylation, sulfation and transfer-RNA mediated addition of amino acids to protein such as arginylation. (See Creighton, T. E., Proteins-Structure and Molecular Properties 2nd Ed., W.H. Freeman and Company, New York (1993); Posttranslational Covalent Modification of Proteins, B. C. Johnson, Ed., Academic Press, New York, pp. 1-12 (1983)). The peptides and polypeptides of the invention also include all "mimetic" and "peptidomimetic" forms, as described in further detail, below.

"Recombinant" polypeptides or proteins refer to polypeptides or proteins produced by recombinant DNA techniques; i.e., produced from cells transformed by an exogenous DNA construct encoding the desired polypeptide or protein. "Synthetic" nucleic acids (including oligonucleotides), polypeptides or proteins of the invention include those prepared by any chemical synthesis, e.g., as described, below. Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

"Fragments" or "enzymatically active fragments" as used herein are a portion of an amino acid sequence (encoding a protein) which retains at least one functional activity of the protein to which it is related. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "proform" molecule, such as a low activity proprotein that can be modified by cleavage to produce a mature enzyme with significantly higher activity.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a xylanase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(═O)—$CH_2$— for —C(═O)—NH—), aminomethylene ($CH_2$—NH), ethylene, olefin (CH═CH), ether ($CH_2$—O), thioether ($CH_2$—S), tetrazole ($CN_4$—), thiazole, retroamide, thioamide, or ester (see, e.g., Spatula (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thienylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidine)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzene-sulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

The invention includes xylanases of the invention with and without signal. The polypeptide comprising a signal sequence of the invention can be a xylanase of the invention or another xylanase or another enzyme or other polypeptide.

The invention includes immobilized xylanases, anti-xylanase antibodies and fragments thereof. The invention provides methods for inhibiting xylanase activity, e.g., using dominant negative mutants or anti-xylanase antibodies of the invention. The invention includes heterocomplexes, e.g., fusion proteins, heterodimers, etc., comprising the xylanases of the invention.

Polypeptides of the invention can have a xylanase activity under various conditions, e.g., extremes in pH and/or temperature, oxidizing agents, and the like. The invention provides methods leading to alternative xylanase preparations with different catalytic efficiencies and stabilities, e.g., towards temperature, oxidizing agents and changing wash conditions. In one aspect, xylanase variants can be produced using techniques of site-directed mutagenesis and/or random mutagenesis. In one aspect, directed evolution can be used to produce a great variety of xylanase variants with alternative specificities and stability.

The proteins of the invention are also useful as research reagents to identify xylanase modulators, e.g., activators or inhibitors of xylanase activity. Briefly, test samples (compounds, broths, extracts, and the like) are added to xylanase assays to determine their ability to inhibit substrate cleavage. Inhibitors identified in this way can be used in industry and research to reduce or prevent undesired proteolysis. As with xylanases, inhibitors can be combined to increase the spectrum of activity.

The enzymes of the invention are also useful as research reagents to digest proteins or in protein sequencing. For example, the xylanases may be used to break polypeptides into smaller fragments for sequencing using, e.g. an automated sequencer.

The invention also provides methods of discovering new xylanases using the nucleic acids, polypeptides and antibodies of the invention. In one aspect, phagemid libraries are screened for expression-based discovery of xylanases. In another aspect, lambda phage libraries are screened for expression-based discovery of xylanases. Screening of the phage or phagemid libraries can allow the detection of toxic clones; improved access to substrate; reduced need for engineering a host, by-passing the potential for any bias resulting from mass excision of the library; and, faster growth at low clone densities. Screening of phage or phagemid libraries can be in liquid phase or in solid phase. In one aspect, the invention provides screening in liquid phase. This gives a greater flexibility in assay conditions; additional substrate flexibility; higher sensitivity for weak clones; and ease of automation over solid phase screening.

The invention provides screening methods using the proteins and nucleic acids of the invention and robotic automation to enable the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

Another aspect of the invention is an isolated or purified polypeptide comprising the sequence of one of the invention and sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Another aspect of the invention is polypeptides or fragments thereof which have at least about 50%, at least about 55%, at least about 60%, at least about 65%, at least about 70%, at least about 75%, at least about 80%, at least about 85%, at least about 90%, at least about 95%, or more than about 95% homology to one of the polypeptides of the invention and sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of the invention, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by xylan hydrolase digestion, gel electrophoresis and/or microsequencing. The sequence of the prospective homologous polypeptide or fragment can be compared to one of the polypeptides of the invention, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of The invention, which retain the enzymatic function of the polypeptides of The invention. For example the fragments or variants of said polypeptides, may be used to catalyze biochemical reactions, which indicate that the fragment or variant retains the enzymatic activity of the polypeptides of the invention.

The assay for determining if fragments of variants retain the enzymatic activity of the polypeptides of the invention includes the steps of: contacting the polypeptide fragment or variant with a substrate molecule under conditions which allow the polypeptide fragment or variant to function and detecting either a decrease in the level of substrate or an increase in the level of the specific reaction product of the reaction between the polypeptide and substrate.

The polypeptides of the invention or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of the invention or polynucleotides encoding such polypeptides for hydrolyzing glycosidic linkages. In such procedures, a substance containing a glycosidic linkage (e.g., a starch) is contacted with one of the polypeptides of The invention, or sequences substantially identical thereto under conditions which facilitate the hydrolysis of the glycosidic linkage.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods.

In a particular aspect, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library which exhibits a desired activity. A specific biocatalytic reaction which produces the modified small molecule of desired activity is identified by systematically eliminating each of the biocatalytic reactions used to produce a portion of the library and then testing the small molecules produced in the portion of the library for the presence or absence of the modified small molecule with the desired activity. The specific biocatalytic reactions which produce the modified small molecule of desired activity is in one aspect (optionally) repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

Xylanase Signal Sequences, Prepro and Catalytic Domains

The invention provides xylanase signal sequences (e.g., signal peptides (SPs)), prepro domains and catalytic domains (CDs). The SPs, prepro domains and/or CDs of the invention can be isolated, synthetic or recombinant peptides or can be part of a fusion protein, e.g., as a heterologous domain in a chimeric protein. The invention provides nucleic acids encoding these catalytic domains (CDs), prepro domains and signal sequences (SPs, e.g., a peptide having a sequence comprising/consisting of amino terminal residues of a polypeptide of the invention). In one aspect, the invention provides a signal sequence comprising a peptide comprising/consisting of a sequence as set forth in residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44, 1 to 45, 1 to 46, 1 to 47, 1 to 48, 1 to 49 or 1 to 50, of a polypeptide of the invention.

The xylanase signal sequences (SPs) and/or prepro sequences of the invention can be isolated peptides, or, sequences joined to another xylanase or a non-xylanase polypeptide, e.g., as a fusion (chimeric) protein. In one aspect, the invention provides polypeptides comprising xylanase signal sequences of the invention. In one aspect, polypeptides comprising xylanase signal sequences SPs and/or prepro of the invention comprise sequences heterologous to a xylanase of the invention (e.g., a fusion protein comprising an SP and/or prepro of the invention and sequences from another xylanase or a non-xylanase protein). In one aspect, the invention provides xylanases of the invention with heterologous SPs and/or prepro sequences, e.g., sequences with a yeast signal sequence. A xylanase of the invention can comprise a heterologous SP and/or prepro in a vector, e.g., a pPIC series vector (Invitrogen, Carlsbad, Calif.).

In one aspect, SPs and/or prepro sequences of the invention are identified following identification of novel xylanase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The signal sequences can vary in length from between about 11 to 41, or between about 13 to 36 amino acid residues. Various methods of recognition of signal sequences are known to those of skill in the art. For example, in one aspect, novel xylanase signal peptides are identified by a method referred to as SignalP. SignalP uses a combined neural network which recognizes both signal peptides and their cleavage sites; see, e.g., Nielsen (1997) "Identification of prokaryotic and eukaryotic signal peptides and prediction of their cleavage sites." Protein Engineering 10:1-6.

It should be understood that in some aspects xylanases of the invention may not have SPs and/or prepro sequences, or "domains" In one aspect, the invention provides the xylanases of the invention lacking all or part of an SP and/or a prepro domain. In one aspect, the invention provides a nucleic acid sequence encoding a signal sequence (SP) and/or prepro from one xylanase operably linked to a nucleic acid sequence of a different xylanase or, in one aspect (optionally), a signal sequence (SPs) and/or prepro domain from a non-xylanase protein may be desired.

The invention also provides isolated, synthetic or recombinant polypeptides comprising signal sequences (SPs), prepro domain and/or catalytic domains (CDs) of the invention and heterologous sequences. The heterologous sequences are sequences not naturally associated (e.g., to a xylanase) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In one aspect, the invention provides an isolated, synthetic or recombinant polypeptide comprising (or consisting of) a polypeptide comprising a signal sequence (SP), prepro domain and/or catalytic domain (CD) of the invention with the proviso that it is not associated with any sequence to which it is naturally associated (e.g., a xylanase sequence). Similarly in one aspect, the invention provides isolated, synthetic or recombinant nucleic acids encoding these polypeptides. Thus, in one aspect, the isolated, synthetic or recombinant nucleic acid of the invention comprises coding sequence for a signal sequence (SP), prepro domain and/or catalytic domain (CD) of the invention and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

Hybrid (Chimeric) Xylanases and Peptide Libraries

In one aspect, the invention provides hybrid xylanases and fusion proteins, including peptide libraries, comprising sequences of the invention. The peptide libraries of the invention can be used to isolate peptide modulators (e.g., activators or inhibitors) of targets, such as xylanase substrates, receptors, enzymes. The peptide libraries of the invention can be used to identify formal binding partners of targets, such as ligands, e.g., cytokines, hormones and the like. In one aspect, the invention provides chimeric proteins comprising a signal sequence (SP), prepro domain and/or catalytic domain (CD) of the invention or a combination thereof and a heterologous sequence (see above).

In one aspect, the fusion proteins of the invention (e.g., the peptide moiety) are conformationally stabilized (relative to linear peptides) to allow a higher binding affinity for targets. The invention provides fusions of xylanases of the invention and other peptides, including known and random peptides. They can be fused in such a manner that the structure of the xylanases is not significantly perturbed and the peptide is metabolically or structurally conformationally stabilized. This allows the creation of a peptide library that is easily monitored both for its presence within cells and its quantity.

Amino acid sequence variants of the invention can be characterized by a predetermined nature of the variation, a feature that sets them apart from a naturally occurring form, e.g., an allelic or interspecies variation of a xylanase sequence. In one aspect, the variants of the invention exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed xylanase variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using, e.g., assays of xylan hydrolysis. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides xylanases where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alphahelical or a beta-sheet structure; a charge or a hydrophobic site of the molecule, which can be at an active site; or a side chain. The invention provides substitutions in polypeptide of the invention where (a) a hydrophilic residues, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e. xylanase activity) although variants can be selected to modify the characteristics of the xylanases as needed.

In one aspect, xylanases of the invention comprise epitopes or purification tags, signal sequences or other fusion sequences, etc. In one aspect, the xylanases of the invention can be fused to a random peptide to form a fusion polypeptide. By "fused" or "operably linked" herein is meant that the random peptide and the xylanase are linked together, in such a manner as to minimize the disruption to the stability of the xylanase structure, e.g., it retains xylanase activity. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor.

Xylanases are multidomain enzymes that consist in one aspect (optionally) of a signal peptide, a carbohydrate binding module, a xylanase catalytic domain, a linker and/or another catalytic domain.

The invention provides a means for generating chimeric polypeptides which may encode biologically active hybrid polypeptides (e.g., hybrid xylanases). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g. high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the polynucleotides of the invention include, but are not limited to, hydrolases, such as xylanases. Glycosidase hydrolases were first classified into families in 1991, see, e.g., Henrissat (1991) Biochem. J. 280:309-316. Since then, the classifications have been continually updated, see, e.g., Henrissat (1993) Biochem. J. 293:781-788; Henrissat (1996) Biochem. J. 316:695-696; Henrissat (2000) Plant Physiology 124:1515-1519. There are 87 identified families of glycosidase hydrolases. In one aspect, the xylanases of the invention may be categorized in families 8, 10, 11, 26 and 30. In one aspect, the invention also provides xylanase-encoding nucleic acids with a common novelty in that they are derived from a common family, e.g., 11.

A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolases, such as: (a) amide (peptide bonds), i.e., xylanases; (b) ester bonds, i.e., esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

Additionally, subcloning may be performed to further isolate sequences of interest. In subcloning, a portion of DNA is amplified, digested, generally by restriction enzymes, to cut out the desired sequence, the desired sequence is ligated into a recipient vector and is amplified. At each step in subcloning, the portion is examined for the activity of interest, in order to ensure that DNA that encodes the structural protein has not been excluded. The insert may be purified at any step of the subcloning, for example, by gel electrophoresis prior to ligation into a vector or where cells containing the recipient vector and cells not containing the recipient vector are placed on selective media containing, for example, an antibiotic, which will kill the cells not containing the recipient vector. Specific methods of subcloning cDNA inserts into vectors are well-known in the art (Sambrook et al., Molecular Cloning: A Laboratory Manual, 2nd Ed., Cold Spring Harbor Laboratory Press (1989)). In another aspect, the enzymes of the invention are subclones. Such subclones may differ from the parent clone by, for example, length, a mutation, a tag or a label.

It should be understood that some of the xylanases of the invention may or may not contain signal sequences. It may be desirable to include a nucleic acid sequence encoding a signal sequence from one xylanase operably linked to a nucleic acid sequence of a different xylanase or, in one aspect (optionally), a signal sequence from a non-xylanase protein may be desired.

The microorganisms from which the polynucleotide may be prepared include prokaryotic microorganisms, such as Eubacteria and Archaebacteria and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such micro organisms may be extremophiles, such as hyperthermophiles, psychrophiles, psychrotrophs, halophiles, barophiles and acidophiles. Polynucleotides encoding enzymes isolated from extremophilic microorganisms can be used. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981) and other cell lines capable of expressing a compatible vector, for example, the C127, 3T3, CHO, HeLa and BHK cell lines. Mammalian expression vectors will comprise an origin of replication, a suitable promoter and enhancer and also any necessary ribosome binding sites, polyadenylation site, splice donor and acceptor sites, transcriptional termination sequences and 5' flanking nontranscribed sequences. DNA sequences derived from the SV40 splice and polyadenylation sites may be used to provide the required nontranscribed genetic elements.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of E. coli. This f-factor of E. coli is a plasmid which affects high-frequency transfer of itself during conjugation and is ideal to achieve and stably propagate large DNA fragments, such as gene clusters from mixed microbial samples. One aspect of the invention is to use cloning vectors, referred to as "fosmids" or bacterial artificial chromosome (BAC) vectors. These are derived from E. coli f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et al., Molecular Cloning: A Laboratory Manual, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one aspect, the invention relates to a method for producing a biologically active hybrid polypeptide and screening such a polypeptide for enhanced activity by:

1) introducing at least a first polynucleotide in operable linkage and a second polynucleotide in operable linkage, the at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

Screening Methodologies and "On-line" Monitoring Devices

In practicing the methods of the invention, a variety of apparatus and methodologies can be used to in conjunction with the polypeptides and nucleic acids of the invention, e.g., to screen polypeptides for xylanase activity (e.g., assays such as hydrolysis of casein in zymograms, the release of fluorescence from gelatin, or the release of p-nitroanalide from various small peptide substrates), to screen compounds as potential modulators, e.g., activators or inhibitors, of a xylanase activity, for antibodies that bind to a polypeptide of the invention, for nucleic acids that hybridize to a nucleic acid of the invention, to screen for cells expressing a polypeptide of the invention and the like. In addition to the array formats described in detail below for screening samples, alternative formats can also be used to practice the methods of the invention. Such formats include, for example, mass spectrometers, chromatographs, e.g., high-throughput HPLC and other forms of liquid chromatography, and smaller formats, such as 1536-well plates, 384-well plates and so on. High throughput screening apparatus can be adapted and used to practice the methods of the invention, see, e.g., U.S. Patent Application No. 20020001809.

Capillary Arrays

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays, such as the GIGAMATRIX™, Diversa Corporation, San Diego, Calif.; and arrays described in, e.g., U.S. Patent Application No. 20020080350 A1; WO 0231203 A; WO 0244336A, provide an alternative apparatus for holding and screening samples. In one aspect, the capillary array includes a plurality of capillaries formed into an array of adjacent capillaries, wherein each capillary comprises at least one wall defining a lumen for retaining a sample. The lumen may be cylindrical, square, hexagonal or any other geometric shape so long as the walls form a lumen for retention of a liquid or sample. The capillaries of the capillary array can be held, together in close proximity to form a planar structure. The capillaries can be bound together, by being fused (e.g., where the capillaries are made of glass), glued, bonded, or clamped side-by-side. Additionally, the capillary array can include interstitial material disposed between adjacent capillaries in the array, thereby forming a solid planar device containing a plurality of through-holes.

A capillary array can be formed of any number of individual capillaries, for example, a range from 100 to 4,000,000 capillaries. Further, a capillary array having about 100,000 or more individual capillaries can be formed into the standard size and shape of a Microtiter® plate for fitment into standard laboratory equipment. The lumens are filled manually or automatically using either capillary action or microinjection using a thin needle. Samples of interest may subsequently be removed from individual capillaries for further analysis or characterization. For example, a thin, needle-like probe is positioned in fluid communication with a selected capillary to either add or withdraw material from the lumen.

In a single-pot screening assay, the assay components are mixed yielding a solution of interest, prior to insertion into the capillary array. The lumen is filled by capillary action when at least a portion of the array is immersed into a solution of interest. Chemical or biological reactions and/or activity in each capillary are monitored for detectable events. A detectable event is often referred to as a "hit", which can usually be distinguished from "non-hit" producing capillaries by optical detection. Thus, capillary arrays allow for massively parallel detection of "hits".

In a multi-pot screening assay, a polypeptide or nucleic acid, e.g., a ligand, can be introduced into a first component, which is introduced into at least a portion of a capillary of a capillary array. An air bubble can then be introduced into the capillary behind the first component. A second component can then be introduced into the capillary, wherein the second component is separated from the first component by the air bubble. The first and second components can then be mixed by applying hydrostatic pressure to both sides of the capillary array to collapse the bubble. The capillary array is then monitored for a detectable event resulting from reaction or non-reaction of the two components.

In a binding screening assay, a sample of interest can be introduced as a first liquid labeled with a detectable particle into a capillary of a capillary array, wherein the lumen of the capillary is coated with a binding material for binding the detectable particle to the lumen. The first liquid may then be removed from the capillary tube, wherein the bound detectable particle is maintained within the capillary, and a second liquid may be introduced into the capillary tube. The capillary is then monitored for a detectable event resulting from reaction or non-reaction of the particle with the second liquid.

Arrays, or "Biochips"

Nucleic acids and/or polypeptides of the invention can be immobilized to or applied to an array, e.g., a "biochip". Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a xylanase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated, synthetic or recombinant antibodies that specifically bind to a xylanase of the invention. These antibodies can be used to isolate, identify or quantify the xylanases of the invention or related polypeptides. These antibodies can be used to isolate other polypeptides within the scope the invention or other related xylanases. The antibodies can be designed to bind to an active site of a xylanase. Thus, the invention provides methods of inhibiting xylanases using the antibodies of the invention (see discussion above regarding applications for anti-xylanase compositions of the invention).

The invention provides fragments of the enzymes of the invention, including immunogenic fragments of a polypeptide of the invention. The invention provides compositions comprising a polypeptide or peptide of the invention and adjuvants or carriers and the like.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VIA and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

The polypeptides of The invention or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of The invention, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of The invention, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding maybe determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays and Western Blots.

Polyclonal antibodies generated against the polypeptides of The invention, or fragments comprising at least 5, 10, 15, 20, 25, 30, 35, 40, 50, 75, 100, or 150 or more consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate, antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975), the trioma technique, the human B-cell hybridoma technique (Kozbor et al., Immunology Today 4:72, 1983) and the EBV-hybridoma technique (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to the polypeptides of The invention, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of The invention, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", Methods in Enzymology, Vol 160, pp. 87-116.

Kits

The invention provides kits comprising the compositions, e.g., nucleic acids, expression cassettes, vectors, cells, transgenic seeds or plants or plant parts, polypeptides (e.g., xylanases) and/or antibodies of the invention. The kits also can contain instructional material teaching the methodologies and industrial, research, medical, pharmaceutical, food and feed and food and feed supplement processing and other applications and processes of the invention, as described herein.

Whole Cell Engineering and Measuring Metabolic Parameters

The methods of the invention provide whole cell evolution, or whole cell engineering, of a cell to develop a new cell strain having a new phenotype, e.g., a new or modified xylanase activity, by modifying the genetic composition of the cell. The genetic composition can be modified by addition to the cell of a nucleic acid of the invention, e.g., a coding sequence for an enzyme of the invention. See, e.g., WO0229032; WO0196551.

To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using the xylanases of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

- identity of all pathway substrates, products and intermediary metabolites
- identity of all the chemical reactions interconverting the pathway metabolites, the stoichiometry of the pathway reactions,
- identity of all the enzymes catalyzing the reactions, the enzyme reaction kinetics,
- the regulatory interactions between pathway components, e.g. allosteric interactions, enzyme-enzyme interactions etc,
- intracellular compartmentalization of enzymes or any other supramolecular organization of the enzymes, and,
- the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript (e.g., a xylanase message) or generating new (e.g., xylanase) transcripts in a cell. This increased or decreased expression can be traced by testing for the presence of a xylanase of the invention or by xylanase activity assays. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide (e.g., a xylanase) or generating new polypeptides in a cell. This increased or decreased expression can be traced by determining the amount of xylanase present or by xylanase activity assays. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immunofluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Industrial, Energy, Pharmaceutical, Medical, Food Processing and other Applications Polypeptides of the invention can be used in any industrial, agricultural, food and feed and food and feed supplement processing, pharmaceutical, medical, research (laboratory) or other process. The invention provides industrial processes using enzymes of the invention, e.g., in the pharmaceutical or nutrient (diet) supplement industry, the energy industry (e.g., to make "clean" biofuels), in the food and feed industries, e.g., in methods for making food and feed products and food and feed additives. In one aspect, the invention provides processes using enzymes of the invention in the medical industry, e.g., to make pharmaceuticals or dietary aids or supplements, or food supplements and additives. In addition, the invention provides methods for using the enzymes of the invention in biofuel production, including, e.g., a bioalcohol such as bioethanol, biomethanol, biobutanol or biopropanol, thus comprising a "clean" fuel production. Enzymes of the invention can be added to industrial processes continuously, in batches or by fed-batch methods. In another aspect, enzymes of the invention can be recycled in the industrial processes, thereby lowering enzyme requirements.

For example, xylanases can be used in the biobleaching and treatment of chemical pulps, for example, as described in U.S. Pat. No. 5,202,249; or for biobleaching and treatment of wood or paper pulps, for example, as described in U.S. Pat. Nos. 5,179,021, 5,116,746, 5,407,827, 5,405,769, 5,395,765, 5,369,024, 5,457,045, 5,434,071, 5,498,534, 5,591,304, 5,645,686, 5,725,732, 5,759,840, 5,834,301, 5,871,730 and 6,057,438; or for reducing lignin in wood and modifying wood, for example, as described in U.S. Pat. Nos. 5,486,468 and/or 5,770,012; or for use as flour, dough and bread improvers, for example, as described in U.S. Pat. Nos. 5,108,765 and/or 5,306,633; or for use as feed additives and/or supplements, for example, as described in U.S. Pat. Nos. 5,432,074; 5,429,828; 5,612,055; 5,720,971; 5,981,233; 5,948,667; 6,099,844; 6,132,727 and/or 6,132,716; or in manufacturing cellulose solntions, for example, as described in U.S. Pat. No. 5,760,211; or in detergent compositions; or used for fruit, vegetables and/or mud and clay compounds, for example, as described in U.S. Pat. No. 5,786,316. Xylanases of this invention also can be used in hydrolysis of hemicellulose, for example, as described in U.S. Pat. No. 4,725,544.

The xylanase enzymes of the invention can be highly selective catalysts. They can catalyze reactions with exquisite stereo-, regio- and chemo-selectivities that are unparalleled in conventional synthetic chemistry. Moreover, enzymes are remarkably versatile. The xylanase enzymes of the invention can be tailored to function in organic solvents, operate at extreme pHs (for example, high pHs and low pHs) extreme temperatures (for example, high temperatures and low temperatures), extreme salinity levels (for example, high salinity and low salinity) and catalyze reactions with compounds that are structurally unrelated to their natural, physiological substrates.

Wood, Paper and Pulp Treatments

The xylanases of the invention can be used in any wood, wood product, wood waste or by-product, paper, paper product, paper or wood pulp, Kraft pulp, or wood or paper recycling treatment or industrial process, e.g., any wood, wood pulp, paper waste, paper or pulp treatment or wood or paper deinking process. In one aspect, xylanases of the invention can be used to treat/pretreat paper pulp, or recycled paper or paper pulp, and the like. In one aspect, enzyme(s) of the invention are used to increase the "brightness" of the paper via their use in treating/pretreating paper pulp, or recycled paper or paper pulp, and the like. The higher the grade of paper, the greater the brightness; paper brightness can impact the scan capability of optical scanning equipment; thus, the enzymes and processes of the invention can be used to make high grade, "bright" paper for, e.g., use in optical scanning equipment, including inkjet, laser and photo printing quality paper.

For example, the enzymes of the invention can be used in any industrial process using xylanases known in the art, e.g., treating waste paper, as described in, e.g., U.S. Pat. Nos. 6,767,728 or 6,426,200; seasoning wood, e.g., for applications in the food industry, as described in, e.g., U.S. Pat. No. 6,623,953; for the production of xylose from a paper-grade hardwood pulp, as described in, e.g., U.S. Pat. No. 6,512,110; treating fibrous lignocellulosic raw material with a xylanase in an aqueous medium as described in, e.g., U.S. Pat. No. 6,287,708; dissolving pulp from cellulosic fiber, as described in, e.g., U.S. Pat. No. 6,254,722; deinking and decolorizing a printed paper or removing color from wood-pulp, as described in, e.g., U.S. Pat. Nos. 6,241,849, 5,834,301 or 5,582,681; bleaching a chemical paper pulp or lignocellulose pulp using a xylanase, as described in, e.g., U.S. Pat. Nos. 5,645,686 or 5,618,386; for treating wood pulp that includes incompletely washed brownstock, as described in, e.g., U.S. Pat. No. 5,591,304; purifying and delignifying a waste lignocellulosic material, as described in, e.g., in U.S. Pat. No. 5,503,709; manufacturing paper or cardboard from recycled cellulose fibers, as described in, e.g., in U.S. Pat. No. 5,110,412; debarking of logs, as described in, e.g., in U.S. Pat. No. 5,103,883; producing fluff pulp with improved shredding properties, as described in, e.g., in U.S. Pat. No. 5,068,009, and the like. The xylanases of the invention can be used to process or treat any cellulosic material, e.g., fibers from wood, cotton, hemp, flax or linen.

In one aspect, the invention provides wood, wood pulp, paper, paper pulp, paper waste or wood or paper recycling treatment processes using a xylanase of the invention. In one aspect, the xylanase of the invention is applicable both in reduction of the need for a chemical decoloring (e.g., bleaching) agent, such as chlorine dioxide, and in high alkaline and high temperature environments. Most lignin is solubilized in the cooking stage of pulping process. The residual lignin is removed from the pulp in the bleaching process. In one aspect, xylanase bleaching of pulp (e.g., using an enzyme of the invention) is based on the partial hydrolysis of xylan, which is the main component of the hemicellulose. The enzymatic action (e.g., of an enzyme of the invention) releases hemicellulose-bound lignin and increases the extractability of lignin from the pulp in the subsequent bleaching process, e.g. using chlorine and oxygen chemicals. In one aspect, xylanases of the invention can be used to increase the final brightness of the pulp at a fixed level of bleaching chemicals. In another aspect, xylanases of the invention can be used to decrease the kappa number of the pulp.

The invention provides wood, wood pulp, paper, paper pulp, paper waste or wood or paper recycling treatment processes (methods) using a xylanase of the invention where the treatment time (the amount of time the xylanase is in contact with the pulp, paper, wood, etc.) and/or retention time can be anywhere from between about 1 minute to 12 hours, or between about 5 minutes to 1 hour, or between about 15 to 30 minutes; or the treatment and/or retention time can be any time up to about 0.1, 0.25, 0.5, 0.75, 1, 1.5, 2, 3, 4, 5, 6, 7, 8, 9, 10, 11, 12 or more hours.

In one aspect, the xylanase of the invention is a thermostable alkaline endoxylanase which in one aspect can effect a greater than 25% reduction in the chlorine dioxide requirement of kraft pulp with a less than 0.5% pulp yield loss. In one aspect, boundary parameters are pH 10, 65-85° C. and treatment time of less than 60 minutes at an enzyme loading of less than 0.001 wt %; in alternative aspects the treatment and/or retention time is less than about 0.1, 0.25, 0.5, 0.75, 1, 1.5, 2, 3, 4, 5, 6, 7, 8, 9, 10, 11 or 12.

A pool of xylanases may be tested for the ability to hydrolyze dye-labeled xylan at, for example, pH 10 and 60° C. The enzymes that test positive under these conditions may then be evaluated at, for example pH 10 and 70° C. Alternatively, enzymes may be tested at pH 8 and pH 10 at 70° C. In discovery of xylanases desirable in the pulp and paper industry libraries from high temperature or highly alkaline environments were targeted. Specifically, these libraries were screened for enzymes functioning at alkaline pH and a temperature of approximately 45° C. In another aspect, the xylanases of the invention are useful in the pulp and paper industry in degradation of a lignin-hemicellulose linkage, in order to release the lignin.

Enzymes of the invention can be used for deinking printed wastepaper, such as newspaper, or for deinking noncontact-printed wastepaper, e.g., xerographic and laser-printed paper, and mixtures of contact and noncontact-printed wastepaper, as described in U.S. Pat. Nos. 6,767,728 or 6,426,200; Neo (1986) J. Wood Chem. Tech. 6(2):147. Enzymes of the invention can be used in processes for the production of xylose from a paper-grade hardwood pulp by extracting xylan contained in pulp into a liquid phase, subjecting the xylan contained in the obtained liquid phase to conditions sufficient to hydrolyze xylan to xylose, and recovering the xylose, where the extracting step includes at least one treatment of an aqueous suspension of pulp or an alkali-soluble material a xylanase enzyme, as described in, e.g., U.S. Pat. No. 6,512,110. Enzymes of the invention can be used in processes for dissolving pulp from cellulosic fibers such as recycled paper products made from hardwood fiber, a mixture of hardwood fiber and softwood fiber, waste paper, e.g., from unprinted envelopes, de-inked envelopes, unprinted ledger paper, deinked ledger paper, and the like, as described in, e.g., U.S. Pat. No. 6,254,722.

In another aspect of the invention, the xylanases of the invention can also be used in any wood, wood product, paper, paper product, paper or wood pulp, Kraft pulp, or wood or paper recycling treatment or industrial process, e.g., any wood, wood pulp, paper waste, paper or pulp treatment or wood or paper deinking process as an antimicrobial or microbial repellent. Alternatively, the xylanases of the invention can be part of a wood, wood product, paper, paper product, paper or wood pulp, Kraft pulp, or recycled paper composition, and/or a composition comprising one or more wood, wood product, paper, paper product, paper or wood pulp, Kraft pulp, or recycled paper compositions, wherein the xylanases of the invention act as an antimicrobial or microbial repellent in the composition.

Treating Fibers and Textiles

The invention provides methods of treating fibers and fabrics using one or more xylanases of the invention. The xylanases can be used in any fiber- or fabric-treating method, which are well known in the art, see, e.g., U.S. Pat. Nos. 6,261,828; 6,077,316; 6,024,766; 6,021,536; 6,017,751; 5,980,581; US Patent Publication No. 20020142438 A1. For example, xylanases of the invention can be used in fiber and/or fabric desizing. In one aspect, the feel and appearance of a fabric is improved by a method comprising contacting the fabric with a xylanase of the invention in a solution. In one aspect, the fabric is treated with the solution under pressure. For example, xylanases of the invention can be used in the removal of stains.

The xylanases of the invention can be used to treat any cellulosic material, including fibers (e.g., fibers from cotton, hemp, flax or linen), sewn and unsewn fabrics, e.g., knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The textile treating processes of the invention (using xylanases of the invention) can be used in conjunction with other textile treatments, e.g., scouring and bleaching. Scouring is the removal of non-cellulosic material from the cotton fiber, e.g., the cuticle (mainly consisting of waxes) and primary cell wall (mainly consisting of pectin, protein and xyloglucan). A proper wax removal is necessary for obtaining a high wettability. This is needed for dyeing. Removal of the primary cell walls by the processes of the invention improves wax removal and ensures a more even dyeing. Treating textiles with the processes of the invention can improve whiteness in the bleaching process. The main chemical used in scouring is sodium, hydroxide in high concentrations and at high temperatures. Bleaching comprises oxidizing the textile. Bleaching typically involves use of hydrogen peroxide as the oxidizing agent in order to obtain either a fully bleached (white) fabric or to ensure a clean shade of the dye.

The invention also provides alkaline xylanases (xylanases active under alkaline conditions). These have wide-ranging applications in textile processing, degumming of plant fibers (e.g., plant bast fibers), treatment of pectic wastewaters, paper-making, and coffee and tea fermentations. See, e.g., Hoondal (2002) Applied Microbiology and Biotechnology 59:409-418.

In another aspect of the invention, the xylanases of the invention can also be used in any fiber- and/or fabric-treating process as an antimicrobial or microbial repellent. Alternatively, the xylanases of the invention can be part of a fiber- and/or fabric-composition, where the xylanases of the invention act as an antimicrobial or microbial repellent in the fiber and/or fabric.

Detergent, Disinfectant and Cleaning Compositions

The invention provides detergent, disinfectant or cleanser (cleaning or cleansing) compositions comprising one or more polypeptides (e.g., xylanases) of the invention, and methods of making and using these compositions. The invention incorporates all methods of making and using detergent, disinfectant or cleanser compositions, see, e.g., U.S. Pat. Nos. 6,413,928; 6,399,561; 6,365,561; 6,380,147. The detergent, disinfectant or cleanser compositions can be a one and two part aqueous composition, a non-aqueous liquid composition, a cast solid, a granular form, a particulate form, a compressed tablet, a gel and/or a paste and a slurry form. The xylanases of the invention can also be used as a detergent, disinfectant or cleanser additive product in a solid or a liquid form. Such additive products are intended to supplement or boost the performance of conventional detergent compositions and can be added at any stage of the cleaning process.

The actual active enzyme content depends upon the method of manufacture of a detergent, disinfectant or cleanser composition and is not critical, assuming the detergent solution has the desired enzymatic activity. In one aspect, the amount of xylanase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the xylanases of the present invention are active in the pH ranges of from about 4 to about 12 and in the temperature range of from about 20° C.

to about 95° C. The detergents of the invention can comprise cationic, semi-polar nonionic or zwitterionic surfactants; or, mixtures thereof.

Xylanases of the invention can be formulated into powdered and liquid detergents, disinfectants or cleansers having pH between 4.0 and 12.0 at levels of about 0.01 to about 5% (preferably 0.1% to 0.5%) by weight. These detergent, disinfectant or cleanser compositions can also include other enzymes such as xylanases, cellulases, lipases, esterases, proteases, or endoglycosidases, endo-beta-1,4-glucanases, beta-glucanases, endo-beta-1,3(4)-glucanases, cutinases, peroxidases, catalases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases and/or transglutaminases. These detergent, disinfectant or cleanser compositions can also include dyes, colorants, odorants, bleaches, buffers, builders, enzyme "enhancing agents" (see, e.g., U.S. Patent application no. 20030096394) and stabilizers.

The addition of xylanases of the invention to conventional cleaning compositions does not create any special use limitation. In other words, any temperature and pH suitable for the detergent is also suitable for the compositions of the invention as long as the enzyme is active at or tolerant of the pH and/or temperature of the intended use. In addition, the xylanases of the invention can be used in a cleaning composition without detergents, again either alone or in combination with builders and stabilizers.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions.

In one aspect, the invention provides a method for washing an object comprising contacting the object with a polypeptide of the invention under conditions sufficient for washing. A xylanase of the invention may be included as a detergent, disinfectant or cleanser additive. The detergent, disinfectant or cleanser composition of the invention may, for example, be formulated as a hand or machine laundry detergent, disinfectant or cleanser composition comprising a polypeptide of the invention. A laundry additive suitable for pre-treatment of stained fabrics can comprise a polypeptide of the invention. A fabric softener composition can comprise a xylanase of the invention. Alternatively, a xylanase of the invention can be formulated as a detergent, disinfectant or cleanser composition for use in general household hard surface cleaning operations. In alternative aspects, detergent, disinfectant or cleanser additives and detergent, disinfectant or cleanser compositions of the invention may comprise one or more other enzymes such as a xylanase, a lipase, a protease, a cutinase, an esterase, another xylanase, a carbohydrase, a cellulase, a pectinase, a mannanase, an arabinase, a galactanase, a xylanase, an oxidase, e.g., a lactase, and/or a peroxidase (see also, above). The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, xylanase enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

When formulated as compositions suitable for use in a laundry machine washing method, the xylanases of the invention can comprise both a surfactant and a builder compound. They can additionally comprise one or more detergent components, e.g., organic polymeric compounds, bleaching agents, additional enzymes, suds suppressors, dispersants, lime-soap dispersants, soil suspension and anti-redeposition agents and corrosion inhibitors. Laundry compositions of the invention can also contain softening agents, as additional detergent components. Such compositions containing carbohydrase can provide fabric cleaning, stain removal, whiteness maintenance, softening, color appearance, dye transfer inhibition and sanitization when formulated as laundry detergent compositions.

The density of the laundry detergent, disinfectant or cleanser compositions of the invention can range from about 200 to 1500 g/liter, or, about 400 to 1200 g/liter, or, about 500 to 950 g/liter, or, 600 to 800 g/liter, of composition; this can be measured at about 20° C.

In one aspect, the "compact" form of laundry detergent, disinfectant or cleanser compositions of the invention is best reflected by density and, in terms of composition, by the amount of inorganic filler salt. Inorganic filler salts are conventional ingredients of detergent compositions in powder form. In conventional detergent compositions, the filler salts are present in substantial amounts, typically 17% to 35% by weight of the total composition. In one aspect of the compact compositions, the filler salt is present in amounts not exceeding 15% of the total composition, or, not exceeding 10%, or, not exceeding 5% by weight of the composition. The inorganic filler salts can be selected from the alkali and alkaline-earth-metal salts of sulphates and chlorides, e.g., sodium sulphate.

Liquid detergent compositions of the invention can also be in a "concentrated form." In one aspect, the liquid detergent, disinfectant or cleanser compositions can contain a lower amount of water, compared to conventional liquid detergents, disinfectants or cleansers. In alternative aspects, the water content of the concentrated liquid detergent is less than 40%, or, less than 30%, or, less than 20% by weight of the detergent, disinfectant or cleanser composition. Detergent, disinfectant or cleanser compounds of the invention can comprise formulations as described in WO 97/01629.

Xylanases of the invention can be useful in formulating various detergent, cleaning, disinfectant or cleanser compositions. A number of known compounds are suitable surfactants including nonionic, anionic, cationic, or zwitterionic detergents, can be used, e.g., as disclosed in U.S. Pat. Nos. 4,404,128; 4,261,868; 5,204,015. In addition, xylanases can be used, for example, in bar or liquid soap applications, dish care formulations, contact lens cleaning solutions or products, peptide hydrolysis, waste treatment, textile applications, as fusion-cleavage enzymes in protein production, and the like. Xylanases may provide enhanced performance in a detergent composition as compared to another detergent xylanase, that is, the enzyme group may increase cleaning of certain enzyme sensitive stains such as grass or blood, as determined by usual evaluation after a standard wash cycle. Xylanases can be formulated into known powdered and liquid detergents having pH between 6.5 and 12.0 at levels of about 0.01 to about 5% (for example, about 0.1% to 0.5%) by weight. These detergent cleaning compositions can also include other enzymes such as known xylanases, xylanases, proteases, amylases, cellulases, mannanases, lipases or endoglycosidases, redox enzymes such as catalases and laccases, as well as builders, stabilizers, fragrances and pigments.

In one aspect, the invention provides detergent, disinfectant or cleanser compositions having xylanase activity (a xylanase of the invention) for use with fruit, vegetables and/or mud and clay compounds (see, for example, U.S. Pat. No. 5,786,316).

In another aspect of the invention, the xylanases of the invention can also be used in any detergent, disinfectant or cleanser (cleaning solution) manufacturing process, wherein the xylanase is used as an antimicrobial or microbial repellent. Alternatively, the xylanases of the invention can be used in any cleansing or washing process, wherein the xylanase is used as an antimicrobial or microbial repellent. In another aspect of the invention, the xylanase of the invention can be included in any detergent or cleanser composition, wherein the xylanases of the invention act as an antimicrobial or microbial repellent in the composition.

Treating Foods and Food Processing

The xylanases of the invention have numerous applications in food processing industry. For example, in one aspect, the xylanases of the invention are used to improve the extraction of oil from oil-rich plant material, e.g., oil-rich seeds, for example, soybean oil from soybeans, olive oil from olives, rapeseed oil from rapeseed and/or sunflower oil from sunflower seeds.

The xylanases of the invention can be used for separation of components of plant cell materials. For example, xylanases of the invention can be used in the separation of xylan-rich material (e.g., plant cells) into components. In one aspect, xylanases of the invention can be used to separate xylan-rich or oil-rich crops into valuable protein and oil and hull fractions. The separation process may be performed by use of methods known in the art.

The xylanases of the invention can be used in the preparation of fruit or vegetable juices, syrups, extracts and the like to increase yield. The xylanases of the invention can be used in the enzymatic treatment (e.g., hydrolysis of xylan-comprising plant materials) of various plant cell wall-derived materials or waste materials, e.g. from cereals, grains, wine or juice production, or agricultural residues such as vegetable hulls, bean hulls, sugar beet pulp, olive pulp, potato pulp, and the like. The xylanases of the invention can be used to modify the consistency and appearance of processed fruit or vegetables. The xylanases of the invention can be used to treat plant material to facilitate processing of plant material, including foods, facilitate purification or extraction of plant components. The xylanases of the invention can be used to improve feed value, decrease the water binding capacity, improve the degradability in waste water plants and/or improve the conversion of plant material to ensilage, and the like.

In one aspect, xylanases of the invention are used in baking applications, e.g., cookies and crackers, to hydrolyze xylans such as arabinoxylans. In one aspect, xylanases of the invention are used to create non-sticky doughs that are not difficult to machine and to reduce biscuit size. Xylanases of the invention can be used to hydrolyze arabinoxylans to prevent rapid rehydration of the baked product resulting in loss of crispiness and reduced shelf-life. In one aspect, xylanases of the invention are used as additives in dough processing. In one aspect, xylanases of the invention are used in dough conditioning, wherein in one aspect the xylanases possess high activity over a temperature range of about 25-35° C. and at near neutral pH (7.0-7.5). In one aspect, dough conditioning enzymes can be inactivated at the extreme temperatures of baking (>500° F.). The enzymes of the invention can be used in conjunction with any dough processing protocol, e.g., as in U.S. Patent App. No. 20050281916.

In one aspect, xylanases of the invention are used as additives in dough processing to perform optimally under dough pH and temperature conditions. In one aspect, an enzyme of the invention is used for dough conditioning. In one aspect, a xylanase of the invention possesses high activity over a temperature range of 25-35° C. and at near neutral pH (7.0-7.5). In one aspect, the enzyme is inactivated at the extreme temperatures of baking, for example, >500° F.

In another aspect of the invention, the xylanases of the invention can also be used in any food or beverage treatment or food or beverage processing process, wherein the xylanase is used as an antimicrobial or microbial repellent. In another aspect of the invention, the xylanase of the invention can be included in any food or bevereage composition, wherein the xylanases of the invention act as an antimicrobial or microbial repellent in the composition.

Animal Feeds and Food or Feed or Food Additives (Supplements)

The invention provides methods for treating animal feeds and foods and food or feed additives (supplements) using xylanases of the invention, animals including mammals (e.g., humans), birds, fish and the like. The invention provides animal feeds, foods, and additives (supplements) comprising xylanases of the invention. In one aspect, treating animal feeds, foods and additives using xylanases of the invention can help in the availability of nutrients, e.g., starch, protein, and the like, in the animal feed or additive (supplements). By breaking down difficult to digest proteins or indirectly or directly unmasking starch (or other nutrients), the xylanase makes nutrients more accessible to other endogenous or exogenous enzymes. The xylanase can also simply cause the release of readily digestible and easily absorbed nutrients and sugars.

When added to animal feed, xylanases of the invention improve the in vivo break-down of plant cell wall material partly due to a reduction of the intestinal viscosity (see, e.g., Bedford et al., Proceedings of the 1st Symposium on Enzymes in Animal Nutrition, 1993, pp. 73-77), whereby a better utilization of the plant nutrients by the animal is achieved. Thus, by using xylanases of the invention in feeds the grow thrate and/or feed conversion ratio (i.e. the weight of ingested feed relative to weight gain) of the animal is improved.

The animal feed additive of the invention may be a granulated enzyme product which may readily be mixed with feed components. Alternatively, feed additives of the invention can form a component of a pre-mix. The granulated enzyme product of the invention may be coated or uncoated. The particle size of the enzyme granulates can be compatible with that of feed and pre-mix components. This provides a safe and convenient mean of incorporating enzymes into feeds. Alternatively, the animal feed additive of the invention may be a stabilized liquid composition. This may be an aqueous or oil-based slurry. See, e.g., U.S. Pat. No. 6,245,546.

Xylanases of the present invention, in the modification of animal feed or a food, can process the food or feed either in vitro (by modifying components of the feed or food) or in vivo. Xylanases can be added to animal feed or food compositions containing high amounts of xylans, e.g. feed or food containing plant material from cereals, grains and the like. When added to the feed or food the xylanase significantly improves the in vivo break-down of xylan-containing material, e.g., plant cell walls, whereby a better utilization of the plant nutrients by the animal (e.g., human) is achieved. In one aspect, the growth rate and/or feed conversion ratio (i.e. the weight of ingested feed relative to weight gain) of the animal is improved. For example a partially or indigestible xylan-comprising protein is fully or partially degraded by a xylanase of the invention, e.g. in combination with another enzyme, e.g., beta-galactosidase, to peptides and galactose and/or galactooligomers. These enzyme digestion products are more digestible by the animal. Thus, xylanases of the invention can contribute to the available energy of the feed or food. Also, by contributing to the degradation of xylan-comprising proteins, a xylanase of the invention can improve the digestibility and uptake of carbohydrate and non-carbohydrate feed or food constituents such as protein, fat and minerals.

In another aspect, xylanase of the invention can be supplied by expressing the enzymes directly in transgenic feed crops (as, e.g., transgenic plants, seeds and the like), such as grains, cereals, corn, soy bean, rape seed, lupin and the like. As discussed above, the invention provides transgenic plants, plant parts and plant cells comprising a nucleic acid sequence encoding a polypeptide of the invention. In one aspect, the nucleic acid is expressed such that the xylanase of the invention is produced in recoverable quantities. The xylanase can be recovered from any plant or plant part. Alternatively, the plant or plant part containing the recombinant polypeptide can be used as such for improving the quality of a food or feed, e.g., improving nutritional value, palatability, and rheological properties, or to destroy an antinutritive factor.

In one aspect, the invention provides methods for removing oligosaccharides from feed prior to consumption by an animal subject using a xylanase of the invention. In this process a feed is formed having an increased metabolizable energy value. In addition to xylanases of the invention, galactosidases, cellulases and combinations thereof can be used. In one aspect, the enzyme is added in an amount equal to between about 0.1% and 1% by weight of the feed material. In one aspect, the feed is a cereal, a wheat, a grain, a soybean (e.g., a ground soybean) material. See, e.g., U.S. Pat. No. 6,399,123.

In another aspect, the invention provides methods for utilizing xylanase as a nutritional supplement in the diets of animals by preparing a nutritional supplement containing a recombinant xylanase enzyme comprising at least thirty contiguous amino acids of a sequence of the invention, and administering the nutritional supplement to an animal to increase the utilization of xylan contained in food ingested by the animal.

In yet another aspect, the invention provides an edible pelletized enzyme delivery matrix and method of use for delivery of xylanase to an animal, for example as a nutritional supplement. The enzyme delivery matrix readily releases a xylanase enzyme, such as one having an amino acid sequence of the invention, or at least 30 contiguous amino acids thereof, in aqueous media, such as, for example, the digestive fluid of an animal. The invention enzyme delivery matrix is prepared from a granulate edible carrier selected from such components as grain germ that is spent of oil, hay, alfalfa, timothy, soy hull, sunflower seed meal, corn meal, soy meal, wheat midd, and the like, that readily disperse the recombinant enzyme contained therein into aqueous media. In use, the edible pelletized enzyme delivery matrix is administered to an animal to delivery of xylanase to the animal. Suitable grain-based substrates may comprise or be derived from any suitable edible grain, such as wheat, corn, soy, sorghum, alfalfa, barley, and the like. An exemplary grain-based substrate is a corn-based substrate. The substrate may be derived from any suitable part of the grain, but is preferably a grain germ approved for animal feed use, such as corn germ that is obtained in a wet or dry milling process. The grain germ preferably comprises spent germ, which is grain germ from which oil has been expelled, such as by pressing or hexane or other solvent extraction. Alternatively, the grain germ is expeller extracted, that is, the oil has been removed by pressing.

The enzyme delivery matrix of the invention is in the form of discrete plural particles, pellets or granules. By "granules" is meant particles that are compressed or compacted, such as by a pelletizing, extrusion, or similar compacting to remove water from the matrix. Such compression or compacting of the particles also promotes intraparticle cohesion of the particles. For example, the granules can be prepared by pelletizing the grain-based substrate in a pellet mill. The pellets prepared thereby are ground or crumbled to a granule size suitable for use as an adjuvant in animal feed. Since the matrix is itself approved for use in animal feed, it can be used as a diluent for delivery of enzymes in animal feed.

The enzyme delivery matrix can be in the form of granules having a granule size ranging from about 4 to about 400 mesh (USS); more preferably, about 8 to about 80 mesh; and most preferably about 14 to about 20 mesh. If the grain germ is spent via solvent extraction, use of a lubricity agent such as corn oil may be necessary in the pelletizer, but such a lubricity agent ordinarily is not necessary if the germ is expeller extracted. In other aspects of the invention, the matrix is prepared by other compacting or compressing processes such as, for example, by extrusion of the grain-based substrate through a die and grinding of the extrudate to a suitable granule size.

The enzyme delivery matrix may further include a polysaccharide component as a cohesiveness agent to enhance the cohesiveness of the matrix granules. The cohesiveness agent is believed to provide additional hydroxyl groups, which enhance the bonding between grain proteins within the matrix granule. It is further believed that the additional hydroxyl groups so function by enhancing the hydrogen bonding of proteins to starch and to other proteins. The cohesiveness agent may be present in any amount suitable to enhance the cohesiveness of the granules of the enzyme delivery matrix. Suitable cohesiveness agents include one or more of dextrins, maltodextrins, starches, such as corn starch, flours, cellulosics, hemicellulosics, and the like. For example, the percentage of grain germ and cohesiveness agent in the matrix (not including the enzyme) is 78% corn germ meal and 20% by weight of corn starch.

Because the enzyme-releasing matrix of the invention is made from biodegradable materials and contains moisture, the matrix may be subject to spoilage, such as by molding. To prevent or inhibit such molding, the matrix may include a mold inhibitor, such as a propionate salt, which may be present in any amount sufficient to inhibit the molding of the enzyme-releasing matrix, thus providing a delivery matrix in a stable formulation that does not require refrigeration.

The xylanase enzyme contained in the invention enzyme delivery matrix and methods is preferably a thermostable xylanase, as described herein, so as to resist inactivation of the xylanase during manufacture where elevated temperatures and/or steam may be employed to prepare the pelletized enzyme delivery matrix. During digestion of feed containing the invention enzyme delivery matrix, aqueous digestive fluids will cause release of the active enzyme.

Other types of thermostable enzymes and nutritional supplements that are thermostable can also be incorporated in the delivery matrix for release under any type of aqueous conditions.

A coating can be applied to the invention enzyme matrix particles for many different purposes, such as to add a flavor or nutrition supplement to animal feed, to delay release of animal feed supplements and enzymes in gastric conditions, and the like. Or, the coating may be applied to achieve a functional goal, for example, whenever it is desirable to slow release of the enzyme from the matrix particles or to control the conditions under which the enzyme will be released. The composition of the coating material can be such that it is selectively broken down by an agent to which it is susceptible (such as heat, acid or base, enzymes or other chemicals). Alternatively, two or more coatings susceptible to different such breakdown agents may be consecutively applied to the matrix particles.

The invention is also directed towards a process for preparing an enzyme-releasing matrix. In accordance with the invention, the process comprises providing discrete plural particles of a grain-based substrate in a particle size suitable for use as an enzyme-releasing matrix, wherein the particles comprise a xylanase enzyme encoded by an amino acid sequence of the invention or at least 30 consecutive amino acids thereof. Preferably, the process includes compacting or compressing the particles of enzyme-releasing matrix into granules, which can be accomplished by palletizing. The mold inhibitor and collusiveness agent, when used, can be added at any suitable time, and can be mixed with the grain-based substrate in the desired proportions prior to pelletizing of the grain-based substrate. Moisture content in the pellet mill feed can be in the ranges set forth above with respect to the moisture content in the finished product, and can be about 14-15%. In one aspect, moisture is added to the feedstock in the form of an aqueous preparation of the enzyme to bring the feedstock to this moisture content. The temperature in the pellet mill can be brought to about 82° C. with steam. The pellet mill may be operated under any conditions that impart sufficient work to the feedstock to provide pellets. The pelleting process itself is a cost-effective process for removing water from the enzyme containing composition.

In one aspect, the pellet mill is operated with a ⅛ in. by 2 inch die at 100 lb./min. pressure at 82° C. to provide pellets, which then are crumbled in a pellet mill crumbler to provide discrete plural particles having a particle size capable of passing through an 8 mesh screen but being retained on a 20 mesh screen.

The thermostable xylanases of the invention can be used in the pellets of the invention. They can have high optimum temperatures and high heat resistance such that an enzyme reaction at a temperature not hitherto carried out can be achieved. The gene encoding the xylanase according to the present invention (e.g. as set forth in any of the sequences in the invention) can be used in preparation of xylanases (e.g. using GSSM as described herein) having characteristics different from those of the xylanases of the inveution (in terms of optimum pH, optimum temperature, heat resistance, stability to solvents, specific activity, affinity to substrate, secretion ability, translation rate, transcription control and the like). Furthermore, a polynucleotide of the invention may be employed for screening of variant xylanases prepared by the methods described herein to determine those having a desired activity, such as improved or modified thermostability or thermotolerance. For example, U.S. Pat. No. 5,830,732, describes a screening assay for determining thermotolerance of a xylanase.

In another aspect of the invention, the xylanases of the invention can also be used in any animal feed, animal food or feed additive production process, wherein the xylanase is used as an antimicrobial or microbial repellent. In another aspect of the invention, the xylanase of the invention can be included in any animal feed, animal food or feed additive composition, wherein the xylanases of the invention act as an antimicrobial or microbial repellent in the composition.

Waste Treatment

The xylanases of the invention can be used in a variety of other industrial applications, e.g., in waste treatment. For example, in one aspect, the invention provides a solid waste digestion process using xylanases of the invention. The methods can comprise reducing the mass and volume of substantially untreated solid waste. Solid waste can be treated with an enzymatic digestive process in the presence of an enzymatic solution (including xylanases of the invention) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796.

In another aspect of the invention, the xylanases of the invention can also be used in any waste treatment process, wherein the xylanase is used as an antimicrobial or microbial repellent. In another aspect of the invention, the xylanase of the invention can be included in any waste treatment composition, wherein the xylanases of the invention act as an antimicrobial or microbial repellent in the composition.

Oral Care Products

The invention provides oral care product comprising xylanases of the invention, including the enzyme mixtures or "cocktails" of the invention. Exemplary oral care products include toothpastes, dental creams, gels or tooth powders, odontics, mouth washes, pre- or post brushing rinse formulations, chewing gums, lozenges, or candy. See, e.g., U.S. Pat. No. 6,264,925.

In another aspect of the invention, the xylanases of the invention, including the enzyme mixtures or "cocktails" of the invention, can also be used in any oral care manufacturing process, wherein the xylanase is used as an antimicrobial or microbial repellent. In another aspect of the invention, the xylanase of the invention, including the enzyme mixtures or "cocktails" of the invention, can be included in any oral care composition, wherein the xylanases of the invention act as an antimicrobial or microbial repellent in the composition.

Brewing and Fermenting

The invention provides methods of brewing (e.g., fermenting) beer comprising xylanases of the invention, including the enzyme mixtures or "cocktails" of the invention. In one exemplary process, starch-containing raw materials are disintegrated and processed to form a malt. A xylanase of the invention is used at any point in the fermentation process. For example, xylanases of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15 to 25° C. for 3 to 6 days when enzyme synthesis is stimulated under the control of gibberellins. In one aspect, xylanases of the invention are added at this (or any other) stage of the process. Xylanases of the invention can be used in any beer or alcoholic beverage producing process, as described, e.g., in U.S. Pat. Nos. 5,762,991; 5,536,650; 5,405,624; 5,021,246; 4,788,066.

In one aspect, an enzyme of the invention is used to improve filterability and wort viscosity and to obtain a more complete hydrolysis of endosperm components. Use of an enzyme of the invention would also increase extract yield. The process of brewing involves germination of the barley grain (malting) followed by the extraction and the breakdown of the stored carbohydrates to yield simple sugars that are used by yeast for alcoholic fermentation. Efficient breakdown of the carbohydrate reserves present in the barley endosperm and brewing adjuncts requires the activity of several different enzymes.

In one aspect, an enzyme of the invention has activity in slightly acidic pH (e.g., 5.5-6.0) in, e.g., the 40° C. to 70° C. temperature range; and, in one aspect, with inactivation at 95° C. Activity under such conditions would be optimal, but are not an essential requirement for efficacy. In one aspect, an enzyme of the invention has activity between 40-75° C., and pH 5.5-6.0; stable at 70° for at least 50 minutes, and, in one aspect, is inactivated at 96-100° C. Enzymes of the invention can be used with other enzymes, e.g., beta-1,4-endoglucanases and amylases.

In another aspect of the invention, the xylanases of the invention, including the enzyme mixtures or "cocktails" of the invention, can also be used in any brewing or fermentation process, wherein the xylanase is used as an antimicrobial or microbial repellent. In another aspect of the invention, the xylanase of the invention can be included in any brewed or fermented composition, wherein the xylanases of the invention act as an antimicrobial or microbial repellent in the composition.

Biomass Conversion and Biofuel Production

The invention provides methods and processes for biomass conversion, e.g., to a biofuel, such as bioethanol, biomethanol, biopropanol and/or biobutanol and the like, using enzymes of the invention, including the enzyme mixtures or "cocktails" of the invention. Thus, the invention provides fuels, e.g., biofuels, such as bioethanols, comprising a polypeptide of the invention, including the enzyme mixtures or "cocktails" of the invention, or a polypeptide encoded by a nucleic acid of the invention. In alternative aspects, the fuel is derived from a plant material, which optionally comprises potatoes, soybean (rapeseed), barley, rye, corn, oats, wheat, beets or sugar cane, and optionally the fuel comprises a bioethanol or a gasoline-ethanol mix.

The invention provides methods for making a fuel comprising contacting a composition comprising a xylan, hemicellulose, cellulose or a fermentable sugar with a polypeptide of the invention, or a polypeptide encoded by a nucleic acid of the invention, or any one of the mixtures or "cocktails" or products of manufacture of the invention. In alternative embodiments, the composition comprising a xylan, hemicellulose, a cellulose or a fermentable sugar comprises a plant, plant product or plant derivative, and the plant or plant product can comprise cane sugar plants or plant products, beets or sugarbeets, wheat, corn, soybeans, potato, rice or barley. In alternative embodiments, the polypeptide has activity comprising catalyzing hydrolysis of internal β-1,4-xylosidic linkages or endo-β-1,4-glucanase linkages; and/or degrading a linear polysaccharide beta-1,4-xylan into xylose. In one aspect, the fuel comprises a bioethanol or a gasoline-ethanol mix, or a biopropanol or a gasoline-propanol mix, or a biobutanol or a gasoline-butanol mix, or a biomethanol or a gasoline-methanol mix, or any combination thereof.

The invention provides methods for making bioethanol, biobutanol, biomethanol and/or a biopropanol comprising contacting a composition comprising a xylan, hemi-cellulose, cellulose or a fermentable sugar with a polypeptide of the invention, or a polypeptide encoded by a nucleic acid of the invention, or any one of the mixtures or "cocktails" or products of manufacture of the invention. In alternative embodiments, the composition comprising a cellulose or a fermentable sugar comprises a plant, plant product or plant derivative, and the plant or plant product can comprise cane sugar plants or plant products, beets or sugarbeets, wheat, corn, soybeans, potato, rice or barley, and the polypeptide can have activity comprising cellulase, glucanase, cellobiohydrolase, beta-glucosidase, xylanase, mannanse, β-xylosidase, and/or arabinofuranosidase activity.

The invention provides enzyme ensembles, or "cocktails", for depolymerization of cellulosic and hemicellulosic polymers, xylans, and polysaccharides to metabolizeable carbon moieties comprising a polypeptide of the invention, or a polypeptide encoded by a nucleic acid of the invention. In alternative embodiments, the polypeptide has activity comprising catalyzing hydrolysis of internal α-1,4-xylosidic linkages or endo-β-1,4-glucanase linkages; and/or degrading a linear polysaccharide beta-1,4-xylan into xylose. The enzyme ensembles, or "cocktails", of the invention can be in the form of a composition (e.g., a formulation, liquid or solid), e.g., as a product of manufacture. The invention further enzymes, enzyme ensembles, or "cocktails" for depolymerization of cellulosic and hemicellulosic polymers, xylans and polysaccharides, to simpler moieties, such as sugars, which are then microbially fermented to generate products such as succinic acid, lactic acid, or acetic acid.

The invention provides compositions (including products of manufacture, enzyme ensembles, or "cocktails") comprising a mixture (or "cocktail") of hemicellulose- and cellulose-hydrolyzing enzymes, wherein the xylan-hydrolyzing enzymes comprise at least one of each of a xylanase of the invention and at least one, several or all of a cellulase, glucanase, a cellobiohydrolase and/or a β-glucosidase. In alternative embodiments, the xylan-hydrolyzing and/or hemicellulose-hydrolyzing mixtures of the invention comprise at least one of each of a xylanase of the invention and at least one or both of a β-xylosidase and/or an arabinofuranosidase.

The invention provides compositions (including products of manufacture, enzyme ensembles, or "cocktails") comprising a mixture (or "cocktail") of xylan-hydrolyzing, hemicellulose- and/or cellulose-hydrolyzing enzymes comprising at least one, several or all of a cellulase, a glucanase, a cellobiohydrolase and/or an arabinofuranosidase, and a xylanase of this invention.

The invention provides compositions (including products of manufacture, enzyme ensembles, or "cocktails") comprising mixture (or "cocktail") of xylan-hydrolyzing, hemicellulose- and/or cellulose-hydrolyzing enzymes comprising at least one, several or all of a cellulase, a glucanase; a cellobiohydrolase; an arabinofuranosidase; a xylanase; a β-glucosidose; a β-xylosidase; and at least one enzyme of the invention.

The invention provides compositions (including products of manufacture, enzyme ensembles, or "cocktails") comprising mixture (or "cocktail") of enzymes comprising, in addition to at least one enzyme of the invention: (1) a glucanase which cleaves internal β-1,4 linkages resulting in shorter glucooligosaccharides, (2) a cellobiohydrolase which acts in an "exo" manner processively releasing cellobiose units (β-1,4 glucose-glucose disaccharide), and/or (3) a β-glucosidase for releasing glucose monomer from short cellooligosaccharides (e.g. cellobiose).

Biomass Conversion and Production of Clean Bio Fuels

The invention provides compositions and processes using enzymes of this invention, including mixtures, or "cocktails" of enzymes of the invention, for the conversion of a biomass, or any organic material, e.g., any xylan-comprising or lignocellulosic material (e.g., any composition comprising a xylan, cellulose, hemicellulose and/or lignin), to a fuel, such as a biofuel (e.g., bioethanol, biobutanol, biomethanol and/or a biopropanol), including biodiesels, in addition to feeds, foods, food or feed supplements (additives), pharmaceuticals and chemicals. Thus, the compositions and methods of the invention provide effective and sustainable alternatives or adjuncts to use of petroleum-based products, e.g., as a mixture of a biofuel (e.g., bioethanol, biobutanol, biomethanol and/or a biopropanol) and gasoline and/or diesel fuel.

The invention provides cells and/or organisms expressing enzymes of the invention (e.g., wherein the cells or organisms comprise as heterologous nucleic acids a sequence of this invention) for participation in chemical cycles involving natural biomass (e.g., plant) conversion. In one aspect, enzymes and methods for the conversion are used in enzyme ensembles (or "cocktails") for the efficient depolymerization of xylan-comprising compositions, or xylan, cellulosic and hemicellulosic polymers, to metabolizeable carbon moieties. The invention provides methods for discovering and implementing the most effective of enzymes to enable these important new "biomass conversion" and alternative energy industrial processes.

The invention provides methods, enzymes and mixtures of enzymes or "cocktails" of the invention, for processing a material, e.g. a biomass material, comprising a cellooligsaccharide, an arabinoxylan oligomer, a lignin, a lignocellulose, a xylan, a glucan, a cellulose and/or a fermentable sugar comprising contacting the composition with a polypeptide of the invention, or a polypeptide encoded by a nucleic acid of the invention, wherein optionally the material is derived from an agricultural crop (e.g., wheat, barley, potatoes, switchgrass, poplar wood), is a byproduct of a food or a feed production, is a lignocellulosic waste product, or is a plant residue or a waste paper or waste paper product, and optionally the plant residue comprise stems, leaves, hulls, husks, corn or corn cobs, corn stover, corn fiber, hay, straw (e.g. rice straw or wheat straw), sugarcane bagasse, sugar beet pulp, citrus pulp, and citrus peels, wood, wood thinnings, wood chips, wood pulp, pulp waste, wood waste, wood shavings and sawdust, construction and/or demolition wastes and debris (e.g. wood, wood shavings and sawdust), and optionally the paper waste comprises discarded or used photocopy paper, computer printer paper, notebook paper, notepad paper, typewriter paper, newspapers, magazines, cardboard and paper-based packaging materials, and recycled paper materials. In addition, urban wastes, e.g. the paper fraction of municipal solid waste, municipal wood waste, and municipal green waste, along with other materials containing sugar, starch, and/or cellulose can be used. Optionally the processing of the material, e.g. the biomass material, generates a bioalcohol, e.g., a bioethanol, biomethanol, biobutanol or biopropanol.

Alternatively, the polypeptide of the invention may be expressed in the biomass plant material or feedstock itself.

The methods of the invention also include taking the converted biomass (e.g., lignocellulosic) material (processed by enzymes of the invention) and making it into a fuel (e.g. a biofuel such as a bioethanol, biobutanol, biomethanol, a biopropanol, or a biodiesel) by fermentation and/or by chemical synthesis. In one aspect, the produced sugars are fermented and/or the non-fermentable products are gasified.

The methods of the invention also include converting algae, virgin vegetable oils, waste vegetable oils, animal fats and greases (e.g. tallow, lard, and yellow grease), or sewage, using enzymes of the invention, and making it into a fuel (e.g. a bioalcohol, e.g., a bioethanol, biomethanol, biobutanol or biopropanol, or biodiesel) by fermentation and/or by chemical synthesis or conversion.

The enzymes of the invention (including, for example, organisms, such as microorganisms, e.g., fungi, yeast or bacteria, and plants and plant cells and plant parts, e.g., seeds, making and in some aspects secreting recombinant enzymes of the invention) can be used in or included/integrated at any stage of any organic matter/biomass conversion process, e.g., at any one step, several steps, or included in all of the steps, or all of the following methods of biomass conversion processes, or all of these biofuel alternatives:

Direct combustion: the burning of material by direct heat and is the simplest biomass technology; can be very economical if a biomass source is nearby.

1 Pyrolysis: is the thermal degradation of biomass by heat in the absence of oxygen. In one aspect, biomass is heated to a temperature between about 800 and 1400 degrees Fahrenheit, but no oxygen is introduced to support combustion resulting in the creation of gas, fuel oil and charcoal.

2 Gasification: biomass can be used to produce methane through heating or anaerobic digestion. Syngas, a mixture of carbon monoxide and hydrogen, can be derived from biomass.

Landfill Gas: is generated by the decay (anaerobic digestion) of buried garbage in landfills. When the organic waste decomposes, it generates gas consisting of approximately 50% methane, the major component of natural gas.

Anaerobic digestion: converts organic matter to a mixture of methane, the major component of natural gas, and carbon dioxide. In one aspect, biomass such as waterwaste (sewage), manure, or food processing waste, is mixed with water and fed into a digester tank without air.

Fermentation

Alcohol Fermentation: fuel alcohol is produced by converting cellulosic mass and/or starch to sugar, fermenting the sugar to alcohol, then separating the alcohol water mixture by distillation. Feedstocks such as dedicated crops (e.g., wheat, barley, potatoes, switchgrass, poplar wood), agricultural residues and wastes (e.g. rice straw, corn stover, wheat straw, sugarcane bagasse, rice hulls, corn fiber, sugar beet pulp, citrus pulp, and citrus peels), forestry wastes (e.g. hardwood and softwood thinnings, hardwood and softwood residues from timber operations, wood shavings, and sawdust), urban wastes (e.g. paper fraction of municipal solid waste, municipal wood waste, municipal green waste), wood wastes (e.g. saw mill waste, pulp mill waste, construction waste, demolition waste, wood shavings, and sawdust), and waste paper or other materials containing sugar, starch, and/or cellulose can be converted to sugars and then to alcohol by fermentation with yeast. Alternatively, materials containing sugars can be converted directly to alcohol by fermentation.

Transesterification: An exemplary reaction for converting oil to biodiesel is called transesterification. The transesterification process reacts an alcohol (like methanol) with the triglyceride oils contained in vegetable oils, animal fats, or recycled greases, forming fatty acid alkyl esters (biodiesel) and glycerin. The reaction requires heat and a strong base catalyst, such as sodium hydroxide or potassium hydroxide.

Biodiesel: Biodiesel is a mixture of fatty acid alkyl esters made from vegetable oils, animal fats or recycled greases. Biodiesel can be used as a fuel for vehicles in its pure form, but it is usually used as a petroleum diesel additive to reduce levels of particulates, carbon monoxide, hydrocarbons and air toxics from diesel-powered vehicles.

Hydrolysis: includes hydrolysis of a compound, e.g., a biomass, such as a lignocellulosic material, catalyzed using an enzyme of the instant invention.

Cogeneration: is the simultaneous production of more than one form of energy using a single fuel and facility. In one aspect, biomass cogeneration has more potential growth than biomass generation alone because cogeneration produces both heat and electricity.

In one aspect, the polypeptides of the invention have sufficient enzymatic activity, e.g. a xylanase, a mannanase and/or a glucanase activity, for, or can be used with other enzymes in a process for, generating a biodiesel or a fuel, (e.g. a bioalcohol, e.g., a bioethanol, biomethanol, biobutanol or biopropanol, or biodiesel) from an organic material, e.g., a biomass, such as compositions derived from plants and animals, including any agricultural crop or other renewable feedstock, an agricultural residue or an animal waste, the organic components of municipal and industrial wastes, or construction or demolition wastes or debris, or microorganisms such as algae or yeast.

In one aspect, polypeptides of the invention are used in processes for converting an organic material, e.g., a biomass, such as a lignocellulosic biomass, to a biofuel, such as a bioethanol, biobutanol, biomethanol, a biopropanol, or otherwise are used in processes for hydrolyzing or digesting biomaterials such that they can be used as a biofuel (including biodiesel or bioethanol, biobutanol, biomethanol or biopropanol), or for making it easier for the biomass to be processed into a fuel. In an alternative aspect, polypeptides of the invention are used in processes for a transesterification process reacting an alcohol (like methanol, butanol, propanol, ethanol) with a triglyceride oil contained in a vegetable oil, animal fat or recycled greases, forming fatty acid alkyl esters (biodiesel) and glycerin. In one aspect, biodiesel is made from soybean oil or recycled cooking oils. Animal's fats, other vegetable oils, and other recycled oils can also be used to produce biodiesel, depending on their costs and availability. In another aspect, blends of all kinds of fats and oils are used to produce a biodiesel fuel of the invention.

Enzymes of the invention can also be used in glycerin refining. The glycerin by-product contains unreacted catalyst and soaps that are neutralized with an acid. Water and alcohol are removed to produce 50% to 80% crude glycerin. The remaining contaminants include unreacted fats and oils, which can be processes using the polypeptides of the invention. In a large biodiesel plants of the invention, the glycerin can be further purified, e.g., to 99% or higher purity, for the pharmaceutical and cosmetic industries.

Fuels (including bioalcohols such as bioethanols, biomethanols, biobutanols or biopropanols, or biodiesels) made using the polypeptides of the invention, including the mixture of enzymes or "cocktails" of the invention, can be used with fuel oxygenates to improve combustion characteristics. Adding oxygen results in more complete combustion, which reduces carbon monoxide emissions. This is another environmental benefit of replacing petroleum fuels with biofuels (e.g., a fuel of the invention). A biofuel made using the compositions and/or methods of this invention can be blended with gasoline to form an E10 blend (about 5% to 10% ethanol and about 90% to 95% gasoline), but it can be used in higher concentrations such as E85 or in its pure form. A biofuel made using the compositions and/or methods of this invention can be blended with petroleum diesel to form a B20 blend (20% biodiesel and 80% petroleum diesel), although other blend levels can be used up to B100 (pure biodiesel).

In one aspect, the polypeptides of this invention are used in processes for converting organic material, e.g., a biomass, such as a lignocellulosic biomass, to methanol, butanol, propanol and/or ethanol. The invention also provides processes for making ethanol ("bioethanol") methanol, butanol and/or propanol from compositions comprising organic material, e.g., a biomass, such as a lignocellulosic biomass. The organic material, e.g., a biomass, such as a lignocellulose biomass material, can be obtained from agricultural crops, as a byproduct of food or feed production, or as biomass waste products, such as plant residues and waste paper or construction and/or demolition wastes or debris. Examples of suitable plant residues for treatment with polypeptides of the invention include grains, seeds, stems, leaves, hulls, husks, corn cobs, corn stover, straw, grasses (e.g., Indian grass, such as Sorghastrum nutans; or, switch grass, e.g., Panicum species, such as Panicum virgatum), and the like, as well as wood, wood chips, wood pulp, and sawdust. Examples of paper waste suitable for treatment with polypeptides of the invention include discard photocopy paper, computer printer paper, notebook paper, notepad paper, typewriter paper, and the like, as well as newspapers, magazines, cardboard, and paper-based packaging materials. Examples of construction and demolition wastes and debris include wood, wood scraps, wood shavings and sawdust.

In one aspect, the enzymes and methods of the invention can be used in conjunction with more "traditional" means of making methanol, butanol, propanol and/or ethanol from biomass, e.g., as methods comprising hydrolyzing biomass (e.g., lignocellulosic materials) by subjecting dried biomass material in a reactor to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660,506; 6,423,145.

Another exemplary method that incorporated use of enzymes of the invention comprises hydrolyzing biomass (e.g., lignocellulosic materials) containing xylan, hemicellulose, cellulose and/or lignin by subjecting the material to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose. See, e.g., U.S. Pat. No. 5,536,325. Enzymes of the invention can be added at any stage of this exemplary process.

Another exemplary method that incorporated use of enzymes of the invention comprises processing a biomass material by one or more stages of dilute acid hydrolysis with about 0.4% to 2% strong acid; and treating an unreacted solid lignocellulosic component of the acid hydrolyzed biomass material by alkaline delignification to produce precursors for biodegradable thermoplastics and derivatives. See, e.g., U.S. Pat. No. 6,409,841. Enzymes of the invention can be added at any stage of this exemplary process.

Another exemplary method that incorporated use of enzymes of the invention comprises prehydrolyzing biomass (e.g., lignocellulosic materials) in a prehydrolysis reactor; adding an acidic liquid to the solid lignocellulosic material to make a mixture; heating the mixture to reaction temperature; maintaining reaction temperature for time sufficient to fractionate the lignocellulosic material into a solubilized portion containing at least about 20% of the lignin from the lignocellulosic material and a solid fraction containing cellulose; removing a solubilized portion from the solid fraction while at or near reaction temperature wherein the cellulose in the solid fraction is rendered more amenable to enzymatic digestion; and recovering a solubilized portion. See, e.g., U.S. Pat. No. 5,705,369. Enzymes of the invention can be added at any stage of this exemplary process.

The invention provides methods for making motor fuel compositions (e.g., for spark ignition motors) based on liquid hydrocarbons blended with a fuel grade alcohol made by using an enzyme or a method of the invention. In one aspect, the fuels made by use of an enzyme of the invention comprise, e.g., coal gas liquid- or natural gas liquid-ethanol blends. In one aspect, a co-solvent is biomass-derived 2-methyltetrahydrofuran (MTHF). See, e.g., U.S. Pat. No. 6,712,866.

In one aspect, methods of the invention for the enzymatic degradation of biomass (e.g., lignocellulosic materials), e.g., for production of a biofuel, e.g., an ethanol, from a biomass or any organic material, can also comprise use of ultrasonic treatment of a biomass material; see, e.g., U.S. Pat. No. 6,333,181.

In another aspect, methods of the invention for producing a biofuel, e.g., an ethanol (a bioethanol) from a biomass (e.g., a cellulosic) substrate comprise providing a reaction mixture in the form of a slurry comprising biomass (e.g., a cellulosic) substrate, an enzyme of this invention and a fermentation agent (e.g., within a reaction vessel, such as a semi-continuously solids-fed bioreactor), and the reaction mixture is reacted under conditions sufficient to initiate and maintain a fermentation reaction (as described, e.g., in U.S. Pat. App. No. 20060014260). In one aspect, experiment or theoretical calculations can determine an optimum feeding frequency. In one aspect, additional quantities of the biomass (e.g., a cellulosic) substrate and the enzyme are provided into the reaction vessel at an interval(s) according to the optimized feeding frequency.

One exemplary process for making a biofuels and biodiesels of the invention is described in U.S. Pat. App. Pub. Nos. 20050069998; 20020164730; and in one aspect comprises stages of grinding the biomass (e.g., lignocellulosic material) (e.g., to a size of 15-30 mm), subjecting the product obtained to steam explosion pre-treatment (e.g., at a temperature of 190-230° C.) for between 1 and 10 minutes in a reactor; collecting the pre-treated material in a cyclone or related product of manufacture; and separating the liquid and solid fractions by filtration in a filter press, introducing the solid fraction in a fermentation deposit and adding one or more enzymes of the invention, and in one aspect, another enzyme is also added, e.g., a cellulase and/or beta-glucosidase enzyme (e.g., dissolved in citrate buffer pH 4.8).

Another exemplary process for making a biofuels and biodiesels of the invention comprising methanol, butanol, propanol and/or ethanol using enzymes of the invention comprises pretreating a starting material comprising a biomass (e.g., a lignocellulosic) feedstock comprising at least a xylan, a hemicellulose and/or a cellulose. In one aspect, the starting material comprises potatoes, soybean (rapeseed), barley, rye, corn, oats, wheat, beets or sugar cane or a component or waste or food or feed production byproduct. The starting material ("feedstock") is reacted at conditions which disrupt the plant's fiber structure to effect at least a partial hydrolysis of the biomass (e.g., hemicellulose and/or cellulose). Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent. This generates a feedstock with increased accessibility to being digested by an enzyme, e.g., a cellulase enzyme of the invention. U.S. Pat. No. 6,090,595.

Exemplary conditions for hydrolysis of biomass (e.g., a lignocellulosic material) by an enzyme of this invention include reactions at temperatures between about 30° C. and 48° C., and/or a pH between about 4.0 and 6.0. Other exemplary conditions include a temperature between about 30° C. and 60° C. and a pH between about 4.0 and 8.0.

Biofuels and Biologically Produced Alcohols

The invention provides biofuels and synthetic fuels, including liquids and gases (e.g., syngas) and biologically produced alcohols, and methods for making them, using the compositions (e.g., enzyme and nucleic acids, and transgenic plants, animal, seeds and microorganisms) and methods of the invention. The invention provides biofuels and biologically produced alcohols comprising enzymes, nucleic acids, transgenic plants, animals (e.g., microorganisms, such as bacteria or yeast) and/or seeds of the invention. In one aspect, these biofuels and biologically produced alcohols are produced from a biomass.

The invention provides biologically produced alcohols, such as ethanol, methanol, propanol and butanol produced by methods of the invention, which include the action of microbes and enzymes of the invention through fermentation (hydrolysis) to result in an alcohol fuel.

Biofuels as a Liquid or a Gas Gasoline

The invention provides biofuels and synthetic fuels in the form of a gas, or gasoline, e.g., a syngas. In one aspect, methods of the invention comprising use of enzymes of the invention for chemical cycles for natural biomass conversion, e.g., for the hydrolysis of a biomass to make a biofuel, e.g., a bioethanol, biopropanol, bio-butanol or a biomethanol, or a synthetic fuel, in the form of a liquid or as a gas, such as a "syngas".

For example, invention provides methods for making biofuel gases and synthetic gas fuels ("syngas") comprising a bioethanol, biopropanol, bio-butanol and/or a biomethanol made using a polypeptide of the invention, or made using a method of the invention; and in one aspect this biofuel gas of the invention is mixed with a natural gas (can also be produced from biomass), e.g., a hydrogen or a hydrocarbon-based gas fuel.

In one aspect, the invention provides methods for processing biomass to a synthetic fuel, e.g., a syngas, such as a syngas produced from a biomass by gasification. In one aspect, the invention provides methods for making an ethanol, propanol, butanol and/or methanol gas from a sugar cane, e.g., a bagasse. In one aspect, this fuel, or gas, is used as motor fuel, e.g., an automotive, truck, airplane, boat, small engine, etc. fuel. In one aspect, the invention provides methods for making an ethanol, propanol, butanol and/or methanol from a plant, e.g., corn, or a plant product, e.g., hay or straw (e.g., a rice straw or a wheat straw, or any the dry stalk of any cereal plant), or an agricultural waste product. Cellulosic ethanol, propanol, butanol and/or methanol can be manufactured from a plant, e.g., corn, or plant product, e.g., hay or straw, or an agricultural waste product (e.g., as processed by Iogen Corporation of Ontario, Canada).

In one aspect, the ethanol, propanol, butanol and/or methanol made using a method of composition of the invention can be used as a fuel (e.g., a gasoline) additive (e.g., an oxygenator) or in a direct use as a fuel. For example, a ethanol, propanol, butanol and/or methanol, including a fuel, made by a method of the invention can be mixed with ethyl tertiary butyl ether (ETBE), or an ETBE mixture such as ETBE containing 47% ethanol as a biofuel, or with MTBE (methyl tertiary-butyl ether). In another aspect, a ethanol, propanol, butanol and/or methanol, including a fuel, made by a method of the invention can be mixed with:

| IUPAC name | Common name |
|---|---|
| but-1-ene | α-butylene |
| cis-but-2-ene | cis-β-butylene |
| trans-but-2-ene | trans-β-butylene |
| 2-methylpropene | isobutylene |

A butanol and/or ethanol made by a method of the invention (e.g., using an enzyme of the invention) can be further processed using "A.B.E." (Acetone, Butanol, Ethanol) fermentation; in one aspect, butanol being the only liquid product. In one aspect, this butanol and/or ethanol is burned "straight" in existing gasoline engines (without modification to the engine or car), produces more energy and is less corrosive and less water soluble than ethanol, and can be distributed via existing infrastructures.

The invention also provides mixed alcohols wherein one, several or all of the alcohols are made by processes comprising at least one method of the invention (e.g., using an enzyme of the invention), e.g., comprising a mixture of ethanol, propanol, butanol, pentanol, hexanol, and heptanol, such as ECALENE™ (Power Energy Fuels, Inc., Lakewood, Colo.), e.g.:

Exemplary Fuel of the Invention

| Component | Weight % |
|---|---|
| Methanol | 0% |
| Ethanol | 75% |
| Propanol | 9% |
| Butanol | 7% |
| Pentanol | 5% |
| Hexanol & Higher | 4% |

In one aspect, one, several or all of these alcohols are made by a process of the invention using an enzyme of the invention, and the process can further comprise a biomass-to-liquid technology, e.g., a gasification process to produce syngas followed by catalytic synthesis, or by a bioconversion of biomass to a mixed alcohol fuel.

The invention also provides processes comprising use of an enzyme of the invention incorporating (or, incorporated into) "gas to liquid", or GTL; or "coal to liquid", or CTL; or "biomass to liquid" or BTL; or "oilsands to liquid", or OTL, processes; and in one aspect these processes of the invention are used to make synthetic fuels. In one aspect, one of these processes of the invention comprises making a biofuel (e.g., a synfuel) out of a biomass using, e.g., the so-called "Fischer Tropsch" process (a catalyzed chemical reaction in which carbon monoxide and hydrogen are converted into liquid hydrocarbons of various forms; typical catalysts used are based on iron and cobalt; the principal purpose of this process is to produce a synthetic petroleum substitute for use as synthetic lubrication oil or as synthetic fuel). In one aspect, this synthetic biofuel of the invention can contain oxygen and can be used as additive in high quality diesel and petrol.

In alternative aspects, the processes of the invention use various pretreatments, which can be grouped into three categories: physical, chemical, and multiple (physical+chemical). Any chemicals can be used as a pretreatment agent, e.g., acids, alkalis, gases, cellulose solvents, alcohols, oxidizing agents and reducing agents. Among these chemicals, alkali is the most popular pretreatment agent because it is relatively inexpensive and results in less cellulose degradation. The common alkalis sodium hydroxide and lime also can be used as pretreatment agents. Although sodium hydroxide increases biomass digestibility significantly, it is difficult to recycle, is relatively expensive, and is dangerous to handle. In contrast, lime has many advantages: it is safe and very inexpensive, and can be recovered by carbonating wash water with carbon dioxide.

In one aspect, the invention provides a multi-enzyme system (including at least one enzyme of this invention) that can hydrolyze polysaccharides in a biomass, e.g. sugarcane, e.g., bagasse, a component of sugarcane processed in sugar mills. In one aspect, the biomass is processed by an enzyme of the invention made by an organism (e.g., transgenic animal, plants, transformed microorganism) and/or byproduct (e.g., harvested plant, fruit, seed) expressing an enzyme of the invention. In one aspect, the enzyme is a recombinant enzyme made by the plant or biomass which is to be processed to a fuel, e.g., the invention provides a transgenic sugarcane bagasse comprising an enzyme of the invention. In one aspect, these compositions and products used in methods of the invention comprising chemical cycles for natural biomass conversion, e.g., for the hydrolysis of a biomass to make a biofuel, e.g., bioethanol, biopropanol, bio-butanol, biomethanol, a synthetic fuel in the form of a liquid or a gas, such as a "syngas".

In one aspect, the invention provides a biofuel, e.g., a biogas, produced by the process of anaerobic digestion of organic material by anaerobes, wherein the process comprises use of an enzyme of the invention or a method of the invention. This biofuel, e.g., a biogas, can be produced either from biodegradable waste materials or by the use of energy crops fed into anaerobic digesters to supplement gas yields. The solid output, digestate, can also be used as a biofuel.

In one aspect, the invention provides a biofuel, e.g., a biogas, comprising a methane, wherein the process comprises use of an enzyme of the invention or a method of the invention. This biofuel, e.g., a biogas, can be recovered in industrial anaerobic digesters and mechanical biological treatment systems. Landfill gas can be further processed using an enzyme of this invention or a process of this invention; before processing landfill gas can be a less clean form of biogas produced in landfills through naturally occurring anaerobic digestion. Paradoxically if landfill gas is allowed to escape into the atmosphere it is a potent greenhouse gas.

The invention provides methods for making biologically produced oils and gases from various wastes, wherein the process comprises use of an enzyme of the invention or a method of the invention. In one aspect, these methods comprise thermal depolymerization of waste to extract methane and other oils similar to petroleum; or, e.g., a bioreactor system that utilizes nontoxic photosynthetic algae to take in smokestacks flue gases and produce biofuels such as biodiesel, biogas and a dry fuel comparable to coal, e.g., as designed by GreenFuel Technologies Corporation, of Cambridge, Mass.

The invention provides methods for making biologically produced oils, including crude oils, and gases that can be used in diesel engines, wherein the process comprises use of an enzyme of the invention or a method of the invention. In one aspect, these methods can refine petroleum, e.g., crude oils, into kerosene, pertroleum, diesel and other fractions.

The invention provides methods (using an enzyme of the invention or a method of the invention) for making biologically produced oils from:

Straight vegetable oil (SVO).

Waste vegetable oil (WVO)—waste cooking oils and greases produced in quantity mostly by commercial kitchens.

Biodiesel obtained from transesterification of animal fats and vegetable oil, directly usable in petroleum diesel engines.

Biologically derived crude oil, together with biogas and carbon solids via the thermal depolymerization of complex organic materials including non oil based materials; for example, waste products such as old tires, offal, wood and plastic.

Pyrolysis oil; which may be produced out of biomass, wood waste etc. using heat only in the flash pyrolysis process (the oil may have to be treated before using in conventional fuel systems or internal combustion engines).

Wood, charcoal, and dried dung.

Medical and Research Applications

Xylanases of the invention, including the enzyme mixtures or "cocktails" of the invention, can be used as antimicrobial agents due to their bacteriolytic properties. Xylanases of the invention can be used to eliminating or protecting animals from salmonellae, as described in e.g., PCT Application Nos. WO0049890 and WO9903497. In another aspect of the invention, the xylanases of the invention can also be used an antimicrobial surface cleanser or microbial repellent.

Other Industrial and Medical Applications

As discussed above, xylanases of the invention, including the enzyme mixtures or "cocktails" of the invention, can be used can be used, e.g., in a wide variety of industrial processes, medical and research (laboratory) applications, and food, animal feed and beverage applications. New xylanases are discovered by screening existing libraries and DNA libraries constructed from diverse mesophilic and moderately thermophilic locations as well as from targeted sources including digestive flora, microorganisms in animal waste, soil bacteria and highly alkaline habitats. Biotrap and primary enrichment strategies using arabinoxylan substrates and/or non-soluble polysaccharide fractions of animal feed material are also useful.

Two screening formats (activity-based and sequence-based) are used in the discovery of novel xylanases. The activity-based approach is direct screening for xylanase activity in agar plates using a substrate such as azo-xylan (Megazyme). Alternatively a sequence-based approach may be used, which relies on bioinformatics and molecular biology to design probes for hybridization and biopanning. See, for example, U.S. Pat. Nos. 6,054,267, 6,030,779, 6,368,798, 6,344,328. Hits from the screening are purified, sequenced, characterized (for example, determination of specificity, temperature and pH optima), analyzed using bioinformatics, subcloned and expressed for basic biochemical characterization. These methods may be used in screening for xylanases useful in a myriad of applications, including dough conditioning and as animal feed additive enzymes.

In characterizing enzymes obtained from screening, the exemplary utility in dough processing and baking applications may be assessed. Characterization may include, for example, measurement of substrate specificity (xylan, arabinoxylan, CMC, BBG), temperature and pH stability and specific activity. A commercial enzyme may be used as a benchmark. In one aspect, the enzymes of the invention have significant activity at pH≥7 and 25-35° C., are inactive on insoluble xylan, are stable and active in 50-67% sucrose.

In another aspect, utility as feed additives may be assessed from characterization of candidate enzymes. Characterization may include, for example, measurement of substrate specificity (xylan, arabinoxylan, CMC, BβG), temperature and pH stability, specific activity and gastric stability. In one aspect the feed is designed for a mono gastric animal and in another aspect the feed is designed for a ruminant animal. In one aspect, the enzymes of the invention have significant activity at pH 2-4 and 35-40° C., a half-life greater than 30 minutes in gastric fluid, formulation (in buffer or cells) half-life greater than 5 minutes at 85° C. and are used as a monogastric animal feed additive. In another aspect, the enzymes of the invention have one or more of the following characteristics: significant activity at pH 6.5-7.0 and 35-40° C., a half-life greater than 30 minutes in rumen fluid, formulation stability as stable as dry powder and are used as a ruminant animal feed additive.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are xylanases which catalyze the breakdown of polypeptides. In organic solution some xylanases can also acylate sugars, a function unrelated to the native function of these enzymes.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds. Each biocatalyst is specific for one functional group, or several related functional groups and can react with many starting compounds containing this functional group. The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, see PCT/US94/09174).

In one aspect, the invention provides a composition comprising at least one mucoadhesive polymer that is capable of forming a hydrogel and at one least water soluble polymer, and one or more enzymes of the invention. This formulation can be used in any industrial, food or feed processing or medical or research application of the invention, i.e., any application using an enzyme or nucleic acid of the invention. In one aspect, the formulation forms a hydrogel in aqueous solution that has mucoadhesive properties; this can be capable of releasing enzymes, microorganisms capable of generating enzymes of the invention, or antibodies of the invention, over an extended period of time. Alternatively, the hydrogel can entrap enzymes, microorganisms capable of generating enzymes of the invention, or antibodies of the invention and release them over a defined (e.g., an extended) period of time.

The invention will be further described with reference to the following examples; however, it is to be understood that the invention is not limited to such examples.

EXAMPLES

Example 1

Xylanase Assay with Wheat Arabinoxylan as Substrate

The following example describes an exemplary xylanase assay that can be used, for example, to determine if an enzyme is within the scope of the invention. Enzymes of the invention, e.g., SEQ ID NO:2 having one or more amino acid residue changes (mutations) as set forth in Table 1 and as described herein, also include a genus of polypeptides having various sequence identities based on the exemplary SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 or SEQ ID NO:24, can be subjected to an assay at pH 8 (Na-phosphate buffer) and 70° C. using wheat arabinoxylan as a substrate.

Example 2

Determination of Melting Temperature and Xylanase Activity

Differential Scanning Calorimetry (DSC)

The melting temperature transition midpoint ($T_m$) for each enzyme of the invention, e.g. SEQ ID NO:2 having one or more amino acid residue changes (mutations) as set forth in Table 1 and as described herein, can be determined by Differential Scanning Calorimetry (DSC). Baseline subtracted DSC data can be normalized for protein concentration.

In one assay, calorimetry can be performed using a Model 6100 NANO II DSC™ apparatus (Calorimetry Sciences Corporation, American Fork, Utah) using the DSCRUN™ (DSCRun) software package for data acquisition, CPCALC™ (CpCalc) for analysis, CPCONVER™ (CpConvert) for conversion into molar heat capacity from microwatts and CPDECONVOLUTE™ (CpDeconvolute) for deconvolution. Analysis can be carried out with 1 mg/ml recombinant protein in 20 mM potassium phosphate (pH 7.0) and 100 mM KCl at a scan rate of 1° C./min. A constant pressure of 5 atm can be maintained during all DSC experiments to prevent possible degassing of the solution on heating. The instrumental baseline can be recorded routinely before the experiments with both cells filled with buffer. Reversibility of the thermally induced transitions can be tested by reheating the solution in the calorimeter cell immediately after cooling the first run.

Alternatively, DSC measurements can be made using a VP-DSC microcalorimeter (Micro-Cal) in duplicate. In one aspect, a required sample volume is 540 μL. The concentrations of the protein can be between 0.1 to 0.5 mg/mL in 50 mM HEPES, pH 7.2; a sample of the dialysis buffer can be retained for base line controls. Each sample can be heated from 40° C. to 110° C. Samples and/or buffer can be heated and cooled at a scan rate of 90° C./h. Buffer baselines were recorded multiple times until the system reached a stable state. The $T_m$ value was the temperature where maximum heat was released.

Xylanase Activity Assays

Enzymatic activities can be determined using 400μL of 2% Azo-xylan as substrate in 550 μl of CP (citrate-phosphate) buffer, pH 6.0 at the indicated temperatures. Activity measurements as a function of pH can be determined using 50 mM Britton and Robinson buffer solutions (pH 3.0, 5.0, 6.0, 7.0, 8.0 and 9.0) prepared by mixing solutions of 0.1 M phosphoric acid solution, 0.1 M boric acid and 0.1 M acetic acid followed by pH adjustment with 1 M sodium hydroxide. Reactions can be initiated by adding 50 μL of 0.1 mg/ml of purified enzyme. Time points can be taken from 0 to 15 minutes where 50 μL of reaction mixture are added to 200 μL of precipitation solution (100% ethanol). When all time points have been taken, samples are mixed, incubated for 10 minutes and centrifuged at 3000 g for 10 minutes at 4° C. Supernatant (150 μL) can be aliquoted into a fresh 96 well plate and absorbance is measured at 590 nm. A 590 values can be plotted against time and the initial rate is determined from the slope of the line.

Polysaccharide Fingerprinting.

Polysaccharide fingerprints can be determined by polysaccharide analysis using carbohydrate gel electrophoresis (PACE). Beechwood xylan (0.1 mg/mL, 100 μL, Sigma, Poole, Dorset, UK) or xylooligosaccharides (1 mM, 20 μL, Megazyme, Wicklow, Ireland) can be treated with enzyme (1-3 μg) in a total volume of 250 μL for 16 hours. The reaction is buffered in 0.1 M ammonium acetate pH 5.5. Controls without substrates or enzymes are performed under the same conditions to identify any unspecific compounds in the enzymes, polysaccharides/oligosaccharides or labeling reagents. The reactions are stopped by boiling for 20 min. Assays can be independently performed at least 2 times for each condition. Derivatization using ANTS (8-aminonaphthalene-1,3,6-trisulfonic acid, Molecular Probes, Leiden, The Netherlands), electrophoresis and imaging are carried out as described (Goubet, F., Jackson, P., Deery, M. and Dupree, P. (2002) Anal. Biochem. 300, 53-68).

Fitness Calculation.

The fitness ($F_n$), for a given enzyme variant, n, can be calculated by equally weighting increase in denaturation temperature transition midpoint ($T_m$) and increase (or decrease) in enzymatic activity relative to the largest difference in each parameter across all variants: $F_n=F_{Tn}+F_{Vn}$, where $F_{Tn}=T_m$ fitness factor of the variant and $F_{Vn}$=activity fitness factor of the variant. The fitness factors for each ($T_m$ and activity) are relative to the largest difference in $T_m$ or rate across all of the variants. $F_{Tn}=(T_m-T_{mL})/(T_{mH}-T_{mL})$ where $T_{mn}$ is the $T_m$ for the given variant, n, and $T_{mL}$ is the lowest $T_m$ across all variants and $T_{mH}$ the highest $T_m$ across all variants and $F_{Vn}=(V_n-V_L)/(V_H-V_L)$ where $V_n$ is the relative rate for the given variant, n, and $V_L$ is the lowest rate across all variants and $V_H$ the highest rate across all variants.

Example 3

Pre-Treating Paper Pulp with Xylanases of the Invention

In one aspect, xylanases of the invention are used to treat/pretreat paper pulp, or recycled paper or paper pulp, waste wood or wood chips, and the like. In one aspect, enzyme(s) of the invention are used to increase the "brightness" of the paper via their use in treating/pretreating paper pulp, or recycled paper or paper pulp, and the like.

In one aspect, xylanases of the invention are used to treat/pretreat paper pulp, or recycled paper or paper pulp, and the like to reduce the Kappa number. Kappa number is defined as a numerical value indicating a paper's relative lignin content—the higher the Kappa number, the higher the lignin content. In some aspects, reduction in Kappa # has benefits when treating unbleached pulp (kappa #70-90), when then is used for, e.g., processing, such as in board manufacture. In some aspects, a reduction in Kappa across the X stage allows lower alkali use in cooking or cooking to a higher target Kappa #. In some aspects, this results in higher pulp strength, less machine refining and higher machine speeds. In some aspects, such results are seen using digester additives (surfactants) in linerboard mills; this can allow for better liquor penetration, and allow lower effective alkali charge leading to higher pulp strength, lower refining and a 200 fpm (feet per minute) increase in machine speed.

This example describes an exemplary routine screening protocol to determine whether a xylanase is useful in pretreating paper pulp; e.g., in reducing the use of bleaching chemicals (e.g., chlorine dioxide, $ClO_2$) when used to pretreat Kraft paper pulp.

The screening protocol has two alternative test parameters: Impact of xylanase treatment after an oxygen delignification step (post-$O_2$ pulp); and, impact of xylanase in a process that does not include oxygen delignification (pre-$O_2$ brownstock).

The invention provides pulp or paper treatment conditions that simulate process conditions in industrial situations, e.g., factories: for example, at about pH 8.0; 70° C.; 60 min duration. For example, an exemplary process of the invention is schematically depicted in the Flow Diagram of FIG. 5; see also FIG. 6. However, the conditions of a process of method of the invention can be adjusted to any temperature, time duration and/or pH, depending on the exemplary enzyme(s) of the invention used and the objective of the process; for example, there are a variety of ways to adjust pH in the various pulp and paper processes of the invention:

adding acid and/or base:
- Hydrochloric acid (HCl)
- Sodium hydroxide (NaOH)
- $H_2SO_4$ (sulfuric acid)
- $NaHSO_4$ (sodium hydrogen sulfate)
- $H_2SO_3$ (sulfurous acid)
- H3PO4 (phosphoric acid)
- HF (hydrofluoric acid)
- $CH_3CO_2H$ (acetic acid)
- $H_2CO_3$ (carbonic acid)
- $H_2S$ (hydrogen sulfide)
- $NaH_2PO_4$ (sodium dihydrogen phosphate)
- $NH_4Cl$ (ammonium chloride)
- HCN (hydrocyanic acid)
- $Na_2SO_4$ (sodium sulfate)
- NaCl (sodium chloride)
- $NaCH_3CO_2$ (sodium acetate)
- $NaHCO_3$ (sodium bicarbonate)
- $Na_2HPO_4$ (sodium hydrogen phosphate)
- $Na_2SO_3$ (sodium sulfite)
- NaCN (sodium cyanide)
- $NH_3$ (aqueous ammonia)
- $Na_2CO_3$ (sodium carbonate)
- $Na_3PO_4$ (sodium phosphate)

bubbling in gas, e.g. $CO_2$ (which forms an acid with water when dissolved)

Dose Response Determination for Xylanases on Pre-02 Brownstock

Conditions for xylanase stage (X-stage) as follows:
- pH 8
- Temperature 70° C.
- Time 60 min
- Kappa factor 0.24
- For no-enzyme control, kappa factor was 0.30

Pretreatment of Intercontinental Pre-$O_2$ Brownstock Xylanase

Determination of $ClO_2$ Dose Response in $D_o$
- Experimental outline
- Pre-$O_2$ Brownstock
- Initial kappa 31.5
- X stage conditions
- Xylanase charge 0.7 U/gm
- Temperature 70° C.
- pH 8
- Treatment time 1 hr
- Pulp consistency 10%
- Bleach sequence $XDE_p$
- Kappa factor 0.22, 0.26 and 0.30 (% D on pulp: 2.63, 3.12 and 3.60)

Determination of $ClO_2$ Dose Response in $D_o$:
- Xylanase 0.7 U/g, pH 8.0, 70° C., 1 hr
- Pulp: Pre-02 Brownstock, initial kappa 31.5

Percentage saving of $ClO_2$ is of little significance to the industry. Their primary concern is lbs of $ClO_2$ required per ton OD pulp. This makes sense when one considers that a lower percentage saving seen with a high initial kappa brownstock can be more valuable in terms of lbs of $ClO_2$ saved than a higher percentage reduction for a low initial kappa pulp which will require a lower total charge of $ClO_2$ to reach target brightness.

Relationship between Brightness, Yield and Kappa Factor for Bleached Control Pulp:

Bleaching with increasing doses of $ClO_2$ to achieve higher target brightness results in increased loss of pulp yield. This is an issue because pulp at this stage of the process has a value of almost $400 per ton and loss of cellulose costs money.

A benefit of xylanase (e.g., a xylanase of the invention) is that use of a lower $ClO_2$ dose can reduce yield losses as long as the action of the xylanase itself doesn't cancel out the gain. Dose Response Data for Pretreatment of Pre-$O_2$ Brownstock with Xylanase Experimental outline Northwood Pre-$O_2$ Brownstock
Initial kappa 28.0
Initial consistency 32.46%
Initial brightness 28.37
X stage conditions
Xylanase charge 0 to 2.70 U/gm
Temperature 58° C. to 61° C.
pH 8.2 to 8.5
Treatment time 1 hr
Bleach sequence $XDE_p$
Kappa factor 0.24
$ClO_2$ saving calculated for Kappa factors between 0.24 and 0.30

The purpose of this experiment is to evaluate xylanases on unwashed SPF brown stock. Results can show dose-dependent increases in final brightness for pulp treated with XYLB (E.c), with brightness achieved in presence of xylanase at lower Kf of 0.24, approaching brightness achieved at higher Kf of 0.30 asymptotically.

Example 4

Novel Biobleaching Assay for Assessing Xylanase Performance in Enhancing the Brightness of Pulp This example describes an exemplary protocol, a "biobleaching assay," that can be used to determine if a polypeptide has xylanase activity and is within the scope of the invention. This assay can be used to assess the performance of an exemplary enzyme of the invention, for example SEQ ID NO:2 having one or more amino acid residue changes (mutations) as set forth in Table 1 and as described herein, or a sequence having a sequence identity (as described herein) to an exemplary SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 or SEQ ID NO:24; in enhancing the brightness of a pulp, e.g., a Kraft Pulp.

The invention provides biobleaching procedures, e.g., a three-stage biobleaching procedure that closely simulates the conditions of an actual pulp mill bleach plant, as illustrated in FIG. 5; including a process as illustrated in FIG. 6. This bleach sequence is designated by (X) DoEp, in which X represents the xylanase treatment stage (using, e.g., an enzyme of the invention), D for chlorine dioxide bleaching stage, and Ep for alkaline peroxide extraction stage. Many different feedstocks may be used, for example, Southern Softwood Kraft Brownstock (without oxygen delignification) and hardwood Kraft pulp (e.g., maple and aspen). Upon completion of each biobleaching round, ensuing pulp can be used to produce TAPPI (Technical Association of Pulp and Paper Industries, the technical association for the worldwide pulp, paper and converting industry)—standard handsheets. The GE % brightness of each handsheet can be measured, and the brightness values can be used as the indication of how well each enzyme performs on the pulp during the enzymatic pretreatment stage (X).

Pulp biobleaching: Pulp was bleached in 10-g batches in sealed plastic bags using a 3-stage (X) DoEp sequence, as illustrated in FIG. 5. The treatment conditions at the three stages can be summarized as follows:

X stage: 10% (w/v) consistency at 65° C. and pH=8 for 60 min
Do stage: 4% (w/v) consistency at 60° C. for 30 min; Kappa Factor=0.18 for enzyme treated samples, and 0.18 and 0.21 for no-enzyme controls.
Ep stage: 10% (w/v) consistency at 75° C. for 90 min; caustic charge: 1.7% (w NaOH/w OD pulp) and $H_2O_2$ charge: 0.5% (w/w)

As noted in FIG. 5, in one aspect, raw pulp is washed to reduce pH to pH 8.5; pulp is filter pressed and divided into bags. At each stage, bags can be incubated in a water bath at the desired temperature and each bag is taken out and kneaded thoroughly every 10 min to ensure uniform mass and heat transfer within the pulp mass. After each treatment, pulp can be filtered, washed with 2 L of DI water and filtered again before receiving the next treatment. The moisture content of the pulp can be measured using a Mettler-Toledo moisture analyzer (Fisher Scientific, USA).

As noted in FIG. 5, in one aspect, after the pulp is filter pressed and divided into bags, in the X stage, the pulp can be resuspended, filter pressed, the pH adjusted; and then, incubated with enzyme at 10% solids, 65° C., 1 hour; then kneaded for 10 minutes. At the Do stage the pulp can be resuspended, washed, pH set to 4.0, and filter pressed; then, impregnated with $C10_2$ at 4% solids (i.e., 4% (w/v) consistency) at 60° C. for 30 min; then kneaded for 10 minutes. At the Do stage the Kappa Factor=18 for enzyme treated samples, and 0.18 and 0.21 for no-enzyme controls. At the Ep stage the pulp can be resuspended, washed, and filter pressed; then, incubated with NaOH and $H_2O_2$ at 10% solids (i.e., 10% (w/v) consistency) at 75° C. for 90 min; then kneaded for 10 minutes. The caustic charge: 1.7% (w NaOH/w OD pulp) and $H_2O_2$ charge: 0.5% (w/w). After kneading, handsheets were formed.

Handsheets: As noted in FIG. 5, in one aspect, handsheets can be formed (4 m pulp, pH about 6.5); handsheets can be made from unbleached and bleached pulp using TAPPI standard equipment (Kalamazoo Paper Chemicals, Richland, Mich.) according to TAPPI method T-272 sp-97. The GE % brightness of each handsheet can be measured using a BRIGHTMETER MICRO S-5/BC™ (Technidyne Corp., New Albany, Ind.) according to TAPPI method T-452 om-98 (reference at 457 nm).

Example 5

Novel Biobleaching Process

This example describes a novel biobleaching process of the invention, as illustrated in FIG. 6. This process can be practiced using any xylanase enzyme, including a polypeptide of the invention, which includes a polypeptide having at 50% to 99% or more sequence identity to an exemplary enzyme of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and also includes any polypeptide having the sequence of SEQ ID NO:2 having one or more amino acid residue changes (mutations) as set forth in Table 1 and as described herein.

This exemplary process of the invention can have a starting material comprising "brownstock," which can be described as: 1) feedstock preparation—logs coming into the paper mill are debarked, chipped and screened to remove overthick chips, fines, knots and foreign matter, 2) pulping—wood chips are cooked at 160° C. to 190° C. under pressure for several hours in a concentrated liquor of sodium hydroxide and sodium sulfide to separate cellulose fibers and increase cellulose content by extracting the majority of unwanted lignin. The output of this step is referred to as "brownstock".

This process of the invention comprises a "Bleaching Step"—a multistage process by which residual lignin and other chromophores are removed to whiten the pulp to target brightness in preparation for making paper or other products. Pulp is treated with oxidizing chemicals, for example chlorine and chlorine dioxide, that attack lignin preferentially. In one aspect the process comprises a bleaching sequence where pulp is reacted with chlorine dioxide, the "$D_o$" stage (see also FIG. 5); extracted with alkali in the presence of hydrogen peroxide, the "Ep" stage (see also FIG. 5, the "Ep" stage); reacted with chlorine dioxide a second time, a "D1" stage; extracted with alkali and hydrogen peroxide, an Ep stage; and, reacted with chlorine dioxide a third time, a D2 stage. In practicing this process, bleaching can be subject to many variations with respect to type and quantity of oxidizing chemicals used and the number of process steps (however, chlorine dioxide is currently the most widely used chemical oxidant). In one aspect, this process comprises pretreatment of cooked pulp with oxygen under pressure; the oxygen reactor can be at high pressure—at about 200 to 230° F. and pH 12 to 14 (this is a common first step in bleaching, known as "oxygen delignification").

In one aspect, this process comprises refining. For example, prior to papermaking bleached pulp is mechanically fined to collapse the cellulose fibers into flat ribbons, fibrilate their surfaces and improve their physical characteristics for papermaking. At any stage of the process following pulping, the pulp may be dewatered, washed and adjusted to a predetermined consistency by the addition of clean water or recyled streams.

Xylanase (e.g., an enzyme of the invention) can be just added after pulping, in the oxygen reactor or in the storage container just before the oxygen reactor. Xylanase (e.g., an enzyme of the invention) can be added at multiple points (one or more or all points) in the bleaching process. In one aspect, a laccase is added to catalyze break-down of lignin. The laccase may be added at any stage of the process, including in the oxygen reactor. Pulp may release various components that self-mediate the laccase. Alternatively, in one aspect, organic or inorganic mediators can be added (see, e.g., DE 19723890 describing an oxidation system comprising an organic mediator and a laccase; alternative exemplary mediators include 2,2'-azinobis(3-ethylbenzthiazoline-5-sulphonate) (ABTS) as an exemplary organic mediator and potassium octacyanomolybdate $[K_4Mo(CN)_8]$ as an exemplary inorganic mediator). Mediators as described in U.S. patent application no. 20030096394, can also be used in the processes of the invention, including any compound capable of enhancing the activities of laccase and laccase-related enzymes.

In one aspect, an esterase, e.g. lipase, or oxidoreductase, e.g. peroxidase is added. In addition, pH and/or temperature can be modified in the reactor. In monitoring reactions of the invention, any lignin content-measuring technique can be used, e.g., see U.S. Patent Application No. 20020144795, describing a method to measure kappa number or lignin content of kraft pulps based on the voltammetric measurement of catalytic reactions involving lignin and redox mediators.

Enzymes of the invention can also be used in with alkali-oxygen bleaching (oxygen delignification) processes as described, e.g., in U.S. Pat. No. 6,824,646, the process comprising bleaching lignocellulose pulp in aqueous alkali solution with oxygen and treating the pulp with a hemicellulase, while a liquid fraction delivered from the enzyme treatment step is separated from the hemicellulase treated reaction mixture, and subjected to a penetration treatment through a separation membrane, for example, reverse osmosis membrane, to separate a permeated fraction from a non-permeated fraction; and then the permeated fraction is fed to the alkali-oxygen bleaching (oxygen delignification) step comprising use of an enzyme of the invention.

In alternative aspects of this or any other process (method) of the invention xylanases (e.g., enzymes of the invention) are used to reduce bleaching chemicals, e.g., chlorine, chlorine dioxide, caustic, peroxide, or any combination thereof; and in alternative aspects, a reduction of up to about 1%, 5%, 10%, 20%, 25%, 30%, 35%, 40%, 45%, 50%, 55%, 60%, 65%, 70%, 75%, 80%, 85%, 90%, 95% or more, or 100%, of chemicals can be seen in practicing the methods and using the enzymes of the invention. In one aspect, a 100% reduction in chemicals can be achieved when the xylanase is used in combination with a laccase or other enzyme, e.g., by use of enzyme cocktails; noting the invention provides enzyme mixtures, or "cocktails" comprising at least one enzyme of the invention and one or more other enzyme(s), which can be another xylanase, or any other enzyme.

In one aspect xylanases of the invention are used to reduce chlorine dioxide to allow recycling of water in the process; thus, there is less water used and less water dumped into the sewer. In one aspect xylanases of the invention are used to allow more lignin-rich pulp to enter the bleaching plant, allowing for better pulp yield and better quality pulp (i.e., less destruction during the cooking process). In one aspect, xylanases of the invention are used to increase the overall brightness of the paper. In one aspect, xylanases of the invention are used to lower the kappa number of the pulp.

Xylanases of the invention can be used, and the processes of the invention can be practiced, on all wood types, including, for example, on hard wood with, e.g., oxygen delignification, hard wood without oxygen delignification, soft wood with oxygen delignification and soft wood without oxygen delignification, and the like. Xylanases of the invention can be used, and the processes of the invention can be practiced for processing of recycled paper and/or pulp.

Oxygen delignification typically requires the addition of a reaction tower between a brownstock washer and a bleach plant. Typically, oxygen and sodium hydroxide are added to brownstock. Reduction of bleaching chemistry by 50% can be achieved in the bleaching process if preceded by oxygen delignification. Washing follows oxygen delignification; effluent can be recovered or discharged. Ozone delignification can be used in place of oxygen delignification.

Example 6

Novel Biobleaching Assay

This example describes assays that can demonstrate xylanase activity in polypeptides of the invention, e.g., the exemplary polypeptides of the invention, or enzymes of the invention, e.g., SEQ ID NO:2 having one or more amino acid residue changes (mutations) as set forth in Table 1 and as described herein, also include a genus of polypeptides having various sequence identities based on the exemplary SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 or SEQ ID NO:24.

These xylanase activity studies can be based on those described by Nelson (1944) J. Biol. Chem. 153:375-380, "Reducing Sugar Assay for Xylanase"; and, Somogyi (1952) J. Biol. Chem. 195:19-23. This "Nelson-Somogyi" assay can be used to determine units of activity; data from "Nelson-Somogyi" assays demonstrating xylanase activity in polypeptides of the invention by determining units of activity is set forth, below.

Enzyme unit determinations also can be determined using the Nelson-Somogyi assay. Biobleaching assays can be based on methods from TAPPI ((Technical Association of Pulp and Paper Industries, see above). Below a description along with references to the TAPPI protocols.

Pulp: In one aspect, two hatches of southern softwood Kraft brownstock are obtained, e.g., from the Department of Wood and Fiber Science at North Carolina State University (Raleigh, N.C.). The pulp Kappa Numbers can be determined, e.g., typically are or are between 21.4 or 29.7, as analyzed using TAPPI method T-236 om-99; see e.g., TAPPI Test Methods (2000-2001, 2003 173).

Pulp Biobleaching: Pulp can be pretreated with xylanase and bleached in 10 g batches in sealed plastic bags using a 3-stage xylanase/chlorine dioxide/alkaline peroxide sequence: (X) DoEp (see explanation above). The treatment conditions at the three stages can be:

X stage: 10% (w/v) consistency at 65° C. and pH 8 for 60 min.

Do stage: 4% (w/v) consistency at 60° C. for 30 min; a Kappa Factor of 0.18 was used for enzyme treated samples, and 0.18 and 0.21 for no-enzyme control samples. The concentration of chlorine dioxide used during the Do stage was calculated using equation (1):

$$ClO_2\,\% = \frac{KF \times K\#}{2.63} \tag{1}$$

Where $ClO_2$% is equal to g pure chlorine dioxide per 100 g oven-dried (OD) pulp KF is the Kappa Factor and K# is the Kappa Number of the pulp as determined by TAPPI method T-236 om-99, TAPPI Test Methods (2000-2001, 2003 173), Ep stage: 10% (w/v) consistency at 75° C. for 90 min; caustic charge is 1.7% on pulp (w/w) and $H_2O_2$ charge is 0.5% on pulp (w/w).

At each stage, replicate bags can be incubated in a water bath at the desired temperature and then removed and kneaded thoroughly every 10 min to ensure uniform mass and heat transfer within the pulp mass. After each stage, pulp can be filtered, e.g., through a Buchner funnel lined with a hard polypropylene filter (297-micron mesh, Spectrum Labs, Ft. Lauderdale, Fla.). The filtrate can be recycled once to catch the fines, and the pulp cake can be washed, e.g., with 2 L of DI water. The pulp cake can then be re-suspended, e.g., in 1.5 L of DI water and pH can be adjusted, e.g., to pH 8 and pH 4 prior to X and Do stages, respectively. The moisture content of the pulp can be measured using a Mettler-Toledo moisture analyzer (Fisher Scientific, USA).

Handsheets can be made from the bleached pulp using TAPPI standard equipment (Kalamazoo Paper Chemicals, Richland, Mich.) according to TAPPI method T-272 sp-97, TAPPI Test Methods (2000-2001, 2003 173). The GE % brightness of each handsheet TAPPI Test Methods (2000-2001, 2003 173) can be measured, e.g., using a Technidyne BRIGHTMETER MICRO S-5BC™ (Technidyne Corp., New Albany, Ind.) according to TAPPI method T-452 om-98.

| COMPONENTS used in assay (1) | |
|---|---|
| 1M NaOH | Solution 1: 12 g $K^+/Na^+$ tartrate; 24 g $Na_2CO_3$; 16 g $NaHCO_3$; 144 g $Na_2SO_4$ in 800 mL $H_2O$ |
| 0.5 M Sodium phosphate buffer pH 8 | Solution 2: 4 g $CuSO_4*5H_2O$; 36 g $Na_2SO_4$ in 200 mL $H_2O$ |
| 1% Arabinoxylan - (Megazyme #P-WAXYM) prepared according to the manufacturer's instructions | Reagent A: Mix 4 volumes of solution 1 with 1 volume of solution 2. Note- make fresh daily |
| Xylose - prepare standards 0.15 mM-2 mM using D-xylose dissolved in $H_2O$ | Reagent B: 25 g $(NH4)_2MoO_4$ in 450 mL $H_2O$; add 21 mL conc. $H_2SO_4$, mix. |
| 96 well PCR plate (Fisher 05 500-48) | Dissolve 3 g $Na_2HAsO_4*7H_2O$ in 25 mL $dH_2O$; mix with ammonium molybdate solution and incubate reagent at 37° C. for 24-48 h. Store solution in a dark bottle i.e. away from light at room temperature. |
| PCR plate seals | |
| Standard 96 well clear plates | |
| 1 mL tubes (E&K 671511-RC) for the 96 well block | |

Procedure

1. Prepare reagent A
2. Pipet 5 uL of 1 M NaOH into each well of a 96 well PCR plate. Keep plate on ice.
3. Prepare reaction mixture. Alternatively, you can make a master mix for multiple samples. Here is the 1× mix. Add to the 1 mL tubes and place into the 96 well block.
   a. 50 uL pH8 Na-phosphate buffer
   b. 250 uL of 1% substrate (to make a final concentration of 0.5%)
   c. 150 uL $H_2O$
4. Preheat reaction mixture to desired temperature for 3 minutes.
5. Dilute the 0.5 M phosphate buffer to 5 mM pH 8 and make enzyme dilutions using this buffer.
6. Pipet 75 uL of diluted enzyme into a well of a 96 well microtiter plate
7. Pipet 50 uL of diluted enzyme into the 1 mL tube containing the reaction mix.
8. At the desired timepoint, pipet 50 uL from each reaction mixture into tubes containing the NaOH (the NaOH will raise the pH to 12, quenching the reaction).
9. Add 50 uL of each standard to separate tubes also containing NaOH. Standards are linear within the range of 0.25 mM xylose to 2.0 mM. Use at least 4 standards to generate the standard curve.
10. Add 50 uL of Reagent A to each well. Seal plate using the Microseal™ 'A' Film.
11. Heat the plate for 20 min. at 100° C. in a PCR machine. Set the machine to cool down to 4° C. after heating the samples.
12. Add 50 uL of reagent B to each tube, mix.

13. —note a significant amount of $CO_2$ is formed after addition of reagent B. Care should be taken so sample does not contaminate adjacent wells.
14. Pipet 100 uL of each sample or standard into separate wells of a 96 well microliter plate.
15. Read plate at 560 nm.
16. Plot standard curve data and express standards as umoles of xylose i.e. 50 uL of 2.5 mM xylose is 0.125 μmoles of xylose.
17. Subtract buffer control from sample data for each time-point and plot the data
18. Divide timepoint curve slope value by the xylose standard curve slope value
19. Multiply by 10 (accounts for the 50 uL samples (1/10 of the total assay volume)
20. Divide by the volume used in the assay (0.05) to get μmoles of xylose released per min per mL of enzyme or U/mL of enzyme.
21. Divide this number by the protein concentration to get U/mg.

"Units of Activity" data from the "Nelson-Somogyi" assays can be used to determine dosing in biobleaching assays (based on TAPPI methods).

As noted above, the enzymes and processes of the invention can also be used in conjunction with a second approach to enzymatic bleaching using oxidative enzymes such as laccase and/or manganese peroxidase (MnP) to delignify pulp. In one aspect of this second approach, of these enzymes, laccase is preferred, because MnP requires hydrogen peroxide, manganese (II) ions and a chelator. Laccase can cause delignification of pulp under slight oxygen pressure, but is considerably more effective when mediators are added, as discussed above.

Catalyst improved delignification methods can also be used in conjunction with the methods of the invention, for example, polysulfide or anthraquinone. Anthraquinone is a pulping reaction catalyst which can increase the speed of pulping, increase yield, and reduce pulping chemical usage by up to 10%. It is possible to use both anthraquinone and polysulfide together.

In one aspect, laccase is used in conjunction with the methods of the invention, as discussed above. For example, laccase is used in an oxygen reactor in a process of the invention, where the laccase breaks down the lignin in the oxygen reactor. While pulp may release various components that self-mediate the laccase, in one aspect organic or inorganic mediators are added (see discussion above, e.g., alternative exemplary mediators include 2,2'-azinobis(3-ethylbenzth-iazoline-5-sulphonate) (ABTS) as an exemplary organic mediator and potassium octacyanomolybdate $[K_4Mo(CN)_8]$ as an exemplary inorganic mediator, or mediators as described in U.S. patent application no. 20030096394). In one aspect, another hydrolase, such as an esterase (e.g., a lipase) and/or an oxidoreductase (e.g., a peroxidase) is also added. In alternative aspects, pH and/or temperature are modified in the reactor.

Example 7

Studies Demonstrating the Enzymatic Activity of Enzymes of the Invention

This example describes studies demonstrating the enzymatic activity of the exemplary xylanase enzymes of the invention, which demonstrates that polypeptides of this invention, which includes a polypeptide having at 50% to 99% or more sequence identity to an exemplary enzyme of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 and/or SEQ ID NO:24, and also includes any polypeptide having the sequence of SEQ ID NO:2 having one or more amino acid residue changes (mutations) as set forth in Table 1 and as described herein, have xylanase activity.

An exemplary assay for evaluating these xylanases:

1. Initial Screen—using an azo-xylan (solution-based) substrate
   a. Enzymatic activity of enzymes can be determined by an azo-xylan assay using MEGAZYME® substrate Birchwood Azo-xylan in 100 mM sodium phosphate, pH 8, according to manufacturer's recommended assay protocol. The concentrations of enzyme samples can be adjusted such that they had equal amounts of xylanase activity at pH8.
   b. The azo-xylan assay are then repeated with normalized samples in 100 mM sodium borate buffer at pH 10.4.
2. Initial Screen—ENZ-CHEK ULTRA XYLANASE ASSAY KIT™ (Invitrogen)
   a. Xylanase enzyme samples can be prepared in the same manner as for the azo-xylan assay (section 1, above).
   b. The level of enzymatic activity of enzymes can be measured by employing commercially available assay kit, e.g., sold by Invitrogen under the name ENZ-CHEK ULTRA XYLANASE ASSAY KIT™ (Product number E33650). The ENZ-CHEK™ kit substrate produces fluorescent signal in the presence of xylanases, which can be used to quantify xylanase activities using kit-supplied standards. The protocol used for testing xylanase enzymes can be slightly modified from any manufacturer-recommended protocol. The modifications can primarily involve, e.g., testing xylanases at different pH and temperature that what is recommended by the manufacturer.
3. Secondary Screen—Exemplary Pulp Assays
   a. The enzymes from azo-xylan assay can be tested for activity on wheat arabinoxylan using, e.g., a Nelson-Somogyi assay as already described herein. They can be then tested in a laboratory scale bleaching assays to determine the amount of chemical savings each can achieved for a given pulp type and chlorine dioxide loading. The ones that meet desired performance characteristics can be tested in TAPPI bag biobleaching assay (e.g., in triplicate) at a range of loadings and pH levels.
4. Exemplary enzyme characterization screen—Temperature profile
   a. Thermotolerance of xylanases can be assayed using azoxylan assay at pH 8 and pH 10.4 at progressively more elevated temperatures; and enzymes of the invention were tested using this assay. The initial rates of reaction at each temperature can be recorded and plotted to determine optimal performance temperature of xylanases.
   b. Residual activity—Another exemplary assay that can be employed for testing thermostability of enzymes is the residual activity method, whereby a sample of enzyme is treated at an elevated temperature at a particular pH for a specific period of time, and then assayed under standard conditions under permissive temperature (typically 37° C.). A half-life at a particular temperature is then determined and provides a measure of a given enzyme fitness under those temperature conditions.

Example 8

Studies Demonstrating the Enzymatic Activity of Enzymes of the Invention

This example describes studies demonstrating the enzymatic activity of the exemplary xylanase enzymes of the invention, including the enzymatic activity of any polypeptide of this invention, which includes a polypeptide having at 50% to 99% or more sequence identity to an exemplary enzyme of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 and/or SEQ ID NO:24, and also includes any polypeptide having the sequence of SEQ ID NO:2 having one or more amino acid residue changes (mutations) as set forth in Table 1 and as described herein, have xylanase activity.

The evolution of endoxylanase SEQ ID NO:2 (Xyl 11) utilizing GSSM technology and xylanase screening identified point mutations (Xyl 11 mutants) having increased xylanase activity, as well increased sugar release from alkaline pretreated corn stover, when used in combination with 7 other cellulosic enzymes (Table 2, below) after 36 hrs in saccharification cocktail assays at 50° C. These assays contain alkaline pretreated dry corn cobs at 5% (w/v) with a total enzyme loading of 10.2 mg/g cellulose in the solids.

TABLE 2

Composition of enzyme cocktail

| Enzyme | SEQ ID NOs: | Conc. mg/g cellulose |
|---|---|---|
| Endoglucanase^ | SEQ ID NO: 4 (encoded by SEQ ID NO: 3) | 1.7 |
| Oligomerase I (beta-glucosidase)^ | SEQ ID NO: 6 (encoded by SEQ ID NO: 5) | 0.5 |
| CBH1 (GH family 7)^ | SEQ ID NO: 8 (encoded by SEQ ID NO: 7) | 5 |
| CBH2 (GH family 6)^ | SEQ ID NO: 10 (encoded by SEQ ID NO: 9) | 1 |
| Xylanase (GH family 11) | VARIES (control*, Xyl 11 or Xyl 11 mutants) | 0.6 |
| Arabinofuranosidase^ | SEQ ID NO: 14 (encoded by SEQ ID NO: 13) | 0.25 |
| Xylanase (GH family10)^ | SEQ ID NO: 16 (encoded by SEQ ID NO: 15) | 0.15 |
| Oligomerase II (beta-xylosidase)^ | SEQ ID NO: 18 (encoded by SEQ ID NO: 17) | 1 |

*control xylanase is SEQ ID NO: 12 (encoded by SEQ ID NO: 11)

^previously described in PCT Publication No. WO 07/094852

The new xylanase mutants improved xylose release over the wild type at 0.6 mg/g cellulose as well as 0.2 mg/g cellulose loading (FIG. 2). At the standard loading of 0.6 mg/g cellulose these new variants achieved conversion rates of up to 90% monomeric xylose released vs. 63% with the wild type. Some of the polypeptides of the invention (the mutants of SEQ ID NO:2), in particular, Xyl 11 mutant 11 and Xyl 11 mutant 14, also achieved greater than 90% xylose release even at the reduced loading of 0.2 mg cellulose. These novel polypeptides of the invention (the mutants of SEQ ID NO:2) therefore not only improve the rate of xylose release but also can do so at a reduced enzyme loading. Similar positive effects on xylose release and enzyme loading could be envisioned for comparable saccharification reactions using different feed stocks (switch grass, hard and soft woods, energy cane, bagasse etc.) applied to alkaline or acidic pretreatments and with different initial enzyme loadings (1 mg-100 mg/g cellulose) and different ratios of cocktail components.

The enzymes of this invention can be used to process/treat cellulosic material for, e.g., biological alcohol (e.g., EtOH, or ethanol) fermentation; cellulosic material that is processed using compositions and methods of the invention can be mainly composed of cellulose (containing glucose), and hemicellulose—which is mostly containing xylose. In one aspect, glucose as well as xylose can be used as a sugar source for EtOH fermentation. In one aspect, xylanases of the invention are active in the enzymatic breakdown of the hemicellulose portion of cellulosic material, releasing a monomeric xylose. In one aspect, the improved xylanase activity of polypeptides of the invention increases the amount of xylose available for fermentation.

In one aspect, by removing the hemicellulose the cellulose becomes more accessible to cellulases, which can also increase the conversion of cellulose to glucose. Using xylanases of the invention, e.g., the sequence variations of the exemplary endoxylanase Xyl 11 (SEQ ID NO:2), including the exemplary 18 amino acid substitutions described herein, an increased specific activity can be achieved over the "wild type" xylanase, as described in Table 1, above. Note: in Table 1 tertiary assay activity is indicated as the Absorbance at 560 nm measured in the BCA assay reached after 9.5 h of hydrolysis. Referencing Table 1, when each of these clones (xylanases of the invention) was evaluated in cocktail saccharification assays with the xylanase as the variable, fourteen of these clones (xylanases of the invention) improved xylose conversion rates when compared to assays with the wild type at the same loading, as noted in Table 3 (see Table 1 for the sequence referenced in Table 3, e.g., Table 1 sets for the sequence of Xyl 11 mutant 5, Xyl 11 mutant 5, etc., based on the exemplary SEQ ID NO:2; note also, "Xyl 11 (WT)" refers to the "wild type" exemplary SEQ ID NO:2):

TABLE 3

Xylose conversion by the cocktail shown in Table 2 (above). Note the xylanase component (Xyl 11 WT or Xyl 11 mutant) varies in each cocktail.

| Xylose Conversion @ 0.2 mg | | | Xylose Conversion @ 0.6 mg | | |
|---|---|---|---|---|---|
| Xyl 11 or Xyl 11 mutant used in cocktail | 36 hr | STDEV | Xyl 11 or Xyl 11 mutant used in cocktail | 36 hr | STDEV |
| Xyl 11 (WT) | 51.57% | 0.01 | Xyl 11 (WT) | 62.84% | 0.02 |
| Xyl 11 mutant 5 | 55.98% | 0.00 | Xyl 11 mutant 16 | 68.10% | 0.01 |
| Xyl 11 mutant 16 | 57.43% | 0.01 | Xyl 11 mutant 5 | 69.69% | 0.00 |
| Xyl 11 mutant 12 | 59.03% | 0.02 | Xyl 11 mutant 12 | 71.75% | 0.01 |
| Xyl 11 mutant 4 | 59.46% | 0.00 | Xyl 11 mutant 7 | 74.25% | 0.00 |
| Xyl 11 mutant 9 | 60.34% | 0.01 | Xyl 11 mutant 9 | 74.45% | 0.00 |
| Xyl 11 mutant 17 | 60.45% | 0.01 | Xyl 11 mutant 17 | 74.76% | 0.01 |
| Xyl 11 mutant 7 | 61.23% | 0.02 | Xyl 11 mutant 4 | 74.94% | 0.01 |
| Xyl 11 mutant 2 | 61.73% | 0.02 | Xyl 11 mutant 13 | 75.30% | 0.01 |
| Xyl 11 mutant 6 | 62.31% | 0.00 | Xyl 11 mutant 2 | 78.24% | 0.05 |
| Xyl 11 mutant 13 | 63.58% | 0.01 | Xyl 11 mutant 15 | 80.03% | 0.00 |
| Xyl 11 | 65.95% | 0.00 | Xyl 11 | 80.36% | 0.09 |

TABLE 3-continued

Xylose conversion by the cocktail shown in Table 2 (above). Note the xylanase component (Xyl 11 WT or Xyl 11 mutant) varies in each cocktail.

| Xylose Conversion @ 0.2 mg | | | Xylose Conversion @ 0.6 mg | | |
|---|---|---|---|---|---|
| Xyl 11 or Xyl 11 mutant used in cocktail | 36 hr | STDEV | Xyl 11 or Xyl 11 mutant used in cocktail | 36 hr | STDEV |
| mutant 15 | | | mutant 6 | | |
| Xyl 11 mutant 10 | 66.34% | 0.00 | Xyl 11 mutant 10 | 80.61% | 0.01 |
| Xyl 11 mutant 11 | 71.76% | 0.01 | Xyl 11 mutant 14 | 84.74% | 0.01 |
| Xyl 11 mutant 14 | 73.69% | 0.03 | Xyl 11 mutant 11 | 90.36% | 0.06 |

Accordingly, the invention provides an enzyme cocktail comprising, or consisting of, the enzymes: Endoglucanase, Oligomerase I (beta-glucosidase), CBH1 (GH family 7), CBH2 (GH family 6), Xylanase (GH family 11), Arabinofuranosidase, Xylanase (GH family 10) and an Oligomerase II (beta-xylosidase); wherein one, two, three, four, five, six, seven and/or all eight of these enzyme are a polypeptide of this invention, and methods for treating polysaccharide compositions using these cocktails, or any cocktail of this invention, for, e.g., treating/processing wood, pulp, paper, waste(s) and the like, or making biofuels or foods or feeds, or any other industrial process or method, e.g., as described herein.

Screens and Assays for Identifying Enzymes of the Invention

The following screens and assays were used in identifying exemplary enzymes of the invention, and in one aspect, these screens and assays can be applied to determine if any polypeptide has sufficient xylanase activity to fall with the scope of this invention—assuming of course it also has the requisite sequence identity, as described herein:

Xylanase Evolution Screen:

Utilizing the GSSM technology (Verenium Corporation, U.S. Pat. No. 6,171,820) an evolution library for endoxylanase Xyl 11 (SEQ ID NO:2) representing all possible amino acid exchanges for each of the 194 residues of this enzyme was created. Point mutations were introduced using degenerate oligonucleotides, one amino acidposition at a time, so that each original codon could be substituted with each of the 20 naturally encoded amino acids. The mutated variants were transformed into XL 1-Blue (recA-strain, Stratagene) and then into Pseudomonas fluorescens MB214 (Dow Global Technologies Inc., US Patent Publication No. 20050130160), using vector pWZ82T (SEQ ID NO:25). All variants were grown and expressed (from Pseudomonas fluorescens MB214) and lysed in 96 well plates. Hydrolysis reactions with the lysates were carried out in 96 well plates (200 ul of 200 mM citrate buffer, pH 5.5, 0.5% dried and milled alkaline pretreated corn stover—CP-15, 50 C). Aliquots were removed from the reaction at 1, 3, 5 and 10 hrs and added to 800 mM carbonate buffer pH 10 to stop the reaction. The extent of hydrolysis at each time point was evaluated via a reducing ends assay (BCA), as described by Johnston et al. 1998 (see below), recording absorption at 560 nm (A560). In addition a quantitative ELISA utilizing Xyl 11 (SEQ ID NO:2) specific antibodies was used to normalize activity to protein expression. Both functional and quantitative assays were automated for high through put. In the primary screen, clones exhibiting normalized activity exceeding Xyl 11 (SEQ ID NO:2) controls on the plate by at least 2 standard deviations (>1.0+2 STDV wt) were moved on to a secondary screen. In the secondary screen, all primary hits were re-screened in duplicate applying the same assay and hit criteria as in the primary screen. Clones that confirmed for both duplicates were then moved onto a tertiary screen. In tertiary screens, these clones again were assayed in duplicate using the BCA assay, but this time with different defined concentrations of protein (0.1, 0.05 and 0.025 mg/ml). Total protein of lysates was determined via Bradford assays (e.g., as described in Bradford 1976, see below) the relative content of xylanase then was determined via densitometry of SDS PAGE gels after running defined amounts of total protein. All clones exceeding wt activity, recorded as absorption at 560 nm (A560), for at least one enzyme concentration in the tertiary screen were then assayed in saccharification assays.

Saccharification/Cocktail Assay:

Cocktail reactions were set up in capped 10 ml glass vials containing two metal ball bearings. The reaction volume was 5 ml (200 mM Sodium Citrate-1 mM Sodium Azide pH 5.5) with 5% solids (size 40 grit milled alkaline pretreated corn stover). Enzyme composition and loadings were according to Table 2, above, only varying the family 11 endoxylanase. Reaction vials were incubated for 36 h at 50 C under shaking at 300 rpm. The concentration of xylose monomers released was determined by HPLC (RI detector, Shodex SP-0810 column, flow rate of 0.5 ml/min) using a set of standards and calibration curves.

Johnston, D. B.; Shoemaker, S. P.; Smith, G. M. and Whitaker, J. R.: Kinetic Measurement of Cellulase Activity on Insoluble Substrates Using Disodium 2,2' Bicinchoninate. Journal of Food Biochemistry (22) Issue 4 pp. 301-319, 1998

Bradford, M. M. (1976) A Rapid and Sensitive Method for the Quantitation of Microgram Quantities of Protein Utilizing the Principle of Protein-Dye Binding. Anal. Biochem. 72:248-25

While the invention has been described in detail with reference to certain preferred aspects thereof, it will be understood that modifications and variations are within the spirit and scope of that which is described and claimed.

SEQUENCE LISTING

```
<160> NUMBER OF SEQ ID NOS: 24

<210> SEQ ID NO 1
<211> LENGTH: 585
<212> TYPE: DNA
<213> ORGANISM: Artificial Sequence
<220> FEATURE:
<223> OTHER INFORMATION: Synthetically engineered
```

<400> SEQUENCE: 1 atggcccaga cctgcctcac gtcgccccaa accggctttc acaatggctt cttctattcc 60 ttctggaagg acagtccggg cacggtgaat ttttgcctgt tggagggcgg ccgttacaca 120 tcgaactgga gcggcatcaa caactgggtg ggcggcaagg gatggcagac cggttcacgc 180 cggaacatca cgtactcggg cagcttcaat acaccgggca acggctacct ggcgctttac 240 ggatggacca ccaatccact cgtcgagtac tacgtcgtcg atagctgggg gagctggcgt 300 ccgccgggtt cggacggaac gttcctgggg acggtcaaca gcgatggcgg aacgtatgac 360 atctatcgcg cgcagcgggt caacgcgccg tccatcatcg gcaacgccac gttctatcaa 420 tactggagcg ttcggcagtc gaagcgggta ggtgggacga tcaccaccgg aaaccacttc 480 gacgcgtggg ccagcgtggg cctgaacctg ggcactcaca actaccagat catggcgacc 540 gagggctacc aaagcagcgg cagctccgac atcacggtga gttga 585

<210> SEQ ID NO 2
<211> LENGTH: 194
<212> TYPE: PRT
<213> ORGANISM: Artificial Sequence
<220> FEATURE:
<223> OTHER INFORMATION: Synthetically engineered

<400> SEQUENCE: 2

Met Ala Gln Thr Cys Leu Thr Ser Pro Gln Thr Gly Phe His Asn Gly
1 5 10 15

Phe Phe Tyr Ser Phe Trp Lys Asp Ser Pro Gly Thr Val Asn Phe Cys
20 25 30

Leu Leu Glu Gly Gly Arg Tyr Thr Ser Asn Trp Ser Gly Ile Asn Asn
35 40 45

Trp Val Gly Gly Lys Gly Trp Gln Thr Gly Ser Arg Arg Asn Ile Thr
50 55 60

Tyr Ser Gly Ser Phe Asn Thr Pro Gly Asn Gly Tyr Leu Ala Leu Tyr
65 70 75 80

Gly Trp Thr Thr Asn Pro Leu Val Glu Tyr Tyr Val Val Asp Ser Trp
85 90 95

Gly Ser Trp Arg Pro Pro Gly Ser Asp Gly Thr Phe Leu Gly Thr Val
100 105 110

Asn Ser Asp Gly Gly Thr Tyr Asp Ile Tyr Arg Ala Gln Arg Val Asn
115 120 125

Ala Pro Ser Ile Ile Gly Asn Ala Thr Phe Tyr Gln Tyr Trp Ser Val
130 135 140

Arg Gln Ser Lys Arg Val Gly Gly Thr Ile Thr Thr Gly Asn His Phe
145 150 155 160

Asp Ala Trp Ala Ser Val Gly Leu Asn Leu Gly Thr His Asn Tyr Gln
165 170 175

Ile Met Ala Thr Glu Gly Tyr Gln Ser Ser Gly Ser Ser Asp Ile Thr
180 185 190

Val Ser

<210> SEQ ID NO 3
<211> LENGTH: 1365
<212> TYPE: DNA
<213> ORGANISM: Clostridium thermocellum

<400> SEQUENCE: 3 gtgaaaaaaa ttgtttcttt ggtttgtgtg cttgtgatgc tggtaagcat cttaggctcg 60

```
ttttcagtcg tagcggcatc accggtaaaa ggctttcagg tatcgggaac aaagcttttg    120

gatgcaagcg gaaacgagct tgtaatgagg ggcatgcgtg atatttcagc aatagatttg    180

gttaaagaaa taaaaatcgg atggaatttg ggaaatactt tggatgctcc tacagagact    240

gcctggggaa atccaaggac aaccaaggca atgatagaaa aggtaaggga aatgggcttt    300

aatgccgtca gagtgcctgt tacctgggat acgcacatcg gacctgctcc ggactataaa    360

attgacgaag catggctgaa cagagttgag gaagtggtaa actatgttct tgactgcggt    420

atgtacgcga tcataaatgt tcaccatgac aatacatgga ttatacctac atatgccaat    480

gagcaaagga gtaaagaaaa acttgtaaaa gtttgggaac aaatagcaac ccgttttaaa    540

gattatgacg accatttgtt gtttgagaca atgaacgaac cgagagaagt aggttcacct    600

atggaatgga tgggcggaac gtatgaaaac cgagatgtga taaacagatt taatttggcg    660

gttgttaata ccatcagagc aagcggcgga aataacgata aaagattcat actggttccg    720

accaatgcgg caaccggcct ggatgttgca ttaaacgacc ttgtcattcc gaacaatgac    780

agcagagtca tagtatccat acatgcttat tcaccgtatt tctttgctat ggatgtcaac    840

ggaacttcat attggggaag tgactatgac aaggcttctc ttacaagtga acttgatgct    900

atttacaaca gatttgtgaa aaacggaagg gctgtaatta tcggagaatt cggaaccatt    960

gacaagaaca acctgtcttc aagggtggct catgccgagc actatgcaag agaagcagtt   1020

tcaagaggaa ttgctgtttt ctggtgggat aacggctatt acaatccggg tgatgcagag   1080

acttatgcat tgctgaacag aaaaactctc tcatggtatt atcctgaaat tgtccaggct   1140

cttatgagag gtgccggcgt tgaaccttta gtttcaccga ctcctacacc tacattaatg   1200

ccgacccccct cgcccacggt gacagcaaat attttgtacg gtgacgtaaa cggggacgga   1260

aaaataaatt ctacagactg tacaatgcta aagagatata ttttgcgtgg catagaagaa   1320

ttcccaagtc ctagcggaat tatagccgct gacgtaaatg cggat                   1365
```

```
<210> SEQ ID NO 4
<211> LENGTH: 455
<212> TYPE: PRT
<213> ORGANISM: Clostridium thermocellum
<220> FEATURE:
<221> NAME/KEY: SIGNAL
<222> LOCATION: (1)...(25)
<220> FEATURE:
<221> NAME/KEY: DOMAIN
<222> LOCATION: (71)...(359)
<223> OTHER INFORMATION: Cellulase (glycosyl hydrolase family 5)
<220> FEATURE:
<221> NAME/KEY: DOMAIN
<222> LOCATION: (415)...(435)
<223> OTHER INFORMATION: Dockerin type I repeat
<220> FEATURE:
<221> NAME/KEY: SITE
<222> LOCATION: (186)...(195)
<223> OTHER INFORMATION: Glycosyl hydrolases family 5 signature. Prosite
      id = PS00659
<220> FEATURE:
<221> NAME/KEY: SITE
<222> LOCATION: (280)...(283)
<223> OTHER INFORMATION: N-glycosylation site. Prosite id = PS00001
<220> FEATURE:
<221> NAME/KEY: SITE
<222> LOCATION: (415)...(434)
<223> OTHER INFORMATION: Clostridium cellulosome enzymes repeated domain
      signature. Prosite id = PS00448
<220> FEATURE:
<221> NAME/KEY: SITE
<222> LOCATION: (423)...(426)
<223> OTHER INFORMATION: N-glycosylation site. Prosite id = PS00001
```

<400> SEQUENCE: 4

Met Lys Lys Ile Val Ser Leu Val Cys Val Leu Val Met Leu Val Ser
1 5 10 15

Ile Leu Gly Ser Phe Ser Val Val Ala Ala Ser Pro Val Lys Gly Phe
20 25 30

Gln Val Ser Gly Thr Lys Leu Leu Asp Ala Ser Gly Asn Glu Leu Val
35 40 45

Met Arg Gly Met Arg Asp Ile Ser Ala Ile Asp Leu Val Lys Glu Ile
50 55 60

Lys Ile Gly Trp Asn Leu Gly Asn Thr Leu Asp Ala Pro Thr Glu Thr
65 70 75 80

Ala Trp Gly Asn Pro Arg Thr Thr Lys Ala Met Ile Glu Lys Val Arg
85 90 95

Glu Met Gly Phe Asn Ala Val Arg Val Pro Val Thr Trp Asp Thr His
100 105 110

Ile Gly Pro Ala Pro Asp Tyr Lys Ile Asp Glu Ala Trp Leu Asn Arg
115 120 125

Val Glu Glu Val Val Asn Tyr Val Leu Asp Cys Gly Met Tyr Ala Ile
130 135 140

Ile Asn Val His His Asp Asn Thr Trp Ile Ile Pro Thr Tyr Ala Asn
145 150 155 160

Glu Gln Arg Ser Lys Glu Lys Leu Val Lys Val Trp Glu Gln Ile Ala
165 170 175

Thr Arg Phe Lys Asp Tyr Asp Asp His Leu Leu Phe Glu Thr Met Asn
180 185 190

Glu Pro Arg Glu Val Gly Ser Pro Met Glu Trp Met Gly Gly Thr Tyr
195 200 205

Glu Asn Arg Asp Val Ile Asn Arg Phe Asn Leu Ala Val Val Asn Thr
210 215 220

Ile Arg Ala Ser Gly Gly Asn Asn Asp Lys Arg Phe Ile Leu Val Pro
225 230 235 240

Thr Asn Ala Ala Thr Gly Leu Asp Val Ala Leu Asn Asp Leu Val Ile
245 250 255

Pro Asn Asn Asp Ser Arg Val Ile Val Ser Ile His Ala Tyr Ser Pro
260 265 270

Tyr Phe Phe Ala Met Asp Val Asn Gly Thr Ser Tyr Trp Gly Ser Asp
275 280 285

Tyr Asp Lys Ala Ser Leu Thr Ser Glu Leu Asp Ala Ile Tyr Asn Arg
290 295 300

Phe Val Lys Asn Gly Arg Ala Val Ile Ile Gly Glu Phe Gly Thr Ile
305 310 315 320

Asp Lys Asn Asn Leu Ser Ser Arg Val Ala His Ala Glu His Tyr Ala
325 330 335

Arg Glu Ala Val Ser Arg Gly Ile Ala Val Phe Trp Trp Asp Asn Gly
340 345 350

Tyr Tyr Asn Pro Gly Asp Ala Glu Thr Tyr Ala Leu Leu Asn Arg Lys
355 360 365

Thr Leu Ser Trp Tyr Tyr Pro Glu Ile Val Gln Ala Leu Met Arg Gly
370 375 380

Ala Gly Val Glu Pro Leu Val Ser Pro Thr Pro Thr Pro Thr Leu Met
385 390 395 400

Pro Thr Pro Ser Pro Thr Val Thr Ala Asn Ile Leu Tyr Gly Asp Val

```
                405                 410                 415

Asn Gly Asp Gly Lys Ile Asn Ser Thr Asp Cys Thr Met Leu Lys Arg
            420                 425                 430

Tyr Ile Leu Arg Gly Ile Glu Glu Phe Pro Ser Pro Ser Gly Ile Ile
        435                 440                 445

Ala Ala Asp Val Asn Ala Asp
    450                 455


<210> SEQ ID NO 5
<211> LENGTH: 2610
<212> TYPE: DNA
<213> ORGANISM: Cochliobolus heterostrophus ATCC 48331

<400> SEQUENCE: 5

atgctgtggc ttgcacaagc attgttggtc ggccttgccc aggcatcgcc caggttccct     60

cgtgctacca acgacaccgg cagtgattct ttgaacaatg cccagagccc gccattctac    120

ccaagtcctt gggtagatcc caccaccaag gactgggcgg ctgcctatga aaaagcaaag    180

gcttttgtta gccaattgac tcttattgag aaggtcaacc tcaccaccgg cactggatgg    240

cagagcgacc actgcgttgg taacgtgggc gctattcctc gccttggctt tgatcccctc    300

tgcctccagg acagccctct cggcatccgt ttcgcagact acgtttctgc tttcccagca    360

ggtggcacca ttgctgcatc atgggaccgc tatgagtttt acacccgcgg taacgagatg    420

ggtaaggagc accgaaggaa gggagtcgac gttcagcttg gtcctgccat tggacctctt    480

ggtcgccacc ccaagggcgg tcgtaactgg gaaggcttca gtcctgatcc tgtactttcc    540

ggtgtggccg tgagcgaaac agtccgcggt atccaggatg ctggtgtcat tgcctgcact    600

aagcacttcc ttctgaacga gcaagaacat ttccgtcagc ccggcagttt cggagatatc    660

ccctttgtcg atgccatcag ctccaatacc gatgacacga ctctacacga gctctacctg    720

tggccctttg ccgacgccgt ccgcgctggt actggtgcca tcatgtgctc ttacaacaag    780

gccaacaact cgcaactctg ccaaaactcg caccttcaaa actatattct caagggcgag    840

cttggcttcc agggtttcat tgtatctgac tgggatgcac agcactcggg cgttgcgtcg    900

gcttatgctg gattggacat gactatgcct ggtgatactg gattcaacac tggactgtcc    960

ttctggggcg ctaacatgac cgtctccatt ctcaacggca ccattcccca gtggcgtctc   1020

gacgatgcgg ccatccgtat catgaccgca tactactttg tcggccttga tgagtctatc   1080

cctgtcaact ttgacagctg gcaaactagc acgtacggat tcgagcattt tttcggaaag   1140

aagggcttcg gtctgatcaa caagcacatt gacgttcgcg aggagcactt ccgctccatc   1200

cgccgctctg ctgccaagtc aaccgttctc ctcaagaact ctggcgtcct tcccctctct   1260

ggaaaggaga agtggactgc tgtatttgga gaagatgctg gcgaaaaccc gctgggcccc   1320

aacggatgcg ctgaccgcgg ctgcgactct ggcaccttgg ccatgggctg gggttcggga   1380

actgcagact tcccttacct cgtcactcct ctcgaagcca tcaagcgtga ggttggcgag   1440

aatggcggcg tgatcacttc ggtcacagac aactacgcca cttcgcagat ccagaccatg   1500

gccagcaggg ccagccactc gattgtcttc gtcaatgccg actctggtga aggttacatc   1560

actgttgata acaacatggg tgaccgcaac aacatgactg tgtggggcaa tggtgatgtg   1620

cttgtcaaga atatctctgc tctgtgcaac aacacgattg tggttatcca ctctgtcggc   1680

ccagtcatta ttgacgcctg gaaggccaac gacaacgtga ctgccattct ctgggctggt   1740

cttcctggcc aggagtctgg taactcgatt gctgacattc tatacggaca ccacaaccct   1800
```

```
ggtggcaagc tccccttcac cattggcagc tcttcagagg agtatggccc tgatgtcatc   1860

tacgagccca cgaacggcat cctcagccct caggccaact ttgaagaggg cgtcttcatt   1920

gactaccgcg cgtttgacaa ggcgggcatt gagcccacgt acgaatttgg ctttggtctt   1980

tcgtacacga cttttgaata ctcggacctc aaggtcactg cgcagtctgc cgaggcttac   2040

aagcctttca ccggccagac ttcggctgcc cctacattcg gaaacttcag caagaacccc   2100

gaggactacc agtaccctcc cggccttgtt taccccgaca cgttcatcta cccctacctc   2160

aactcgactg acctcaagac ggcatctcag gatcccgagt acggcctcaa cgttacctgg   2220

cccaagggct ctaccgatgg ctcgcctcag acccgcattg cggctggtgg tgcgcccggc   2280

ggtaaccccc agctctggga cgttttgttc aaggtcgagg ccacgatcac caacactggt   2340

cacgttgctg gtgacgaggt ggcccaggcg tacatctcgc ttggtggccc caacgacccc   2400

aaggtgctac tccgtgactt tgaccgcttg accatcaagc ctggtgagag cgctgttttc   2460

acagccaaca tcacccgccg tgatgtcagc aactgggaca ctgtcagcca gaactgggtc   2520

attaccgagt accccaagac gatccacgtt ggtgccagtt cgaggaacct tcctctttct   2580

gccccactgg acactagcag ctttagataa                                    2610
```

```
<210> SEQ ID NO 6
<211> LENGTH: 869
<212> TYPE: PRT
<213> ORGANISM: Cochliobolus heterostrophus ATCC 48331
<220> FEATURE:
<221> NAME/KEY: DOMAIN
<222> LOCATION: (89)...(310)
<223> OTHER INFORMATION: Glycosyl hydrolase family 3 N terminal domain
<220> FEATURE:
<221> NAME/KEY: DOMAIN
<222> LOCATION: (408)...(642)
<223> OTHER INFORMATION: Glycosyl hydrolase family 3 C terminal domain
<220> FEATURE:
<221> NAME/KEY: SITE
<222> LOCATION: (24)...(27)
<223> OTHER INFORMATION: N-glycosylation site. Prosite id = PS00001
<220> FEATURE:
<221> NAME/KEY: SITE
<222> LOCATION: (73)...(76)
<223> OTHER INFORMATION: N-glycosylation site. Prosite id = PS00001
<220> FEATURE:
<221> NAME/KEY: SITE
<222> LOCATION: (262)...(265)
<223> OTHER INFORMATION: N-glycosylation site. Prosite id = PS00001
<220> FEATURE:
<221> NAME/KEY: SITE
<222> LOCATION: (276)...(293)
<223> OTHER INFORMATION: Glycosyl hydrolases family 3 active site.
      Prosite id = PS00775
<220> FEATURE:
<221> NAME/KEY: SITE
<222> LOCATION: (332)...(335)
<223> OTHER INFORMATION: N-glycosylation site. Prosite id = PS00001
<220> FEATURE:
<221> NAME/KEY: SITE
<222> LOCATION: (539)...(542)
<223> OTHER INFORMATION: N-glycosylation site. Prosite id = PS00001
<220> FEATURE:
<221> NAME/KEY: SITE
<222> LOCATION: (531)...(534)
<223> OTHER INFORMATION: N-glycosylation site. Prosite id = PS00001
<220> FEATURE:
<221> NAME/KEY: SITE
<222> LOCATION: (550)...(553)
<223> OTHER INFORMATION: N-glycosylation site. Prosite id = PS00001
<220> FEATURE:
<221> NAME/KEY: SITE
<222> LOCATION: (572)...(575)
<223> OTHER INFORMATION: N-glycosylation site. Prosite id = PS00001
<220> FEATURE:
```

<221> NAME/KEY: SITE
<222> LOCATION: (695)...(698)
<223> OTHER INFORMATION: N-glycosylation site. Prosite id = PS00001
<220> FEATURE:
<221> NAME/KEY: SITE
<222> LOCATION: (721)...(724)
<223> OTHER INFORMATION: N-glycosylation site. Prosite id = PS00001
<220> FEATURE:
<221> NAME/KEY: SITE
<222> LOCATION: (737)...(740)
<223> OTHER INFORMATION: N-glycosylation site. Prosite id = PS00001
<220> FEATURE:
<221> NAME/KEY: SITE
<222> LOCATION: (823)...(826)
<223> OTHER INFORMATION: N-glycosylation site. Prosite id = PS00001

<400> SEQUENCE: 6

```
Met Leu Trp Leu Ala Gln Ala Leu Leu Val Gly Leu Ala Gln Ala Ser
1               5                   10                  15

Pro Arg Phe Pro Arg Ala Thr Asn Asp Thr Gly Ser Asp Ser Leu Asn
            20                  25                  30

Asn Ala Gln Ser Pro Pro Phe Tyr Pro Ser Pro Trp Val Asp Pro Thr
        35                  40                  45

Thr Lys Asp Trp Ala Ala Ala Tyr Glu Lys Ala Lys Ala Phe Val Ser
    50                  55                  60

Gln Leu Thr Leu Ile Glu Lys Val Asn Leu Thr Thr Gly Thr Gly Trp
65                  70                  75                  80

Gln Ser Asp His Cys Val Gly Asn Val Gly Ala Ile Pro Arg Leu Gly
                85                  90                  95

Phe Asp Pro Leu Cys Leu Gln Asp Ser Pro Leu Gly Ile Arg Phe Ala
            100                 105                 110

Asp Tyr Val Ser Ala Phe Pro Ala Gly Gly Thr Ile Ala Ala Ser Trp
        115                 120                 125

Asp Arg Tyr Glu Phe Tyr Thr Arg Gly Asn Glu Met Gly Lys Glu His
    130                 135                 140

Arg Arg Lys Gly Val Asp Val Gln Leu Gly Pro Ala Ile Gly Pro Leu
145                 150                 155                 160

Gly Arg His Pro Lys Gly Gly Arg Asn Trp Glu Gly Phe Ser Pro Asp
                165                 170                 175

Pro Val Leu Ser Gly Val Ala Val Ser Glu Thr Val Arg Gly Ile Gln
            180                 185                 190

Asp Ala Gly Val Ile Ala Cys Thr Lys His Phe Leu Leu Asn Glu Gln
        195                 200                 205

Glu His Phe Arg Gln Pro Gly Ser Phe Gly Asp Ile Pro Phe Val Asp
    210                 215                 220

Ala Ile Ser Ser Asn Thr Asp Asp Thr Thr Leu His Glu Leu Tyr Leu
225                 230                 235                 240

Trp Pro Phe Ala Asp Ala Val Arg Ala Gly Thr Gly Ala Ile Met Cys
                245                 250                 255

Ser Tyr Asn Lys Ala Asn Asn Ser Gln Leu Cys Gln Asn Ser His Leu
            260                 265                 270

Gln Asn Tyr Ile Leu Lys Gly Glu Leu Gly Phe Gln Gly Phe Ile Val
        275                 280                 285

Ser Asp Trp Asp Ala Gln His Ser Gly Val Ala Ser Ala Tyr Ala Gly
    290                 295                 300

Leu Asp Met Thr Met Pro Gly Asp Thr Gly Phe Asn Thr Gly Leu Ser
305                 310                 315                 320

Phe Trp Gly Ala Asn Met Thr Val Ser Ile Leu Asn Gly Thr Ile Pro
```

```
                325                 330                 335

Gln Trp Arg Leu Asp Asp Ala Ala Ile Arg Ile Met Thr Ala Tyr Tyr
            340                 345                 350

Phe Val Gly Leu Asp Glu Ser Ile Pro Val Asn Phe Asp Ser Trp Gln
        355                 360                 365

Thr Ser Thr Tyr Gly Phe Glu His Phe Phe Gly Lys Lys Gly Phe Gly
    370                 375                 380

Leu Ile Asn Lys His Ile Asp Val Arg Glu Glu His Phe Arg Ser Ile
385                 390                 395                 400

Arg Arg Ser Ala Ala Lys Ser Thr Val Leu Leu Lys Asn Ser Gly Val
                405                 410                 415

Leu Pro Leu Ser Gly Lys Glu Lys Trp Thr Ala Val Phe Gly Glu Asp
            420                 425                 430

Ala Gly Glu Asn Pro Leu Gly Pro Asn Gly Cys Ala Asp Arg Gly Cys
        435                 440                 445

Asp Ser Gly Thr Leu Ala Met Gly Trp Gly Ser Gly Thr Ala Asp Phe
    450                 455                 460

Pro Tyr Leu Val Thr Pro Leu Glu Ala Ile Lys Arg Glu Val Gly Glu
465                 470                 475                 480

Asn Gly Gly Val Ile Thr Ser Val Thr Asp Asn Tyr Ala Thr Ser Gln
                485                 490                 495

Ile Gln Thr Met Ala Ser Arg Ala Ser His Ser Ile Val Phe Val Asn
            500                 505                 510

Ala Asp Ser Gly Glu Gly Tyr Ile Thr Val Asp Asn Asn Met Gly Asp
        515                 520                 525

Arg Asn Asn Met Thr Val Trp Gly Asn Gly Asp Val Leu Val Lys Asn
    530                 535                 540

Ile Ser Ala Leu Cys Asn Asn Thr Ile Val Val Ile His Ser Val Gly
545                 550                 555                 560

Pro Val Ile Ile Asp Ala Trp Lys Ala Asn Asp Asn Val Thr Ala Ile
                565                 570                 575

Leu Trp Ala Gly Leu Pro Gly Gln Glu Ser Gly Asn Ser Ile Ala Asp
            580                 585                 590

Ile Leu Tyr Gly His His Asn Pro Gly Gly Lys Leu Pro Phe Thr Ile
        595                 600                 605

Gly Ser Ser Ser Glu Glu Tyr Gly Pro Asp Val Ile Tyr Glu Pro Thr
    610                 615                 620

Asn Gly Ile Leu Ser Pro Gln Ala Asn Phe Glu Glu Gly Val Phe Ile
625                 630                 635                 640

Asp Tyr Arg Ala Phe Asp Lys Ala Gly Ile Glu Pro Thr Tyr Glu Phe
                645                 650                 655

Gly Phe Gly Leu Ser Tyr Thr Thr Phe Glu Tyr Ser Asp Leu Lys Val
            660                 665                 670

Thr Ala Gln Ser Ala Glu Ala Tyr Lys Pro Phe Thr Gly Gln Thr Ser
        675                 680                 685

Ala Ala Pro Thr Phe Gly Asn Phe Ser Lys Asn Pro Glu Asp Tyr Gln
    690                 695                 700

Tyr Pro Pro Gly Leu Val Tyr Pro Asp Thr Phe Ile Tyr Pro Tyr Leu
705                 710                 715                 720

Asn Ser Thr Asp Leu Lys Thr Ala Ser Gln Asp Pro Glu Tyr Gly Leu
                725                 730                 735

Asn Val Thr Trp Pro Lys Gly Ser Thr Asp Gly Ser Pro Gln Thr Arg
            740                 745                 750
```

```
Ile Ala Ala Gly Gly Ala Pro Gly Gly Asn Pro Gln Leu Trp Asp Val
        755                 760                 765

Leu Phe Lys Val Glu Ala Thr Ile Thr Asn Thr Gly His Val Ala Gly
    770                 775                 780

Asp Glu Val Ala Gln Ala Tyr Ile Ser Leu Gly Gly Pro Asn Asp Pro
785                 790                 795                 800

Lys Val Leu Leu Arg Asp Phe Asp Arg Leu Thr Ile Lys Pro Gly Glu
                805                 810                 815

Ser Ala Val Phe Thr Ala Asn Ile Thr Arg Arg Asp Val Ser Asn Trp
            820                 825                 830

Asp Thr Val Ser Gln Asn Trp Val Ile Thr Glu Tyr Pro Lys Thr Ile
        835                 840                 845

His Val Gly Ala Ser Ser Arg Asn Leu Pro Leu Ser Ala Pro Leu Asp
    850                 855                 860

Thr Ser Ser Phe Arg
865


<210> SEQ ID NO 7
<211> LENGTH: 1527
<212> TYPE: DNA
<213> ORGANISM: Unknown
<220> FEATURE:
<223> OTHER INFORMATION: Obtained from environmental sample

<400> SEQUENCE: 7

atgtaccgca ttctcgccac cgcctcggct ctgctggcaa ccgcccgtgc ccagcaagcc     60

tgcaccctca acgccgaaag caagcctgcc ttgacctggt ccaagtgcac atccagcggc    120

tgcagcaacg tccgcggatc tgtcgtggtt gacgccaact ggcgatggac ccatagcacc    180

tccagcagca ccaactgcta caccggcaac acctgggaca agactctctg ccccgatgga    240

aagacctgcg ctgacaagtg ctgtcttgat ggtgccgact actctggcac ctacggagtc    300

acctcgagcg gcaaccagct caacctcaag tttgtgactg ttggaccata cagcaccaat    360

gttggcagcc gtctctacct catggaggat gagaacaact accagatgtt cgacctcctg    420

ggcaacgaat tcacctttga tgtcgatgtc aacaacatcg gatgcggcct gaacggcgcc    480

ctctacttcg tctccatgga caaggatggt ggcaagagcc gcttcagcac caacaaggct    540

ggtgccaagt acggaactgg ctactgcgat gcccagtgcc ctcgcgatgt caagttcatc    600

aacggagttg ccaactccga cgactggcag ccctccgcca gcgacaagaa cgccggtgtt    660

ggcaagtacg gcacctgctg ccctgagatg gatatctggg aggccaacaa gatctccacg    720

gcttacactc cccatccctg caagagcctc acccagcagt cctgcgaggg cgatgcctgc    780

ggtggcacct actcttctac tcgctatgct ggaacttgcg atcccgatgg ttgcgatttc    840

aacccttacc gccagggcaa ccacaccttc tacggtcccg gctccggctt caacgttgat    900

accaccaaga aggtgactgt cgtgacccag ttcatcaagg gcagcgacgg caagctctct    960

gagatcaagc gtctctatgt tcagaacggc aaggtcattg gcaacccccca gtccgagatt   1020

gccaacaacc ccggcagctc cgtcaccgac agcttctgca aggcccagaa ggttgcattc   1080

aacgaccccg atgacttcaa caagaagggt ggctggagcg gcatgaacga cgccctcgcc   1140

aagcccatgg ttctcgtcat gagcctgtgg cacgaccact acgccaacat gctctggctc   1200

gactctacct accccaaggg ctccaagact cccggctctg ctcgtggctc ttgccctgag   1260

gactctggtg tccccgccac tctcgagaag gaggtcccca actccagcgt cagcttctcc   1320
```

```
aacatcaagt tcggtcccat cggcagcacc tactccggca ccggcggcaa caaccccgac   1380

cccgaggagc ctgaggagcc cgaggagcct gtcggcaccg tcccccagtg gggccagtgc   1440

ggcggcatca actacagcgg ccccaccgcc tgcgtgtctc cctacaagtg caacaagatc   1500

aacgactact actcccagtg ctactag                                       1527


<210> SEQ ID NO 8
<211> LENGTH: 508
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(20)
<220> FEATURE:
<221> NAME/KEY: DOMAIN
<222> LOCATION: (19)...(453)
<223> OTHER INFORMATION: Glycosyl hydrolase family 7
<220> FEATURE:
<221> NAME/KEY: DOMAIN
<222> LOCATION: (476)...(504)
<223> OTHER INFORMATION: Fungal cellulose binding domain

<400> SEQUENCE: 8

Met Tyr Arg Ile Leu Ala Thr Ala Ser Ala Leu Leu Ala Thr Ala Arg
1               5                   10                  15

Ala Gln Gln Ala Cys Thr Leu Asn Ala Glu Ser Lys Pro Ala Leu Thr
            20                  25                  30

Trp Ser Lys Cys Thr Ser Ser Gly Cys Ser Asn Val Arg Gly Ser Val
        35                  40                  45

Val Val Asp Ala Asn Trp Arg Trp Thr His Ser Thr Ser Ser Ser Thr
    50                  55                  60

Asn Cys Tyr Thr Gly Asn Thr Trp Asp Lys Thr Leu Cys Pro Asp Gly
65                  70                  75                  80

Lys Thr Cys Ala Asp Lys Cys Cys Leu Asp Gly Ala Asp Tyr Ser Gly
                85                  90                  95

Thr Tyr Gly Val Thr Ser Ser Gly Asn Gln Leu Asn Leu Lys Phe Val
            100                 105                 110

Thr Val Gly Pro Tyr Ser Thr Asn Val Gly Ser Arg Leu Tyr Leu Met
        115                 120                 125

Glu Asp Glu Asn Asn Tyr Gln Met Phe Asp Leu Leu Gly Asn Glu Phe
    130                 135                 140

Thr Phe Asp Val Asp Val Asn Asn Ile Gly Cys Gly Leu Asn Gly Ala
145                 150                 155                 160

Leu Tyr Phe Val Ser Met Asp Lys Asp Gly Gly Lys Ser Arg Phe Ser
                165                 170                 175

Thr Asn Lys Ala Gly Ala Lys Tyr Gly Thr Gly Tyr Cys Asp Ala Gln
            180                 185                 190

Cys Pro Arg Asp Val Lys Phe Ile Asn Gly Val Ala Asn Ser Asp Asp
        195                 200                 205

Trp Gln Pro Ser Ala Ser Asp Lys Asn Ala Gly Val Gly Lys Tyr Gly
    210                 215                 220

Thr Cys Cys Pro Glu Met Asp Ile Trp Glu Ala Asn Lys Ile Ser Thr
225                 230                 235                 240

Ala Tyr Thr Pro His Pro Cys Lys Ser Leu Thr Gln Gln Ser Cys Glu
                245                 250                 255

Gly Asp Ala Cys Gly Gly Thr Tyr Ser Ser Thr Arg Tyr Ala Gly Thr
            260                 265                 270
```

```
Cys Asp Pro Asp Gly Cys Asp Phe Asn Pro Tyr Arg Gln Gly Asn His
        275                 280                 285

Thr Phe Tyr Gly Pro Gly Ser Gly Phe Asn Val Asp Thr Thr Lys Lys
    290                 295                 300

Val Thr Val Val Thr Gln Phe Ile Lys Gly Ser Asp Gly Lys Leu Ser
305                 310                 315                 320

Glu Ile Lys Arg Leu Tyr Val Gln Asn Gly Lys Val Ile Gly Asn Pro
                325                 330                 335

Gln Ser Glu Ile Ala Asn Asn Pro Gly Ser Ser Val Thr Asp Ser Phe
            340                 345                 350

Cys Lys Ala Gln Lys Val Ala Phe Asn Asp Pro Asp Asp Phe Asn Lys
        355                 360                 365

Lys Gly Gly Trp Ser Gly Met Asn Asp Ala Leu Ala Lys Pro Met Val
    370                 375                 380

Leu Val Met Ser Leu Trp His Asp His Tyr Ala Asn Met Leu Trp Leu
385                 390                 395                 400

Asp Ser Thr Tyr Pro Lys Gly Ser Lys Thr Pro Gly Ser Ala Arg Gly
                405                 410                 415

Ser Cys Pro Glu Asp Ser Gly Val Pro Ala Thr Leu Glu Lys Glu Val
            420                 425                 430

Pro Asn Ser Ser Val Ser Phe Ser Asn Ile Lys Phe Gly Pro Ile Gly
        435                 440                 445

Ser Thr Tyr Ser Gly Thr Gly Gly Asn Asn Pro Asp Pro Glu Glu Pro
    450                 455                 460

Glu Glu Pro Glu Glu Pro Val Gly Thr Val Pro Gln Trp Gly Gln Cys
465                 470                 475                 480

Gly Gly Ile Asn Tyr Ser Gly Pro Thr Ala Cys Val Ser Pro Tyr Lys
                485                 490                 495

Cys Asn Lys Ile Asn Asp Tyr Tyr Ser Gln Cys Tyr
            500                 505


<210> SEQ ID NO 9
<211> LENGTH: 1413
<212> TYPE: DNA
<213> ORGANISM: Unknown
<220> FEATURE:
<223> OTHER INFORMATION: Obtained from an environmental sample

<400> SEQUENCE: 9

atgcgctata catggtcggt cgcggcggcg ctgctgccat gcgcaatcca ggctcagcaa      60

accctctatg gacaatgtgg tggtcagggc tactccggac tcaccagctg cgtggcggga     120

gcaacatgct ccaccgtaaa tgaatactac gctcagtgta cgccagcagc aggcagcgcc     180

acttccacca ccttgaagac aactacgacc accgctgggg cgacgacgac gacgactagc     240

aagacttctg cttcccagac gtctactact aaaacctcaa ccagtaccgc ctcaacaacc     300

acggctacaa ccacggccag cgcgagcggc aacccgttca gtgggtacca gctctacgtg     360

aacccctact actcctccga agtggcctcc ctggctatcc catccctcac ggggacactt     420

tcctcgctcc aggctgcagc cacagccgca gccaaggtgc cctctttcgt ctggctggac     480

gtggctgcca aggtgccgac gatggccacc tacctggccg acatcaaagc ccagaatgca     540

gcgggagcca accccccgt cgccggccag tttgtggtct acgacctccc tgaccgcgac     600

tgcgccgcgc tggccagcaa cggcgagtac tccatcgcca acaacggtgt ggccaactac     660

aaggcctaca tcgactccat ccgcaaggtc ctggtgcagt actcggatgt gcacaccatt     720
```

```
ctggtgatcg agcccgacag tctcgccaac ctggtgacca acctcaatgt ggccaaatgt    780

gccaacgctc agagcgccta cctcgaatgc accaactatg ccctggagca gctgaacctc    840

cccaacgtgg ccatgtatct tgatgccgga cacgccggct ggctcggctg gcccgcgaac    900

cagcaaccgg ccgccaatct gtacgcgagc gtgtacaaga acgccagctc gcccgccgca    960

gtgcgcggcc tggccacgaa cgtcgccaac tacaacgcct tcaccatcgc ctcgtgcccg   1020

tcgtacaccc agggcaacag cgtctgcgac gagcagcagt acatcaacgc gatcgccccg   1080

ctcctgtcag cgcagggctt caacgcccac ttcatcgtcg acaccggccg caacggcaaa   1140

cagcccaccg gccaacaagc ctggggcgac tggtgcaacg tcatcaacac ggggttcggc   1200

gtgcgcccga ccaccaacac gggcgacgcg ctcgtcgacg ccttcgtctg ggtcaagccc   1260

ggcggcgaga gcgacggcac ctccgatagc tcggcgaccc gctacgacgc ccactgcggg   1320

tacagcgatg ccttgcagcc ggcgccggag gcggggacct ggttccaggc ctacttcgta   1380

caattgctct cgaacgccaa tccggctttc tag                                1413
```

```
<210> SEQ ID NO 10
<211> LENGTH: 470
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(18)
<220> FEATURE:
<221> NAME/KEY: DOMAIN
<222> LOCATION: (22)...(50)
<223> OTHER INFORMATION: Fungal cellulose binding domain
<220> FEATURE:
<221> NAME/KEY: DOMAIN
<222> LOCATION: (120)...(437)
<223> OTHER INFORMATION: Glycosyl hydrolases family 6
<220> FEATURE:
<221> NAME/KEY: SITE
<222> LOCATION: (26)...(53)
<223> OTHER INFORMATION: Cellulose-binding domain, fungal type. Prosite
      id = PS00562
<220> FEATURE:
<221> NAME/KEY: SITE
<222> LOCATION: (240)...(249)
<223> OTHER INFORMATION: Glycosyl hydrolases family 6 signature 2.
      Prosite id = PS00656
<220> FEATURE:
<221> NAME/KEY: SITE
<222> LOCATION: (314)...(317)
<223> OTHER INFORMATION: N-glycosylation site. Prosite id = PS00001

<400> SEQUENCE: 10

Met Arg Tyr Thr Trp Ser Val Ala Ala Ala Leu Leu Pro Cys Ala Ile
1               5                   10                  15

Gln Ala Gln Gln Thr Leu Tyr Gly Gln Cys Gly Gly Gln Gly Tyr Ser
            20                  25                  30

Gly Leu Thr Ser Cys Val Ala Gly Ala Thr Cys Ser Thr Val Asn Glu
        35                  40                  45

Tyr Tyr Ala Gln Cys Thr Pro Ala Ala Gly Ser Ala Thr Ser Thr Thr
    50                  55                  60

Leu Lys Thr Thr Thr Thr Thr Ala Gly Ala Thr Thr Thr Thr Thr Ser
65                  70                  75                  80

Lys Thr Ser Ala Ser Gln Thr Ser Thr Thr Lys Thr Ser Thr Ser Thr
                85                  90                  95

Ala Ser Thr Thr Thr Ala Thr Thr Thr Ala Ser Ala Ser Gly Asn Pro
```

```
            100                 105                 110

Phe Ser Gly Tyr Gln Leu Tyr Val Asn Pro Tyr Tyr Ser Ser Glu Val
        115                 120                 125

Ala Ser Leu Ala Ile Pro Ser Leu Thr Gly Thr Leu Ser Ser Leu Gln
    130                 135                 140

Ala Ala Ala Thr Ala Ala Ala Lys Val Pro Ser Phe Val Trp Leu Asp
145                 150                 155                 160

Val Ala Ala Lys Val Pro Thr Met Ala Thr Tyr Leu Ala Asp Ile Lys
                165                 170                 175

Ala Gln Asn Ala Ala Gly Ala Asn Pro Pro Val Ala Gly Gln Phe Val
            180                 185                 190

Val Tyr Asp Leu Pro Asp Arg Asp Cys Ala Ala Leu Ala Ser Asn Gly
        195                 200                 205

Glu Tyr Ser Ile Ala Asn Asn Gly Val Ala Asn Tyr Lys Ala Tyr Ile
    210                 215                 220

Asp Ser Ile Arg Lys Val Leu Val Gln Tyr Ser Asp Val His Thr Ile
225                 230                 235                 240

Leu Val Ile Glu Pro Asp Ser Leu Ala Asn Leu Val Thr Asn Leu Asn
                245                 250                 255

Val Ala Lys Cys Ala Asn Ala Gln Ser Ala Tyr Leu Glu Cys Thr Asn
            260                 265                 270

Tyr Ala Leu Glu Gln Leu Asn Leu Pro Asn Val Ala Met Tyr Leu Asp
        275                 280                 285

Ala Gly His Ala Gly Trp Leu Gly Trp Pro Ala Asn Gln Gln Pro Ala
    290                 295                 300

Ala Asn Leu Tyr Ala Ser Val Tyr Lys Asn Ala Ser Ser Pro Ala Ala
305                 310                 315                 320

Val Arg Gly Leu Ala Thr Asn Val Ala Asn Tyr Asn Ala Phe Thr Ile
                325                 330                 335

Ala Ser Cys Pro Ser Tyr Thr Gln Gly Asn Ser Val Cys Asp Glu Gln
            340                 345                 350

Gln Tyr Ile Asn Ala Ile Ala Pro Leu Leu Ser Ala Gln Gly Phe Asn
        355                 360                 365

Ala His Phe Ile Val Asp Thr Gly Arg Asn Gly Lys Gln Pro Thr Gly
    370                 375                 380

Gln Gln Ala Trp Gly Asp Trp Cys Asn Val Ile Asn Thr Gly Phe Gly
385                 390                 395                 400

Val Arg Pro Thr Thr Asn Thr Gly Asp Ala Leu Val Asp Ala Phe Val
                405                 410                 415

Trp Val Lys Pro Gly Gly Glu Ser Asp Gly Thr Ser Asp Ser Ser Ala
            420                 425                 430

Thr Arg Tyr Asp Ala His Cys Gly Tyr Ser Asp Ala Leu Gln Pro Ala
        435                 440                 445

Pro Glu Ala Gly Thr Trp Phe Gln Ala Tyr Phe Val Gln Leu Leu Ser
    450                 455                 460

Asn Ala Asn Pro Ala Phe
465                 470
```

<210> SEQ ID NO 11
<211> LENGTH: 594
<212> TYPE: DNA
<213> ORGANISM: Artificial Sequence
<220> FEATURE:
<223> OTHER INFORMATION: Synthetically generated

<400> SEQUENCE: 11 atggcccaga cctgcctcac gtcgagtcaa accggcacta acaatggctt ctattattcc 60 ttctggaagg acagtccggg cacggtgaat ttttgcctgc agtccggcgg ccgttacaca 120 tcgaactgga gcggcatcaa caactgggtg ggcggcaagg gatggcagac cggttcacgc 180 cggaacatca cgtactcggg cagcttcaat tcaccgggca acggctacct ggcgctttac 240 ggatggacca ccaatccact cgtcgagtac tacgtcgtcg atagctgggg gagctggcgt 300 ccgccgggtt cggacggaac gttcctgggg acggtcaaca gcgatggcgg aacgtatgac 360 atctatcgcg cgcagcgggt caacgcgccg tccatcatcg gcaacgccac gttctatcaa 420 tactggagcg ttcggcagtc gaagcgggta ggtgggacga tcaccaccgg aaaccacttc 480 gacgcgtggg ccagcgtggg cctgaacctg ggcactcaca actaccagat catggcgacc 540 gagggctacc aaagcagcgg cagctccgac atcacggtga gtgaaggcgg ttga 594

<210> SEQ ID NO 12
<211> LENGTH: 197
<212> TYPE: PRT
<213> ORGANISM: Artificial Sequence
<220> FEATURE:
<223> OTHER INFORMATION: Synthetically generated

<400> SEQUENCE: 12

Met Ala Gln Thr Cys Leu Thr Ser Ser Gln Thr Gly Thr Asn Asn Gly
1 5 10 15

Phe Tyr Tyr Ser Phe Trp Lys Asp Ser Pro Gly Thr Val Asn Phe Cys
20 25 30

Leu Gln Ser Gly Gly Arg Tyr Thr Ser Asn Trp Ser Gly Ile Asn Asn
35 40 45

Trp Val Gly Gly Lys Gly Trp Gln Thr Gly Ser Arg Arg Asn Ile Thr
50 55 60

Tyr Ser Gly Ser Phe Asn Ser Pro Gly Asn Gly Tyr Leu Ala Leu Tyr
65 70 75 80

Gly Trp Thr Thr Asn Pro Leu Val Glu Tyr Tyr Val Val Asp Ser Trp
85 90 95

Gly Ser Trp Arg Pro Pro Gly Ser Asp Gly Thr Phe Leu Gly Thr Val
100 105 110

Asn Ser Asp Gly Gly Thr Tyr Asp Ile Tyr Arg Ala Gln Arg Val Asn
115 120 125

Ala Pro Ser Ile Ile Gly Asn Ala Thr Phe Tyr Gln Tyr Trp Ser Val
130 135 140

Arg Gln Ser Lys Arg Val Gly Gly Thr Ile Thr Thr Gly Asn His Phe
145 150 155 160

Asp Ala Trp Ala Ser Val Gly Leu Asn Leu Gly Thr His Asn Tyr Gln
165 170 175

Ile Met Ala Thr Glu Gly Tyr Gln Ser Ser Gly Ser Ser Asp Ile Thr
180 185 190

Val Ser Glu Gly Gly
195

<210> SEQ ID NO 13
<211> LENGTH: 2637
<212> TYPE: DNA
<213> ORGANISM: Unknown
<220> FEATURE:
<223> OTHER INFORMATION: Obtained from environmental sample

<400> SEQUENCE: 13 atgactagtg gacgaaacac atgtgtgtgt ctgttgttga ttgtgctggc gatcggtctt 60 ctgtcaaagc caccggcgag cgcgcaaaat gaggcgcctt ataaagccac gctgacgatc 120 cggttggacc aaccgggagc ggtgatcaat cgcaacatct acggccagtt tgcggagcat 180 ctcggacgtt tgatctacga cgggctctgg gttggtgaag gatcgtcgat cccgaacacg 240 cgcggattgc gtaacgacgt cgttacggcg ttaaaagaat tgcatgtgcc tgtgctgcgt 300 tggcccggcg gctgttttgc cgacgagtat cactggcgtg acggcattgg accacgcgac 360 aagcgtccgc ggcggccgaa cgcgagttgg ggcggcgtcg attcgaatgc gtttggcacg 420 catgagttca tggagctgtg cgagatgttg ggcgcagacg cttatatcaa tggcaacgtc 480 ggcagcggca cgccgcagga gatgatggaa tggatcgagt acatgacttc cgattccgat 540 tcggatctcg ccaacctgcg ccgtcgcaat ggccgcgaca agccgtggaa ggtgccgtat 600 ttcgccgtcg gcaatgagac gtggggctgt ggtggaaata tgcggccgga gttttacgcc 660 gacgtgtatc gccagtacgc cacgttcatc aagaaccatt caggcaatcg cattcagaaa 720 ctcgcgagcg gtggttacga caacaattac aactggaccg aggtgctgat ggcgcaggcg 780 gcgaagcaga tcgatggcct gtcgttgcac tattacacgc tgcccaccgg caactgggac 840 aagaaaggat cggcgacgga attcggcgaa agcgagtggc acgcgacgct cgccaggacg 900 ttgcgcatcg aggagttcat tcagaagcac agcgcgatca tggacaagca cgatccgcag 960 aagcgcgtcg gtttgatggt tgacgagtgg ggcacgtggt acgaccgcga cgagggccgc 1020 gacatgggcg cgctttatca gcagaacacg ttgcgcgatg cggttgcggc cggtatcaat 1080 ctcaatatct ttcacaagta tgccgatcgc gtgcgcatgg cgaacatcgc gcagatggtg 1140 aacgtgttgc aggcgatggt gttgacggac aaagagaaaa tggtgctgac gccgacgtat 1200 cacgtttttc ggatgtatcg cgtgcatcag ggagcgacgc tgatcccggt cgaggttagt 1260 gcgccgcagt acacgctggg tggtgcgtct gtgccgtcgt tgagcgtgtc ggcttcgcgt 1320 gacggtgaag gacgggtgca tctgtcgatc gtgaatctcg atccagcgcg ggcggcggag 1380 atcgatgcga acggaccgtt cagcagtgtc aagggagaag tattgactgc gccggcggtg 1440 aatgcgctga atactttcga tcacccggat agtgtcaagc ccgtgtcttt taatggatat 1500 aaattagaag gctctaaatt aatcctgaat attccggcga aatccgtggt ggtgttggaa 1560 cttggaccac agaaacaagc aacgctcaaa gatgcattca aaaacgattt catgatcggc 1620 gcggcgctca accggcgaca gttcttcgaa gaagacgctc gcggcgcaga gatcgtgcgc 1680 atgcatttca actcgatcac gccggagaac gtgttgaagt gggggctggt ccatcccgaa 1740 ccgaacaagt acgacttcac cgctcccgat cgcttcgtcg aattcggcga gaagcacggc 1800 atgttcgtcg tcggacacac gctcgtctgg cataaccaaa cgccgcgctg ggtttttgaa 1860 gacgaaaaga aacagccgct cgatcgcgag acgttgctga aacgaatgcg cgatcacatc 1920 ttcaccgtcg tcggccgtta caagggacgc attaaaggct gggacgtagt caacgaggcg 1980 ctgaatcagg atggcacgat gcggcagtcg ccgtggttca agatcatcgg cgaggattat 2040 ctcgtcaaag cgtttgagtt tgcccacgag gccgatccag ccgccgagct ttattacaac 2100 gactacgatc tcgagctgcc ggcgaagcgc gcaggcgccg tcgaactgct gaagaaactg 2160 aaagccgcgg gtgtgtcgct tgctggtgtg ggattgcaga accacagtct catggagtgg 2220 ccgtcagccg cagatgtgga tgcgacgatc gcggcgttcg cgaatctggg tttgaaggtt 2280 cacatcacgg aactcgacgt cgacgtgctg ccgcgcacga cgaaacccgg tgcggattac 2340

```
gcagtcgacg tgaaggtgac gccgcagttg aacccgtatc tcgacggctt accggaggcg   2400

cgacagtcgg cgttggcgag gcgttatgcg gagctgtttc acgtgtttag aaaacatcgc   2460

gacgcgatcg agcgtgtgac gttctgggga gttgcggacg gcgattcgtg gttgaacaac   2520

tggcccatcc gcggcaggac aaactatccg ctgctcttcg atcgttccgg ccaaccgaaa   2580

ccggcgttag cgtcggtgat cgaaaccgct aattattcaa cggaacgtcg acggtga      2637


<210> SEQ ID NO 14
<211> LENGTH: 878
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(28)
<220> FEATURE:
<221> NAME/KEY: DOMAIN
<222> LOCATION: (328)...(515)
<223> OTHER INFORMATION: Alpha-L-arabinofuranosidase C-terminus
<220> FEATURE:
<221> NAME/KEY: DOMAIN
<222> LOCATION: (528)...(870)
<223> OTHER INFORMATION: Glycosyl hydrolase family 10
<220> FEATURE:
<221> NAME/KEY: SITE
<222> LOCATION: (127)...(130)
<223> OTHER INFORMATION: N-glycosylation site. Prosite id = PS00001
<220> FEATURE:
<221> NAME/KEY: SITE
<222> LOCATION: (205)...(208)
<223> OTHER INFORMATION: N-glycosylation site. Prosite id = PS00001
<220> FEATURE:
<221> NAME/KEY: SITE
<222> LOCATION: (232)...(235)
<223> OTHER INFORMATION: N-glycosylation site. Prosite id = PS00001
<220> FEATURE:
<221> NAME/KEY: SITE
<222> LOCATION: (251)...(254)
<223> OTHER INFORMATION: N-glycosylation site. Prosite id = PS00001
<220> FEATURE:
<221> NAME/KEY: SITE
<222> LOCATION: (734)...(737)
<223> OTHER INFORMATION: N-glycosylation site. Prosite id = PS00001
<220> FEATURE:
<221> NAME/KEY: SITE
<222> LOCATION: (757)...(767)
<223> OTHER INFORMATION: Glycosyl hydrolases family 10 active site.
      Prosite id = PS00591
<220> FEATURE:
<221> NAME/KEY: SITE
<222> LOCATION: (871)...(874)
<223> OTHER INFORMATION: N-glycosylation site. Prosite id = PS00001

<400> SEQUENCE: 14

Met Thr Ser Gly Arg Asn Thr Cys Val Cys Leu Leu Leu Ile Val Leu
1               5                   10                  15

Ala Ile Gly Leu Leu Ser Lys Pro Pro Ala Ser Ala Gln Asn Glu Ala
            20                  25                  30

Pro Tyr Lys Ala Thr Leu Thr Ile Arg Leu Asp Gln Pro Gly Ala Val
        35                  40                  45

Ile Asn Arg Asn Ile Tyr Gly Gln Phe Ala Glu His Leu Gly Arg Leu
    50                  55                  60

Ile Tyr Asp Gly Leu Trp Val Gly Glu Gly Ser Ser Ile Pro Asn Thr
65                  70                  75                  80

Arg Gly Leu Arg Asn Asp Val Val Thr Ala Leu Lys Glu Leu His Val
                85                  90                  95
```

```
Pro Val Leu Arg Trp Pro Gly Gly Cys Phe Ala Asp Glu Tyr His Trp
            100                 105                 110

Arg Asp Gly Ile Gly Pro Arg Asp Lys Arg Pro Arg Arg Pro Asn Ala
        115                 120                 125

Ser Trp Gly Gly Val Asp Ser Asn Ala Phe Gly Thr His Glu Phe Met
    130                 135                 140

Glu Leu Cys Glu Met Leu Gly Ala Asp Ala Tyr Ile Asn Gly Asn Val
145                 150                 155                 160

Gly Ser Gly Thr Pro Gln Glu Met Met Glu Trp Ile Glu Tyr Met Thr
                165                 170                 175

Ser Asp Ser Asp Ser Asp Leu Ala Asn Leu Arg Arg Arg Asn Gly Arg
            180                 185                 190

Asp Lys Pro Trp Lys Val Pro Tyr Phe Ala Val Gly Asn Glu Thr Trp
        195                 200                 205

Gly Cys Gly Gly Asn Met Arg Pro Glu Phe Tyr Ala Asp Val Tyr Arg
    210                 215                 220

Gln Tyr Ala Thr Phe Ile Lys Asn His Ser Gly Asn Arg Ile Gln Lys
225                 230                 235                 240

Leu Ala Ser Gly Gly Tyr Asp Asn Asn Tyr Asn Trp Thr Glu Val Leu
                245                 250                 255

Met Ala Gln Ala Ala Lys Gln Ile Asp Gly Leu Ser Leu His Tyr Tyr
            260                 265                 270

Thr Leu Pro Thr Gly Asn Trp Asp Lys Lys Gly Ser Ala Thr Glu Phe
        275                 280                 285

Gly Glu Ser Glu Trp His Ala Thr Leu Ala Arg Thr Leu Arg Ile Glu
    290                 295                 300

Glu Phe Ile Gln Lys His Ser Ala Ile Met Asp Lys His Asp Pro Gln
305                 310                 315                 320

Lys Arg Val Gly Leu Met Val Asp Glu Trp Gly Thr Trp Tyr Asp Arg
                325                 330                 335

Asp Glu Gly Arg Asp Met Gly Ala Leu Tyr Gln Gln Asn Thr Leu Arg
            340                 345                 350

Asp Ala Val Ala Ala Gly Ile Asn Leu Asn Ile Phe His Lys Tyr Ala
        355                 360                 365

Asp Arg Val Arg Met Ala Asn Ile Ala Gln Met Val Asn Val Leu Gln
    370                 375                 380

Ala Met Val Leu Thr Asp Lys Glu Lys Met Val Leu Thr Pro Thr Tyr
385                 390                 395                 400

His Val Phe Arg Met Tyr Arg Val His Gln Gly Ala Thr Leu Ile Pro
                405                 410                 415

Val Glu Val Ser Ala Pro Gln Tyr Thr Leu Gly Gly Ala Ser Val Pro
            420                 425                 430

Ser Leu Ser Val Ser Ala Ser Arg Asp Gly Glu Gly Arg Val His Leu
        435                 440                 445

Ser Ile Val Asn Leu Asp Pro Ala Arg Ala Ala Glu Ile Asp Ala Asn
    450                 455                 460

Gly Pro Phe Ser Ser Val Lys Gly Glu Val Leu Thr Ala Pro Ala Val
465                 470                 475                 480

Asn Ala Leu Asn Thr Phe Asp His Pro Asp Ser Val Lys Pro Val Ser
                485                 490                 495

Phe Asn Gly Tyr Lys Leu Glu Gly Ser Lys Leu Ile Leu Asn Ile Pro
            500                 505                 510

Ala Lys Ser Val Val Val Leu Glu Leu Gly Pro Gln Lys Gln Ala Thr
```

```
        515                 520                 525

Leu Lys Asp Ala Phe Lys Asn Asp Phe Met Ile Gly Ala Ala Leu Asn
    530                 535                 540

Arg Arg Gln Phe Phe Glu Glu Asp Ala Arg Gly Ala Glu Ile Val Arg
545                 550                 555                 560

Met His Phe Asn Ser Ile Thr Pro Glu Asn Val Leu Lys Trp Gly Leu
                565                 570                 575

Val His Pro Glu Pro Asn Lys Tyr Asp Phe Thr Ala Pro Asp Arg Phe
            580                 585                 590

Val Glu Phe Gly Glu Lys His Gly Met Phe Val Val Gly His Thr Leu
        595                 600                 605

Val Trp His Asn Gln Thr Pro Arg Trp Val Phe Glu Asp Glu Lys Lys
    610                 615                 620

Gln Pro Leu Asp Arg Glu Thr Leu Leu Lys Arg Met Arg Asp His Ile
625                 630                 635                 640

Phe Thr Val Val Gly Arg Tyr Lys Gly Arg Ile Lys Gly Trp Asp Val
                645                 650                 655

Val Asn Glu Ala Leu Asn Gln Asp Gly Thr Met Arg Gln Ser Pro Trp
            660                 665                 670

Phe Lys Ile Ile Gly Glu Asp Tyr Leu Val Lys Ala Phe Glu Phe Ala
        675                 680                 685

His Glu Ala Asp Pro Ala Ala Glu Leu Tyr Tyr Asn Asp Tyr Asp Leu
    690                 695                 700

Glu Leu Pro Ala Lys Arg Ala Gly Ala Val Glu Leu Leu Lys Lys Leu
705                 710                 715                 720

Lys Ala Ala Gly Val Ser Leu Ala Gly Val Gly Leu Gln Asn His Ser
                725                 730                 735

Leu Met Glu Trp Pro Ser Ala Ala Asp Val Asp Ala Thr Ile Ala Ala
            740                 745                 750

Phe Ala Asn Leu Gly Leu Lys Val His Ile Thr Glu Leu Asp Val Asp
        755                 760                 765

Val Leu Pro Arg Thr Thr Lys Pro Gly Ala Asp Tyr Ala Val Asp Val
    770                 775                 780

Lys Val Thr Pro Gln Leu Asn Pro Tyr Leu Asp Gly Leu Pro Glu Ala
785                 790                 795                 800

Arg Gln Ser Ala Leu Ala Arg Arg Tyr Ala Glu Leu Phe His Val Phe
                805                 810                 815

Arg Lys His Arg Asp Ala Ile Glu Arg Val Thr Phe Trp Gly Val Ala
            820                 825                 830

Asp Gly Asp Ser Trp Leu Asn Asn Trp Pro Ile Arg Gly Arg Thr Asn
        835                 840                 845

Tyr Pro Leu Leu Phe Asp Arg Ser Gly Gln Pro Lys Pro Ala Leu Ala
    850                 855                 860

Ser Val Ile Glu Thr Ala Asn Tyr Ser Thr Glu Arg Arg Arg
865                 870                 875


<210> SEQ ID NO 15
<211> LENGTH: 1725
<212> TYPE: DNA
<213> ORGANISM: Clostridium thermocellum

<400> SEQUENCE: 15

gtgtggaagc ccggattgtg gaatttcctt caaatggcag atgaagccgg attgacgagg     60

gatggaaaca ctccggttcc gacacccagt ccaaagccgg ctaacacacg tattgaagcg    120
```

```
gaagattatg acggtattaa ttcttcaagt attgagataa taggtgttcc acctgaagga    180
ggcagaggaa taggttatat taccagtggt gattatctgg tatacaagag tatagacttt    240
ggaaacggag caacgtcgtt taaggccaag gttgcaaatg caaatacttc caatattgaa    300
cttagattaa acggtccgaa tggtactctc ataggcacac tctcggtaaa atccacagga    360
gattggaata catatgagga gcaaacttgc agcattagca aagtcaccgg aataaatgat    420
ttgtacttgg tattcaaagg ccctgtaaac atagactggt tcacttttgg cgttgaaagc    480
agttccacag gtctgggggga tttaaatggt gacggaaata ttaactcgtc ggaccttcag    540
gcgttaaaga ggcatttgct cggtatatca ccgcttacgg gagaggctct tttaagagcg    600
gatgtaaata ggagcggcaa agtggattct actgactatt cagtgctgaa aagatatata    660
ctccgcatta ttacagagtt ccccggacaa ggtgatgtac agacacccaa tccgtctgtt    720
actccgacac aaactcctat ccccacgatt tcgggaaatg ctcttaggga ttatgcggag    780
gcaaggggaa taaaaatcgg aacatgtgtc aactatccgt tttacaacaa ttcagatcca    840
acctacaaca gcattttgca aagagaattt tcaatggttg tatgtgaaaa tgaaatgaag    900
tttgatgctt tgcagccgag acaaaacgtt tttgattttt cgaaaggaga ccagttgctt    960
gcttttgcag aaagaaacgg tatgcagatg aggggacata cgttgatttg gcacaatcaa   1020
aacccgtcat ggcttacaaa cggtaactgg aaccgggatt cgctgcttgc ggtaatgaaa   1080
aatcacatta ccactgttat gacccattac aaaggtaaaa ttgttgagtg ggatgtggca   1140
aacgaatgta tggatgattc cggcaacggc ttaagaagca gcatatggag aaatgtaatc   1200
ggtcaggact accttgacta tgctttcagg tatgcaagag aagcagatcc cgatgcactt   1260
cttttctaca atgattataa tattgaagac ttgggtccaa agtccaatgc ggtatttaac   1320
atgattaaaa gtatgaagga aagaggtgtg ccgattgacg gagtaggatt ccaatgccac   1380
tttatcaatg gaatgagccc cgagtacctt gccagcattg atcaaaatat taagagatat   1440
gcggaaatag gcgttatagt atcctttacc gaaatagata tacgcatacc tcagtcggaa   1500
aacccggcaa ctgcattcca ggtacaggca aacaactata aggaacttat gaaaatttgt   1560
ctggcaaacc ccaattgcaa tacctttgta atgtggggat tcacagataa atacacatgg   1620
attccgggaa ctttcccagg atatggcaat ccattgattt atgacagcaa ttacaatccg   1680
aaaccggcat acaatgcaat aaaggaagct cttatgggct attga                   1725
```

<210> SEQ ID NO 16
<211> LENGTH: 574
<212> TYPE: PRT
<213> ORGANISM: Clostridium thermocellum
<220> FEATURE:
<221> NAME/KEY: DOMAIN
<222> LOCATION: (39)...(158)
<223> OTHER INFORMATION: Carbohydrate binding module (family 6)
<220> FEATURE:
<221> NAME/KEY: DOMAIN
<222> LOCATION: (167)...(187)
<223> OTHER INFORMATION: Dockerin type I repeat
<220> FEATURE:
<221> NAME/KEY: DOMAIN
<222> LOCATION: (201)...(221)
<223> OTHER INFORMATION: Dockerin type I repeat
<220> FEATURE:
<221> NAME/KEY: DOMAIN
<222> LOCATION: (254)...(571)
<223> OTHER INFORMATION: Glycosyl hydrolase family 10
<220> FEATURE:
<221> NAME/KEY: SITE
<222> LOCATION: (47)...(50)

<223> OTHER INFORMATION: N-glycosylation site. Prosite id = PS00001
<220> FEATURE:
<221> NAME/KEY: SITE
<222> LOCATION: (95)...(98)
<223> OTHER INFORMATION: N-glycosylation site. Prosite id = PS00001
<220> FEATURE:
<221> NAME/KEY: SITE
<222> LOCATION: (107)...(110)
<223> OTHER INFORMATION: N-glycosylation site. Prosite id = PS00001
<220> FEATURE:
<221> NAME/KEY: SITE
<222> LOCATION: (167)...(179)
<223> OTHER INFORMATION: EF-hand calcium-binding domain. Prosite id = PS00018
<220> FEATURE:
<221> NAME/KEY: SITE
<222> LOCATION: (167)...(186)
<223> OTHER INFORMATION: Clostridium cellulosome enzymes repeated domain signature. Prosite id = PS00448
<220> FEATURE:
<221> NAME/KEY: SITE
<222> LOCATION: (175)...(178)
<223> OTHER INFORMATION: N-glycosylation site. Prosite id = PS00001
<220> FEATURE:
<221> NAME/KEY: SITE
<222> LOCATION: (204)...(216)
<223> OTHER INFORMATION: EF-hand calcium-binding domain. Prosite id = PS00018
<220> FEATURE:
<221> NAME/KEY: SITE
<222> LOCATION: (201)...(213)
<223> OTHER INFORMATION: Clostridium cellulosome enzymes repeated domain signature. Prosite id = PS00448
<220> FEATURE:
<221> NAME/KEY: SITE
<222> LOCATION: (203)...(206)
<223> OTHER INFORMATION: N-glycosylation site. Prosite id = PS00001
<220> FEATURE:
<221> NAME/KEY: SITE
<222> LOCATION: (276)...(279)
<223> OTHER INFORMATION: N-glycosylation site. Prosite id = PS00001
<220> FEATURE:
<221> NAME/KEY: SITE
<222> LOCATION: (484)...(594)
<223> OTHER INFORMATION: Glycosyl hydrolases family 10 active site. Prosite id = PS00591

<400> SEQUENCE: 16

```
Met Trp Lys Pro Gly Leu Trp Asn Phe Leu Gln Met Ala Asp Glu Ala
1               5                   10                  15

Gly Leu Thr Arg Asp Gly Asn Thr Pro Val Pro Thr Pro Ser Pro Lys
            20                  25                  30

Pro Ala Asn Thr Arg Ile Glu Ala Glu Asp Tyr Asp Gly Ile Asn Ser
        35                  40                  45

Ser Ser Ile Glu Ile Ile Gly Val Pro Pro Glu Gly Gly Arg Gly Ile
    50                  55                  60

Gly Tyr Ile Thr Ser Gly Asp Tyr Leu Val Tyr Lys Ser Ile Asp Phe
65                  70                  75                  80

Gly Asn Gly Ala Thr Ser Phe Lys Ala Lys Val Ala Asn Ala Asn Thr
                85                  90                  95

Ser Asn Ile Glu Leu Arg Leu Asn Gly Pro Asn Gly Thr Leu Ile Gly
            100                 105                 110

Thr Leu Ser Val Lys Ser Thr Gly Asp Trp Asn Thr Tyr Glu Glu Gln
        115                 120                 125

Thr Cys Ser Ile Ser Lys Val Thr Gly Ile Asn Asp Leu Tyr Leu Val
    130                 135                 140

Phe Lys Gly Pro Val Asn Ile Asp Trp Phe Thr Phe Gly Val Glu Ser
145                 150                 155                 160
```

```
Ser Ser Thr Gly Leu Gly Asp Leu Asn Gly Asp Gly Asn Ile Asn Ser
                165                 170                 175

Ser Asp Leu Gln Ala Leu Lys Arg His Leu Leu Gly Ile Ser Pro Leu
            180                 185                 190

Thr Gly Glu Ala Leu Leu Arg Ala Asp Val Asn Arg Ser Gly Lys Val
        195                 200                 205

Asp Ser Thr Asp Tyr Ser Val Leu Lys Arg Tyr Ile Leu Arg Ile Ile
    210                 215                 220

Thr Glu Phe Pro Gly Gln Gly Asp Val Gln Thr Pro Asn Pro Ser Val
225                 230                 235                 240

Thr Pro Thr Gln Thr Pro Ile Pro Thr Ile Ser Gly Asn Ala Leu Arg
                245                 250                 255

Asp Tyr Ala Glu Ala Arg Gly Ile Lys Ile Gly Thr Cys Val Asn Tyr
            260                 265                 270

Pro Phe Tyr Asn Asn Ser Asp Pro Thr Tyr Asn Ser Ile Leu Gln Arg
        275                 280                 285

Glu Phe Ser Met Val Val Cys Glu Asn Glu Met Lys Phe Asp Ala Leu
    290                 295                 300

Gln Pro Arg Gln Asn Val Phe Asp Phe Ser Lys Gly Asp Gln Leu Leu
305                 310                 315                 320

Ala Phe Ala Glu Arg Asn Gly Met Gln Met Arg Gly His Thr Leu Ile
                325                 330                 335

Trp His Asn Gln Asn Pro Ser Trp Leu Thr Asn Gly Asn Trp Asn Arg
            340                 345                 350

Asp Ser Leu Leu Ala Val Met Lys Asn His Ile Thr Thr Val Met Thr
        355                 360                 365

His Tyr Lys Gly Lys Ile Val Glu Trp Asp Val Ala Asn Glu Cys Met
    370                 375                 380

Asp Asp Ser Gly Asn Gly Leu Arg Ser Ser Ile Trp Arg Asn Val Ile
385                 390                 395                 400

Gly Gln Asp Tyr Leu Asp Tyr Ala Phe Arg Tyr Ala Arg Glu Ala Asp
                405                 410                 415

Pro Asp Ala Leu Leu Phe Tyr Asn Asp Tyr Asn Ile Glu Asp Leu Gly
            420                 425                 430

Pro Lys Ser Asn Ala Val Phe Asn Met Ile Lys Ser Met Lys Glu Arg
        435                 440                 445

Gly Val Pro Ile Asp Gly Val Gly Phe Gln Cys His Phe Ile Asn Gly
    450                 455                 460

Met Ser Pro Glu Tyr Leu Ala Ser Ile Asp Gln Asn Ile Lys Arg Tyr
465                 470                 475                 480

Ala Glu Ile Gly Val Ile Val Ser Phe Thr Glu Ile Asp Ile Arg Ile
                485                 490                 495

Pro Gln Ser Glu Asn Pro Ala Thr Ala Phe Gln Val Gln Ala Asn Asn
            500                 505                 510

Tyr Lys Glu Leu Met Lys Ile Cys Leu Ala Asn Pro Asn Cys Asn Thr
        515                 520                 525

Phe Val Met Trp Gly Phe Thr Asp Lys Tyr Thr Trp Ile Pro Gly Thr
    530                 535                 540

Phe Pro Gly Tyr Gly Asn Pro Leu Ile Tyr Asp Ser Asn Tyr Asn Pro
545                 550                 555                 560

Lys Pro Ala Tyr Asn Ala Ile Lys Glu Ala Leu Met Gly Tyr
                565                 570
```

<210> SEQ ID NO 17
<211> LENGTH: 2232
<212> TYPE: DNA
<213> ORGANISM: Cochliobolus heterostrophus ATCC 48331

<400> SEQUENCE: 17 gcaatcggtc ctgattgtac caatggtccc ctgagtacca atgcaatttg cgatgtcaat 60 gcgcctcctc atgagagggc agcggctcta gtcgcagcta tggaaccgca agaaaagcta 120 gataacctcg tcagtaaatc caaaggtgtg tcgagattag gtcttccagc gtataactgg 180 tggggcgaag ctctacacgg tgtagctgga gcgccaggaa tcaaattcgt cgaaccttat 240 aaaaacgcta cttcgtttcc tatgccaatc cttatgtcgg cagcttttga tgatgatctc 300 attttcaaaa ttgccaatat tatcgggaac gaggcccgag ccttcggaaa tggtggagtc 360 gctcctatgg actattggac ccctgacatc aatcccgtcc gcgatatacg atggggccga 420 gccagtgaat cacccggaga ggacattcga cgaataaaag ggtacaccaa ggctctgctt 480 gctggcctcg aaggtgacca agcccaaagg aagatcattg caacatgcaa acactatgtg 540 ggttacgaca tggaagcttg gggaggatac gatcgacaca acttcagtgc aaagatcacc 600 atgcaagacc tcgcagagta ctacatgccg ccattccagc aatgtgcgcg tgactcgaag 660 gtcgggtcat tcatgtgcag ctacaatgca gtcaacggtg ttccaacatg cgctgacacc 720 tacgttcttc aaacaatcct gagggaccac tggaactgga cagatagcaa taactacatt 780 actagcgatt gcgaagccgt tgcggatatc tctgagaacc acaaatatgt cgaaaccctt 840 gcgcaaggca ccgcacttgc ttttgccaag ggtatggatc ttagctgtga atacagtgga 900 tcgtcagata tcccaggagc ttggtcacaa ggtcttctga atctttctgt tatcgacaaa 960 gcattgactc gacaatatga aggcttagtc catgccggct actttgatgg cgcgaaggcg 1020 acttacgcaa acttgagtta taatgacatc aacacacccg aagcacgaca gctatccttg 1080 caagttacct ctgaaggttt ggtcatgcta aagaacgatc acacacttcc attgcctctc 1140 acgaagggat caaaggtggc tatgataggt ttctgggcca acgactcttc caaactccag 1200 ggcatctaca gcggtccacc tccttaccgg cactctccag tattcgctgg tgaacaaatg 1260 ggattagata tggccatagc ctggggccca atgattcaga actcaagtgt gcccgacaac 1320 tggactacca acgcgctcga cgcggccgag aagtccgact atattctcta ctttggtggt 1380 caagactgga cagtggcgca agaaggctac gatcgcacta caatcagttt tcctcaagtg 1440 caaatcgacc ttcttgccaa actggctaaa cttggcaagc cgcttgttgt catcacgctt 1500 ggtgatatga ctgatcactc ccctctcttg tccatggaag gcatcaactc aattatctgg 1560 gcgaattggc ctggccaaga tggcggtcca gcgatactaa acgtgatttc cggtgtgcat 1620 gctcctgcag gtcgtttgcc aataacggaa tacccggcag attatgtcaa gctctctatg 1680 cttgacatga acttgcgacc acatgccgag agccctggcc gtacttatcg ctggttcaat 1740 gagtctgttc agccatttgg cttcggtcta cattacacta cttttgaggc tggttttgct 1800 agcgaagaag gtctaaccta cgatatccag gaaaccttgg atagctgtac acagcagtac 1860 aaggatttgt gtgaggttgc accactggag gtcaccgtgg caaacaaggg taaccgaaca 1920 tcggatttcg tcgctctcgc tttcatcaag ggcgaggttg gacctaagcc atacccacta 1980 aagactctga ttacgtacgg gaggctcaga gatatccatg ggggcgcgaa gaagtcggcg 2040 tcacttccgc ttacacttgg agaattggcc agagtggatc aatcaggcaa caccgttatc 2100 tatcccggcg aatacaccct gctccttgac gagcctactc aggctgagct gaaattgact 2160

```
attacgggcg aggagacaat tctggacaaa tggccccagc cgccaaacgg aggcaatcgg   2220

accgtgcttt ga                                                       2232


<210> SEQ ID NO 18
<211> LENGTH: 743
<212> TYPE: PRT
<213> ORGANISM: Cochliobolus heterostrophus ATCC 48331
<220> FEATURE:
<221> NAME/KEY: DOMAIN
<222> LOCATION: (47)...(297)
<223> OTHER INFORMATION: Glycosyl hydrolase family 3 N terminal domain
<220> FEATURE:
<221> NAME/KEY: DOMAIN
<222> LOCATION: (367)...(594)
<223> OTHER INFORMATION: Glycosyl hydrolase family 3 C terminal domain
<220> FEATURE:
<221> NAME/KEY: SITE
<222> LOCATION: (82)...(85)
<223> OTHER INFORMATION: N-glycosylation site. Prosite id = PS00001
<220> FEATURE:
<221> NAME/KEY: SITE
<222> LOCATION: (252)...(255)
<223> OTHER INFORMATION: N-glycosylation site. Prosite id = PS00001
<220> FEATURE:
<221> NAME/KEY: SITE
<222> LOCATION: (314)...(317)
<223> OTHER INFORMATION: N-glycosylation site. Prosite id = PS00001
<220> FEATURE:
<221> NAME/KEY: SITE
<222> LOCATION: (344)...(347)
<223> OTHER INFORMATION: N-glycosylation site. Prosite id = PS00001
<220> FEATURE:
<221> NAME/KEY: SITE
<222> LOCATION: (394)...(397)
<223> OTHER INFORMATION: N-glycosylation site. Prosite id = PS00001
<220> FEATURE:
<221> NAME/KEY: SITE
<222> LOCATION: (434)...(437)
<223> OTHER INFORMATION: N-glycosylation site. Prosite id = PS00001
<220> FEATURE:
<221> NAME/KEY: SITE
<222> LOCATION: (440)...(443)
<223> OTHER INFORMATION: N-glycosylation site. Prosite id = PS00001
<220> FEATURE:
<221> NAME/KEY: SITE
<222> LOCATION: (580)...(583)
<223> OTHER INFORMATION: N-glycosylation site. Prosite id = PS00001
<220> FEATURE:
<221> NAME/KEY: SITE
<222> LOCATION: (638)...(641)
<223> OTHER INFORMATION: N-glycosylation site. Prosite id = PS00001
<220> FEATURE:
<221> NAME/KEY: SITE
<222> LOCATION: (739)...(742)
<223> OTHER INFORMATION: N-glycosylation site. Prosite id = PS00001

<400> SEQUENCE: 18

Ala Ile Gly Pro Asp Cys Thr Asn Gly Pro Leu Ser Thr Asn Ala Ile
1               5                   10                  15

Cys Asp Val Asn Ala Pro Pro His Glu Arg Ala Ala Ala Leu Val Ala
            20                  25                  30

Ala Met Glu Pro Gln Glu Lys Leu Asp Asn Leu Val Ser Lys Ser Lys
        35                  40                  45

Gly Val Ser Arg Leu Gly Leu Pro Ala Tyr Asn Trp Trp Gly Glu Ala
    50                  55                  60

Leu His Gly Val Ala Gly Ala Pro Gly Ile Lys Phe Val Glu Pro Tyr
65                  70                  75                  80

Lys Asn Ala Thr Ser Phe Pro Met Pro Ile Leu Met Ser Ala Ala Phe
                85                  90                  95

Asp Asp Asp Leu Ile Phe Lys Ile Ala Asn Ile Ile Gly Asn Glu Ala
```

```
            100                 105                 110

Arg Ala Phe Gly Asn Gly Gly Val Ala Pro Met Asp Tyr Trp Thr Pro
        115                 120                 125

Asp Ile Asn Pro Val Arg Asp Ile Arg Trp Gly Arg Ala Ser Glu Ser
    130                 135                 140

Pro Gly Glu Asp Ile Arg Arg Ile Lys Gly Tyr Thr Lys Ala Leu Leu
145                 150                 155                 160

Ala Gly Leu Glu Gly Asp Gln Ala Gln Arg Lys Ile Ile Ala Thr Cys
                165                 170                 175

Lys His Tyr Val Gly Tyr Asp Met Glu Ala Trp Gly Gly Tyr Asp Arg
            180                 185                 190

His Asn Phe Ser Ala Lys Ile Thr Met Gln Asp Leu Ala Glu Tyr Tyr
        195                 200                 205

Met Pro Pro Phe Gln Gln Cys Ala Arg Asp Ser Lys Val Gly Ser Phe
    210                 215                 220

Met Cys Ser Tyr Asn Ala Val Asn Gly Val Pro Thr Cys Ala Asp Thr
225                 230                 235                 240

Tyr Val Leu Gln Thr Ile Leu Arg Asp His Trp Asn Trp Thr Asp Ser
                245                 250                 255

Asn Asn Tyr Ile Thr Ser Asp Cys Glu Ala Val Ala Asp Ile Ser Glu
            260                 265                 270

Asn His Lys Tyr Val Glu Thr Leu Ala Gln Gly Thr Ala Leu Ala Phe
        275                 280                 285

Ala Lys Gly Met Asp Leu Ser Cys Glu Tyr Ser Gly Ser Ser Asp Ile
    290                 295                 300

Pro Gly Ala Trp Ser Gln Gly Leu Leu Asn Leu Ser Val Ile Asp Lys
305                 310                 315                 320

Ala Leu Thr Arg Gln Tyr Glu Gly Leu Val His Ala Gly Tyr Phe Asp
                325                 330                 335

Gly Ala Lys Ala Thr Tyr Ala Asn Leu Ser Tyr Asn Asp Ile Asn Thr
            340                 345                 350

Pro Glu Ala Arg Gln Leu Ser Leu Gln Val Thr Ser Glu Gly Leu Val
        355                 360                 365

Met Leu Lys Asn Asp His Thr Leu Pro Leu Pro Leu Thr Lys Gly Ser
    370                 375                 380

Lys Val Ala Met Ile Gly Phe Trp Ala Asn Asp Ser Ser Lys Leu Gln
385                 390                 395                 400

Gly Ile Tyr Ser Gly Pro Pro Pro Tyr Arg His Ser Pro Val Phe Ala
                405                 410                 415

Gly Glu Gln Met Gly Leu Asp Met Ala Ile Ala Trp Gly Pro Met Ile
            420                 425                 430

Gln Asn Ser Ser Val Pro Asp Asn Trp Thr Thr Asn Ala Leu Asp Ala
        435                 440                 445

Ala Glu Lys Ser Asp Tyr Ile Leu Tyr Phe Gly Gly Gln Asp Trp Thr
    450                 455                 460

Val Ala Gln Glu Gly Tyr Asp Arg Thr Thr Ile Ser Phe Pro Gln Val
465                 470                 475                 480

Gln Ile Asp Leu Leu Ala Lys Leu Ala Lys Leu Gly Lys Pro Leu Val
                485                 490                 495

Val Ile Thr Leu Gly Asp Met Thr Asp His Ser Pro Leu Leu Ser Met
            500                 505                 510

Glu Gly Ile Asn Ser Ile Ile Trp Ala Asn Trp Pro Gly Gln Asp Gly
        515                 520                 525
```

```
Gly Pro Ala Ile Leu Asn Val Ile Ser Gly Val His Ala Pro Ala Gly
    530                 535                 540

Arg Leu Pro Ile Thr Glu Tyr Pro Ala Asp Tyr Val Lys Leu Ser Met
545                 550                 555                 560

Leu Asp Met Asn Leu Arg Pro His Ala Glu Ser Pro Gly Arg Thr Tyr
                565                 570                 575

Arg Trp Phe Asn Glu Ser Val Gln Pro Phe Gly Phe Gly Leu His Tyr
            580                 585                 590

Thr Thr Phe Glu Ala Gly Phe Ala Ser Glu Glu Gly Leu Thr Tyr Asp
        595                 600                 605

Ile Gln Glu Thr Leu Asp Ser Cys Thr Gln Gln Tyr Lys Asp Leu Cys
    610                 615                 620

Glu Val Ala Pro Leu Glu Val Thr Val Ala Asn Lys Gly Asn Arg Thr
625                 630                 635                 640

Ser Asp Phe Val Ala Leu Ala Phe Ile Lys Gly Glu Val Gly Pro Lys
                645                 650                 655

Pro Tyr Pro Leu Lys Thr Leu Ile Thr Tyr Gly Arg Leu Arg Asp Ile
            660                 665                 670

His Gly Gly Ala Lys Lys Ser Ala Ser Leu Pro Leu Thr Leu Gly Glu
        675                 680                 685

Leu Ala Arg Val Asp Gln Ser Gly Asn Thr Val Ile Tyr Pro Gly Glu
    690                 695                 700

Tyr Thr Leu Leu Leu Asp Glu Pro Thr Gln Ala Glu Leu Lys Leu Thr
705                 710                 715                 720

Ile Thr Gly Glu Glu Thr Ile Leu Asp Lys Trp Pro Gln Pro Pro Asn
                725                 730                 735

Gly Gly Asn Arg Thr Val Leu
            740


<210> SEQ ID NO 19
<211> LENGTH: 1362
<212> TYPE: DNA
<213> ORGANISM: Unknown
<220> FEATURE:
<223> OTHER INFORMATION: Bacterial DNA

<400> SEQUENCE: 19

atgcttcagt ttccgaaaga ttttatttgg ggagctgcaa cttcatcgta tcaaattgaa     60

ggaacagcga ctggagaaga taaaatttac tcgatctggg atcacttttc ccgcattcct    120

ggcaaagtag cgaatgggga taatggcgat atcgcaattg atcattacaa tcgttatgtt    180

gaagacatcg cattaatgaa agcgcttcat ttgaaagcgt atcgattttc gactagttgg    240

gcgagacttt attgtgaaac gccagggaag tttaacgaaa aaggtttaga tttttataag    300

cgtcttgtac atgaattgct agagaacggt atcgagccaa tgttgaccat ttatcattgg    360

gatatgccac aagctcttca agagaaaggt ggctgggaaa atcgtgatat cgttcactac    420

ttccaagaat acgctgcttt cctttacgag aatcttgggg atgtcgtgaa aaaatggatt    480

acgcataatg agccgtgggt tgtcacctat ttaggatatg ggaatggcga acatgcccca    540

gggattcaaa actttacatc atttttaaaa gcagcacatc atgttcttct ctcacacggg    600

gaagcggtaa aagcgtttcg agcaatcggt tcgaaagatg gggaaattgg tattacgttg    660

aatttgacac ctggatatgc ggtcgatccg aaagatgaaa aagcagttga tgccgctcga    720

aaatgggacg gctttatgaa tcgttggttt ttagatcctg tatttaaggg acaatatcca    780
```

```
gcagatatgt tagaagtgta taaagattat ttaccagacg tttacaaaga gggagattta    840

caaacgattc agcaaccgat cgactttttc ggatttaact attattcaac agcaacatta    900

aaagattgga aaacaggtga ccgtgaaccg atcgtatttg aacatgtgag cacaggaaga    960

cctgtgacgg atatgaattg ggaagtgaat ccaaacggtt tgtttgattt aatggtgcga   1020

ttgaaaaaag attatggcga tattccatta tacattaccg aaaacggtgc tgcatacaaa   1080

gatcgcgtca acgaacaagg tgaagtagaa gatgatgagc gagttgctta tatacgggag   1140

catttaatcg cttgccaccg cgcgattgaa caaggcgtca atttaaaagg atattatgta   1200

tggtcgctgt tcgataattt tgagtgggca tttggatatg ataagcgctt tgggattgta   1260

tacgtggatt atgaaacgct agagcgcatc ccgaaaaaga gtgcattatg gtacaaggaa   1320

acgattataa acaacggatt gcaagtagac aatgacaaat aa                      1362


<210> SEQ ID NO 20
<211> LENGTH: 453
<212> TYPE: PRT
<213> ORGANISM: Unknown
<220> FEATURE:
<223> OTHER INFORMATION: Bacterial protein
<220> FEATURE:
<221> NAME/KEY: DOMAIN
<222> LOCATION: (1)...(447)
<223> OTHER INFORMATION: Glycosyl hydrolase family 1
<220> FEATURE:
<221> NAME/KEY: SITE
<222> LOCATION: (8)...(22)
<223> OTHER INFORMATION: Glycosyl hydrolases family 1 N-terminal
      signature. Prosite id = PS00653
<220> FEATURE:
<221> NAME/KEY: SITE
<222> LOCATION: (184)...(187)
<223> OTHER INFORMATION: N-glycosylation site. Prosite id = PS00001
<220> FEATURE:
<221> NAME/KEY: SITE
<222> LOCATION: (350)...(358)
<223> OTHER INFORMATION: Glycosyl hydrolases family 1 active site.
      Prosite id = PS00572

<400> SEQUENCE: 20

Met Leu Gln Phe Pro Lys Asp Phe Ile Trp Gly Ala Ala Thr Ser Ser
1               5                   10                  15

Tyr Gln Ile Glu Gly Thr Ala Thr Gly Glu Asp Lys Ile Tyr Ser Ile
            20                  25                  30

Trp Asp His Phe Ser Arg Ile Pro Gly Lys Val Ala Asn Gly Asp Asn
        35                  40                  45

Gly Asp Ile Ala Ile Asp His Tyr Asn Arg Tyr Val Glu Asp Ile Ala
    50                  55                  60

Leu Met Lys Ala Leu His Leu Lys Ala Tyr Arg Phe Ser Thr Ser Trp
65                  70                  75                  80

Ala Arg Leu Tyr Cys Glu Thr Pro Gly Lys Phe Asn Glu Lys Gly Leu
                85                  90                  95

Asp Phe Tyr Lys Arg Leu Val His Glu Leu Leu Glu Asn Gly Ile Glu
            100                 105                 110

Pro Met Leu Thr Ile Tyr His Trp Asp Met Pro Gln Ala Leu Gln Glu
        115                 120                 125

Lys Gly Gly Trp Glu Asn Arg Asp Ile Val His Tyr Phe Gln Glu Tyr
    130                 135                 140

Ala Ala Phe Leu Tyr Glu Asn Leu Gly Asp Val Val Lys Lys Trp Ile
145                 150                 155                 160

Thr His Asn Glu Pro Trp Val Val Thr Tyr Leu Gly Tyr Gly Asn Gly
```

```
                165                 170                 175

Glu His Ala Pro Gly Ile Gln Asn Phe Thr Ser Phe Leu Lys Ala Ala
            180                 185                 190

His His Val Leu Leu Ser His Gly Glu Ala Val Lys Ala Phe Arg Ala
        195                 200                 205

Ile Gly Ser Lys Asp Gly Glu Ile Gly Ile Thr Leu Asn Leu Thr Pro
    210                 215                 220

Gly Tyr Ala Val Asp Pro Lys Asp Glu Lys Ala Val Asp Ala Ala Arg
225                 230                 235                 240

Lys Trp Asp Gly Phe Met Asn Arg Trp Phe Leu Asp Pro Val Phe Lys
                245                 250                 255

Gly Gln Tyr Pro Ala Asp Met Leu Glu Val Tyr Lys Asp Tyr Leu Pro
            260                 265                 270

Asp Val Tyr Lys Glu Gly Asp Leu Gln Thr Ile Gln Gln Pro Ile Asp
        275                 280                 285

Phe Phe Gly Phe Asn Tyr Tyr Ser Thr Ala Thr Leu Lys Asp Trp Lys
    290                 295                 300

Thr Gly Asp Arg Glu Pro Ile Val Phe Glu His Val Ser Thr Gly Arg
305                 310                 315                 320

Pro Val Thr Asp Met Asn Trp Glu Val Asn Pro Asn Gly Leu Phe Asp
                325                 330                 335

Leu Met Val Arg Leu Lys Lys Asp Tyr Gly Asp Ile Pro Leu Tyr Ile
            340                 345                 350

Thr Glu Asn Gly Ala Ala Tyr Lys Asp Arg Val Asn Glu Gln Gly Glu
        355                 360                 365

Val Glu Asp Asp Glu Arg Val Ala Tyr Ile Arg Glu His Leu Ile Ala
    370                 375                 380

Cys His Arg Ala Ile Glu Gln Gly Val Asn Leu Lys Gly Tyr Tyr Val
385                 390                 395                 400

Trp Ser Leu Phe Asp Asn Phe Glu Trp Ala Phe Gly Tyr Asp Lys Arg
                405                 410                 415

Phe Gly Ile Val Tyr Val Asp Tyr Glu Thr Leu Glu Arg Ile Pro Lys
            420                 425                 430

Lys Ser Ala Leu Trp Tyr Lys Glu Thr Ile Ile Asn Asn Gly Leu Gln
        435                 440                 445

Val Asp Asn Asp Lys
    450


<210> SEQ ID NO 21
<211> LENGTH: 930
<212> TYPE: DNA
<213> ORGANISM: Cochliobolus heterostrophus ATCC 48331

<400> SEQUENCE: 21

gtgtcgccca agcaggacag ccgtcaaatc cagggtatca aggacccgac gattatccag      60

aacaatggtg tataccatgt ctttgccagc acggccaagg aagcgggata caacctagtc     120

tacttcaact ttaccgactt cagcagggcc aaccaggcgc cattcttcta cctcgaccag     180

tcaggtatcg gcacaggtta ccgtgctgct cctcaagtct tctacttcgc cccccagaag     240

ctctggtacc tcatctacca aaacggcaat gcagcataca gcaccaaccc cgacatttcc     300

aacccacgag gctggaccgc cccgcaagtc ttctacccca acggaacccc ccagacgatc     360

caaaacggcc taggaacgac cggctactgg gtcgacatgt gggtaatctg cgacacggcc     420

ctctgccacc tgtactcatc cgacgacaac ggcggcctat accgcagcca aacgcccgtc     480
```

```
tcgcaattcc cacgcggcat gaacgagccc gtggtaacgc tcaaggccaa caaaaacgac    540

ctctttgaag cctcgaccgt gtacaacatt gtaaacacca gcacctacct cctcatggtc    600

gaatgcatcg gctccggcaa ctcccccggc ggcctgcgct acttccgctc ctggaccacc    660

cagtccctca ccagcgacaa gtggactccc cttgccgcat cccagcaaac ccctttcctc    720

ggcgccgcta acacccagtt ccccgccggc cgctggtccc agagcttgtc ccacggcgag    780

ctcgttcgca caaatgtaga ccagaggctc cagattcgcc cctgtgaaat gaggtacctc    840

taccagggta tcgatcctaa tgctacgggc acttacaatg ccctgccctg gaaactcgcc    900

cttgcaaccc agacaaactc caagtgttag                                     930


<210> SEQ ID NO 22
<211> LENGTH: 309
<212> TYPE: PRT
<213> ORGANISM: Cochliobolus heterostrophus ATCC 48331
<220> FEATURE:
<221> NAME/KEY: DOMAIN
<222> LOCATION: (3)...(276)
<223> OTHER INFORMATION: Glycosyl hydrolase family 62
<220> FEATURE:
<221> NAME/KEY: SITE
<222> LOCATION: (43)...(46)
<223> OTHER INFORMATION: N-glycosylation site. Prosite id = PS00001
<220> FEATURE:
<221> NAME/KEY: SITE
<222> LOCATION: (192)...(195)
<223> OTHER INFORMATION: N-glycosylation site. Prosite id = PS00001
<220> FEATURE:
<221> NAME/KEY: SITE
<222> LOCATION: (287)...(290)
<223> OTHER INFORMATION: N-glycosylation site. Prosite id = PS00001

<400> SEQUENCE: 22

Met Ser Pro Lys Gln Asp Ser Arg Gln Ile Gln Gly Ile Lys Asp Pro
1               5                   10                  15

Thr Ile Ile Gln Asn Asn Gly Val Tyr His Val Phe Ala Ser Thr Ala
            20                  25                  30

Lys Glu Ala Gly Tyr Asn Leu Val Tyr Phe Asn Phe Thr Asp Phe Ser
        35                  40                  45

Arg Ala Asn Gln Ala Pro Phe Phe Tyr Leu Asp Gln Ser Gly Ile Gly
    50                  55                  60

Thr Gly Tyr Arg Ala Ala Pro Gln Val Phe Tyr Phe Ala Pro Gln Lys
65                  70                  75                  80

Leu Trp Tyr Leu Ile Tyr Gln Asn Gly Asn Ala Ala Tyr Ser Thr Asn
                85                  90                  95

Pro Asp Ile Ser Asn Pro Arg Gly Trp Thr Ala Pro Gln Val Phe Tyr
            100                 105                 110

Pro Asn Gly Thr Pro Gln Thr Ile Gln Asn Gly Leu Gly Thr Thr Gly
        115                 120                 125

Tyr Trp Val Asp Met Trp Val Ile Cys Asp Thr Ala Leu Cys His Leu
    130                 135                 140

Tyr Ser Ser Asp Asp Asn Gly Gly Leu Tyr Arg Ser Gln Thr Pro Val
145                 150                 155                 160

Ser Gln Phe Pro Arg Gly Met Asn Glu Pro Val Val Thr Leu Lys Ala
                165                 170                 175

Asn Lys Asn Asp Leu Phe Glu Ala Ser Thr Val Tyr Asn Ile Val Asn
            180                 185                 190

Thr Ser Thr Tyr Leu Leu Met Val Glu Cys Ile Gly Ser Gly Asn Ser
        195                 200                 205
```

```
Pro Gly Gly Leu Arg Tyr Phe Arg Ser Trp Thr Thr Gln Ser Leu Thr
    210                 215                 220

Ser Asp Lys Trp Thr Pro Leu Ala Ala Ser Gln Gln Thr Pro Phe Leu
225                 230                 235                 240

Gly Ala Ala Asn Thr Gln Phe Pro Ala Gly Arg Trp Ser Gln Ser Leu
                245                 250                 255

Ser His Gly Glu Leu Val Arg Thr Asn Val Asp Gln Arg Leu Gln Ile
            260                 265                 270

Arg Pro Cys Glu Met Arg Tyr Leu Tyr Gln Gly Ile Asp Pro Asn Ala
        275                 280                 285

Thr Gly Thr Tyr Asn Ala Leu Pro Trp Lys Leu Ala Leu Ala Thr Gln
    290                 295                 300

Thr Asn Ser Lys Cys
305


<210> SEQ ID NO 23
<211> LENGTH: 2163
<212> TYPE: DNA
<213> ORGANISM: Unknown
<220> FEATURE:
<223> OTHER INFORMATION: Obtained from environmental sample

<400> SEQUENCE: 23

atgaaacatc acaactataa cgcgcatcat tcgccaatcg gcgctttcgg ctcattcacg     60

ctcggttttc gtggtgctca gggcggcctc ggactggagt taggcggccc ggccaatcac    120

aacatgtaca tcggagtgga agacgagcag cgcaccttcc attgccttcc ctttttggg    180

gatgctgctg caggggccga ggaagcactg cgctacgatg tggaaggcag ccaatccagt    240

gacgatccac tggccggcgc ctatgtcgga cacccagagg atgcgccatc gctgcctccg    300

gccaagttgc gtgcgctgga ccaaagcgcc atctcacggg attttcaact tacgaccgac    360

acctggacag caccggattt ctcactcacg atctattcgc cggtacgcgg cgtgcccgat    420

ccgacaacgg ctgcggaaga cgaattgaaa gccattcttg tgcccgctgt actctgcgag    480

ttgacggtgg ataactcgag tgggcagcag tctcggcgtg cgctctttgg tttcaccggg    540

aacgatcctt attggggaac gcggcgcctt gatgatgtag cgaatagtgc gttcgtgggg    600

gttggcgagg gaaatcatct ggccattgcg tcacgagatg aaggagtgac ggcggcgctg    660

ggcttcaaca tcaatggcgt tatcaacgag actttgcctg agaattacgc ctttggtctg    720

ggcaaatgcg cagttttgct ctgcgaggtg cctgccggtg aaaagcgcac gttccatatc    780

gccgtctgtt ttcatcggag cggcatcgcc accaccggtt tgaagatgcg ctattattac    840

acgcgctttt tccctgacat cgaaagcgta gccgcttatg cactggagca gttcgattct    900

ctcaaaagtg cagctctcca agacaatcaa ctagtggaga acgcgtcgct ttcagaagac    960

cagaaatgga tgttctgcca cgcggtgcgc tcgtactatg gctcaacgga gttgctggag   1020

tataacgaca atccggtgtg ggtggtcaac gaaggcgaat atcgtatgat gaacaccttc   1080

gacttgacgg tggatcatct ctactgggaa ctgcgcctga atccctgggt tgtgaaaaat   1140

cagctcgact ggtttgtgga tcgctactcg tatgaggaca aggtgcgctt tcctggtgac   1200

aaaactgagt acccatgcgg tctctccttc acgcacgata tgggcgtgac gaatgtgtgg   1260

tcgcgccccg gctattcgtc ttatgagaag cagggactca agggtgtctt ttcgtatatg   1320

acgcacgagc aactcgtcaa ctggctctgc tgcgccacgg tgtatgtgga acagaccggt   1380

gaccaggagt ggcttgaaca acggtggccg attttcaaca ggtgctttga gagtttgctc   1440
```

```
aaccgcgatc accccgatcc tgaaaagcgg cgcggcttaa tgcaactcga ttcgacccgt   1500

tgcgccggtg gtgcggagat caccacttac gacagccttg atgtctcgct ggggcagtca   1560

cgcaacaaca cctatctggg tgggaaaatc tgggcgagct atctggcact cgaaaaattg   1620

ttccgcgagc gcggcgacgt ggaaagagcg caagtggcgc atcaacaggc gcatcgcacg   1680

gcgcaaacgc tgctggagaa tgtcggcgag aatgggacga ttcccgccgt actcgaaggc   1740

agcaatcagt cgagaatcat tcccgtgatt gaggggttga tcttccccta cttcaccggg   1800

cgcaaggatg tcctcagttc cgatggcgac ttcggcgaga tgttttcggc actcaagcgc   1860

catcttgaag ccgtgctaaa acccggtatc tgtctgtttg aagatggtgg ctggaagtta   1920

agttcaacct ctgataactc gtggctgagc aaaatctacc tgtgccagtt cgtcgcgcgc   1980

cagatattgg gccgtgaacg cgatgacatt gacaagcgcg ccgatgccgc gcacgtgggc   2040

tggctgctcg atgagcgcaa tgcctacttc gcgtggagtg accagatgct ggccggcttt   2100

gcggaaggct ccaagtacta cccgcgcggt gtgaccagcg cattgtggtt gctggaaggc   2160

tga                                                                 2163
```

```
<210> SEQ ID NO 24
<211> LENGTH: 720
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (19)...(456)
<223> OTHER INFORMATION: Glycosyl hydrolase family 52
<220> FEATURE:
<221> NAME/KEY: SITE
<222> LOCATION: (165)...(168)
<223> OTHER INFORMATION: N-glycosylation site. Prosite id = PS00001
<220> FEATURE:
<221> NAME/KEY: SITE
<222> LOCATION: (229)...(232)
<223> OTHER INFORMATION: N-glycosylation site. Prosite id = PS00001
<220> FEATURE:
<221> NAME/KEY: SITE
<222> LOCATION: (314)...(317)
<223> OTHER INFORMATION: N-glycosylation site. Prosite id = PS00001
<220> FEATURE:
<221> NAME/KEY: SITE
<222> LOCATION: (522)...(525)
<223> OTHER INFORMATION: N-glycosylation site. Prosite id = PS00001
<220> FEATURE:
<221> NAME/KEY: SITE
<222> LOCATION: (571)...(574)
<223> OTHER INFORMATION: N-glycosylation site. Prosite id = PS00001
<220> FEATURE:
<221> NAME/KEY: SITE
<222> LOCATION: (582)...(585)
<223> OTHER INFORMATION: N-glycosylation site. Prosite id = PS00001

<400> SEQUENCE: 24

Met Lys His His Asn Tyr Asn Ala His His Ser Pro Ile Gly Ala Phe
1               5                   10                  15

Gly Ser Phe Thr Leu Gly Phe Arg Gly Ala Gln Gly Gly Leu Gly Leu
            20                  25                  30

Glu Leu Gly Gly Pro Ala Asn His Asn Met Tyr Ile Gly Val Glu Asp
        35                  40                  45

Glu Gln Arg Thr Phe His Cys Leu Pro Phe Phe Gly Asp Ala Ala Ala
    50                  55                  60

Gly Ala Glu Glu Ala Leu Arg Tyr Asp Val Glu Gly Ser Gln Ser Ser
65                  70                  75                  80
```

```
Asp Asp Pro Leu Ala Gly Ala Tyr Val Gly His Pro Glu Asp Ala Pro
                85                  90                  95

Ser Leu Pro Pro Ala Lys Leu Arg Ala Leu Asp Gln Ser Ala Ile Ser
            100                 105                 110

Arg Asp Phe Gln Leu Thr Thr Asp Thr Trp Thr Ala Pro Asp Phe Ser
        115                 120                 125

Leu Thr Ile Tyr Ser Pro Val Arg Gly Val Pro Asp Pro Thr Thr Ala
    130                 135                 140

Ala Glu Asp Glu Leu Lys Ala Ile Leu Val Pro Ala Val Leu Cys Glu
145                 150                 155                 160

Leu Thr Val Asp Asn Ser Ser Gly Gln Gln Ser Arg Arg Ala Leu Phe
                165                 170                 175

Gly Phe Thr Gly Asn Asp Pro Tyr Trp Gly Thr Arg Arg Leu Asp Asp
            180                 185                 190

Val Ala Asn Ser Ala Phe Val Gly Val Gly Glu Gly Asn His Leu Ala
        195                 200                 205

Ile Ala Ser Arg Asp Glu Gly Val Thr Ala Ala Leu Gly Phe Asn Ile
    210                 215                 220

Asn Gly Val Ile Asn Glu Thr Leu Pro Glu Asn Tyr Ala Phe Gly Leu
225                 230                 235                 240

Gly Lys Cys Ala Val Leu Leu Cys Glu Val Pro Ala Gly Glu Lys Arg
                245                 250                 255

Thr Phe His Ile Ala Val Cys Phe His Arg Ser Gly Ile Ala Thr Thr
            260                 265                 270

Gly Leu Lys Met Arg Tyr Tyr Tyr Thr Arg Phe Phe Pro Asp Ile Glu
        275                 280                 285

Ser Val Ala Ala Tyr Ala Leu Glu Gln Phe Asp Ser Leu Lys Ser Ala
    290                 295                 300

Ala Leu Gln Asp Asn Gln Leu Val Glu Asn Ala Ser Leu Ser Glu Asp
305                 310                 315                 320

Gln Lys Trp Met Phe Cys His Ala Val Arg Ser Tyr Tyr Gly Ser Thr
                325                 330                 335

Glu Leu Leu Glu Tyr Asn Asp Asn Pro Val Trp Val Val Asn Glu Gly
            340                 345                 350

Glu Tyr Arg Met Met Asn Thr Phe Asp Leu Thr Val Asp His Leu Tyr
        355                 360                 365

Trp Glu Leu Arg Leu Asn Pro Trp Val Val Lys Asn Gln Leu Asp Trp
    370                 375                 380

Phe Val Asp Arg Tyr Ser Tyr Glu Asp Lys Val Arg Phe Pro Gly Asp
385                 390                 395                 400

Lys Thr Glu Tyr Pro Cys Gly Leu Ser Phe Thr His Asp Met Gly Val
                405                 410                 415

Thr Asn Val Trp Ser Arg Pro Gly Tyr Ser Ser Tyr Glu Lys Gln Gly
            420                 425                 430

Leu Lys Gly Val Phe Ser Tyr Met Thr His Glu Gln Leu Val Asn Trp
        435                 440                 445

Leu Cys Cys Ala Thr Val Tyr Val Glu Gln Thr Gly Asp Gln Glu Trp
    450                 455                 460

Leu Glu Gln Arg Trp Pro Ile Phe Asn Arg Cys Phe Glu Ser Leu Leu
465                 470                 475                 480

Asn Arg Asp His Pro Asp Pro Glu Lys Arg Arg Gly Leu Met Gln Leu
                485                 490                 495
```

-continued

```
Asp Ser Thr Arg Cys Ala Gly Gly Ala Glu Ile Thr Thr Tyr Asp Ser
            500                 505                 510

Leu Asp Val Ser Leu Gly Gln Ser Arg Asn Asn Thr Tyr Leu Gly Gly
        515                 520                 525

Lys Ile Trp Ala Ser Tyr Leu Ala Leu Glu Lys Leu Phe Arg Glu Arg
    530                 535                 540

Gly Asp Val Glu Arg Ala Gln Val Ala His Gln Gln Ala His Arg Thr
545                 550                 555                 560

Ala Gln Thr Leu Leu Glu Asn Val Gly Glu Asn Gly Thr Ile Pro Ala
                565                 570                 575

Val Leu Glu Gly Ser Asn Gln Ser Arg Ile Ile Pro Val Ile Glu Gly
            580                 585                 590

Leu Ile Phe Pro Tyr Phe Thr Gly Arg Lys Asp Val Leu Ser Ser Asp
        595                 600                 605

Gly Asp Phe Gly Glu Met Phe Ser Ala Leu Lys Arg His Leu Glu Ala
    610                 615                 620

Val Leu Lys Pro Gly Ile Cys Leu Phe Glu Asp Gly Gly Trp Lys Leu
625                 630                 635                 640

Ser Ser Thr Ser Asp Asn Ser Trp Leu Ser Lys Ile Tyr Leu Cys Gln
                645                 650                 655

Phe Val Ala Arg Gln Ile Leu Gly Arg Glu Arg Asp Asp Ile Asp Lys
            660                 665                 670

Arg Ala Asp Ala Ala His Val Gly Trp Leu Leu Asp Glu Arg Asn Ala
        675                 680                 685

Tyr Phe Ala Trp Ser Asp Gln Met Leu Ala Gly Phe Ala Glu Gly Ser
    690                 695                 700

Lys Tyr Tyr Pro Arg Gly Val Thr Ser Ala Leu Trp Leu Leu Glu Gly
705                 710                 715                 720
```

What is claimed is:

1. An isolated, synthetic, or recombinant polypeptide having a xylanase activity, wherein the polypeptide comprises an amino acid sequence having at least 95% sequence identity to SEQ ID NO: 2, and amino acid residue change at amino acid residue 44 such that amino acid residue 44 Serine, Ser (or "S") is changed to Threonine, "Thr" (or "T").

2. A protein preparation, or an immobilized polypeptide comprising the polypeptide of claim 1, wherein the protein preparation comprises a liquid, a solid or a gel.

3. The polypeptide of claim 1, wherein the polypeptide specifically binds to an antibody and the antibody is a monoclonal, a polyclonal antibody, or a single chained antibody.

4. A method for hydrolyzing, liquefying, breaking up, or disrupting a xylan-, cellulose- or hemicellulose-comprising composition, comprising: contacting the polypeptide of claim 1 with the composition comprising a xylan, a cellulose, or a hemicellulose under conditions wherein the polypeptide hydrolyze, liquefy, breakup, or disrupt the xylan, cellulose, or hemicellulose-comprising composition, wherein optionally the composition comprises a plant cell, or a bacterial cell.

5. A biomass, wood, wood pulp, wood product, paper pulp, paper product, newspaper or paper waste comprising the polypeptide of claim 1.

6. An enzyme cocktail comprising the polypeptide of claim 1, and one or more enzymes selected from a group consisting of: a xylanase, a mannanase, a glucanase, a cellulose, a lipase, an esterase, a protease, an endoglycosidase, an endo-beta.-1,4-glucanase, a beta-glucanase, an endo-beta-1,3(4)-glucanase, a cutinase, a peroxidase, a catalase, a laccase, an amylase, a glucoamylase, a pectinase, a reductase, an oxidase, a phenoloxidase, a ligninase, a pullulanase, an arabinanase, a hemicellulase, a mannanase, a xyloglucanase, a xylanase, a mannanase, a glucanase, a pectin acetyl esterase, a rhamnogalacturonan acetyl esterase, a polygalacturonase, a rhamnogalacturonase, a galactanase, a pectin lyase, a pectin methylesterase, a cellobiohydrolase, a transglutaminase, or a combination thereof.

7. A process for hydrolyzing xylans, celluloses, or hemicelluloses in any organic compound, plant or wood or wood product or byproduct, wood waste, paper pulp, paper product or paper waste or byproduct with the polypeptide of claim 1.

8. A composition comprising the polypeptide of claim 1.

9. The enzyme cocktail of claim 6, further comprising at least one additional enzyme selected from: an Endo glucanase, an Oligomerase I (beta glucosidase), a CBHI (GH family 7), a CBH2 (GH family 6), a Xylanase (GH family 11), an Arabinofuranosidase, a Xylanase (GH family 10), and an Oligomerase II (beta-xylosidase).

10. A fabric, yarn, cloth or textile comprising the polypeptide of claim 1 wherein the fabric, yarn, cloth or textile comprises a non-cotton cellulosic fabric, yarn, cloth, or textile.

11. A food, a feed, or a nutritional supplement comprising the polypeptide of claim 1.

12. The polypeptide of claim 1, further comprising a heterologous amino acid sequence.

13. The polypeptide of claim 12, wherein the heterologous amino acid sequence comprises:

(a) a heterologous signal sequence, a heterologous carbohydrate binding module, a heterologous dockerin domain, a heterologous catalytic domain (CD), or a combination thereof;

(b) the sequence of (a), wherein the heterologous signal sequence, carbohydrate binding module or heterologous catalytic domain (CD) is derived from a heterologous enzyme; a tag, an epitope, a targeting peptide, a cleavable sequence, a detectable moiety or an enzyme; or (c) the sequence of (a), wherein the heterologous carbohydrate binding module (CBM) comprises, a xylan binding module, a cellulose binding module, a lignin binding module, a xylose binding module, a mannanse binding module, a xyloglucan-specific module or a arabinofuranosidase binding module.

14. The polypeptide of claim 1, wherein the amino acid sequence further comprising a second amino acid change selected from a group consisting of:

(a) a change at amino acid residue 4 such that amino acid residue 4 Threonine, or "Thr" (or "T") is changed to Asparagine, or Asn (or "N");

(b) a change at amino acid residue 4 such that amino acid residue 4 Threonine, or "Thr" (or "T") is changed to Arginine, Arg (or "R");

(c) a change at amino acid residue 4 such that amino acid residue 4 Threonine, or "Thr" (or "T") is changed to Histidine, His (or "H");

(d) a change at amino acid residue 73 such that amino acid residue 73 Glycine, Gly (or "G") is changed to Tyrosine, "Tyr" (or "Y");

(e) a change at amino acid residue 63 such that amino acid residue 63 Isoleucine, Ile (or "I") is changed to Valine, "Val" (or "V");

(f) a change at amino acid residue 17 such that amino acid residue 17 Phenylalanine, Phe (or "F") is changed to Valine, "Val" (or "V");

(g) a change at amino acid residue 38 such that amino acid residue 38 Arginine, Arg (or "R") is changed to Histidine, His (or "H");

(h) a change at amino acid residue 33 such that amino acid residue 33 Leucine, Leu (or "L") is changed to Alaninw, Ala (or "A");

(i) a change at amino acid residue 73 such that amino acid residue 73 Glycine, Gly (or "G") is changed to Glutamate, Glu (or "E");

(j) a change at amino acid residue 73 such that amino acid residue 73 Glycine, Gly (or "G") is changed to Valine, "Val" (or "V");

(k) a change at amino acid residue 125 such that amino acid residue 125 Glutamine, Gln (or "Q") is changed to Tyrosine, "Tyr" (or "Y"):

(l) a change at amino acid residue 188 such that amino acid residue 188 Serine, Ser (or "S") is changed to Glutamate, Glu (or "E");

(m) a change at amino acid residue 9, such that amino acid residue 9 Proline, Pro (or "P") is changed to Aspartate, Asp (or "D");

(n) a change at amino acid residue 150, such that amino acid residue 150 Valine, Val (or "V") is changed to Alanine, Ala (or "A");

(o) a change at amino acid residue 189, such that amino acid residue 189 Serine, Ser (or "S") is changed to Glutamine, Gln (or "Q");

(p) a change at amino acid residue 21, such that amino acid residue 21 Phenylalanine, Phe (or "F") is changed to Tyrosine, "Tyr" (or "Y"); and (q) any combination of the changes (a) to (m).

15. A method for reducing the amount of lignin (delignification), or solubilizing a lignin, in a paper or paper product, a wood, wood pulp or wood product, or a wood or paper recycling composition, comprising: contacting the paper or paper product, wood, wood pulp or wood product, or wood or paper recycling composition with the polypeptide of claim 1 thereby reducing the amount of lignin.

16. A method for an enzymatic decoloring of paper, hemp, or flax pulp comprising: contacting the paper, hemp, or flax pulp with the polypeptide of claim 1 and a decoloring agent, wherein optionally the decoloring agent comprises oxygen or hydrogen peroxide under conditions suitable for enzymatic decoloring.

17. A method for an enzymatic deinking of paper, paper waste, paper recycled product, deinking toner from non-contact printed wastepaper or mixtures of non-contact and contact printed wastepaper, comprising: contacting the paper, paper waste, paper recycled product, non-contact printed wastepaper, or contact printed wastepaper with the polypeptide of claim 1 under conditions suitable for enzymatic deinking.

18. A method for decoloring a fabric, yarn, cloth, or textile comprising: contacting the fabric, yarn, cloth, or textile with the polypeptide of claim 1 under conditions suitable to produce a whitening of the textile, wherein optionally the fabric, yarn, cloth, or textile comprises a non-cotton cellulosic fabric, yarn, cloth, or textile, under conditions suitable for enzymatic decoloring.

19. The polypeptide of claim 1, wherein the amino acid sequence is a fragment of SEQ ID NO:2 having xylanase activity.

20. A method for hydrolyzing celluloses, hemicelluloses, or xylans in a biomass, a wood, wood product, paper pulp, paper product or paper waste comprising contacting the wood, wood product, paper pulp, paper product or paper waste with the polypeptide of claim 1.

21. A method for using the polypeptide of claim 1 for converting biomass to methanol, butanol, ethanol or propanol.

22. The polypeptide of claim 1, wherein the amino acid sequence has least 96% sequence identity to SEQ ID NO: 2.

23. The polypeptide of claim 1, wherein the amino acid sequence has least 97% sequence identity to SEQ ID NO: 2.

24. The polypeptide of claim 1, wherein the amino acid sequence has least 98% sequence identity to SEQ ID NO: 2.

25. The polypeptide of claim 1, wherein the amino acid sequence has least 99% sequence identity to SEQ ID NO: 2.

26. The polypeptide of claim 1, wherein the amino acid sequence is the [sequences] *sequence* set forth in SEQ ID NO: 2, *wherein an amino acid residue is changed at amino acid residue 44 such that amino acid residue 44 Serine, Ser (or "S") is changed to Threonine, "Thr" (or "T").*

*27. The polypeptide of claim 1, produced by the method comprising:*

*(a) transforming a cell with a vector comprising polynucleotide sequence encoding the polypeptide of claim 1; and*

*(b) culturing the transformed cell under conditions to produce the polypeptide.*

*28. The polypeptide of claim 27 further comprising disrupting the cells and collecting the resulting extract comprising the polypeptide.*

*29. The polypeptide of claim 27, wherein the transformed cell is a bacterial cell or a fungal cell.*

*30. The polypeptide of claim 27, wherein the polynucleotide sequence is operably linked to a promoter.*

* * * * *